United States Patent
Corbett et al.

(10) Patent No.: US 6,911,545 B2
(45) Date of Patent: Jun. 28, 2005

(54) CRYSTALS OF GLUCOKINASE AND METHODS OF GROWING THEM

(75) Inventors: Wendy Lea Corbett, Randolph, NJ (US); Robert Lewis Crowther, East Stroudsburg, PA (US); Pete William Dunten, Mountain View, CA (US); R. Ursula Kammlott, Fair Lawn, NJ (US); Christine Maria Lukacs, Millburn, NJ (US)

(73) Assignee: Hoffman-La Roche Inc., Nutley, NJ (US)

(*) Notice: Subject to any disclaimer, the term of this patent is extended or adjusted under 35 U.S.C. 154(b) by 0 days.

(21) Appl. No.: 10/318,308

(22) Filed: Dec. 12, 2002

(65) Prior Publication Data

US 2003/0219887 A1 Nov. 27, 2003

Related U.S. Application Data

(60) Provisional application No. 60/341,988, filed on Dec. 19, 2001.

(51) Int. Cl.⁷ ............................................. C07D 417/02
(52) U.S. Cl. ................................................... 546/270.7
(58) Field of Search ....................... 546/270.7

(56) References Cited

U.S. PATENT DOCUMENTS 6,320,050 B1  11/2001  Bizzarro et al.

OTHER PUBLICATIONS

Aleshin et al., Structure 6, pp. 39–50, 1998.
Bennett, Jr. et al., J. Mol. Biol. vol. 140, pp. 183–209, 1978.
Ito et al., Structure 9, pp. 205–214, 2001.
Colowick, S. P., The Enzymes, vol. 9 (P. Boyer, ed.) Academic Press, New York, NY pp. 1–48, 1973.
Chipkin, S. R., et al., Joslin's Diabetes (C.R. Khan & G. C. Wier, eds.), Lea & Febiger, Philadelphia, PA, pp. 97–115, 1994.
Printz, R. G., et al., Ann. Rev. Nutrition, vol. 13, (R. E. Olson, D. M. Bier, & D. B. McCormick eds.) pp. 463–496, 1993.
Meglasson, M. D. et al., Amer. J. Physiol. vol. 246 pp. E1–E13, 1984.
Grupe, A., et al., Cell vol. 83, pp. 69–78, 1995.
Ferrie T. et al., FASB J. vol. 10, pp. 1213–1218, 1996.
Liang, Y. et al., Biochem. J. vol. 309, pp. 167–173, 1995.
Glaser, B. et al., New England J. Med. vol. 338, pp. 226–230, 1998.
Aleshin Alexander E., et al., FEBS Letters, XP002253654, vol. 391, No. 1–2, pp. 9–10 (1996).
Aleshin Alexander E., et a., Journal of Molecular Biology, XP002253657, vol. 296, No. 4 pp. 1001–1015 (2000).
Tongleli Li, J. Biomaterials Sci. Polymer Edn., XP002918057, vol. 9, No. 4, pp. 327–344 (1998).
Tsuge, et al., Protein Science, vol. 11, pp. 2456–2463 (2002).
Mahalingam, et al., vol. 48, pp. 1698–1705 (1999).

*Primary Examiner*—Zinna Northington Davis
(74) *Attorney, Agent, or Firm*—George W. Johnston; Dennis P. Tramaloni; Eileen M. Ebel

(57) ABSTRACT

Crystalline forms of mammalian Gluckokinase of sufficient size and quality to obtain structural data by X-ray crystallography are presented. Methods of growing such crystals are also disclosed.

1 Claim, 65 Drawing Sheets

Figure 2. The amino-acid sequence of the GST-GK fusion protein. The GST sequence was taken from GenBank entry U13852. Residue 229 of the fusion protein is the first residue of GK.

```
  1 MSPILGYWKI KGLVQPTRLL LEYLEEKYEE HLYERDEGDK WRNKKFELGL EFPNLPYYID
 61 GDVKLTQSMA IIRYIADKHN MLGGCPKERA EISMLEGAVL DIRYGVSRIA YSKDFETLKV
121 DFLSKLPEML KMFEDRLCHK TYLNGDHVTH PDFMLYDALD VVLYMDPMCL DAFPKLVCFK
181 KRIEAIPQID KYLKSSKYIA WPLQGWQATF GGGDHPPKSD LIEGRGIHMP RPRSQLPQPN
241 SQVEQILAEF QLQEEDLKKV MRRMQKEMDR GLRLETHEEA SVKMLPTYVR STPEGSEVGD
301 FLSLDLGGTN FRVMLVKVGE GEEGQWSVKT KHQMYSIPED AMTGTAEMLF DYISECISDF
361 LDKHQMKHKK LPLGFTFSFP VRHEDIDKGI LLNWTKGFKA SGAEGNNVVG LLRDAIKRRG
421 DFEMDVVAMV NDTVATMISC YYEDHQCEVG MIVGTGCNAC YMEEMQNVEL VEGDEGRMCV
481 NTEWGAFGDS GELDEFLLEY DRLVDESSAN PGQQLYEKLI GGKYMGELVR LVLLRLVDEN
541 LLFHGEASEQ LRTRGAFETR FVSQVESDTG DRKQIYNILS TLGLRPSTTD CDIVRRACES
601 VSTRAAHMCS AGLAGVINRM RESRSEDVMR ITVGVDGSVY KLHPSFKERF HASVRRLTPS
661 CEITFIESEE GSGRGAALVS AVACKKACML GQ
```

| Atom No. | Atom Type | A.A. Type | A.A.# | X | Y | Z | OCC | B |
|---|---|---|---|---|---|---|---|---|
| ATOM | 1 | CB | SER | 8 | -0.421 | 63.744 | 24.899 | 1.00 | 50.68 |
| ATOM | 2 | OG | SER | 8 | -0.752 | 63.605 | 23.524 | 1.00 | 50.85 |
| ATOM | 3 | C | SER | 8 | 1.865 | 64.216 | 24.094 | 1.00 | 50.72 |
| ATOM | 4 | O | SER | 8 | 2.308 | 63.644 | 23.102 | 1.00 | 51.79 |
| ATOM | 5 | N | SER | 8 | 1.473 | 63.793 | 26.507 | 1.00 | 50.36 |
| ATOM | 6 | CA | SER | 8 | 1.057 | 63.446 | 25.120 | 1.00 | 50.55 |
| ATOM | 7 | N | GLN | 9 | 2.041 | 65.515 | 24.314 | 1.00 | 49.84 |
| ATOM | 8 | CA | GLN | 9 | 2.831 | 66.312 | 23.385 | 1.00 | 48.95 |
| ATOM | 9 | CB | GLN | 9 | 2.983 | 67.745 | 23.895 | 1.00 | 49.08 |
| ATOM | 10 | CG | GLN | 9 | 3.676 | 68.686 | 22.925 | 1.00 | 50.25 |
| ATOM | 11 | CD | GLN | 9 | 3.206 | 70.127 | 23.085 | 1.00 | 51.06 |
| ATOM | 12 | OE1 | GLN | 9 | 2.037 | 70.433 | 22.846 | 1.00 | 51.38 |
| ATOM | 13 | NE2 | GLN | 9 | 4.112 | 71.017 | 23.499 | 1.00 | 51.44 |
| ATOM | 14 | C | GLN | 9 | 4.190 | 65.633 | 23.294 | 1.00 | 48.56 |
| ATOM | 15 | O | GLN | 9 | 4.884 | 65.741 | 22.285 | 1.00 | 48.75 |
| ATOM | 16 | N | VAL | 10 | 4.560 | 64.926 | 24.361 | 1.00 | 47.77 |
| ATOM | 17 | CA | VAL | 10 | 5.823 | 64.198 | 24.392 | 1.00 | 46.87 |
| ATOM | 18 | CB | VAL | 10 | 6.293 | 63.902 | 25.842 | 1.00 | 46.39 |
| ATOM | 19 | CG1 | VAL | 10 | 7.303 | 62.782 | 25.841 | 1.00 | 46.41 |
| ATOM | 20 | CG2 | VAL | 10 | 6.952 | 65.135 | 26.436 | 1.00 | 46.79 |
| ATOM | 21 | C | VAL | 10 | 5.616 | 62.885 | 23.653 | 1.00 | 46.17 |
| ATOM | 22 | O | VAL | 10 | 6.521 | 62.384 | 22.991 | 1.00 | 46.18 |
| ATOM | 23 | N | GLU | 11 | 4.423 | 62.317 | 23.768 | 1.00 | 45.28 |
| ATOM | 24 | CA | GLU | 11 | 4.159 | 61.071 | 23.069 | 1.00 | 45.19 |
| ATOM | 25 | CB | GLU | 11 | 2.905 | 60.393 | 23.616 | 1.00 | 45.21 |
| ATOM | 26 | CG | GLU | 11 | 3.105 | 59.709 | 24.967 | 1.00 | 46.05 |
| ATOM | 27 | CD | GLU | 11 | 4.224 | 58.664 | 24.957 | 1.00 | 46.30 |
| ATOM | 28 | OE1 | GLU | 11 | 4.350 | 57.918 | 23.948 | 1.00 | 46.28 |
| ATOM | 29 | OE2 | GLU | 11 | 4.963 | 58.583 | 25.972 | 1.00 | 45.66 |
| ATOM | 30 | C | GLU | 11 | 4.002 | 61.345 | 21.580 | 1.00 | 44.48 |
| ATOM | 31 | O | GLU | 11 | 4.068 | 60.430 | 20.755 | 1.00 | 44.48 |
| ATOM | 32 | N | GLN | 12 | 3.807 | 62.614 | 21.239 | 1.00 | 43.86 |
| ATOM | 33 | CA | GLN | 12 | 3.646 | 62.996 | 19.845 | 1.00 | 42.86 |
| ATOM | 34 | CB | GLN | 12 | 2.972 | 64.368 | 19.715 | 1.00 | 44.49 |
| ATOM | 35 | CG | GLN | 12 | 2.833 | 64.840 | 18.259 | 1.00 | 46.49 |
| ATOM | 36 | CD | GLN | 12 | 1.986 | 66.099 | 18.113 | 1.00 | 47.74 |
| ATOM | 37 | OE1 | GLN | 12 | 2.055 | 66.799 | 17.088 | 1.00 | 48.30 |
| ATOM | 38 | NE2 | GLN | 12 | 1.174 | 66.388 | 19.131 | 1.00 | 47.51 |
| ATOM | 39 | C | GLN | 12 | 5.014 | 63.023 | 19.192 | 1.00 | 41.14 |
| ATOM | 40 | O | GLN | 12 | 5.139 | 62.739 | 18.002 | 1.00 | 41.76 |
| ATOM | 41 | N | ILE | 13 | 6.038 | 63.360 | 19.971 | 1.00 | 38.51 |
| ATOM | 42 | CA | ILE | 13 | 7.398 | 63.388 | 19.450 | 1.00 | 36.48 |
| ATOM | 43 | CB | ILE | 13 | 8.274 | 64.351 | 20.261 | 1.00 | 35.85 |
| ATOM | 44 | CG2 | ILE | 13 | 9.731 | 64.228 | 19.827 | 1.00 | 35.71 |
| ATOM | 45 | CG1 | ILE | 13 | 7.740 | 65.777 | 20.079 | 1.00 | 35.77 |
| ATOM | 46 | CD1 | ILE | 13 | 8.584 | 66.867 | 20.710 | 1.00 | 35.91 |
| ATOM | 47 | C | ILE | 13 | 8.018 | 61.981 | 19.452 | 1.00 | 36.01 |
| ATOM | 48 | O | ILE | 13 | 8.572 | 61.528 | 18.442 | 1.00 | 35.99 |
| ATOM | 49 | N | LEU | 14 | 7.903 | 61.288 | 20.580 | 1.00 | 34.88 |
| ATOM | 50 | CA | LEU | 14 | 8.430 | 59.934 | 20.711 | 1.00 | 33.91 |
| ATOM | 51 | CB | LEU | 14 | 8.230 | 59.432 | 22.141 | 1.00 | 33.29 |
| ATOM | 52 | CG | LEU | 14 | 8.853 | 60.321 | 23.215 | 1.00 | 33.43 |
| ATOM | 53 | CD1 | LEU | 14 | 8.510 | 59.781 | 24.594 | 1.00 | 33.04 |

*FIG. 4A*

| ATOM | 54 | CD2 | LEU | 14 | 10.354 | 60.398 | 23.001 | 1.00 | 33.04 |
|------|-----|-----|-----|----|--------|--------|--------|------|-------|
| ATOM | 55 | C | LEU | 14 | 7.766 | 58.957 | 19.730 | 1.00 | 33.55 |
| ATOM | 56 | O | LEU | 14 | 8.208 | 57.812 | 19.578 | 1.00 | 33.21 |
| ATOM | 57 | N | ALA | 15 | 6.710 | 59.403 | 19.065 | 1.00 | 32.69 |
| ATOM | 58 | CA | ALA | 15 | 6.021 | 58.551 | 18.104 | 1.00 | 32.59 |
| ATOM | 59 | CB | ALA | 15 | 4.628 | 59.104 | 17.821 | 1.00 | 31.95 |
| ATOM | 60 | C | ALA | 15 | 6.838 | 58.449 | 16.808 | 1.00 | 32.79 |
| ATOM | 61 | O | ALA | 15 | 6.664 | 57.519 | 16.018 | 1.00 | 33.05 |
| ATOM | 62 | N | GLU | 16 | 7.746 | 59.395 | 16.599 | 1.00 | 32.33 |
| ATOM | 63 | CA | GLU | 16 | 8.575 | 59.369 | 15.403 | 1.00 | 32.74 |
| ATOM | 64 | CB | GLU | 16 | 9.566 | 60.531 | 15.401 | 1.00 | 34.23 |
| ATOM | 65 | CG | GLU | 16 | 8.950 | 61.910 | 15.298 | 1.00 | 38.39 |
| ATOM | 66 | CD | GLU | 16 | 10.017 | 62.998 | 15.162 | 1.00 | 41.11 |
| ATOM | 67 | OE1 | GLU | 16 | 10.445 | 63.269 | 14.012 | 1.00 | 40.68 |
| ATOM | 68 | OE2 | GLU | 16 | 10.438 | 63.562 | 16.212 | 1.00 | 42.77 |
| ATOM | 69 | C | GLU | 16 | 9.369 | 58.073 | 15.279 | 1.00 | 31.93 |
| ATOM | 70 | O | GLU | 16 | 9.570 | 57.568 | 14.179 | 1.00 | 33.41 |
| ATOM | 71 | N | PHE | 17 | 9.841 | 57.539 | 16.401 | 1.00 | 30.37 |
| ATOM | 72 | CA | PHE | 17 | 10.640 | 56.321 | 16.369 | 1.00 | 27.71 |
| ATOM | 73 | CB | PHE | 17 | 11.346 | 56.129 | 17.711 | 1.00 | 26.32 |
| ATOM | 74 | CG | PHE | 17 | 12.309 | 57.230 | 18.045 | 1.00 | 24.22 |
| ATOM | 75 | CD1 | PHE | 17 | 11.846 | 58.500 | 18.389 | 1.00 | 23.88 |
| ATOM | 76 | CD2 | PHE | 17 | 13.680 | 57.010 | 17.981 | 1.00 | 22.24 |
| ATOM | 77 | CE1 | PHE | 17 | 12.741 | 59.531 | 18.660 | 1.00 | 22.63 |
| ATOM | 78 | CE2 | PHE | 17 | 14.574 | 58.027 | 18.250 | 1.00 | 21.23 |
| ATOM | 79 | CZ | PHE | 17 | 14.105 | 59.291 | 18.589 | 1.00 | 22.01 |
| ATOM | 80 | C | PHE | 17 | 9.836 | 55.077 | 16.012 | 1.00 | 27.77 |
| ATOM | 81 | O | PHE | 17 | 10.400 | 54.004 | 15.802 | 1.00 | 27.38 |
| ATOM | 82 | N | GLN | 18 | 8.517 | 55.213 | 15.957 | 1.00 | 28.12 |
| ATOM | 83 | CA | GLN | 18 | 7.684 | 54.080 | 15.593 | 1.00 | 29.17 |
| ATOM | 84 | CB | GLN | 18 | 6.216 | 54.484 | 15.599 | 1.00 | 30.98 |
| ATOM | 85 | CG | GLN | 18 | 5.446 | 54.017 | 16.806 | 1.00 | 32.94 |
| ATOM | 86 | CD | GLN | 18 | 4.152 | 54.785 | 16.974 | 1.00 | 34.65 |
| ATOM | 87 | OE1 | GLN | 18 | 3.389 | 54.976 | 16.014 | 1.00 | 37.17 |
| ATOM | 88 | NE2 | GLN | 18 | 3.892 | 55.228 | 18.190 | 1.00 | 33.67 |
| ATOM | 89 | C | GLN | 18 | 8.068 | 53.602 | 14.193 | 1.00 | 28.97 |
| ATOM | 90 | O | GLN | 18 | 8.471 | 54.399 | 13.346 | 1.00 | 28.83 |
| ATOM | 91 | N | LEU | 19 | 7.931 | 52.298 | 13.971 | 1.00 | 29.02 |
| ATOM | 92 | CA | LEU | 19 | 8.235 | 51.659 | 12.704 | 1.00 | 29.94 |
| ATOM | 93 | CB | LEU | 19 | 9.641 | 51.069 | 12.749 | 1.00 | 29.78 |
| ATOM | 94 | CG | LEU | 19 | 10.782 | 51.813 | 12.037 | 1.00 | 30.77 |
| ATOM | 95 | CD1 | LEU | 19 | 10.886 | 53.251 | 12.477 | 1.00 | 30.67 |
| ATOM | 96 | CD2 | LEU | 19 | 12.083 | 51.087 | 12.339 | 1.00 | 32.05 |
| ATOM | 97 | C | LEU | 19 | 7.199 | 50.549 | 12.511 | 1.00 | 31.41 |
| ATOM | 98 | O | LEU | 19 | 7.288 | 49.484 | 13.137 | 1.00 | 31.35 |
| ATOM | 99 | N | GLN | 20 | 6.205 | 50.801 | 11.663 | 1.00 | 32.64 |
| ATOM | 100 | CA | GLN | 20 | 5.153 | 49.817 | 11.422 | 1.00 | 34.95 |
| ATOM | 101 | CB | GLN | 20 | 4.024 | 50.413 | 10.570 | 1.00 | 35.78 |
| ATOM | 102 | CG | GLN | 20 | 3.301 | 51.622 | 11.175 | 1.00 | 37.65 |
| ATOM | 103 | CD | GLN | 20 | 3.048 | 51.486 | 12.669 | 1.00 | 39.03 |
| ATOM | 104 | OE1 | GLN | 20 | 2.603 | 50.441 | 13.152 | 1.00 | 40.92 |
| ATOM | 105 | NE2 | GLN | 20 | 3.324 | 52.552 | 13.410 | 1.00 | 40.04 |
| ATOM | 106 | C | GLN | 20 | 5.692 | 48.568 | 10.730 | 1.00 | 35.83 |
| ATOM | 107 | O | GLN | 20 | 6.827 | 48.547 | 10.247 | 1.00 | 36.56 |
| ATOM | 108 | N | GLU | 21 | 4.864 | 47.531 | 10.681 | 1.00 | 36.52 |
| ATOM | 109 | CA | GLU | 21 | 5.240 | 46.279 | 10.062 | 1.00 | 37.80 |
| ATOM | 110 | CB | GLU | 21 | 4.024 | 45.357 | 9.998 | 1.00 | 39.22 |

*FIG. 4B*

| ATOM | 111 | CG | GLU | 21 | 4.298 | 43.898 | 9.625 | 1.00 | 42.88 |
|------|-----|-----|-----|-----|--------|--------|--------|------|-------|
| ATOM | 112 | CD | GLU | 21 | 4.568 | 43.009 | 10.844 | 1.00 | 44.63 |
| ATOM | 113 | OE1 | GLU | 21 | 4.540 | 41.758 | 10.699 | 1.00 | 45.40 |
| ATOM | 114 | OE2 | GLU | 21 | 4.810 | 43.564 | 11.943 | 1.00 | 45.89 |
| ATOM | 115 | C | GLU | 21 | 5.770 | 46.549 | 8.654 | 1.00 | 38.20 |
| ATOM | 116 | O | GLU | 21 | 6.892 | 46.183 | 8.324 | 1.00 | 38.71 |
| ATOM | 117 | N | GLU | 22 | 4.972 | 47.208 | 7.826 | 1.00 | 38.54 |
| ATOM | 118 | CA | GLU | 22 | 5.386 | 47.478 | 6.457 | 1.00 | 39.08 |
| ATOM | 119 | CB | GLU | 22 | 4.308 | 48.267 | 5.703 | 1.00 | 40.61 |
| ATOM | 120 | CG | GLU | 22 | 3.123 | 47.406 | 5.313 | 1.00 | 43.51 |
| ATOM | 121 | CD | GLU | 22 | 3.556 | 46.039 | 4.773 | 1.00 | 45.80 |
| ATOM | 122 | OE1 | GLU | 22 | 4.243 | 45.999 | 3.719 | 1.00 | 46.20 |
| ATOM | 123 | OE2 | GLU | 22 | 3.215 | 45.007 | 5.414 | 1.00 | 46.87 |
| ATOM | 124 | C | GLU | 22 | 6.711 | 48.197 | 6.359 | 1.00 | 38.74 |
| ATOM | 125 | O | GLU | 22 | 7.482 | 47.954 | 5.423 | 1.00 | 39.26 |
| ATOM | 126 | N | ASP | 23 | 6.988 | 49.084 | 7.308 | 1.00 | 37.74 |
| ATOM | 127 | CA | ASP | 23 | 8.258 | 49.795 | 7.276 | 1.00 | 37.23 |
| ATOM | 128 | CB | ASP | 23 | 8.356 | 50.779 | 8.437 | 1.00 | 38.62 |
| ATOM | 129 | CG | ASP | 23 | 7.240 | 51.789 | 8.427 | 1.00 | 40.46 |
| ATOM | 130 | OD1 | ASP | 23 | 7.104 | 52.508 | 7.408 | 1.00 | 41.26 |
| ATOM | 131 | OD2 | ASP | 23 | 6.495 | 51.861 | 9.438 | 1.00 | 41.77 |
| ATOM | 132 | C | ASP | 23 | 9.371 | 48.760 | 7.382 | 1.00 | 35.54 |
| ATOM | 133 | O | ASP | 23 | 10.267 | 48.698 | 6.536 | 1.00 | 35.43 |
| ATOM | 134 | N | LEU | 24 | 9.294 | 47.937 | 8.420 | 1.00 | 33.31 |
| ATOM | 135 | CA | LEU | 24 | 10.288 | 46.910 | 8.631 | 1.00 | 32.04 |
| ATOM | 136 | CB | LEU | 24 | 9.898 | 46.062 | 9.842 | 1.00 | 31.35 |
| ATOM | 137 | CG | LEU | 24 | 9.920 | 46.801 | 11.196 | 1.00 | 31.20 |
| ATOM | 138 | CD1 | LEU | 24 | 9.710 | 45.815 | 12.343 | 1.00 | 29.48 |
| ATOM | 139 | CD2 | LEU | 24 | 11.253 | 47.526 | 11.367 | 1.00 | 31.51 |
| ATOM | 140 | C | LEU | 24 | 10.509 | 46.041 | 7.385 | 1.00 | 31.61 |
| ATOM | 141 | O | LEU | 24 | 11.645 | 45.723 | 7.049 | 1.00 | 31.67 |
| ATOM | 142 | N | LYS | 25 | 9.434 | 45.673 | 6.693 | 1.00 | 31.58 |
| ATOM | 143 | CA | LYS | 25 | 9.551 | 44.863 | 5.486 | 1.00 | 31.41 |
| ATOM | 144 | CB | LYS | 25 | 8.186 | 44.347 | 5.061 | 1.00 | 31.91 |
| ATOM | 145 | CG | LYS | 25 | 7.574 | 43.372 | 6.033 | 1.00 | 34.39 |
| ATOM | 146 | CD | LYS | 25 | 6.224 | 42.901 | 5.531 | 1.00 | 36.61 |
| ATOM | 147 | CE | LYS | 25 | 5.414 | 42.232 | 6.640 | 1.00 | 38.71 |
| ATOM | 148 | NZ | LYS | 25 | 3.978 | 42.086 | 6.235 | 1.00 | 39.39 |
| ATOM | 149 | C | LYS | 25 | 10.166 | 45.679 | 4.352 | 1.00 | 31.50 |
| ATOM | 150 | O | LYS | 25 | 10.969 | 45.170 | 3.568 | 1.00 | 30.92 |
| ATOM | 151 | N | LYS | 26 | 9.784 | 46.947 | 4.261 | 1.00 | 31.82 |
| ATOM | 152 | CA | LYS | 26 | 10.332 | 47.819 | 3.229 | 1.00 | 32.63 |
| ATOM | 153 | CB | LYS | 26 | 9.695 | 49.203 | 3.315 | 1.00 | 33.38 |
| ATOM | 154 | CG | LYS | 26 | 10.053 | 50.129 | 2.177 | 1.00 | 35.11 |
| ATOM | 155 | CD | LYS | 26 | 9.424 | 51.502 | 2.400 | 1.00 | 37.48 |
| ATOM | 156 | CE | LYS | 26 | 9.364 | 52.312 | 1.104 | 1.00 | 39.72 |
| ATOM | 157 | NZ | LYS | 26 | 8.706 | 53.645 | 1.307 | 1.00 | 42.62 |
| ATOM | 158 | C | LYS | 26 | 11.845 | 47.919 | 3.441 | 1.00 | 32.91 |
| ATOM | 159 | O | LYS | 26 | 12.614 | 48.012 | 2.479 | 1.00 | 32.90 |
| ATOM | 160 | N | VAL | 27 | 12.265 | 47.901 | 4.705 | 1.00 | 33.16 |
| ATOM | 161 | CA | VAL | 27 | 13.687 | 47.956 | 5.046 | 1.00 | 33.43 |
| ATOM | 162 | CB | VAL | 27 | 13.903 | 48.281 | 6.555 | 1.00 | 32.58 |
| ATOM | 163 | CG1 | VAL | 27 | 15.335 | 47.960 | 6.963 | 1.00 | 32.13 |
| ATOM | 164 | CG2 | VAL | 27 | 13.622 | 49.755 | 6.818 | 1.00 | 31.04 |
| ATOM | 165 | C | VAL | 27 | 14.305 | 46.586 | 4.727 | 1.00 | 33.90 |
| ATOM | 166 | O | VAL | 27 | 15.323 | 46.482 | 4.036 | 1.00 | 33.83 |
| ATOM | 167 | N | MSE | 28 | 13.668 | 45.536 | 5.223 | 1.00 | 34.26 |

*FIG. 4C*

| ATOM | 168 | CA | MSE | 28 | 14.140 | 44.193 | 4.983 | 1.00 | 34.84 |
|------|-----|-----|-----|-----|--------|--------|-------|------|-------|
| ATOM | 169 | CB | MSE | 28 | 13.072 | 43.198 | 5.393 | 1.00 | 35.83 |
| ATOM | 170 | CG | MSE | 28 | 13.456 | 41.784 | 5.144 | 1.00 | 38.88 |
| ATOM | 171 | SE | MSE | 28 | 12.108 | 40.670 | 5.608 | 1.00 | 45.40 |
| ATOM | 172 | CE | MSE | 28 | 11.054 | 40.713 | 4.095 | 1.00 | 42.96 |
| ATOM | 173 | C | MSE | 28 | 14.465 | 44.016 | 3.505 | 1.00 | 35.32 |
| ATOM | 174 | O | MSE | 28 | 15.571 | 43.621 | 3.144 | 1.00 | 35.22 |
| ATOM | 175 | N | ARG | 29 | 13.495 | 44.331 | 2.655 | 1.00 | 36.22 |
| ATOM | 176 | CA | ARG | 29 | 13.665 | 44.191 | 1.218 | 1.00 | 36.59 |
| ATOM | 177 | CB | ARG | 29 | 12.352 | 44.520 | 0.509 | 1.00 | 37.37 |
| ATOM | 178 | CG | ARG | 29 | 11.223 | 43.542 | 0.827 | 1.00 | 38.96 |
| ATOM | 179 | CD | ARG | 29 | 9.913 | 43.960 | 0.152 | 1.00 | 40.89 |
| ATOM | 180 | NE | ARG | 29 | 8.760 | 43.281 | 0.744 | 1.00 | 42.88 |
| ATOM | 181 | CZ | ARG | 29 | 7.621 | 43.889 | 1.081 | 1.00 | 43.80 |
| ATOM | 182 | NH1 | ARG | 29 | 7.475 | 45.201 | 0.881 | 1.00 | 43.07 |
| ATOM | 183 | NH2 | ARG | 29 | 6.631 | 43.188 | 1.636 | 1.00 | 44.12 |
| ATOM | 184 | C | ARG | 29 | 14.814 | 45.008 | 0.625 | 1.00 | 36.30 |
| ATOM | 185 | O | ARG | 29 | 15.615 | 44.469 | -0.133 | 1.00 | 35.58 |
| ATOM | 186 | N | ARG | 30 | 14.906 | 46.296 | 0.948 | 1.00 | 36.85 |
| ATOM | 187 | CA | ARG | 30 | 16.008 | 47.091 | 0.410 | 1.00 | 38.41 |
| ATOM | 188 | CB | ARG | 30 | 15.944 | 48.543 | 0.894 | 1.00 | 39.31 |
| ATOM | 189 | CG | ARG | 30 | 14.676 | 49.285 | 0.513 | 1.00 | 41.96 |
| ATOM | 190 | CD | ARG | 30 | 14.742 | 50.763 | 0.933 | 1.00 | 44.07 |
| ATOM | 191 | NE | ARG | 30 | 13.415 | 51.384 | 0.995 | 1.00 | 45.48 |
| ATOM | 192 | CZ | ARG | 30 | 13.179 | 52.628 | 1.416 | 1.00 | 45.93 |
| ATOM | 193 | NH1 | ARG | 30 | 14.175 | 53.403 | 1.810 | 1.00 | 45.92 |
| ATOM | 194 | NH2 | ARG | 30 | 11.937 | 53.091 | 1.467 | 1.00 | 45.68 |
| ATOM | 195 | C | ARG | 30 | 17.338 | 46.461 | 0.843 | 1.00 | 39.05 |
| ATOM | 196 | O | ARG | 30 | 18.286 | 46.404 | 0.061 | 1.00 | 38.99 |
| ATOM | 197 | N | MSE | 31 | 17.408 | 45.999 | 2.092 | 1.00 | 39.11 |
| ATOM | 198 | CA | MSE | 31 | 18.615 | 45.348 | 2.596 | 1.00 | 38.96 |
| ATOM | 199 | CB | MSE | 31 | 18.374 | 44.784 | 4.002 | 1.00 | 40.43 |
| ATOM | 200 | CG | MSE | 31 | 19.512 | 43.922 | 4.599 | 1.00 | 42.62 |
| ATOM | 201 | SE | MSE | 31 | 21.083 | 44.819 | 5.027 | 1.00 | 48.46 |
| ATOM | 202 | CE | MSE | 31 | 20.438 | 45.988 | 6.389 | 1.00 | 45.46 |
| ATOM | 203 | C | MSE | 31 | 18.901 | 44.209 | 1.633 | 1.00 | 38.25 |
| ATOM | 204 | O | MSE | 31 | 19.973 | 44.132 | 1.038 | 1.00 | 38.18 |
| ATOM | 205 | N | GLN | 32 | 17.915 | 43.334 | 1.478 | 1.00 | 37.93 |
| ATOM | 206 | CA | GLN | 32 | 18.037 | 42.199 | 0.589 | 1.00 | 37.33 |
| ATOM | 207 | CB | GLN | 32 | 16.708 | 41.475 | 0.480 | 1.00 | 36.41 |
| ATOM | 208 | CG | GLN | 32 | 16.219 | 40.905 | 1.780 | 1.00 | 37.04 |
| ATOM | 209 | CD | GLN | 32 | 15.304 | 39.723 | 1.561 | 1.00 | 37.28 |
| ATOM | 210 | OE1 | GLN | 32 | 15.740 | 38.682 | 1.072 | 1.00 | 38.23 |
| ATOM | 211 | NE2 | GLN | 32 | 14.027 | 39.874 | 1.912 | 1.00 | 37.39 |
| ATOM | 212 | C | GLN | 32 | 18.475 | 42.641 | -0.791 | 1.00 | 37.81 |
| ATOM | 213 | O | GLN | 32 | 19.215 | 41.929 | -1.466 | 1.00 | 37.79 |
| ATOM | 214 | N | LYS | 33 | 18.019 | 43.819 | -1.205 | 1.00 | 38.80 |
| ATOM | 215 | CA | LYS | 33 | 18.362 | 44.345 | -2.516 | 1.00 | 39.85 |
| ATOM | 216 | CB | LYS | 33 | 17.525 | 45.588 | -2.830 | 1.00 | 40.63 |
| ATOM | 217 | CG | LYS | 33 | 17.591 | 45.992 | -4.298 | 1.00 | 42.21 |
| ATOM | 218 | CD | LYS | 33 | 16.924 | 47.336 | -4.561 | 1.00 | 43.78 |
| ATOM | 219 | CE | LYS | 33 | 17.160 | 47.803 | -6.006 | 1.00 | 44.42 |
| ATOM | 220 | NZ | LYS | 33 | 16.639 | 49.187 | -6.256 | 1.00 | 44.23 |
| ATOM | 221 | C | LYS | 33 | 19.843 | 44.695 | -2.574 | 1.00 | 40.37 |
| ATOM | 222 | O | LYS | 33 | 20.519 | 44.411 | -3.564 | 1.00 | 40.53 |
| ATOM | 223 | N | GLU | 34 | 20.331 | 45.312 | -1.500 | 1.00 | 40.59 |
| ATOM | 224 | CA | GLU | 34 | 21.730 | 45.712 | -1.378 | 1.00 | 40.95 |

*FIG. 4D*

| ATOM | 225 | CB  | GLU | 34 | 21.912 | 46.641 | -0.179 | 1.00 | 41.24 |
| ATOM | 226 | CG  | GLU | 34 | 21.229 | 47.956 | -0.359 | 1.00 | 41.42 |
| ATOM | 227 | CD  | GLU | 34 | 21.476 | 48.506 | -1.741 | 1.00 | 42.21 |
| ATOM | 228 | OE1 | GLU | 34 | 22.650 | 48.810 | -2.063 | 1.00 | 42.30 |
| ATOM | 229 | OE2 | GLU | 34 | 20.493 | 48.613 | -2.507 | 1.00 | 43.29 |
| ATOM | 230 | C   | GLU | 34 | 22.667 | 44.528 | -1.221 | 1.00 | 40.87 |
| ATOM | 231 | O   | GLU | 34 | 23.770 | 44.527 | -1.767 | 1.00 | 41.06 |
| ATOM | 232 | N   | MSE | 35 | 22.233 | 43.534 | -0.456 | 1.00 | 41.15 |
| ATOM | 233 | CA  | MSE | 35 | 23.038 | 42.350 | -0.232 | 1.00 | 41.36 |
| ATOM | 234 | CB  | MSE | 35 | 22.289 | 41.354 | 0.648  | 1.00 | 41.62 |
| ATOM | 235 | CG  | MSE | 35 | 22.320 | 41.711 | 2.117  | 1.00 | 43.28 |
| ATOM | 236 | SE  | MSE | 35 | 21.428 | 40.506 | 3.120  | 1.00 | 46.51 |
| ATOM | 237 | CE  | MSE | 35 | 22.217 | 38.947 | 2.587  | 1.00 | 45.63 |
| ATOM | 238 | C   | MSE | 35 | 23.376 | 41.701 | -1.554 | 1.00 | 41.91 |
| ATOM | 239 | O   | MSE | 35 | 24.532 | 41.367 | -1.824 | 1.00 | 42.73 |
| ATOM | 240 | N   | ASP | 36 | 22.367 | 41.533 | -2.395 | 1.00 | 42.15 |
| ATOM | 241 | CA  | ASP | 36 | 22.593 | 40.898 | -3.675 | 1.00 | 41.96 |
| ATOM | 242 | CB  | ASP | 36 | 21.264 | 40.633 | -4.369 | 1.00 | 43.56 |
| ATOM | 243 | CG  | ASP | 36 | 21.446 | 39.947 | -5.699 | 1.00 | 45.91 |
| ATOM | 244 | OD1 | ASP | 36 | 21.821 | 40.652 | -6.675 | 1.00 | 46.71 |
| ATOM | 245 | OD2 | ASP | 36 | 21.232 | 38.707 | -5.754 | 1.00 | 46.76 |
| ATOM | 246 | C   | ASP | 36 | 23.502 | 41.717 | -4.578 | 1.00 | 41.03 |
| ATOM | 247 | O   | ASP | 36 | 24.406 | 41.178 | -5.217 | 1.00 | 40.61 |
| ATOM | 248 | N   | ARG | 37 | 23.257 | 43.021 | -4.620 | 1.00 | 40.36 |
| ATOM | 249 | CA  | ARG | 37 | 24.034 | 43.937 | -5.446 | 1.00 | 39.76 |
| ATOM | 250 | CB  | ARG | 37 | 23.498 | 45.355 | -5.283 | 1.00 | 39.56 |
| ATOM | 251 | CG  | ARG | 37 | 22.252 | 45.621 | -6.112 | 1.00 | 40.04 |
| ATOM | 252 | CD  | ARG | 37 | 21.465 | 46.815 | -5.590 | 1.00 | 41.19 |
| ATOM | 253 | NE  | ARG | 37 | 22.278 | 48.002 | -5.307 | 1.00 | 41.70 |
| ATOM | 254 | CZ  | ARG | 37 | 22.938 | 48.711 | -6.221 | 1.00 | 42.38 |
| ATOM | 255 | NH1 | ARG | 37 | 22.899 | 48.362 | -7.505 | 1.00 | 42.59 |
| ATOM | 256 | NH2 | ARG | 37 | 23.615 | 49.792 | -5.851 | 1.00 | 41.94 |
| ATOM | 257 | C   | ARG | 37 | 25.524 | 43.908 | -5.152 | 1.00 | 39.94 |
| ATOM | 258 | O   | ARG | 37 | 26.335 | 43.732 | -6.059 | 1.00 | 40.39 |
| ATOM | 259 | N   | GLY | 38 | 25.893 | 44.076 | -3.890 | 1.00 | 39.94 |
| ATOM | 260 | CA  | GLY | 38 | 27.305 | 44.063 | -3.557 | 1.00 | 39.60 |
| ATOM | 261 | C   | GLY | 38 | 27.933 | 42.689 | -3.699 | 1.00 | 39.23 |
| ATOM | 262 | O   | GLY | 38 | 29.163 | 42.546 | -3.695 | 1.00 | 39.59 |
| ATOM | 263 | N   | LEU | 39 | 27.087 | 41.677 | -3.834 | 1.00 | 38.16 |
| ATOM | 264 | CA  | LEU | 39 | 27.545 | 40.307 | -3.960 | 1.00 | 37.65 |
| ATOM | 265 | CB  | LEU | 39 | 26.428 | 39.376 | -3.495 | 1.00 | 35.76 |
| ATOM | 266 | CG  | LEU | 39 | 26.821 | 38.029 | -2.900 | 1.00 | 34.52 |
| ATOM | 267 | CD1 | LEU | 39 | 27.899 | 38.248 | -1.857 | 1.00 | 33.52 |
| ATOM | 268 | CD2 | LEU | 39 | 25.606 | 37.348 | -2.284 | 1.00 | 32.44 |
| ATOM | 269 | C   | LEU | 39 | 27.931 | 39.989 | -5.407 | 1.00 | 39.20 |
| ATOM | 270 | O   | LEU | 39 | 28.594 | 38.980 | -5.681 | 1.00 | 39.88 |
| ATOM | 271 | N   | ARG | 40 | 27.537 | 40.866 | -6.329 | 1.00 | 40.51 |
| ATOM | 272 | CA  | ARG | 40 | 27.809 | 40.656 | -7.751 | 1.00 | 41.77 |
| ATOM | 273 | CB  | ARG | 40 | 26.494 | 40.686 | -8.526 | 1.00 | 42.80 |
| ATOM | 274 | CG  | ARG | 40 | 25.735 | 39.392 | -8.377 | 1.00 | 44.75 |
| ATOM | 275 | CD  | ARG | 40 | 24.257 | 39.551 | -8.636 | 1.00 | 46.47 |
| ATOM | 276 | NE  | ARG | 40 | 23.639 | 38.239 | -8.797 | 1.00 | 48.71 |
| ATOM | 277 | CZ  | ARG | 40 | 22.331 | 38.034 | -8.890 | 1.00 | 50.01 |
| ATOM | 278 | NH1 | ARG | 40 | 21.497 | 39.064 | -8.831 | 1.00 | 51.43 |
| ATOM | 279 | NH2 | ARG | 40 | 21.861 | 36.804 | -9.060 | 1.00 | 50.46 |
| ATOM | 280 | C   | ARG | 40 | 28.802 | 41.623 | -8.374 | 1.00 | 42.16 |
| ATOM | 281 | O   | ARG | 40 | 28.783 | 42.819 | -8.097 | 1.00 | 42.42 |

*FIG. 4E*

| | | | | | | | | |
|---|---|---|---|---|---|---|---|---|
| ATOM | 282 | N | LEU | 41 | 29.650 | 41.087 | -9.247 | 1.00 42.03 |
| ATOM | 283 | CA | LEU | 41 | 30.689 | 41.864 | -9.902 | 1.00 42.00 |
| ATOM | 284 | CB | LEU | 41 | 31.307 | 41.044 | -11.041 | 1.00 42.00 |
| ATOM | 285 | CG | LEU | 41 | 32.577 | 41.650 | -11.660 | 1.00 41.78 |
| ATOM | 286 | CD1 | LEU | 41 | 33.638 | 41.836 | -10.583 | 1.00 40.20 |
| ATOM | 287 | CD2 | LEU | 41 | 33.087 | 40.747 | -12.773 | 1.00 41.95 |
| ATOM | 288 | C | LEU | 41 | 30.278 | 43.237 | -10.428 | 1.00 42.57 |
| ATOM | 289 | O | LEU | 41 | 30.920 | 44.243 | -10.110 | 1.00 42.64 |
| ATOM | 290 | N | GLU | 42 | 29.219 | 43.292 | -11.227 | 1.00 43.03 |
| ATOM | 291 | CA | GLU | 42 | 28.788 | 44.562 | -11.803 | 1.00 44.63 |
| ATOM | 292 | CB | GLU | 42 | 27.494 | 44.369 | -12.607 | 1.00 43.97 |
| ATOM | 293 | CG | GLU | 42 | 26.436 | 43.533 | -11.922 | 1.00 44.02 |
| ATOM | 294 | CD | GLU | 42 | 26.546 | 42.057 | -12.248 | 1.00 43.71 |
| ATOM | 295 | OE1 | GLU | 42 | 27.673 | 41.527 | -12.245 | 1.00 45.13 |
| ATOM | 296 | OE2 | GLU | 42 | 25.504 | 41.416 | -12.496 | 1.00 43.50 |
| ATOM | 297 | C | GLU | 42 | 28.616 | 45.714 | -10.805 | 1.00 46.21 |
| ATOM | 298 | O | GLU | 42 | 28.963 | 46.860 | -11.103 | 1.00 46.22 |
| ATOM | 299 | N | THR | 43 | 28.105 | 45.413 | -9.616 | 1.00 47.90 |
| ATOM | 300 | CA | THR | 43 | 27.873 | 46.443 | -8.608 | 1.00 49.10 |
| ATOM | 301 | CB | THR | 43 | 26.370 | 46.533 | -8.285 | 1.00 48.63 |
| ATOM | 302 | OG1 | THR | 43 | 25.772 | 45.242 | -8.465 | 1.00 47.66 |
| ATOM | 303 | CG2 | THR | 43 | 25.679 | 47.531 | -9.192 | 1.00 48.90 |
| ATOM | 304 | C | THR | 43 | 28.629 | 46.226 | -7.302 | 1.00 50.94 |
| ATOM | 305 | O | THR | 43 | 28.481 | 47.008 | -6.362 | 1.00 51.52 |
| ATOM | 306 | N | HIS | 44 | 29.456 | 45.185 | -7.249 | 1.00 52.58 |
| ATOM | 307 | CA | HIS | 44 | 30.204 | 44.854 | -6.037 | 1.00 53.89 |
| ATOM | 308 | CB | HIS | 44 | 31.210 | 43.727 | -6.311 | 1.00 54.68 |
| ATOM | 309 | CG | HIS | 44 | 32.552 | 44.208 | -6.775 | 1.00 55.77 |
| ATOM | 310 | CD2 | HIS | 44 | 33.748 | 44.257 | -6.139 | 1.00 55.82 |
| ATOM | 311 | ND1 | HIS | 44 | 32.758 | 44.772 | -8.017 | 1.00 56.36 |
| ATOM | 312 | CE1 | HIS | 44 | 34.020 | 45.146 | -8.125 | 1.00 56.30 |
| ATOM | 313 | NE2 | HIS | 44 | 34.643 | 44.845 | -6.999 | 1.00 56.06 |
| ATOM | 314 | C | .HIS | 44 | 30.950 | 46.013 | -5.398 | 1.00 54.87 |
| ATOM | 315 | O | HIS | 44 | 30.823 | 46.254 | -4.199 | 1.00 55.06 |
| ATOM | 316 | N | GLU | 45 | 31.724 | 46.732 | -6.203 | 1.00 56.25 |
| ATOM | 317 | CA | GLU | 45 | 32.540 | 47.826 | -5.703 | 1.00 57.17 |
| ATOM | 318 | CB | GLU | 45 | 33.618 | 48.180 | -6.721 | 1.00 59.35 |
| ATOM | 319 | CG | GLU | 45 | 33.146 | 49.127 | -7.800 | 1.00 61.61 |
| ATOM | 320 | CD | GLU | 45 | 34.107 | 50.279 | -7.985 | 1.00 63.07 |
| ATOM | 321 | OE1 | GLU | 45 | 35.228 | 50.038 | -8.487 | 1.00 63.72 |
| ATOM | 322 | OE2 | GLU | 45 | 33.747 | 51.420 | -7.613 | 1.00 64.00 |
| ATOM | 323 | C | GLU | 45 | 31.762 | 49.074 | -5.356 | 1.00 56.66 |
| ATOM | 324 | O | GLU | 45 | 32.295 | 49.985 | -4.732 | 1.00 56.54 |
| ATOM | 325 | N | GLU | 46 | 30.508 | 49.135 | -5.772 | 1.00 56.24 |
| ATOM | 326 | CA | GLU | 46 | 29.708 | 50.306 | -5.456 | 1.00 56.37 |
| ATOM | 327 | CB | GLU | 46 | 29.542 | 51.157 | -6.704 | 1.00 57.92 |
| ATOM | 328 | CG | GLU | 46 | 30.881 | 51.645 | -7.212 | 1.00 60.77 |
| ATOM | 329 | CD | GLU | 46 | 30.782 | 52.400 | -8.515 | 1.00 62.28 |
| ATOM | 330 | OE1 | GLU | 46 | 30.566 | 51.762 | -9.571 | 1.00 62.25 |
| ATOM | 331 | OE2 | GLU | 46 | 30.914 | 53.641 | -8.474 | 1.00 63.95 |
| ATOM | 332 | C | GLU | 46 | 28.366 | 49.891 | -4.873 | 1.00 55.40 |
| ATOM | 333 | O | GLU | 46 | 27.309 | 50.123 | -5.457 | 1.00 55.75 |
| ATOM | 334 | N | ALA | 47 | 28.440 | 49.264 | -3.704 | 1.00 53.89 |
| ATOM | 335 | CA | ALA | 47 | 27.273 | 48.783 | -2.987 | 1.00 51.80 |
| ATOM | 336 | CB | ALA | 47 | 27.140 | 47.280 | -3.159 | 1.00 52.36 |
| ATOM | 337 | C | ALA | 47 | 27.470 | 49.111 | -1.524 | 1.00 49.98 |
| ATOM | 338 | O | ALA | 47 | 28.448 | 48.664 | -0.923 | 1.00 50.36 |

*FIG. 4F*

| ATOM | 339 | N | SER | 48 | 26.553 | 49.894 | -0.960 | 1.00 | 47.18 |
| --- | --- | --- | --- | --- | --- | --- | --- | --- | --- |
| ATOM | 340 | CA | SER | 48 | 26.630 | 50.267 | 0.444 | 1.00 | 44.70 |
| ATOM | 341 | CB | SER | 48 | 25.299 | 50.860 | 0.897 | 1.00 | 46.13 |
| ATOM | 342 | OG | SER | 48 | 24.243 | 49.927 | 0.720 | 1.00 | 47.87 |
| ATOM | 343 | C | SER | 48 | 26.965 | 49.041 | 1.287 | 1.00 | 42.45 |
| ATOM | 344 | O | SER | 48 | 27.841 | 49.082 | 2.147 | 1.00 | 42.01 |
| ATOM | 345 | N | VAL | 49 | 26.261 | 47.946 | 1.037 | 1.00 | 40.48 |
| ATOM | 346 | CA | VAL | 49 | 26.516 | 46.713 | 1.762 | 1.00 | 38.96 |
| ATOM | 347 | CB | VAL | 49 | 25.231 | 45.849 | 1.875 | 1.00 | 38.62 |
| ATOM | 348 | CG1 | VAL | 49 | 25.496 | 44.625 | 2.740 | 1.00 | 38.40 |
| ATOM | 349 | CG2 | VAL | 49 | 24.102 | 46.672 | 2.472 | 1.00 | 37.16 |
| ATOM | 350 | C | VAL | 49 | 27.572 | 45.997 | 0.929 | 1.00 | 37.97 |
| ATOM | 351 | O | VAL | 49 | 27.266 | 45.474 | -0.137 | 1.00 | 38.42 |
| ATOM | 352 | N | LYS | 50 | 28.810 | 45.982 | 1.422 | 1.00 | 36.51 |
| ATOM | 353 | CA | LYS | 50 | 29.937 | 45.385 | 0.703 | 1.00 | 34.95 |
| ATOM | 354 | CB | LYS | 50 | 31.250 | 45.843 | 1.334 | 1.00 | 35.51 |
| ATOM | 355 | CG | LYS | 50 | 31.574 | 47.322 | 1.091 | 1.00 | 36.68 |
| ATOM | 356 | CD | LYS | 50 | 30.676 | 48.249 | 1.913 | 1.00 | 39.05 |
| ATOM | 357 | CE | LYS | 50 | 30.865 | 48.018 | 3.419 | 1.00 | 39.54 |
| ATOM | 358 | NZ | LYS | 50 | 32.316 | 48.157 | 3.792 | 1.00 | 40.04 |
| ATOM | 359 | C | LYS | 50 | 30.012 | 43.879 | 0.482 | 1.00 | 33.72 |
| ATOM | 360 | O | LYS | 50 | 30.845 | 43.421 | -0.293 | 1.00 | 33.30 |
| ATOM | 361 | N | MSE | 51 | 29.171 | 43.100 | 1.147 | 1.00 | 33.02 |
| ATOM | 362 | CA | MSE | 51 | 29.209 | 41.647 | 0.967 | 1.00 | 32.08 |
| ATOM | 363 | CB | MSE | 51 | 28.291 | 41.257 | -0.190 | 1.00 | 34.01 |
| ATOM | 364 | CG | MSE | 51 | 26.867 | 41.744 | -0.025 | 1.00 | 36.03 |
| ATOM | 365 | SE | MSE | 51 | 26.148 | 41.146 | 1.529 | 1.00 | 40.73 |
| ATOM | 366 | CE | MSE | 51 | 25.558 | 39.411 | 1.085 | 1.00 | 37.98 |
| ATOM | 367 | C | MSE | 51 | 30.637 | 41.180 | 0.666 | 1.00 | 30.17 |
| ATOM | 368 | O | MSE | 51 | 30.928 | 40.723 | -0.437 | 1.00 | 30.22 |
| ATOM | 369 | N | LEU | 52 | 31.518 | 41.295 | 1.650 | 1.00 | 28.96 |
| ATOM | 370 | CA | LEU | 52 | 32.920 | 40.928 | 1.487 | 1.00 | 27.43 |
| ATOM | 371 | CB | LEU | 52 | 33.769 | 41.839 | 2.357 | 1.00 | 28.05 |
| ATOM | 372 | CG | LEU | 52 | 33.649 | 43.319 | 1.991 | 1.00 | 28.52 |
| ATOM | 373 | CD1 | LEU | 52 | 34.222 | 44.171 | 3.116 | 1.00 | 28.77 |
| ATOM | 374 | CD2 | LEU | 52 | 34.369 | 43.583 | 0.658 | 1.00 | 28.75 |
| ATOM | 375 | C | LEU | 52 | 33.273 | 39.482 | 1.803 | 1.00 | 26.61 |
| ATOM | 376 | O | LEU | 52 | 32.997 | 38.995 | 2.893 | 1.00 | 25.26 |
| ATOM | 377 | N | PRO | 53 | 33.911 | 38.774 | 0.844 | 1.00 | 27.04 |
| ATOM | 378 | CD | PRO | 53 | 34.270 | 39.142 | -0.540 | 1.00 | 25.69 |
| ATOM | 379 | CA | PRO | 53 | 34.264 | 37.375 | 1.133 | 1.00 | 27.99 |
| ATOM | 380 | CB | PRO | 53 | 34.807 | 36.864 | -0.204 | 1.00 | 26.92 |
| ATOM | 381 | CG | PRO | 53 | 34.184 | 37.825 | -1.241 | 1.00 | 25.77 |
| ATOM | 382 | C | PRO | 53 | 35.314 | 37.361 | 2.239 | 1.00 | 28.40 |
| ATOM | 383 | O | PRO | 53 | 36.152 | 38.271 | 2.317 | 1.00 | 28.36 |
| ATOM | 384 | N | THR | 54 | 35.255 | 36.329 | 3.080 | 1.00 | 29.46 |
| ATOM | 385 | CA | THR | 54 | 36.149 | 36.142 | 4.226 | 1.00 | 30.53 |
| ATOM | 386 | CB | THR | 54 | 35.317 | 35.951 | 5.502 | 1.00 | 29.48 |
| ATOM | 387 | OG1 | THR | 54 | 34.589 | 34.711 | 5.418 | 1.00 | 27.97 |
| ATOM | 388 | CG2 | THR | 54 | 34.324 | 37.084 | 5.659 | 1.00 | 29.42 |
| ATOM | 389 | C | THR | 54 | 37.018 | 34.884 | 4.071 | 1.00 | 31.60 |
| ATOM | 390 | O | THR | 54 | 37.657 | 34.423 | 5.025 | 1.00 | 32.25 |
| ATOM | 391 | N | TYR | 55 | 37.017 | 34.311 | 2.877 | 1.00 | 32.63 |
| ATOM | 392 | CA | TYR | 55 | 37.763 | 33.089 | 2.615 | 1.00 | 34.41 |
| ATOM | 393 | CB | TYR | 55 | 39.249 | 33.421 | 2.405 | 1.00 | 33.07 |
| ATOM | 394 | CG | TYR | 55 | 39.458 | 34.175 | 1.101 | 1.00 | 32.58 |
| ATOM | 395 | CD1 | TYR | 55 | 39.518 | 35.571 | 1.067 | 1.00 | 32.44 |

*FIG. 4G*

| ATOM | 396 | CE1 | TYR | 55 | 39.572 | 36.263 | -0.157 | 1.00 | 32.48 |
| ATOM | 397 | CD2 | TYR | 55 | 39.467 | 33.492 | -0.117 | 1.00 | 31.97 |
| ATOM | 398 | CE2 | TYR | 55 | 39.516 | 34.172 | -1.335 | 1.00 | 31.83 |
| ATOM | 399 | CZ | TYR | 55 | 39.566 | 35.548 | -1.351 | 1.00 | 32.18 |
| ATOM | 400 | OH | TYR | 55 | 39.575 | 36.200 | -2.568 | 1.00 | 32.67 |
| ATOM | 401 | C | TYR | 55 | 37.559 | 31.956 | 3.637 | 1.00 | 36.06 |
| ATOM | 402 | O | TYR | 55 | 38.314 | 30.991 | 3.665 | 1.00 | 37.61 |
| ATOM | 403 | N | VAL | 56 | 36.518 | 32.059 | 4.459 | 1.00 | 38.03 |
| ATOM | 404 | CA | VAL | 56 | 36.199 | 31.006 | 5.429 | 1.00 | 39.87 |
| ATOM | 405 | CB | VAL | 56 | 35.483 | 31.586 | 6.663 | 1.00 | 38.75 |
| ATOM | 406 | CG1 | VAL | 56 | 35.202 | 30.492 | 7.669 | 1.00 | 38.10 |
| ATOM | 407 | CG2 | VAL | 56 | 36.336 | 32.660 | 7.285 | 1.00 | 38.76 |
| ATOM | 408 | C | VAL | 56 | 35.249 | 30.032 | 4.706 | 1.00 | 42.20 |
| ATOM | 409 | O | VAL | 56 | 34.098 | 30.376 | 4.418 | 1.00 | 42.02 |
| ATOM | 410 | N | ARG | 57 | 35.718 | 28.821 | 4.414 | 1.00 | 44.49 |
| ATOM | 411 | CA | ARG | 57 | 34.896 | 27.860 | 3.676 | 1.00 | 47.07 |
| ATOM | 412 | CB | ARG | 57 | 35.688 | 27.288 | 2.499 | 1.00 | 48.02 |
| ATOM | 413 | CG | ARG | 57 | 36.209 | 28.310 | 1.508 | 1.00 | 49.08 |
| ATOM | 414 | CD | ARG | 57 | 36.558 | 27.626 | 0.185 | 1.00 | 49.69 |
| ATOM | 415 | NE | ARG | 57 | 37.239 | 28.528 | -0.737 | 1.00 | 49.50 |
| ATOM | 416 | CZ | ARG | 57 | 38.367 | 29.167 | -0.447 | 1.00 | 48.83 |
| ATOM | 417 | NH1 | ARG | 57 | 38.938 | 28.997 | 0.745 | 1.00 | 48.13 |
| ATOM | 418 | NH2 | ARG | 57 | 38.915 | 29.978 | -1.345 | 1.00 | 47.51 |
| ATOM | 419 | C | ARG | 57 | 34.311 | 26.695 | 4.449 | 1.00 | 48.57 |
| ATOM | 420 | O | ARG | 57 | 34.810 | 26.310 | 5.500 | 1.00 | 48.65 |
| ATOM | 421 | N | SER | 58 | 33.256 | 26.117 | 3.891 | 1.00 | 51.15 |
| ATOM | 422 | CA | SER | 58 | 32.589 | 24.973 | 4.501 | 1.00 | 54.78 |
| ATOM | 423 | CB | SER | 58 | 31.204 | 24.793 | 3.882 | 1.00 | 54.26 |
| ATOM | 424 | OG | SER | 58 | 31.258 | 24.980 | 2.475 | 1.00 | 54.39 |
| ATOM | 425 | C | SER | 58 | 33.419 | 23.708 | 4.295 | 1.00 | 57.39 |
| ATOM | 426 | O | SER | 58 | 33.097 | 22.645 | 4.823 | 1.00 | 57.47 |
| ATOM | 427 | N | THR | 59 | 34.484 | 23.840 | 3.510 | 1.00 | 60.71 |
| ATOM | 428 | CA | THR | 59 | 35.392 | 22.740 | 3.216 | 1.00 | 64.02 |
| ATOM | 429 | CB | THR | 59 | 35.886 | 22.823 | 1.758 | 1.00 | 63.73 |
| ATOM | 430 | OG1 | THR | 59 | 36.637 | 24.029 | 1.570 | 1.00 | 63.22 |
| ATOM | 431 | CG2 | THR | 59 | 34.704 | 22.843 | 0.801 | 1.00 | 63.87 |
| ATOM | 432 | C | THR | 59 | 36.571 | 22.880 | 4.176 | 1.00 | 67.10 |
| ATOM | 433 | O | THR | 59 | 37.554 | 23.562 | 3.884 | 1.00 | 67.44 |
| ATOM | 434 | N | PRO | 60 | 36.480 | 22.238 | 5.349 | 1.00 | 69.75 |
| ATOM | 435 | CD | PRO | 60 | 35.366 | 21.412 | 5.854 | 1.00 | 70.63 |
| ATOM | 436 | CA | PRO | 60 | 37.556 | 22.320 | 6.337 | 1.00 | 71.72 |
| ATOM | 437 | CB | PRO | 60 | 36.841 | 21.982 | 7.636 | 1.00 | 71.72 |
| ATOM | 438 | CG | PRO | 60 | 35.909 | 20.881 | 7.182 | 1.00 | 71.50 |
| ATOM | 439 | C | PRO | 60 | 38.709 | 21.370 | 6.056 | 1.00 | 73.48 |
| ATOM | 440 | O | PRO | 60 | 39.522 | 21.609 | 5.158 | 1.00 | 73.53 |
| ATOM | 441 | N | GLU | 61 | 38.754 | 20.287 | 6.830 | 1.00 | 75.48 |
| ATOM | 442 | CA | GLU | 61 | 39.808 | 19.283 | 6.731 | 1.00 | 76.98 |
| ATOM | 443 | CB | GLU | 61 | 39.969 | 18.788 | 5.289 | 1.00 | 78.43 |
| ATOM | 444 | CG | GLU | 61 | 40.806 | 17.516 | 5.161 | 1.00 | 80.68 |
| ATOM | 445 | CD | GLU | 61 | 42.177 | 17.744 | 4.530 | 1.00 | 81.88 |
| ATOM | 446 | OE1 | GLU | 61 | 42.993 | 18.498 | 5.100 | 1.00 | 82.28 |
| ATOM | 447 | OE2 | GLU | 61 | 42.442 | 17.156 | 3.458 | 1.00 | 82.68 |
| ATOM | 448 | C | GLU | 61 | 41.083 | 19.969 | 7.194 | 1.00 | 77.00 |
| ATOM | 449 | O | GLU | 61 | 41.942 | 20.327 | 6.389 | 1.00 | 77.10 |
| ATOM | 450 | N | GLY | 62 | 41.177 | 20.181 | 8.502 | 1.00 | 76.85 |
| ATOM | 451 | CA | GLY | 62 | 42.344 | 20.826 | 9.069 | 1.00 | 76.72 |
| ATOM | 452 | C | GLY | 62 | 42.415 | 20.539 | 10.555 | 1.00 | 76.65 |

FIG. 4H

| ATOM | 453 | O | GLY | 62 | 42.507 | 19.380 | 10.969 | 1.00 | 76.79 |
|------|-----|-----|-----|----|--------|--------|--------|------|-------|
| ATOM | 454 | N | SER | 63 | 42.361 | 21.594 | 11.362 | 1.00 | 76.25 |
| ATOM | 455 | CA | SER | 63 | 42.417 | 21.458 | 12.814 | 1.00 | 75.06 |
| ATOM | 456 | CB | SER | 63 | 41.401 | 20.413 | 13.300 | 1.00 | 75.92 |
| ATOM | 457 | OG | SER | 63 | 41.350 | 20.363 | 14.718 | 1.00 | 76.69 |
| ATOM | 458 | C | SER | 63 | 43.818 | 21.062 | 13.259 | 1.00 | 73.60 |
| ATOM | 459 | O | SER | 63 | 44.090 | 19.899 | 13.561 | 1.00 | 73.10 |
| ATOM | 460 | N | GLU | 64 | 44.705 | 22.045 | 13.280 | 1.00 | 71.83 |
| ATOM | 461 | CA | GLU | 64 | 46.071 | 21.819 | 13.703 | 1.00 | 70.12 |
| ATOM | 462 | CB | GLU | 64 | 46.996 | 22.824 | 13.011 | 1.00 | 71.42 |
| ATOM | 463 | CG | GLU | 64 | 48.464 | 22.726 | 13.417 | 1.00 | 73.74 |
| ATOM | 464 | CD | GLU | 64 | 49.014 | 21.309 | 13.342 | 1.00 | 74.84 |
| ATOM | 465 | OE1 | GLU | 64 | 48.623 | 20.466 | 14.187 | 1.00 | 75.26 |
| ATOM | 466 | OE2 | GLU | 64 | 49.837 | 21.041 | 12.434 | 1.00 | 75.45 |
| ATOM | 467 | C | GLU | 64 | 46.136 | 21.971 | 15.221 | 1.00 | 67.97 |
| ATOM | 468 | O | GLU | 64 | 46.775 | 22.886 | 15.734 | 1.00 | 68.33 |
| ATOM | 469 | N | VAL | 65 | 45.448 | 21.076 | 15.927 | 1.00 | 65.13 |
| ATOM | 470 | CA | VAL | 65 | 45.400 | 21.067 | 17.391 | 1.00 | 62.32 |
| ATOM | 471 | CB | VAL | 65 | 45.335 | 19.621 | 17.918 | 1.00 | 62.48 |
| ATOM | 472 | CG1 | VAL | 65 | 45.487 | 19.607 | 19.430 | 1.00 | 62.45 |
| ATOM | 473 | CG2 | VAL | 65 | 44.011 | 18.975 | 17.508 | 1.00 | 62.79 |
| ATOM | 474 | C | VAL | 65 | 46.587 | 21.752 | 18.055 | 1.00 | 60.42 |
| ATOM | 475 | O | VAL | 65 | 47.703 | 21.708 | 17.540 | 1.00 | 60.54 |
| ATOM | 476 | N | GLY | 66 | 46.354 | 22.386 | 19.200 | 1.00 | 58.26 |
| ATOM | 477 | CA | GLY | 66 | 47.454 | 23.043 | 19.888 | 1.00 | 55.67 |
| ATOM | 478 | C | GLY | 66 | 47.081 | 24.174 | 20.823 | 1.00 | 53.42 |
| ATOM | 479 | O | GLY | 66 | 46.153 | 24.052 | 21.615 | 1.00 | 54.08 |
| ATOM | 480 | N | ASP | 67 | 47.832 | 25.267 | 20.739 | 1.00 | 51.06 |
| ATOM | 481 | CA | ASP | 67 | 47.614 | 26.460 | 21.549 | 1.00 | 48.67 |
| ATOM | 482 | CB | ASP | 67 | 48.617 | 26.531 | 22.703 | 1.00 | 49.14 |
| ATOM | 483 | CG | ASP | 67 | 48.381 | 25.462 | 23.751 | 1.00 | 49.34 |
| ATOM | 484 | OD1 | ASP | 67 | 48.201 | 24.287 | 23.365 | 1.00 | 49.37 |
| ATOM | 485 | OD2 | ASP | 67 | 48.386 | 25.791 | 24.956 | 1.00 | 49.62 |
| ATOM | 486 | C | ASP | 67 | 47.832 | 27.634 | 20.612 | 1.00 | 47.26 |
| ATOM | 487 | O | ASP | 67 | 48.786 | 27.635 | 19.827 | 1.00 | 47.44 |
| ATOM | 488 | N | PHE | 68 | 46.955 | 28.632 | 20.678 | 1.00 | 45.41 |
| ATOM | 489 | CA | PHE | 68 | 47.075 | 29.778 | 19.785 | 1.00 | 43.60 |
| ATOM | 490 | CB | PHE | 68 | 46.031 | 29.682 | 18.667 | 1.00 | 41.17 |
| ATOM | 491 | CG | PHE | 68 | 46.032 | 28.361 | 17.946 | 1.00 | 39.29 |
| ATOM | 492 | CD1 | PHE | 68 | 45.621 | 27.199 | 18.592 | 1.00 | 38.55 |
| ATOM | 493 | CD2 | PHE | 68 | 46.468 | 28.272 | 16.623 | 1.00 | 38.76 |
| ATOM | 494 | CE1 | PHE | 68 | 45.647 | 25.966 | 17.934 | 1.00 | 38.24 |
| ATOM | 495 | CE2 | PHE | 68 | 46.498 | 27.050 | 15.959 | 1.00 | 37.31 |
| ATOM | 496 | CZ | PHE | 68 | 46.086 | 25.893 | 16.619 | 1.00 | 37.76 |
| ATOM | 497 | C | PHE | 68 | 46.918 | 31.096 | 20.514 | 1.00 | 43.33 |
| ATOM | 498 | O | PHE | 68 | 46.395 | 31.147 | 21.621 | 1.00 | 43.27 |
| ATOM | 499 | N | LEU | 69 | 47.386 | 32.166 | 19.889 | 1.00 | 43.51 |
| ATOM | 500 | CA | LEU | 69 | 47.274 | 33.475 | 20.497 | 1.00 | 44.73 |
| ATOM | 501 | CB | LEU | 69 | 48.625 | 34.197 | 20.518 | 1.00 | 45.26 |
| ATOM | 502 | CG | LEU | 69 | 48.781 | 34.949 | 21.848 | 1.00 | 46.33 |
| ATOM | 503 | CD1 | LEU | 69 | 49.166 | 33.928 | 22.932 | 1.00 | 46.09 |
| ATOM | 504 | CD2 | LEU | 69 | 49.811 | 36.072 | 21.748 | 1.00 | 45.48 |
| ATOM | 505 | C | LEU | 69 | 46.275 | 34.278 | 19.681 | 1.00 | 45.37 |
| ATOM | 506 | O | LEU | 69 | 46.448 | 34.451 | 18.470 | 1.00 | 45.62 |
| ATOM | 507 | N | SER | 70 | 45.228 | 34.758 | 20.351 | 1.00 | 45.75 |
| ATOM | 508 | CA | SER | 70 | 44.177 | 35.528 | 19.697 | 1.00 | 44.98 |
| ATOM | 509 | CB | SER | 70 | 42.794 | 34.984 | 20.074 | 1.00 | 44.61 |

*FIG. 4I*

| | | | | | | | | |
|---|---|---|---|---|---|---|---|---|
| ATOM | 510 | OG | SER | 70 | 42.697 | 33.589 | 19.844 | 1.00 44.25 |
| ATOM | 511 | C | SER | 70 | 44.250 | 36.978 | 20.109 | 1.00 44.92 |
| ATOM | 512 | O | SER | 70 | 44.451 | 37.289 | 21.277 | 1.00 44.67 |
| ATOM | 513 | N | LEU | 71 | 44.095 | 37.858 | 19.130 | 1.00 45.85 |
| ATOM | 514 | CA | LEU | 71 | 44.092 | 39.294 | 19.366 | 1.00 47.27 |
| ATOM | 515 | CB | LEU | 71 | 45.064 | 40.000 | 18.421 | 1.00 47.71 |
| ATOM | 516 | CG | LEU | 71 | 46.552 | 39.942 | 18.787 | 1.00 49.06 |
| ATOM | 517 | CD1 | LEU | 71 | 47.008 | 38.497 | 19.039 | 1.00 49.69 |
| ATOM | 518 | CD2 | LEU | 71 | 47.348 | 40.572 | 17.656 | 1.00 49.35 |
| ATOM | 519 | C | LEU | 71 | 42.668 | 39.752 | 19.082 | 1.00 47.94 |
| ATOM | 520 | O | LEU | 71 | 41.873 | 38.997 | 18.499 | 1.00 48.06 |
| ATOM | 521 | N | ASP | 72 | 42.333 | 40.976 | 19.479 | 1.00 48.20 |
| ATOM | 522 | CA | ASP | 72 | 40.985 | 41.451 | 19.244 | 1.00 48.67 |
| ATOM | 523 | CB | ASP | 72 | 40.043 | 40.807 | 20.262 | 1.00 48.71 |
| ATOM | 524 | CG | ASP | 72 | 38.668 | 41.420 | 20.243 | 1.00 49.13 |
| ATOM | 525 | OD1 | ASP | 72 | 38.090 | 41.549 | 19.144 | 1.00 49.57 |
| ATOM | 526 | OD2 | ASP | 72 | 38.168 | 41.777 | 21.331 | 1.00 50.11 |
| ATOM | 527 | C | ASP | 72 | 40.819 | 42.962 | 19.258 | 1.00 48.98 |
| ATOM | 528 | O | ASP | 72 | 40.247 | 43.530 | 20.187 | 1.00 48.82 |
| ATOM | 529 | N | LEU | 73 | 41.312 | 43.613 | 18.214 | 1.00 49.73 |
| ATOM | 530 | CA | LEU | 73 | 41.193 | 45.060 | 18.117 | 1.00 51.48 |
| ATOM | 531 | CB | LEU | 73 | 42.199 | 45.603 | 17.096 | 1.00 50.80 |
| ATOM | 532 | CG | LEU | 73 | 42.160 | 47.096 | 16.774 | 1.00 50.07 |
| ATOM | 533 | CD1 | LEU | 73 | 42.358 | 47.902 | 18.045 | 1.00 50.10 |
| ATOM | 534 | CD2 | LEU | 73 | 43.223 | 47.421 | 15.738 | 1.00 49.97 |
| ATOM | 535 | C | LEU | 73 | 39.764 | 45.392 | 17.687 | 1.00 52.93 |
| ATOM | 536 | O | LEU | 73 | 38.909 | 44.507 | 17.628 | 1.00 52.38 |
| ATOM | 537 | N | GLY | 74 | 39.504 | 46.665 | 17.401 | 1.00 54.88 |
| ATOM | 538 | CA | GLY | 74 | 38.177 | 47.068 | 16.983 | 1.00 56.88 |
| ATOM | 539 | C | GLY | 74 | 37.285 | 47.420 | 18.148 | 1.00 58.48 |
| ATOM | 540 | O | GLY | 74 | 36.476 | 48.348 | 18.071 | 1.00 58.31 |
| ATOM | 541 | N | GLY | 75 | 37.428 | 46.668 | 19.233 | 1.00 60.27 |
| ATOM | 542 | CA | GLY | 75 | 36.621 | 46.925 | 20.410 | 1.00 62.46 |
| ATOM | 543 | C | GLY | 75 | 37.020 | 48.230 | 21.074 | 1.00 63.75 |
| ATOM | 544 | O | GLY | 75 | 37.824 | 49.005 | 20.536 | 1.00 64.06 |
| ATOM | 545 | N | THR | 76 | 36.452 | 48.481 | 22.248 | 1.00 64.50 |
| ATOM | 546 | CA | THR | 76 | 36.759 | 49.697 | 22.991 | 1.00 65.42 |
| ATOM | 547 | CB | THR | 76 | 35.905 | 49.776 | 24.266 | 1.00 66.28 |
| ATOM | 548 | OG1 | THR | 76 | 36.361 | 48.791 | 25.203 | 1.00 67.43 |
| ATOM | 549 | CG2 | THR | 76 | 34.425 | 49.505 | 23.938 | 1.00 66.14 |
| ATOM | 550 | C | THR | 76 | 38.238 | 49.651 | 23.385 | 1.00 65.25 |
| ATOM | 551 | O | THR | 76 | 39.005 | 50.595 | 23.152 | 1.00 65.01 |
| ATOM | 552 | N | ASN | 77 | 38.622 | 48.528 | 23.980 | 1.00 64.74 |
| ATOM | 553 | CA | ASN | 77 | 39.987 | 48.309 | 24.412 | 1.00 64.17 |
| ATOM | 554 | CB | ASN | 77 | 40.015 | 47.966 | 25.903 | 1.00 65.44 |
| ATOM | 555 | CG | ASN | 77 | 39.346 | 49.027 | 26.765 | 1.00 66.47 |
| ATOM | 556 | OD1 | ASN | 77 | 39.656 | 50.219 | 26.663 | 1.00 67.13 |
| ATOM | 557 | ND2 | ASN | 77 | 38.431 | 48.596 | 27.629 | 1.00 66.65 |
| ATOM | 558 | C | ASN | 77 | 40.547 | 47.149 | 23.603 | 1.00 63.19 |
| ATOM | 559 | O | ASN | 77 | 39.795 | 46.303 | 23.120 | 1.00 62.58 |
| ATOM | 560 | N | PHE | 78 | 41.866 | 47.123 | 23.446 | 1.00 62.14 |
| ATOM | 561 | CA | PHE | 78 | 42.526 | 46.051 | 22.708 | 1.00 61.12 |
| ATOM | 562 | CB | PHE | 78 | 43.887 | 46.514 | 22.172 | 1.00 61.81 |
| ATOM | 563 | CG | PHE | 78 | 44.684 | 45.420 | 21.516 | 1.00 62.50 |
| ATOM | 564 | CD1 | PHE | 78 | 44.347 | 44.956 | 20.245 | 1.00 62.81 |
| ATOM | 565 | CD2 | PHE | 78 | 45.741 | 44.818 | 22.189 | 1.00 62.99 |
| ATOM | 566 | CE1 | PHE | 78 | 45.051 | 43.899 | 19.655 | 1.00 62.72 |

*FIG. 4J*

| ATOM | 567 | CE2 | PHE | 78 | 46.450 | 43.763 | 21.607 | 1.00 | 63.38 |
|------|-----|-----|-----|----|--------|--------|--------|------|-------|
| ATOM | 568 | CZ  | PHE | 78 | 46.103 | 43.301 | 20.336 | 1.00 | 63.01 |
| ATOM | 569 | C   | PHE | 78 | 42.732 | 44.893 | 23.668 | 1.00 | 60.09 |
| ATOM | 570 | O   | PHE | 78 | 43.065 | 45.100 | 24.834 | 1.00 | 60.08 |
| ATOM | 571 | N   | ARG | 79 | 42.528 | 43.675 | 23.184 | 1.00 | 58.63 |
| ATOM | 572 | CA  | ARG | 79 | 42.706 | 42.504 | 24.025 | 1.00 | 57.40 |
| ATOM | 573 | CB  | ARG | 79 | 41.367 | 41.819 | 24.280 | 1.00 | 57.06 |
| ATOM | 574 | CG  | ARG | 79 | 41.481 | 40.637 | 25.222 | 1.00 | 57.49 |
| ATOM | 575 | CD  | ARG | 79 | 40.221 | 39.819 | 25.219 | 1.00 | 57.47 |
| ATOM | 576 | NE  | ARG | 79 | 39.062 | 40.646 | 25.504 | 1.00 | 57.16 |
| ATOM | 577 | CZ  | ARG | 79 | 37.818 | 40.266 | 25.267 | 1.00 | 57.69 |
| ATOM | 578 | NH1 | ARG | 79 | 37.586 | 39.071 | 24.738 | 1.00 | 57.38 |
| ATOM | 579 | NH2 | ARG | 79 | 36.812 | 41.080 | 25.555 | 1.00 | 58.45 |
| ATOM | 580 | C   | ARG | 79 | 43.663 | 41.522 | 23.368 | 1.00 | 56.71 |
| ATOM | 581 | O   | ARG | 79 | 43.926 | 41.619 | 22.170 | 1.00 | 57.24 |
| ATOM | 582 | N   | VAL | 80 | 44.180 | 40.590 | 24.167 | 1.00 | 55.50 |
| ATOM | 583 | CA  | VAL | 80 | 45.114 | 39.557 | 23.724 | 1.00 | 54.27 |
| ATOM | 584 | CB  | VAL | 80 | 46.576 | 39.947 | 23.996 | 1.00 | 54.31 |
| ATOM | 585 | CG1 | VAL | 80 | 47.491 | 38.779 | 23.674 | 1.00 | 54.49 |
| ATOM | 586 | CG2 | VAL | 80 | 46.960 | 41.158 | 23.166 | 1.00 | 54.39 |
| ATOM | 587 | C   | VAL | 80 | 44.806 | 38.327 | 24.555 | 1.00 | 54.04 |
| ATOM | 588 | O   | VAL | 80 | 44.517 | 38.447 | 25.738 | 1.00 | 53.31 |
| ATOM | 589 | N   | MSE | 81 | 44.881 | 37.144 | 23.957 | 1.00 | 54.52 |
| ATOM | 590 | CA  | MSE | 81 | 44.568 | 35.935 | 24.703 | 1.00 | 54.59 |
| ATOM | 591 | CB  | MSE | 81 | 43.053 | 35.804 | 24.828 | 1.00 | 57.08 |
| ATOM | 592 | CG  | MSE | 81 | 42.300 | 36.025 | 23.520 | 1.00 | 60.39 |
| ATOM | 593 | SE  | MSE | 81 | 40.534 | 36.437 | 23.792 | 1.00 | 65.62 |
| ATOM | 594 | CE  | MSE | 81 | 39.999 | 34.926 | 24.679 | 1.00 | 62.03 |
| ATOM | 595 | C   | MSE | 81 | 45.142 | 34.645 | 24.146 | 1.00 | 53.56 |
| ATOM | 596 | O   | MSE | 81 | 45.598 | 34.582 | 23.007 | 1.00 | 52.99 |
| ATOM | 597 | N   | LEU | 82 | 45.096 | 33.611 | 24.978 | 1.00 | 52.63 |
| ATOM | 598 | CA  | LEU | 82 | 45.602 | 32.292 | 24.638 | 1.00 | 51.86 |
| ATOM | 599 | CB  | LEU | 82 | 46.660 | 31.863 | 25.665 | 1.00 | 52.75 |
| ATOM | 600 | CG  | LEU | 82 | 47.261 | 30.455 | 25.542 | 1.00 | 53.22 |
| ATOM | 601 | CD1 | LEU | 82 | 48.562 | 30.521 | 24.736 | 1.00 | 52.42 |
| ATOM | 602 | CD2 | LEU | 82 | 47.523 | 29.882 | 26.937 | 1.00 | 53.00 |
| ATOM | 603 | C   | LEU | 82 | 44.461 | 31.286 | 24.650 | 1.00 | 51.18 |
| ATOM | 604 | O   | LEU | 82 | 43.718 | 31.186 | 25.632 | 1.00 | 51.20 |
| ATOM | 605 | N   | VAL | 83 | 44.333 | 30.535 | 23.563 | 1.00 | 50.58 |
| ATOM | 606 | CA  | VAL | 83 | 43.292 | 29.522 | 23.448 | 1.00 | 50.00 |
| ATOM | 607 | CB  | VAL | 83 | 42.274 | 29.887 | 22.362 | 1.00 | 49.63 |
| ATOM | 608 | CG1 | VAL | 83 | 41.213 | 28.794 | 22.262 | 1.00 | 49.26 |
| ATOM | 609 | CG2 | VAL | 83 | 41.660 | 31.244 | 22.670 | 1.00 | 48.32 |
| ATOM | 610 | C   | VAL | 83 | 43.914 | 28.187 | 23.080 | 1.00 | 50.53 |
| ATOM | 611 | O   | VAL | 83 | 44.759 | 28.122 | 22.192 | 1.00 | 50.93 |
| ATOM | 612 | N   | LYS | 84 | 43.496 | 27.127 | 23.763 | 1.00 | 51.05 |
| ATOM | 613 | CA  | LYS | 84 | 44.017 | 25.788 | 23.504 | 1.00 | 51.89 |
| ATOM | 614 | CB  | LYS | 84 | 44.338 | 25.061 | 24.826 | 1.00 | 51.79 |
| ATOM | 615 | CG  | LYS | 84 | 44.716 | 23.581 | 24.659 | 1.00 | 51.85 |
| ATOM | 616 | CD  | LYS | 84 | 44.951 | 22.870 | 26.009 | 1.00 | 51.58 |
| ATOM | 617 | CE  | LYS | 84 | 46.429 | 22.848 | 26.422 | 1.00 | 50.92 |
| ATOM | 618 | NZ  | LYS | 84 | 47.041 | 24.198 | 26.592 | 1.00 | 50.33 |
| ATOM | 619 | C   | LYS | 84 | 42.997 | 24.983 | 22.708 | 1.00 | 52.68 |
| ATOM | 620 | O   | LYS | 84 | 42.115 | 24.327 | 23.282 | 1.00 | 53.00 |
| ATOM | 621 | N   | VAL | 85 | 43.124 | 25.038 | 21.383 | 1.00 | 52.91 |
| ATOM | 622 | CA  | VAL | 85 | 42.224 | 24.319 | 20.488 | 1.00 | 52.70 |
| ATOM | 623 | CB  | VAL | 85 | 42.399 | 24.805 | 19.048 | 1.00 | 51.79 |

*FIG. 4K*

| | | | | | | | | |
|---|---|---|---|---|---|---|---|---|
| ATOM | 624 | CG1 | VAL | 85 | 41.302 | 24.232 | 18.176 | 1.00 52.19 |
| ATOM | 625 | CG2 | VAL | 85 | 42.389 | 26.319 | 19.017 | 1.00 51.59 |
| ATOM | 626 | C | VAL | 85 | 42.525 | 22.823 | 20.548 | 1.00 53.51 |
| ATOM | 627 | O | VAL | 85 | 43.637 | 22.389 | 20.243 | 1.00 53.87 |
| ATOM | 628 | N | GLY | 86 | 41.534 | 22.037 | 20.952 | 1.00 54.38 |
| ATOM | 629 | CA | GLY | 86 | 41.726 | 20.603 | 21.053 | 1.00 55.35 |
| ATOM | 630 | C | GLY | 86 | 40.901 | 19.810 | 20.060 | 1.00 56.21 |
| ATOM | 631 | O | GLY | 86 | 40.136 | 20.370 | 19.278 | 1.00 55.63 |
| ATOM | 632 | N | GLU | 87 | 41.050 | 18.493 | 20.106 | 1.00 57.81 |
| ATOM | 633 | CA | GLU | 87 | 40.339 | 17.611 | 19.195 | 1.00 59.64 |
| ATOM | 634 | CB | GLU | 87 | 41.290 | 16.529 | 18.673 | 1.00 60.88 |
| ATOM | 635 | CG | GLU | 87 | 40.680 | 15.648 | 17.611 | 1.00 62.26 |
| ATOM | 636 | CD | GLU | 87 | 40.215 | 16.457 | 16.423 | 1.00 63.21 |
| ATOM | 637 | OE1 | GLU | 87 | 41.072 | 16.931 | 15.644 | 1.00 63.20 |
| ATOM | 638 | OE2 | GLU | 87 | 38.989 | 16.631 | 16.278 | 1.00 64.58 |
| ATOM | 639 | C | GLU | 87 | 39.133 | 16.959 | 19.859 | 1.00 60.12 |
| ATOM | 640 | O | GLU | 87 | 39.271 | 16.187 | 20.810 | 1.00 60.00 |
| ATOM | 641 | N | GLY | 88 | 37.948 | 17.273 | 19.347 | 1.00 60.93 |
| ATOM | 642 | CA | GLY | 88 | 36.735 | 16.707 | 19.902 | 1.00 61.61 |
| ATOM | 643 | C | GLY | 88 | 35.840 | 16.120 | 18.833 | 1.00 62.11 |
| ATOM | 644 | O | GLY | 88 | 36.038 | 16.346 | 17.638 | 1.00 61.67 |
| ATOM | 645 | N | GLU | 89 | 34.845 | 15.363 | 19.274 | 1.00 62.79 |
| ATOM | 646 | CA | GLU | 89 | 33.898 | 14.724 | 18.372 | 1.00 63.90 |
| ATOM | 647 | CB | GLU | 89 | 32.782 | 14.089 | 19.203 | 1.00 63.50 |
| ATOM | 648 | CG | GLU | 89 | 33.304 | 13.137 | 20.275 | 1.00 62.64 |
| ATOM | 649 | CD | GLU | 89 | 32.214 | 12.623 | 21.203 | 1.00 62.46 |
| ATOM | 650 | OE1 | GLU | 89 | 32.510 | 11.728 | 22.019 | 1.00 62.39 |
| ATOM | 651 | OE2 | GLU | 89 | 31.064 | 13.110 | 21.128 | 1.00 62.11 |
| ATOM | 652 | C | GLU | 89 | 33.312 | 15.688 | 17.325 | 1.00 65.16 |
| ATOM | 653 | O | GLU | 89 | 32.975 | 16.837 | 17.634 | 1.00 64.98 |
| ATOM | 654 | N | GLU | 90 | 33.204 | 15.205 | 16.087 | 1.00 66.03 |
| ATOM | 655 | CA | GLU | 90 | 32.667 | 15.977 | 14.958 | 1.00 66.67 |
| ATOM | 656 | CB | GLU | 90 | 31.135 | 15.974 | 14.978 | 1.00 67.21 |
| ATOM | 657 | CG | GLU | 90 | 30.495 | 14.620 | 14.717 | 1.00 66.83 |
| ATOM | 658 | CD | GLU | 90 | 28.986 | 14.662 | 14.869 | 1.00 67.49 |
| ATOM | 659 | OE1 | GLU | 90 | 28.308 | 15.273 | 14.009 | 1.00 67.17 |
| ATOM | 660 | OE2 | GLU | 90 | 28.480 | 14.090 | 15.858 | 1.00 66.84 |
| ATOM | 661 | C | GLU | 90 | 33.149 | 17.421 | 14.871 | 1.00 66.91 |
| ATOM | 662 | O | GLU | 90 | 32.623 | 18.212 | 14.080 | 1.00 66.74 |
| ATOM | 663 | N | GLY | 91 | 34.149 | 17.769 | 15.671 | 1.00 67.05 |
| ATOM | 664 | CA | GLY | 91 | 34.649 | 19.126 | 15.628 | 1.00 67.38 |
| ATOM | 665 | C | GLY | 91 | 36.036 | 19.339 | 16.201 | 1.00 67.42 |
| ATOM | 666 | O | GLY | 91 | 37.025 | 18.797 | 15.708 | 1.00 68.24 |
| ATOM | 667 | N | GLN | 92 | 36.094 | 20.154 | 17.246 | 1.00 66.86 |
| ATOM | 668 | CA | GLN | 92 | 37.335 | 20.492 | 17.929 | 1.00 65.93 |
| ATOM | 669 | CB | GLN | 92 | 38.395 | 20.968 | 16.924 | 1.00 66.17 |
| ATOM | 670 | CG | GLN | 92 | 38.007 | 22.215 | 16.159 | 1.00 66.24 |
| ATOM | 671 | CD | GLN | 92 | 38.564 | 22.236 | 14.750 | 1.00 66.57 |
| ATOM | 672 | OE1 | GLN | 92 | 38.432 | 21.260 | 14.007 | 1.00 66.37 |
| ATOM | 673 | NE2 | GLN | 92 | 39.177 | 23.356 | 14.367 | 1.00 66.54 |
| ATOM | 674 | C | GLN | 92 | 36.999 | 21.605 | 18.920 | 1.00 65.21 |
| ATOM | 675 | O | GLN | 92 | 36.625 | 22.721 | 18.530 | 1.00 65.44 |
| ATOM | 676 | N | TRP | 93 | 37.111 | 21.278 | 20.204 | 1.00 63.62 |
| ATOM | 677 | CA | TRP | 93 | 36.820 | 22.227 | 21.261 | 1.00 61.61 |
| ATOM | 678 | CB | TRP | 93 | 36.859 | 21.540 | 22.626 | 1.00 62.77 |
| ATOM | 679 | CG | TRP | 93 | 38.050 | 20.641 | 22.857 | 1.00 63.86 |
| ATOM | 680 | CD2 | TRP | 93 | 39.213 | 20.943 | 23.637 | 1.00 64.17 |

*FIG. 4L*

```
ATOM    681  CE2 TRP    93      40.026  19.787  23.645  1.00 64.21
ATOM    682  CE3 TRP    93      39.647  22.080  24.336  1.00 64.11
ATOM    683  CD1 TRP    93      38.206  19.349  22.424  1.00 63.84
ATOM    684  NE1 TRP    93      39.387  18.830  22.897  1.00 63.69
ATOM    685  CZ2 TRP    93      41.246  19.731  24.324  1.00 64.43
ATOM    686  CZ3 TRP    93      40.859  22.026  25.009  1.00 64.63
ATOM    687  CH2 TRP    93      41.645  20.857  24.999  1.00 64.71
ATOM    688  C   TRP    93      37.784  23.393  21.248  1.00 59.53
ATOM    689  O   TRP    93      38.733  23.420  20.474  1.00 59.18
ATOM    690  N   SER    94      37.521  24.366  22.106  1.00 57.94
ATOM    691  CA  SER    94      38.353  25.549  22.207  1.00 56.46
ATOM    692  CB  SER    94      37.880  26.615  21.219  1.00 56.58
ATOM    693  OG  SER    94      36.504  26.899  21.412  1.00 56.78
ATOM    694  C   SER    94      38.185  26.050  23.624  1.00 55.56
ATOM    695  O   SER    94      37.142  25.822  24.237  1.00 55.36
ATOM    696  N   VAL    95      39.208  26.722  24.146  1.00 54.53
ATOM    697  CA  VAL    95      39.152  27.248  25.504  1.00 53.17
ATOM    698  CB  VAL    95      39.511  26.183  26.549  1.00 52.17
ATOM    699  CG1 VAL    95      39.742  26.844  27.891  1.00 52.13
ATOM    700  CG2 VAL    95      38.396  25.172  26.666  1.00 51.73
ATOM    701  C   VAL    95      40.099  28.399  25.719  1.00 52.74
ATOM    702  O   VAL    95      41.268  28.315  25.357  1.00 53.14
ATOM    703  N   LYS    96      39.587  29.469  26.318  1.00 52.63
ATOM    704  CA  LYS    96      40.402  30.637  26.629  1.00 52.93
ATOM    705  CB  LYS    96      39.513  31.849  26.932  1.00 53.25
ATOM    706  CG  LYS    96      40.277  33.129  27.231  1.00 53.79
ATOM    707  CD  LYS    96      39.910  33.706  28.595  1.00 54.80
ATOM    708  CE  LYS    96      38.427  34.102  28.682  1.00 55.69
ATOM    709  NZ  LYS    96      38.027  35.162  27.696  1.00 55.59
ATOM    710  C   LYS    96      41.154  30.218  27.882  1.00 52.96
ATOM    711  O   LYS    96      40.546  29.733  28.834  1.00 52.93
ATOM    712  N   THR    97      42.470  30.384  27.886  1.00 53.38
ATOM    713  CA  THR    97      43.253  29.980  29.050  1.00 53.93
ATOM    714  CB  THR    97      44.238  28.850  28.684  1.00 53.99
ATOM    715  OG1 THR    97      43.512  27.736  28.151  1.00 52.99
ATOM    716  CG2 THR    97      44.998  28.394  29.918  1.00 55.29
ATOM    717  C   THR    97      44.036  31.132  29.670  1.00 53.82
ATOM    718  O   THR    97      44.330  31.123  30.866  1.00 53.34
ATOM    719  N   LYS    98      44.373  32.117  28.848  1.00 53.85
ATOM    720  CA  LYS    98      45.115  33.276  29.315  1.00 54.60
ATOM    721  CB  LYS    98      46.627  33.096  29.087  1.00 55.51
ATOM    722  CG  LYS    98      47.220  31.809  29.652  1.00 56.78
ATOM    723  CD  LYS    98      47.074  31.733  31.162  1.00 58.23
ATOM    724  CE  LYS    98      47.553  30.389  31.713  1.00 58.82
ATOM    725  NZ  LYS    98      47.404  30.320  33.201  1.00 58.98
ATOM    726  C   LYS    98      44.644  34.479  28.518  1.00 54.54
ATOM    727  O   LYS    98      44.323  34.360  27.329  1.00 54.79
ATOM    728  N   HIS    99      44.590  35.632  29.173  1.00 54.03
ATOM    729  CA  HIS    99      44.193  36.853  28.496  1.00 54.03
ATOM    730  CB  HIS    99      42.720  36.793  28.052  1.00 55.02
ATOM    731  CG  HIS    99      41.732  36.872  29.172  1.00 55.71
ATOM    732  CD2 HIS    99      40.682  37.704  29.373  1.00 55.66
ATOM    733  ND1 HIS    99      41.739  35.999  30.239  1.00 56.19
ATOM    734  CE1 HIS    99      40.736  36.288  31.049  1.00 56.30
ATOM    735  NE2 HIS    99      40.080  37.319  30.546  1.00 56.72
ATOM    736  C   HIS    99      44.445  38.082  29.351  1.00 53.46
ATOM    737  O   HIS    99      44.526  38.007  30.577  1.00 53.47
```

*FIG. 4M*

| | | | | | | | | |
|---|---|---|---|---|---|---|---|---|
| ATOM | 738 | N | GLN | 100 | 44.583 | 39.214 | 28.683 | 1.00 52.94 |
| ATOM | 739 | CA | GLN | 100 | 44.841 | 40.468 | 29.349 | 1.00 53.34 |
| ATOM | 740 | CB | GLN | 100 | 46.354 | 40.649 | 29.513 | 1.00 53.39 |
| ATOM | 741 | CG | GLN | 100 | 46.790 | 42.001 | 30.055 | 1.00 54.26 |
| ATOM | 742 | CD | GLN | 100 | 46.168 | 42.345 | 31.394 | 1.00 54.43 |
| ATOM | 743 | OE1 | GLN | 100 | 46.349 | 41.629 | 32.384 | 1.00 55.27 |
| ATOM | 744 | NE2 | GLN | 100 | 45.433 | 43.452 | 31.432 | 1.00 53.60 |
| ATOM | 745 | C | GLN | 100 | 44.243 | 41.567 | 28.481 | 1.00 53.43 |
| ATOM | 746 | O | GLN | 100 | 44.416 | 41.569 | 27.260 | 1.00 53.75 |
| ATOM | 747 | N | THR | 101 | 43.527 | 42.493 | 29.105 | 1.00 52.90 |
| ATOM | 748 | CA | THR | 101 | 42.905 | 43.576 | 28.367 | 1.00 53.12 |
| ATOM | 749 | CB | THR | 101 | 41.495 | 43.826 | 28.894 | 1.00 52.52 |
| ATOM | 750 | OG1 | THR | 101 | 40.789 | 42.582 | 28.925 | 1.00 52.85 |
| ATOM | 751 | CG2 | THR | 101 | 40.752 | 44.808 | 27.999 | 1.00 52.23 |
| ATOM | 752 | C | THR | 101 | 43.731 | 44.845 | 28.499 | 1.00 53.61 |
| ATOM | 753 | O | THR | 101 | 44.285 | 45.108 | 29.563 | 1.00 53.95 |
| ATOM | 754 | N | TYR | 102 | 43.809 | 45.628 | 27.422 | 1.00 54.10 |
| ATOM | 755 | CA | TYR | 102 | 44.585 | 46.869 | 27.422 | 1.00 55.36 |
| ATOM | 756 | CB | TYR | 102 | 45.878 | 46.708 | 26.608 | 1.00 54.89 |
| ATOM | 757 | CG | TYR | 102 | 46.788 | 45.569 | 27.015 | 1.00 54.25 |
| ATOM | 758 | CD1 | TYR | 102 | 46.382 | 44.241 | 26.888 | 1.00 54.08 |
| ATOM | 759 | CE1 | TYR | 102 | 47.227 | 43.197 | 27.226 | 1.00 53.44 |
| ATOM | 760 | CD2 | TYR | 102 | 48.069 | 45.822 | 27.497 | 1.00 53.79 |
| ATOM | 761 | CE2 | TYR | 102 | 48.922 | 44.785 | 27.840 | 1.00 53.76 |
| ATOM | 762 | CZ | TYR | 102 | 48.498 | 43.475 | 27.701 | 1.00 53.85 |
| ATOM | 763 | OH | TYR | 102 | 49.355 | 42.442 | 28.021 | 1.00 54.03 |
| ATOM | 764 | C | TYR | 102 | 43.813 | 48.041 | 26.822 | 1.00 56.65 |
| ATOM | 765 | O | TYR | 102 | 43.173 | 47.899 | 25.781 | 1.00 56.91 |
| ATOM | 766 | N | SER | 103 | 43.891 | 49.203 | 27.462 | 1.00 58.50 |
| ATOM | 767 | CA | SER | 103 | 43.217 | 50.385 | 26.938 | 1.00 60.94 |
| ATOM | 768 | CB | SER | 103 | 42.997 | 51.411 | 28.049 | 1.00 61.09 |
| ATOM | 769 | OG | SER | 103 | 44.231 | 51.829 | 28.602 | 1.00 62.50 |
| ATOM | 770 | C | SER | 103 | 44.090 | 50.985 | 25.833 | 1.00 62.31 |
| ATOM | 771 | O | SER | 103 | 45.293 | 50.729 | 25.771 | 1.00 62.27 |
| ATOM | 772 | N | ALA | 104 | 43.487 | 51.783 | 24.960 | 1.00 64.47 |
| ATOM | 773 | CA | ALA | 104 | 44.226 | 52.386 | 23.856 | 1.00 67.01 |
| ATOM | 774 | CB | ALA | 104 | 43.516 | 52.093 | 22.526 | 1.00 67.01 |
| ATOM | 775 | C | ALA | 104 | 44.410 | 53.888 | 24.025 | 1.00 68.66 |
| ATOM | 776 | O | ALA | 104 | 43.458 | 54.658 | 23.902 | 1.00 69.01 |
| ATOM | 777 | N | PRO | 105 | 45.648 | 54.327 | 24.305 | 1.00 70.09 |
| ATOM | 778 | CD | PRO | 105 | 46.878 | 53.522 | 24.397 | 1.00 70.06 |
| ATOM | 779 | CA | PRO | 105 | 45.946 | 55.751 | 24.485 | 1.00 71.25 |
| ATOM | 780 | CB | PRO | 105 | 47.443 | 55.748 | 24.783 | 1.00 70.79 |
| ATOM | 781 | CG | PRO | 105 | 47.929 | 54.535 | 24.046 | 1.00 70.54 |
| ATOM | 782 | C | PRO | 105 | 45.592 | 56.586 | 23.251 | 1.00 72.81 |
| ATOM | 783 | O | PRO | 105 | 45.837 | 56.170 | 22.117 | 1.00 73.09 |
| ATOM | 784 | N | GLU | 106 | 45.012 | 57.762 | 23.479 | 1.00 74.39 |
| ATOM | 785 | CA | GLU | 106 | 44.619 | 58.652 | 22.391 | 1.00 76.25 |
| ATOM | 786 | CB | GLU | 106 | 43.991 | 59.921 | 22.950 | 1.00 76.77 |
| ATOM | 787 | CG | GLU | 106 | 42.702 | 59.673 | 23.680 | 1.00 78.35 |
| ATOM | 788 | CD | GLU | 106 | 42.397 | 60.775 | 24.657 | 1.00 79.28 |
| ATOM | 789 | OE1 | GLU | 106 | 42.239 | 61.934 | 24.214 | 1.00 79.74 |
| ATOM | 790 | OE2 | GLU | 106 | 42.326 | 60.478 | 25.871 | 1.00 80.03 |
| ATOM | 791 | C | GLU | 106 | 45.784 | 59.028 | 21.494 | 1.00 77.33 |
| ATOM | 792 | O | GLU | 106 | 45.600 | 59.262 | 20.300 | 1.00 77.48 |
| ATOM | 793 | N | ASP | 107 | 46.980 | 59.104 | 22.068 | 1.00 78.72 |
| ATOM | 794 | CA | ASP | 107 | 48.161 | 59.440 | 21.284 | 1.00 80.10 |

*FIG. 4N*

| ATOM | 795 | CB  | ASP | 107 | 49.431 | 59.316 | 22.134 | 1.00 | 80.44 |
| ATOM | 796 | CG  | ASP | 107 | 49.965 | 57.889 | 22.185 | 1.00 | 81.03 |
| ATOM | 797 | OD1 | ASP | 107 | 49.198 | 56.976 | 22.569 | 1.00 | 81.42 |
| ATOM | 798 | OD2 | ASP | 107 | 51.151 | 57.682 | 21.839 | 1.00 | 80.86 |
| ATOM | 799 | C   | ASP | 107 | 48.212 | 58.424 | 20.151 | 1.00 | 80.92 |
| ATOM | 800 | O   | ASP | 107 | 48.724 | 58.703 | 19.065 | 1.00 | 81.29 |
| ATOM | 801 | N   | ALA | 108 | 47.670 | 57.241 | 20.428 | 1.00 | 81.68 |
| ATOM | 802 | CA  | ALA | 108 | 47.628 | 56.151 | 19.463 | 1.00 | 82.45 |
| ATOM | 803 | CB  | ALA | 108 | 47.605 | 54.813 | 20.200 | 1.00 | 82.45 |
| ATOM | 804 | C   | ALA | 108 | 46.406 | 56.275 | 18.553 | 1.00 | 82.91 |
| ATOM | 805 | O   | ALA | 108 | 46.536 | 56.351 | 17.331 | 1.00 | 82.98 |
| ATOM | 806 | N   | MSE | 109 | 45.221 | 56.303 | 19.157 | 1.00 | 83.41 |
| ATOM | 807 | CA  | MSE | 109 | 43.974 | 56.414 | 18.407 | 1.00 | 83.78 |
| ATOM | 808 | CB  | MSE | 109 | 42.787 | 56.519 | 19.368 | 1.00 | 85.45 |
| ATOM | 809 | CG  | MSE | 109 | 41.581 | 55.678 | 18.972 | 1.00 | 87.01 |
| ATOM | 810 | SE  | MSE | 109 | 41.933 | 53.898 | 19.096 | 1.00 | 90.12 |
| ATOM | 811 | CE  | MSE | 109 | 42.665 | 53.581 | 17.453 | 1.00 | 88.95 |
| ATOM | 812 | C   | MSE | 109 | 43.992 | 57.633 | 17.494 | 1.00 | 83.17 |
| ATOM | 813 | O   | MSE | 109 | 43.235 | 57.710 | 16.527 | 1.00 | 83.19 |
| ATOM | 814 | N   | THR | 110 | 44.854 | 58.590 | 17.820 | 1.00 | 82.51 |
| ATOM | 815 | CA  | THR | 110 | 44.986 | 59.815 | 17.040 | 1.00 | 82.00 |
| ATOM | 816 | CB  | THR | 110 | 45.289 | 61.022 | 17.949 | 1.00 | 82.44 |
| ATOM | 817 | OG1 | THR | 110 | 44.302 | 61.103 | 18.986 | 1.00 | 83.00 |
| ATOM | 818 | CG2 | THR | 110 | 45.283 | 62.313 | 17.142 | 1.00 | 82.69 |
| ATOM | 819 | C   | THR | 110 | 46.150 | 59.640 | 16.082 | 1.00 | 81.25 |
| ATOM | 820 | O   | THR | 110 | 46.127 | 60.123 | 14.949 | 1.00 | 80.95 |
| ATOM | 821 | N   | GLY | 111 | 47.168 | 58.933 | 16.559 | 1.00 | 80.84 |
| ATOM | 822 | CA  | GLY | 111 | 48.358 | 58.691 | 15.768 | 1.00 | 80.12 |
| ATOM | 823 | C   | GLY | 111 | 48.121 | 57.986 | 14.450 | 1.00 | 79.53 |
| ATOM | 824 | O   | GLY | 111 | 47.018 | 57.531 | 14.148 | 1.00 | 79.54 |
| ATOM | 825 | N   | THR | 112 | 49.181 | 57.904 | 13.658 | 1.00 | 78.87 |
| ATOM | 826 | CA  | THR | 112 | 49.129 | 57.254 | 12.360 | 1.00 | 78.09 |
| ATOM | 827 | CB  | THR | 112 | 50.427 | 57.553 | 11.561 | 1.00 | 78.67 |
| ATOM | 828 | OG1 | THR | 112 | 50.329 | 57.001 | 10.240 | 1.00 | 79.18 |
| ATOM | 829 | CG2 | THR | 112 | 51.644 | 56.956 | 12.279 | 1.00 | 78.48 |
| ATOM | 830 | C   | THR | 112 | 48.992 | 55.748 | 12.579 | 1.00 | 77.09 |
| ATOM | 831 | O   | THR | 112 | 49.231 | 55.254 | 13.685 | 1.00 | 76.48 |
| ATOM | 832 | N   | ALA | 113 | 48.601 | 55.027 | 11.529 | 1.00 | 76.26 |
| ATOM | 833 | CA  | ALA | 113 | 48.443 | 53.573 | 11.603 | 1.00 | 75.60 |
| ATOM | 834 | CB  | ALA | 113 | 48.184 | 53.001 | 10.208 | 1.00 | 76.00 |
| ATOM | 835 | C   | ALA | 113 | 49.711 | 52.965 | 12.191 | 1.00 | 74.65 |
| ATOM | 836 | O   | ALA | 113 | 49.665 | 52.006 | 12.968 | 1.00 | 74.58 |
| ATOM | 837 | N   | GLU | 114 | 50.845 | 53.538 | 11.803 | 1.00 | 73.24 |
| ATOM | 838 | CA  | GLU | 114 | 52.139 | 53.088 | 12.288 | 1.00 | 71.57 |
| ATOM | 839 | CB  | GLU | 114 | 53.246 | 53.971 | 11.700 | 1.00 | 72.34 |
| ATOM | 840 | CG  | GLU | 114 | 53.130 | 54.167 | 10.188 | 1.00 | 71.64 |
| ATOM | 841 | CD  | GLU | 114 | 53.325 | 52.877 | 9.401  | 1.00 | 72.49 |
| ATOM | 842 | OE1 | GLU | 114 | 53.192 | 51.781 | 9.994  | 1.00 | 72.24 |
| ATOM | 843 | OE2 | GLU | 114 | 53.600 | 52.960 | 8.183  | 1.00 | 71.83 |
| ATOM | 844 | C   | GLU | 114 | 52.085 | 53.233 | 13.801 | 1.00 | 70.37 |
| ATOM | 845 | O   | GLU | 114 | 52.297 | 52.266 | 14.537 | 1.00 | 69.92 |
| ATOM | 846 | N   | MET | 115 | 51.778 | 54.450 | 14.246 | 1.00 | 68.75 |
| ATOM | 847 | CA  | MET | 115 | 51.657 | 54.760 | 15.669 | 1.00 | 66.97 |
| ATOM | 848 | CB  | MET | 115 | 51.013 | 56.140 | 15.866 | 1.00 | 67.15 |
| ATOM | 849 | CG  | MET | 115 | 51.999 | 57.277 | 16.040 | 1.00 | 66.94 |
| ATOM | 850 | SD  | MET | 115 | 53.203 | 56.869 | 17.320 | 1.00 | 67.61 |
| ATOM | 851 | CE  | MET | 115 | 52.137 | 56.732 | 18.788 | 1.00 | 66.65 |

*FIG. 40*

| ATOM | 852 | C | MET | 115 | 50.799 | 53.718 | 16.374 | 1.00 | 65.81 |
|------|-----|-----|-----|-----|--------|--------|--------|------|-------|
| ATOM | 853 | O | MET | 115 | 51.266 | 53.010 | 17.275 | 1.00 | 65.94 |
| ATOM | 854 | N | LEU | 116 | 49.542 | 53.635 | 15.940 | 1.00 | 63.70 |
| ATOM | 855 | CA | LEU | 116 | 48.561 | 52.711 | 16.504 | 1.00 | 61.63 |
| ATOM | 856 | CB | LEU | 116 | 47.287 | 52.720 | 15.650 | 1.00 | 60.89 |
| ATOM | 857 | CG | LEU | 116 | 45.948 | 52.226 | 16.205 | 1.00 | 59.42 |
| ATOM | 858 | CD1 | LEU | 116 | 44.953 | 52.182 | 15.051 | 1.00 | 58.84 |
| ATOM | 859 | CD2 | LEU | 116 | 46.081 | 50.858 | 16.847 | 1.00 | 58.86 |
| ATOM | 860 | C | LEU | 116 | 49.083 | 51.285 | 16.613 | 1.00 | 60.35 |
| ATOM | 861 | O | LEU | 116 | 48.977 | 50.665 | 17.667 | 1.00 | 60.48 |
| ATOM | 862 | N | PHE | 117 | 49.641 | 50.756 | 15.531 | 1.00 | 59.14 |
| ATOM | 863 | CA | PHE | 117 | 50.138 | 49.391 | 15.580 | 1.00 | 58.14 |
| ATOM | 864 | CB | PHE | 117 | 50.298 | 48.819 | 14.173 | 1.00 | 57.03 |
| ATOM | 865 | CG | PHE | 117 | 49.055 | 48.144 | 13.669 | 1.00 | 56.22 |
| ATOM | 866 | CD1 | PHE | 117 | 48.005 | 48.889 | 13.143 | 1.00 | 55.49 |
| ATOM | 867 | CD2 | PHE | 117 | 48.909 | 46.763 | 13.783 | 1.00 | 55.59 |
| ATOM | 868 | CE1 | PHE | 117 | 46.830 | 48.270 | 12.741 | 1.00 | 55.25 |
| ATOM | 869 | CE2 | PHE | 117 | 47.736 | 46.134 | 13.384 | 1.00 | 55.20 |
| ATOM | 870 | CZ | PHE | 117 | 46.695 | 46.887 | 12.862 | 1.00 | 55.23 |
| ATOM | 871 | C | PHE | 117 | 51.415 | 49.204 | 16.382 | 1.00 | 57.89 |
| ATOM | 872 | O | PHE | 117 | 51.799 | 48.073 | 16.690 | 1.00 | 57.80 |
| ATOM | 873 | N | ALA | 118 | 52.078 | 50.303 | 16.725 | 1.00 | 57.35 |
| ATOM | 874 | CA | ALA | 118 | 53.275 | 50.193 | 17.537 | 1.00 | 56.79 |
| ATOM | 875 | CB | ALA | 118 | 54.004 | 51.533 | 17.594 | 1.00 | 56.42 |
| ATOM | 876 | C | ALA | 118 | 52.747 | 49.792 | 18.922 | 1.00 | 56.46 |
| ATOM | 877 | O | ALA | 118 | 53.220 | 48.829 | 19.536 | 1.00 | 56.68 |
| ATOM | 878 | N | ALA | 119 | 51.733 | 50.515 | 19.391 | 1.00 | 55.57 |
| ATOM | 879 | CA | ALA | 119 | 51.142 | 50.226 | 20.693 | 1.00 | 55.05 |
| ATOM | 880 | CB | ALA | 119 | 49.931 | 51.135 | 20.952 | 1.00 | 53.91 |
| ATOM | 881 | C | ALA | 119 | 50.719 | 48.769 | 20.763 | 1.00 | 54.96 |
| ATOM | 882 | O | ALA | 119 | 51.090 | 48.052 | 21.698 | 1.00 | 54.94 |
| ATOM | 883 | N | ILE | 120 | 49.948 | 48.338 | 19.763 | 1.00 | 55.10 |
| ATOM | 884 | CA | ILE | 120 | 49.443 | 46.969 | 19.715 | 1.00 | 55.51 |
| ATOM | 885 | CB | ILE | 120 | 48.679 | 46.679 | 18.397 | 1.00 | 54.45 |
| ATOM | 886 | CG2 | ILE | 120 | 47.922 | 45.363 | 18.525 | 1.00 | 53.30 |
| ATOM | 887 | CG1 | ILE | 120 | 47.688 | 47.808 | 18.089 | 1.00 | 53.32 |
| ATOM | 888 | CD1 | ILE | 120 | 46.871 | 47.581 | 16.820 | 1.00 | 51.70 |
| ATOM | 889 | C | ILE | 120 | 50.575 | 45.957 | 19.846 | 1.00 | 56.57 |
| ATOM | 890 | O | ILE | 120 | 50.477 | 45.006 | 20.632 | 1.00 | 56.52 |
| ATOM | 891 | N | SER | 121 | 51.645 | 46.169 | 19.076 | 1.00 | 57.78 |
| ATOM | 892 | CA | SER | 121 | 52.814 | 45.284 | 19.093 | 1.00 | 58.54 |
| ATOM | 893 | CB | SER | 121 | 53.844 | 45.730 | 18.045 | 1.00 | 58.96 |
| ATOM | 894 | OG | SER | 121 | 53.377 | 45.507 | 16.720 | 1.00 | 59.32 |
| ATOM | 895 | C | SER | 121 | 53.457 | 45.280 | 20.473 | 1.00 | 58.74 |
| ATOM | 896 | O | SER | 121 | 54.007 | 44.265 | 20.918 | 1.00 | 57.56 |
| ATOM | 897 | N | GLU | 122 | 53.379 | 46.422 | 21.151 | 1.00 | 59.50 |
| ATOM | 898 | CA | GLU | 122 | 53.947 | 46.529 | 22.484 | 1.00 | 60.44 |
| ATOM | 899 | CB | GLU | 122 | 54.003 | 47.986 | 22.941 | 1.00 | 60.60 |
| ATOM | 900 | CG | GLU | 122 | 55.104 | 48.241 | 23.952 | 1.00 | 60.45 |
| ATOM | 901 | CD | GLU | 122 | 54.706 | 49.252 | 25.003 | 1.00 | 61.76 |
| ATOM | 902 | OE1 | GLU | 122 | 54.152 | 50.312 | 24.630 | 1.00 | 61.92 |
| ATOM | 903 | OE2 | GLU | 122 | 54.950 | 48.986 | 26.202 | 1.00 | 62.20 |
| ATOM | 904 | C | GLU | 122 | 53.091 | 45.725 | 23.452 | 1.00 | 60.63 |
| ATOM | 905 | O | GLU | 122 | 53.565 | 44.761 | 24.048 | 1.00 | 60.82 |
| ATOM | 906 | N | CYS | 123 | 51.831 | 46.120 | 23.605 | 1.00 | 60.96 |
| ATOM | 907 | CA | CYS | 123 | 50.936 | 45.410 | 24.510 | 1.00 | 61.79 |
| ATOM | 908 | CB | CYS | 123 | 49.481 | 45.840 | 24.278 | 1.00 | 61.63 |

*FIG. 4P*

| ATOM | 909 | SG  | CYS | 123 | 49.191 | 47.636 | 24.439 | 1.00 | 62.83 |
| ATOM | 910 | C   | CYS | 123 | 51.107 | 43.922 | 24.233 | 1.00 | 61.90 |
| ATOM | 911 | O   | CYS | 123 | 51.028 | 43.095 | 25.147 | 1.00 | 61.89 |
| ATOM | 912 | N   | ILE | 124 | 51.350 | 43.588 | 22.966 | 1.00 | 62.36 |
| ATOM | 913 | CA  | ILE | 124 | 51.561 | 42.197 | 22.588 | 1.00 | 62.79 |
| ATOM | 914 | CB  | ILE | 124 | 52.033 | 42.061 | 21.109 | 1.00 | 62.52 |
| ATOM | 915 | CG2 | ILE | 124 | 52.618 | 40.676 | 20.877 | 1.00 | 61.07 |
| ATOM | 916 | CG1 | ILE | 124 | 50.866 | 42.280 | 20.138 | 1.00 | 61.53 |
| ATOM | 917 | CD1 | ILE | 124 | 50.016 | 41.038 | 19.888 | 1.00 | 61.77 |
| ATOM | 918 | C   | ILE | 124 | 52.673 | 41.706 | 23.499 | 1.00 | 62.76 |
| ATOM | 919 | O   | ILE | 124 | 52.475 | 40.807 | 24.320 | 1.00 | 62.23 |
| ATOM | 920 | N   | SER | 125 | 53.839 | 42.327 | 23.347 | 1.00 | 63.43 |
| ATOM | 921 | CA  | SER | 125 | 55.020 | 42.002 | 24.138 | 1.00 | 64.63 |
| ATOM | 922 | CB  | SER | 125 | 56.062 | 43.117 | 23.986 | 1.00 | 65.05 |
| ATOM | 923 | OG  | SER | 125 | 57.324 | 42.745 | 24.523 | 1.00 | 67.01 |
| ATOM | 924 | C   | SER | 125 | 54.646 | 41.840 | 25.610 | 1.00 | 64.32 |
| ATOM | 925 | O   | SER | 125 | 54.886 | 40.794 | 26.219 | 1.00 | 64.46 |
| ATOM | 926 | N   | ASP | 126 | 54.047 | 42.884 | 26.169 | 1.00 | 64.43 |
| ATOM | 927 | CA  | ASP | 126 | 53.626 | 42.894 | 27.562 | 1.00 | 64.86 |
| ATOM | 928 | CB  | ASP | 126 | 52.660 | 44.060 | 27.788 | 1.00 | 64.95 |
| ATOM | 929 | CG  | ASP | 126 | 52.390 | 44.323 | 29.253 | 1.00 | 65.38 |
| ATOM | 930 | OD1 | ASP | 126 | 51.952 | 43.389 | 29.955 | 1.00 | 65.74 |
| ATOM | 931 | OD2 | ASP | 126 | 52.613 | 45.467 | 29.706 | 1.00 | 65.92 |
| ATOM | 932 | C   | ASP | 126 | 52.968 | 41.572 | 27.980 | 1.00 | 64.65 |
| ATOM | 933 | O   | ASP | 126 | 53.424 | 40.918 | 28.924 | 1.00 | 64.28 |
| ATOM | 934 | N   | PHE | 127 | 51.902 | 41.189 | 27.274 | 1.00 | 64.96 |
| ATOM | 935 | CA  | PHE | 127 | 51.177 | 39.948 | 27.565 | 1.00 | 65.21 |
| ATOM | 936 | CB  | PHE | 127 | 50.145 | 39.657 | 26.468 | 1.00 | 64.22 |
| ATOM | 937 | CG  | PHE | 127 | 49.569 | 38.258 | 26.525 | 1.00 | 63.67 |
| ATOM | 938 | CD1 | PHE | 127 | 48.774 | 37.857 | 27.594 | 1.00 | 63.64 |
| ATOM | 939 | CD2 | PHE | 127 | 49.830 | 37.343 | 25.512 | 1.00 | 63.42 |
| ATOM | 940 | CE1 | PHE | 127 | 48.247 | 36.564 | 27.652 | 1.00 | 63.40 |
| ATOM | 941 | CE2 | PHE | 127 | 49.308 | 36.051 | 25.560 | 1.00 | 63.55 |
| ATOM | 942 | CZ  | PHE | 127 | 48.516 | 35.661 | 26.632 | 1.00 | 63.49 |
| ATOM | 943 | C   | PHE | 127 | 52.154 | 38.791 | 27.631 | 1.00 | 65.83 |
| ATOM | 944 | O   | PHE | 127 | 52.195 | 38.030 | 28.600 | 1.00 | 65.71 |
| ATOM | 945 | N   | LEU | 128 | 52.931 | 38.684 | 26.562 | 1.00 | 66.57 |
| ATOM | 946 | CA  | LEU | 128 | 53.942 | 37.656 | 26.387 | 1.00 | 67.52 |
| ATOM | 947 | CB  | LEU | 128 | 54.773 | 38.022 | 25.166 | 1.00 | 67.64 |
| ATOM | 948 | CG  | LEU | 128 | 53.926 | 38.452 | 23.969 | 1.00 | 67.42 |
| ATOM | 949 | CD1 | LEU | 128 | 54.819 | 39.108 | 22.941 | 1.00 | 67.90 |
| ATOM | 950 | CD2 | LEU | 128 | 53.195 | 37.251 | 23.387 | 1.00 | 67.65 |
| ATOM | 951 | C   | LEU | 128 | 54.850 | 37.502 | 27.609 | 1.00 | 68.09 |
| ATOM | 952 | O   | LEU | 128 | 54.829 | 36.468 | 28.285 | 1.00 | 67.92 |
| ATOM | 953 | N   | ASP | 129 | 55.654 | 38.530 | 27.878 | 1.00 | 68.62 |
| ATOM | 954 | CA  | ASP | 129 | 56.565 | 38.514 | 29.018 | 1.00 | 69.22 |
| ATOM | 955 | CB  | ASP | 129 | 57.135 | 39.907 | 29.287 | 1.00 | 68.93 |
| ATOM | 956 | CG  | ASP | 129 | 58.115 | 40.342 | 28.239 | 1.00 | 68.90 |
| ATOM | 957 | OD1 | ASP | 129 | 59.100 | 39.606 | 28.011 | 1.00 | 69.12 |
| ATOM | 958 | OD2 | ASP | 129 | 57.900 | 41.423 | 27.650 | 1.00 | 69.22 |
| ATOM | 959 | C   | ASP | 129 | 55.843 | 38.059 | 30.267 | 1.00 | 69.59 |
| ATOM | 960 | O   | ASP | 129 | 56.063 | 36.956 | 30.761 | 1.00 | 69.41 |
| ATOM | 961 | N   | LYS | 130 | 54.973 | 38.940 | 30.753 | 1.00 | 70.10 |
| ATOM | 962 | CA  | LYS | 130 | 54.190 | 38.733 | 31.958 | 1.00 | 70.67 |
| ATOM | 963 | CB  | LYS | 130 | 53.285 | 39.946 | 32.159 | 1.00 | 70.80 |
| ATOM | 964 | CG  | LYS | 130 | 54.076 | 41.252 | 32.052 | 1.00 | 70.54 |
| ATOM | 965 | CD  | LYS | 130 | 53.218 | 42.479 | 32.266 | 1.00 | 70.22 |

*FIG. 4Q*

| | | | | | | | | |
|---|---|---|---|---|---|---|---|---|
| ATOM | 966 | CE | LYS | 130 | 54.021 | 43.746 | 32.011 | 1.00 70.07 |
| ATOM | 967 | NZ | LYS | 130 | 53.204 | 44.977 | 32.195 | 1.00 69.69 |
| ATOM | 968 | C | LYS | 130 | 53.394 | 37.441 | 31.982 | 1.00 71.17 |
| ATOM | 969 | O | LYS | 130 | 52.381 | 37.331 | 32.673 | 1.00 70.99 |
| ATOM | 970 | N | HIS | 131 | 53.883 | 36.468 | 31.221 | 1.00 72.01 |
| ATOM | 971 | CA | HIS | 131 | 53.301 | 35.139 | 31.125 | 1.00 73.44 |
| ATOM | 972 | CB | HIS | 131 | 52.313 | 35.065 | 29.965 | 1.00 73.00 |
| ATOM | 973 | CG | HIS | 131 | 50.881 | 35.076 | 30.397 | 1.00 72.93 |
| ATOM | 974 | CD2 | HIS | 131 | 49.960 | 34.085 | 30.454 | 1.00 72.73 |
| ATOM | 975 | ND1 | HIS | 131 | 50.256 | 36.210 | 30.869 | 1.00 72.87 |
| ATOM | 976 | CE1 | HIS | 131 | 49.010 | 35.917 | 31.196 | 1.00 73.01 |
| ATOM | 977 | NE2 | HIS | 131 | 48.806 | 34.634 | 30.954 | 1.00 73.04 |
| ATOM | 978 | C | HIS | 131 | 54.424 | 34.124 | 30.908 | 1.00 74.61 |
| ATOM | 979 | O | HIS | 131 | 54.419 | 33.049 | 31.514 | 1.00 74.70 |
| ATOM | 980 | N | GLN | 132 | 55.374 | 34.502 | 30.046 | 1.00 76.14 |
| ATOM | 981 | CA | GLN | 132 | 56.566 | 33.727 | 29.658 | 1.00 77.30 |
| ATOM | 982 | CB | GLN | 132 | 56.536 | 32.293 | 30.218 | 1.00 77.68 |
| ATOM | 983 | CG | GLN | 132 | 55.424 | 31.387 | 29.676 | 1.00 78.41 |
| ATOM | 984 | CD | GLN | 132 | 55.823 | 30.611 | 28.436 | 1.00 78.88 |
| ATOM | 985 | OE1 | GLN | 132 | 56.016 | 31.179 | 27.356 | 1.00 78.50 |
| ATOM | 986 | NE2 | GLN | 132 | 55.951 | 29.294 | 28.587 | 1.00 79.41 |
| ATOM | 987 | C | GLN | 132 | 56.673 | 33.682 | 28.134 | 1.00 77.86 |
| ATOM | 988 | O | GLN | 132 | 57.769 | 33.638 | 27.574 | 1.00 77.91 |
| ATOM | 989 | N | MSE | 133 | 55.520 | 33.703 | 27.472 | 1.00 78.39 |
| ATOM | 990 | CA | MSE | 133 | 55.450 | 33.662 | 26.017 | 1.00 78.88 |
| ATOM | 991 | CB | MSE | 133 | 53.989 | 33.684 | 25.551 | 1.00 80.96 |
| ATOM | 992 | CG | MSE | 133 | 53.278 | 32.347 | 25.586 | 1.00 83.34 |
| ATOM | 993 | SE | MSE | 133 | 51.991 | 32.273 | 26.846 | 1.00 87.09 |
| ATOM | 994 | CE | MSE | 133 | 52.168 | 30.521 | 27.421 | 1.00 84.33 |
| ATOM | 995 | C | MSE | 133 | 56.174 | 34.812 | 25.333 | 1.00 77.90 |
| ATOM | 996 | O | MSE | 133 | 55.552 | 35.548 | 24.567 | 1.00 78.34 |
| ATOM | 997 | N | LYS | 134 | 57.470 | 34.973 | 25.587 | 1.00 75.97 |
| ATOM | 998 | CA | LYS | 134 | 58.225 | 36.053 | 24.949 | 1.00 73.96 |
| ATOM | 999 | CB | LYS | 134 | 58.976 | 36.879 | 25.997 | 1.00 73.14 |
| ATOM | 1000 | CG | LYS | 134 | 59.676 | 38.125 | 25.454 | 1.00 72.28 |
| ATOM | 1001 | CD | LYS | 134 | 58.697 | 39.250 | 25.141 | 1.00 70.99 |
| ATOM | 1002 | CE | LYS | 134 | 59.415 | 40.586 | 24.935 | 1.00 70.06 |
| ATOM | 1003 | NZ | LYS | 134 | 60.234 | 40.640 | 23.687 | 1.00 69.46 |
| ATOM | 1004 | C | LYS | 134 | 59.211 | 35.443 | 23.964 | 1.00 72.94 |
| ATOM | 1005 | O | LYS | 134 | 59.727 | 36.123 | 23.077 | 1.00 72.63 |
| ATOM | 1006 | N | HIS | 135 | 59.457 | 34.148 | 24.132 | 1.00 72.28 |
| ATOM | 1007 | CA | HIS | 135 | 60.377 | 33.411 | 23.275 | 1.00 71.52 |
| ATOM | 1008 | CB | HIS | 135 | 61.359 | 32.584 | 24.119 | 1.00 71.15 |
| ATOM | 1009 | CG | HIS | 135 | 60.719 | 31.448 | 24.859 | 1.00 70.88 |
| ATOM | 1010 | CD2 | HIS | 135 | 60.908 | 30.109 | 24.773 | 1.00 70.87 |
| ATOM | 1011 | ND1 | HIS | 135 | 59.750 | 31.635 | 25.822 | 1.00 70.81 |
| ATOM | 1012 | CE1 | HIS | 135 | 59.370 | 30.462 | 26.298 | 1.00 70.56 |
| ATOM | 1013 | NE2 | HIS | 135 | 60.057 | 29.519 | 25.678 | 1.00 70.85 |
| ATOM | 1014 | C | HIS | 135 | 59.584 | 32.482 | 22.365 | 1.00 71.26 |
| ATOM | 1015 | O | HIS | 135 | 60.152 | 31.818 | 21.499 | 1.00 71.53 |
| ATOM | 1016 | N | LYS | 136 | 58.272 | 32.434 | 22.574 | 1.00 70.85 |
| ATOM | 1017 | CA | LYS | 136 | 57.393 | 31.590 | 21.766 | 1.00 70.33 |
| ATOM | 1018 | CB | LYS | 136 | 56.077 | 31.329 | 22.508 | 1.00 69.64 |
| ATOM | 1019 | CG | LYS | 136 | 56.225 | 30.694 | 23.886 | 1.00 68.45 |
| ATOM | 1020 | CD | LYS | 136 | 56.740 | 29.271 | 23.783 | 1.00 68.01 |
| ATOM | 1021 | CE | LYS | 136 | 56.698 | 28.560 | 25.128 | 1.00 67.56 |
| ATOM | 1022 | NZ | LYS | 136 | 55.303 | 28.356 | 25.623 | 1.00 66.87 |

*FIG. 4R*

| ATOM | 1023 | C   | LYS | 136 | 57.088 | 32.296 | 20.443 | 1.00 | 70.46 |
|------|------|-----|-----|-----|--------|--------|--------|------|-------|
| ATOM | 1024 | O   | LYS | 136 | 57.100 | 33.530 | 20.371 | 1.00 | 70.94 |
| ATOM | 1025 | N   | LYS | 137 | 56.828 | 31.519 | 19.396 | 1.00 | 70.16 |
| ATOM | 1026 | CA  | LYS | 137 | 56.505 | 32.096 | 18.096 | 1.00 | 69.80 |
| ATOM | 1027 | CB  | LYS | 137 | 57.505 | 31.642 | 17.023 | 1.00 | 71.09 |
| ATOM | 1028 | CG  | LYS | 137 | 57.602 | 30.132 | 16.801 | 1.00 | 71.73 |
| ATOM | 1029 | CD  | LYS | 137 | 58.567 | 29.840 | 15.654 | 1.00 | 72.44 |
| ATOM | 1030 | CE  | LYS | 137 | 58.915 | 28.363 | 15.545 | 1.00 | 72.39 |
| ATOM | 1031 | NZ  | LYS | 137 | 59.919 | 28.136 | 14.463 | 1.00 | 72.59 |
| ATOM | 1032 | C   | LYS | 137 | 55.097 | 31.685 | 17.702 | 1.00 | 68.73 |
| ATOM | 1033 | O   | LYS | 137 | 54.799 | 31.476 | 16.524 | 1.00 | 69.92 |
| ATOM | 1034 | N   | LEU | 138 | 54.243 | 31.579 | 18.716 | 1.00 | 66.57 |
| ATOM | 1035 | CA  | LEU | 138 | 52.841 | 31.193 | 18.586 | 1.00 | 63.82 |
| ATOM | 1036 | CB  | LEU | 138 | 52.057 | 31.788 | 19.748 | 1.00 | 63.11 |
| ATOM | 1037 | CG  | LEU | 138 | 52.364 | 31.145 | 21.092 | 1.00 | 62.89 |
| ATOM | 1038 | CD1 | LEU | 138 | 51.924 | 32.068 | 22.220 | 1.00 | 62.68 |
| ATOM | 1039 | CD2 | LEU | 138 | 51.669 | 29.786 | 21.150 | 1.00 | 61.80 |
| ATOM | 1040 | C   | LEU | 138 | 52.114 | 31.553 | 17.294 | 1.00 | 62.26 |
| ATOM | 1041 | O   | LEU | 138 | 52.416 | 32.566 | 16.647 | 1.00 | 62.54 |
| ATOM | 1042 | N   | PRO | 139 | 51.149 | 30.708 | 16.894 | 1.00 | 60.11 |
| ATOM | 1043 | CD  | PRO | 139 | 50.841 | 29.394 | 17.489 | 1.00 | 59.82 |
| ATOM | 1044 | CA  | PRO | 139 | 50.356 | 30.937 | 15.682 | 1.00 | 57.91 |
| ATOM | 1045 | CB  | PRO | 139 | 49.761 | 29.564 | 15.398 | 1.00 | 58.05 |
| ATOM | 1046 | CG  | PRO | 139 | 49.573 | 28.999 | 16.772 | 1.00 | 59.12 |
| ATOM | 1047 | C   | PRO | 139 | 49.302 | 31.968 | 16.101 | 1.00 | 55.89 |
| ATOM | 1048 | O   | PRO | 139 | 48.469 | 31.693 | 16.973 | 1.00 | 55.71 |
| ATOM | 1049 | N   | LEU | 140 | 49.358 | 33.154 | 15.501 | 1.00 | 53.40 |
| ATOM | 1050 | CA  | LEU | 140 | 48.440 | 34.237 | 15.850 | 1.00 | 50.78 |
| ATOM | 1051 | CB  | LEU | 140 | 49.195 | 35.576 | 15.834 | 1.00 | 49.87 |
| ATOM | 1052 | CG  | LEU | 140 | 48.452 | 36.893 | 16.091 | 1.00 | 49.01 |
| ATOM | 1053 | CD1 | LEU | 140 | 49.414 | 37.933 | 16.646 | 1.00 | 48.17 |
| ATOM | 1054 | CD2 | LEU | 140 | 47.825 | 37.389 | 14.801 | 1.00 | 48.88 |
| ATOM | 1055 | C   | LEU | 140 | 47.169 | 34.359 | 15.018 | 1.00 | 49.13 |
| ATOM | 1056 | O   | LEU | 140 | 47.211 | 34.368 | 13.785 | 1.00 | 49.12 |
| ATOM | 1057 | N   | GLY | 141 | 46.040 | 34.441 | 15.722 | 1.00 | 46.93 |
| ATOM | 1058 | CA  | GLY | 141 | 44.743 | 34.613 | 15.086 | 1.00 | 43.70 |
| ATOM | 1059 | C   | GLY | 141 | 44.324 | 36.041 | 15.402 | 1.00 | 41.11 |
| ATOM | 1060 | O   | GLY | 141 | 44.277 | 36.414 | 16.569 | 1.00 | 41.46 |
| ATOM | 1061 | N   | PHE | 142 | 44.018 | 36.842 | 14.388 | 1.00 | 38.27 |
| ATOM | 1062 | CA  | PHE | 142 | 43.659 | 38.232 | 14.629 | 1.00 | 36.42 |
| ATOM | 1063 | CB  | PHE | 142 | 44.648 | 39.118 | 13.882 | 1.00 | 34.58 |
| ATOM | 1064 | CG  | PHE | 142 | 44.403 | 40.593 | 14.037 | 1.00 | 33.28 |
| ATOM | 1065 | CD1 | PHE | 142 | 43.941 | 41.124 | 15.229 | 1.00 | 32.86 |
| ATOM | 1066 | CD2 | PHE | 142 | 44.702 | 41.465 | 12.992 | 1.00 | 32.75 |
| ATOM | 1067 | CE1 | PHE | 142 | 43.784 | 42.505 | 15.375 | 1.00 | 32.95 |
| ATOM | 1068 | CE2 | PHE | 142 | 44.551 | 42.845 | 13.125 | 1.00 | 31.57 |
| ATOM | 1069 | CZ  | PHE | 142 | 44.094 | 43.365 | 14.313 | 1.00 | 32.24 |
| ATOM | 1070 | C   | PHE | 142 | 42.224 | 38.652 | 14.300 | 1.00 | 36.83 |
| ATOM | 1071 | O   | PHE | 142 | 41.843 | 38.801 | 13.124 | 1.00 | 36.76 |
| ATOM | 1072 | N   | THR | 143 | 41.423 | 38.848 | 15.347 | 1.00 | 35.96 |
| ATOM | 1073 | CA  | THR | 143 | 40.047 | 39.288 | 15.156 | 1.00 | 34.35 |
| ATOM | 1074 | CB  | THR | 143 | 39.179 | 38.997 | 16.373 | 1.00 | 33.98 |
| ATOM | 1075 | OG1 | THR | 143 | 38.947 | 37.586 | 16.472 | 1.00 | 33.45 |
| ATOM | 1076 | CG2 | THR | 143 | 37.854 | 39.750 | 16.255 | 1.00 | 33.35 |
| ATOM | 1077 | C   | THR | 143 | 40.081 | 40.793 | 14.964 | 1.00 | 33.92 |
| ATOM | 1078 | O   | THR | 143 | 40.190 | 41.544 | 15.928 | 1.00 | 34.30 |
| ATOM | 1079 | N   | PHE | 144 | 40.009 | 41.227 | 13.716 | 1.00 | 33.00 |

*FIG. 4S*

| ATOM | 1080 | CA  | PHE | 144 | 40.029 | 42.649 | 13.383 | 1.00 | 31.69 |
|------|------|-----|-----|-----|--------|--------|--------|------|-------|
| ATOM | 1081 | CB  | PHE | 144 | 40.891 | 42.842 | 12.132 | 1.00 | 29.18 |
| ATOM | 1082 | CG  | PHE | 144 | 41.189 | 44.264 | 11.807 | 1.00 | 26.95 |
| ATOM | 1083 | CD1 | PHE | 144 | 41.727 | 45.108 | 12.763 | 1.00 | 26.21 |
| ATOM | 1084 | CD2 | PHE | 144 | 40.956 | 44.755 | 10.533 | 1.00 | 25.39 |
| ATOM | 1085 | CE1 | PHE | 144 | 42.026 | 46.428 | 12.450 | 1.00 | 26.79 |
| ATOM | 1086 | CE2 | PHE | 144 | 41.250 | 46.070 | 10.212 | 1.00 | 25.46 |
| ATOM | 1087 | CZ  | PHE | 144 | 41.785 | 46.910 | 11.167 | 1.00 | 25.80 |
| ATOM | 1088 | C   | PHE | 144 | 38.562 | 42.981 | 13.112 | 1.00 | 32.02 |
| ATOM | 1089 | O   | PHE | 144 | 37.929 | 42.280 | 12.333 | 1.00 | 33.96 |
| ATOM | 1090 | N   | SER | 145 | 38.025 | 44.027 | 13.744 | 1.00 | 32.29 |
| ATOM | 1091 | CA  | SER | 145 | 36.602 | 44.387 | 13.600 | 1.00 | 31.56 |
| ATOM | 1092 | CB  | SER | 145 | 35.993 | 44.689 | 14.968 | 1.00 | 31.79 |
| ATOM | 1093 | OG  | SER | 145 | 35.997 | 43.539 | 15.790 | 1.00 | 33.15 |
| ATOM | 1094 | C   | SER | 145 | 36.271 | 45.546 | 12.679 | 1.00 | 30.95 |
| ATOM | 1095 | O   | SER | 145 | 35.601 | 46.508 | 13.082 | 1.00 | 30.63 |
| ATOM | 1096 | N   | PHE | 146 | 36.723 | 45.456 | 11.439 | 1.00 | 30.27 |
| ATOM | 1097 | CA  | PHE | 146 | 36.452 | 46.513 | 10.489 | 1.00 | 29.49 |
| ATOM | 1098 | CB  | PHE | 146 | 37.573 | 47.541 | 10.535 | 1.00 | 29.01 |
| ATOM | 1099 | CG  | PHE | 146 | 37.848 | 48.054 | 11.908 | 1.00 | 27.96 |
| ATOM | 1100 | CD1 | PHE | 146 | 38.654 | 47.336 | 12.775 | 1.00 | 28.87 |
| ATOM | 1101 | CD2 | PHE | 146 | 37.245 | 49.221 | 12.359 | 1.00 | 27.88 |
| ATOM | 1102 | CE1 | PHE | 146 | 38.852 | 47.777 | 14.078 | 1.00 | 29.72 |
| ATOM | 1103 | CE2 | PHE | 146 | 37.434 | 49.670 | 13.659 | 1.00 | 26.92 |
| ATOM | 1104 | CZ  | PHE | 146 | 38.232 | 48.955 | 14.520 | 1.00 | 28.49 |
| ATOM | 1105 | C   | PHE | 146 | 36.318 | 45.937 | 9.093  | 1.00 | 29.49 |
| ATOM | 1106 | O   | PHE | 146 | 36.668 | 44.778 | 8.846  | 1.00 | 29.56 |
| ATOM | 1107 | N   | PRO | 147 | 35.805 | 46.738 | 8.152  | 1.00 | 29.02 |
| ATOM | 1108 | CD  | PRO | 147 | 35.452 | 48.167 | 8.211  | 1.00 | 28.09 |
| ATOM | 1109 | CA  | PRO | 147 | 35.662 | 46.212 | 6.798  | 1.00 | 30.12 |
| ATOM | 1110 | CB  | PRO | 147 | 34.852 | 47.309 | 6.099  | 1.00 | 28.65 |
| ATOM | 1111 | CG  | PRO | 147 | 35.377 | 48.540 | 6.749  | 1.00 | 28.13 |
| ATOM | 1112 | C   | PRO | 147 | 37.047 | 45.969 | 6.179  | 1.00 | 30.89 |
| ATOM | 1113 | O   | PRO | 147 | 37.938 | 46.821 | 6.263  | 1.00 | 32.17 |
| ATOM | 1114 | N   | VAL | 148 | 37.221 | 44.807 | 5.557  | 1.00 | 31.62 |
| ATOM | 1115 | CA  | VAL | 148 | 38.499 | 44.453 | 4.957  | 1.00 | 32.00 |
| ATOM | 1116 | CB  | VAL | 148 | 39.399 | 43.733 | 6.002  | 1.00 | 32.44 |
| ATOM | 1117 | CG1 | VAL | 148 | 40.471 | 42.940 | 5.311  | 1.00 | 33.36 |
| ATOM | 1118 | CG2 | VAL | 148 | 40.035 | 44.758 | 6.934  | 1.00 | 32.04 |
| ATOM | 1119 | C   | VAL | 148 | 38.351 | 43.557 | 3.733  | 1.00 | 31.54 |
| ATOM | 1120 | O   | VAL | 148 | 37.937 | 42.402 | 3.858  | 1.00 | 30.91 |
| ATOM | 1121 | N   | ALA | 149 | 38.688 | 44.091 | 2.560  | 1.00 | 31.66 |
| ATOM | 1122 | CA  | ALA | 149 | 38.610 | 43.316 | 1.324  | 1.00 | 32.33 |
| ATOM | 1123 | CB  | ALA | 149 | 38.834 | 44.213 | 0.120  | 1.00 | 31.16 |
| ATOM | 1124 | C   | ALA | 149 | 39.723 | 42.288 | 1.428  | 1.00 | 33.43 |
| ATOM | 1125 | O   | ALA | 149 | 40.882 | 42.653 | 1.431  | 1.00 | 35.59 |
| ATOM | 1126 | N   | HIS | 150 | 39.387 | 41.008 | 1.535  | 1.00 | 33.73 |
| ATOM | 1127 | CA  | HIS | 150 | 40.410 | 39.980 | 1.666  | 1.00 | 33.88 |
| ATOM | 1128 | CB  | HIS | 150 | 39.868 | 38.780 | 2.450  | 1.00 | 34.82 |
| ATOM | 1129 | CG  | HIS | 150 | 39.879 | 38.961 | 3.933  | 1.00 | 35.58 |
| ATOM | 1130 | CD2 | HIS | 150 | 40.344 | 38.162 | 4.921  | 1.00 | 36.49 |
| ATOM | 1131 | ND1 | HIS | 150 | 39.329 | 40.061 | 4.555  | 1.00 | 36.45 |
| ATOM | 1132 | CE1 | HIS | 150 | 39.454 | 39.930 | 5.865  | 1.00 | 36.79 |
| ATOM | 1133 | NE2 | HIS | 150 | 40.067 | 38.786 | 6.114  | 1.00 | 36.38 |
| ATOM | 1134 | C   | HIS | 150 | 40.960 | 39.442 | 0.353  | 1.00 | 34.39 |
| ATOM | 1135 | O   | HIS | 150 | 40.245 | 39.364 | -0.655 | 1.00 | 34.56 |
| ATOM | 1136 | N   | ALA | 151 | 42.239 | 39.068 | 0.380  | 1.00 | 34.73 |

*FIG. 4T*

| ATOM | 1137 | CA | ALA | 151 | 42.898 | 38.440 | -0.762 | 1.00 | 34.53 |
|------|------|-----|-----|-----|--------|--------|--------|------|-------|
| ATOM | 1138 | CB | ALA | 151 | 44.334 | 38.949 | -0.919 | 1.00 | 34.86 |
| ATOM | 1139 | C | ALA | 151 | 42.894 | 36.968 | -0.338 | 1.00 | 34.46 |
| ATOM | 1140 | O | ALA | 151 | 42.734 | 36.065 | -1.161 | 1.00 | 34.16 |
| ATOM | 1141 | N | ASP | 152 | 43.050 | 36.754 | 0.970 | 1.00 | 34.36 |
| ATOM | 1142 | CA | ASP | 152 | 43.045 | 35.422 | 1.562 | 1.00 | 35.45 |
| ATOM | 1143 | CB | ASP | 152 | 44.335 | 34.687 | 1.214 | 1.00 | 37.69 |
| ATOM | 1144 | CG | ASP | 152 | 44.233 | 33.185 | 1.431 | 1.00 | 40.20 |
| ATOM | 1145 | OD1 | ASP | 152 | 43.219 | 32.717 | 2.007 | 1.00 | 40.73 |
| ATOM | 1146 | OD2 | ASP | 152 | 45.177 | 32.464 | 1.018 | 1.00 | 42.29 |
| ATOM | 1147 | C | ASP | 152 | 42.901 | 35.549 | 3.088 | 1.00 | 35.53 |
| ATOM | 1148 | O | ASP | 152 | 43.048 | 36.642 | 3.642 | 1.00 | 35.08 |
| ATOM | 1149 | N | ILE | 153 | 42.627 | 34.433 | 3.762 | 1.00 | 35.49 |
| ATOM | 1150 | CA | ILE | 153 | 42.436 | 34.427 | 5.213 | 1.00 | 35.75 |
| ATOM | 1151 | CB | ILE | 153 | 42.258 | 32.984 | 5.754 | 1.00 | 35.32 |
| ATOM | 1152 | CG2 | ILE | 153 | 43.609 | 32.316 | 5.937 | 1.00 | 34.16 |
| ATOM | 1153 | CG1 | ILE | 153 | 41.593 | 33.022 | 7.130 | 1.00 | 35.44 |
| ATOM | 1154 | CD1 | ILE | 153 | 40.225 | 33.697 | 7.131 | 1.00 | 36.43 |
| ATOM | 1155 | C | ILE | 153 | 43.571 | 35.079 | 6.011 | 1.00 | 36.77 |
| ATOM | 1156 | O | ILE | 153 | 43.450 | 35.278 | 7.229 | 1.00 | 36.40 |
| ATOM | 1157 | N | ASP | 154 | 44.665 | 35.411 | 5.332 | 1.00 | 37.10 |
| ATOM | 1158 | CA | ASP | 154 | 45.815 | 36.003 | 6.000 | 1.00 | 37.27 |
| ATOM | 1159 | CB | ASP | 154 | 46.982 | 35.013 | 5.991 | 1.00 | 38.98 |
| ATOM | 1160 | CG | ASP | 154 | 47.795 | 35.079 | 4.703 | 1.00 | 41.58 |
| ATOM | 1161 | OD1 | ASP | 154 | 47.215 | 34.890 | 3.605 | 1.00 | 42.46 |
| ATOM | 1162 | OD2 | ASP | 154 | 49.022 | 35.331 | 4.789 | 1.00 | 42.65 |
| ATOM | 1163 | C | ASP | 154 | 46.233 | 37.287 | 5.307 | 1.00 | 36.74 |
| ATOM | 1164 | O | ASP | 154 | 47.360 | 37.751 | 5.471 | 1.00 | 37.07 |
| ATOM | 1165 | N | ALA | 155 | 45.328 | 37.865 | 4.531 | 1.00 | 35.91 |
| ATOM | 1166 | CA | ALA | 155 | 45.650 | 39.093 | 3.830 | 1.00 | 36.20 |
| ATOM | 1167 | CB | ALA | 155 | 46.522 | 38.771 | 2.621 | 1.00 | 36.22 |
| ATOM | 1168 | C | ALA | 155 | 44.412 | 39.864 | 3.387 | 1.00 | 36.20 |
| ATOM | 1169 | O | ALA | 155 | 43.490 | 39.289 | 2.820 | 1.00 | 36.87 |
| ATOM | 1170 | N | GLY | 156 | 44.402 | 41.168 | 3.642 | 1.00 | 36.26 |
| ATOM | 1171 | CA | GLY | 156 | 43.279 | 41.997 | 3.245 | 1.00 | 37.08 |
| ATOM | 1172 | C | GLY | 156 | 43.481 | 43.446 | 3.647 | 1.00 | 38.10 |
| ATOM | 1173 | O | GLY | 156 | 44.027 | 43.727 | 4.711 | 1.00 | 38.52 |
| ATOM | 1174 | N | ILE | 157 | 43.052 | 44.377 | 2.805 | 1.00 | 39.16 |
| ATOM | 1175 | CA | ILE | 157 | 43.203 | 45.789 | 3.125 | 1.00 | 41.42 |
| ATOM | 1176 | CB | ILE | 157 | 43.389 | 46.646 | 1.842 | 1.00 | 42.84 |
| ATOM | 1177 | CG2 | ILE | 157 | 44.844 | 46.550 | 1.349 | 1.00 | 44.32 |
| ATOM | 1178 | CG1 | ILE | 157 | 42.399 | 46.193 | 0.761 | 1.00 | 43.93 |
| ATOM | 1179 | CD1 | ILE | 157 | 42.630 | 46.838 | -0.615 | 1.00 | 44.55 |
| ATOM | 1180 | C | ILE | 157 | 42.010 | 46.331 | 3.921 | 1.00 | 42.26 |
| ATOM | 1181 | O | ILE | 157 | 40.864 | 45.912 | 3.732 | 1.00 | 42.28 |
| ATOM | 1182 | N | LEU | 158 | 42.300 | 47.259 | 4.824 | 1.00 | 42.54 |
| ATOM | 1183 | CA | LEU | 158 | 41.283 | 47.873 | 5.648 | 1.00 | 43.22 |
| ATOM | 1184 | CB | LEU | 158 | 41.928 | 48.504 | 6.884 | 1.00 | 44.12 |
| ATOM | 1185 | CG | LEU | 158 | 41.090 | 49.514 | 7.670 | 1.00 | 44.84 |
| ATOM | 1186 | CD1 | LEU | 158 | 40.020 | 48.782 | 8.472 | 1.00 | 45.23 |
| ATOM | 1187 | CD2 | LEU | 158 | 42.006 | 50.320 | 8.590 | 1.00 | 45.09 |
| ATOM | 1188 | C | LEU | 158 | 40.548 | 48.947 | 4.855 | 1.00 | 43.56 |
| ATOM | 1189 | O | LEU | 158 | 40.984 | 50.099 | 4.801 | 1.00 | 43.77 |
| ATOM | 1190 | N | LEU | 159 | 39.434 | 48.569 | 4.239 | 1.00 | 43.40 |
| ATOM | 1191 | CA | LEU | 159 | 38.634 | 49.508 | 3.465 | 1.00 | 43.01 |
| ATOM | 1192 | CB | LEU | 159 | 37.238 | 48.935 | 3.280 | 1.00 | 43.36 |
| ATOM | 1193 | CG | LEU | 159 | 37.279 | 47.599 | 2.539 | 1.00 | 43.44 |

*FIG. 4U*

```
ATOM   1194  CD1 LEU   159      36.020  46.808   2.829  1.00 44.00
ATOM   1195  CD2 LEU   159      37.443  47.857   1.050  1.00 42.93
ATOM   1196  C   LEU   159      38.564  50.879   4.139  1.00 42.62
ATOM   1197  O   LEU   159      38.745  51.905   3.488  1.00 43.03
ATOM   1198  N   ASN   160      38.297  50.902   5.440  1.00 42.20
ATOM   1199  CA  ASN   160      38.243  52.169   6.170  1.00 41.99
ATOM   1200  CB  ASN   160      37.347  53.197   5.447  1.00 42.23
ATOM   1201  CG  ASN   160      35.913  52.733   5.295  1.00 43.38
ATOM   1202  OD1 ASN   160      35.225  53.102   4.334  1.00 42.38
ATOM   1203  ND2 ASN   160      35.444  51.934   6.250  1.00 44.48
ATOM   1204  C   ASN   160      37.813  51.988   7.616  1.00 41.13
ATOM   1205  O   ASN   160      37.359  50.913   8.011  1.00 41.17
ATOM   1206  N   TRP   161      37.980  53.043   8.403  1.00 40.24
ATOM   1207  CA  TRP   161      37.652  53.004   9.824  1.00 39.69
ATOM   1208  CB  TRP   161      38.522  54.003  10.602  1.00 39.33
ATOM   1209  CG  TRP   161      39.987  53.640  10.769  1.00 39.07
ATOM   1210  CD2 TRP   161      40.527  52.469  11.411  1.00 38.63
ATOM   1211  CE2 TRP   161      41.931  52.616  11.438  1.00 38.27
ATOM   1212  CE3 TRP   161      39.960  51.317  11.972  1.00 38.43
ATOM   1213  CD1 TRP   161      41.060  54.417  10.436  1.00 38.40
ATOM   1214  NE1 TRP   161      42.228  53.812  10.840  1.00 38.42
ATOM   1215  CZ2 TRP   161      42.778  51.659  12.000  1.00 38.26
ATOM   1216  CZ3 TRP   161      40.809  50.357  12.538  1.00 38.07
ATOM   1217  CH2 TRP   161      42.200  50.540  12.545  1.00 38.37
ATOM   1218  C   TRP   161      36.196  53.301  10.150  1.00 39.07
ATOM   1219  O   TRP   161      35.578  54.193   9.562  1.00 39.38
ATOM   1220  N   THR   162      35.668  52.555  11.114  1.00 38.45
ATOM   1221  CA  THR   162      34.302  52.734  11.593  1.00 38.37
ATOM   1222  CB  THR   162      33.381  51.600  11.125  1.00 37.71
ATOM   1223  OG1 THR   162      33.926  50.338  11.548  1.00 37.02
ATOM   1224  CG2 THR   162      33.226  51.635   9.617  1.00 36.52
ATOM   1225  C   THR   162      34.357  52.702  13.121  1.00 38.24
ATOM   1226  O   THR   162      35.405  52.443  13.703  1.00 37.86
ATOM   1227  N   LYS   163      33.231  52.968  13.770  1.00 38.99
ATOM   1228  CA  LYS   163      33.192  52.941  15.222  1.00 39.72
ATOM   1229  CB  LYS   163      33.510  51.528  15.728  1.00 38.16
ATOM   1230  CG  LYS   163      32.467  50.487  15.311  1.00 36.62
ATOM   1231  CD  LYS   163      32.727  49.108  15.918  1.00 34.66
ATOM   1232  CE  LYS   163      33.829  48.349  15.195  1.00 33.22
ATOM   1233  NZ  LYS   163      34.068  47.031  15.850  1.00 32.19
ATOM   1234  C   LYS   163      34.142  53.956  15.848  1.00 40.71
ATOM   1235  O   LYS   163      34.690  53.723  16.931  1.00 40.69
ATOM   1236  N   GLY   164      34.338  55.076  15.156  1.00 41.81
ATOM   1237  CA  GLY   164      35.187  56.139  15.672  1.00 43.90
ATOM   1238  C   GLY   164      36.685  56.031  15.463  1.00 45.41
ATOM   1239  O   GLY   164      37.375  57.055  15.381  1.00 45.25
ATOM   1240  N   PHE   165      37.190  54.802  15.397  1.00 47.06
ATOM   1241  CA  PHE   165      38.613  54.560  15.197  1.00 48.70
ATOM   1242  CB  PHE   165      38.852  53.117  14.767  1.00 47.20
ATOM   1243  CG  PHE   165      39.290  52.222  15.870  1.00 45.64
ATOM   1244  CD1 PHE   165      38.443  51.937  16.929  1.00 45.87
ATOM   1245  CD2 PHE   165      40.544  51.632  15.833  1.00 45.19
ATOM   1246  CE1 PHE   165      38.840  51.064  17.945  1.00 46.28
ATOM   1247  CE2 PHE   165      40.952  50.763  16.834  1.00 45.80
ATOM   1248  CZ  PHE   165      40.098  50.475  17.896  1.00 45.96
ATOM   1249  C   PHE   165      39.250  55.471  14.154  1.00 50.94
ATOM   1250  O   PHE   165      38.633  55.823  13.143  1.00 50.36
```

*FIG. 4V*

| ATOM | 1251 | N | LYS | 166 | 40.500 | 55.838 | 14.415 | 1.00 | 53.77 |
|------|------|----|-----|-----|--------|--------|--------|------|-------|
| ATOM | 1252 | CA | LYS | 166 | 41.275 | 56.680 | 13.514 | 1.00 | 56.56 |
| ATOM | 1253 | CB | LYS | 166 | 41.050 | 58.170 | 13.822 | 1.00 | 56.16 |
| ATOM | 1254 | CG | LYS | 166 | 39.720 | 58.697 | 13.290 | 1.00 | 56.44 |
| ATOM | 1255 | CD | LYS | 166 | 39.524 | 58.320 | 11.812 | 1.00 | 56.54 |
| ATOM | 1256 | CE | LYS | 166 | 38.131 | 58.694 | 11.305 | 1.00 | 56.74 |
| ATOM | 1257 | NZ | LYS | 166 | 37.863 | 58.198 | 9.922  | 1.00 | 56.86 |
| ATOM | 1258 | C  | LYS | 166 | 42.751 | 56.322 | 13.640 | 1.00 | 58.33 |
| ATOM | 1259 | O  | LYS | 166 | 43.180 | 55.747 | 14.651 | 1.00 | 58.69 |
| ATOM | 1260 | N  | ALA | 167 | 43.510 | 56.647 | 12.597 | 1.00 | 59.76 |
| ATOM | 1261 | CA | ALA | 167 | 44.943 | 56.375 | 12.543 | 1.00 | 61.43 |
| ATOM | 1262 | CB | ALA | 167 | 45.220 | 54.901 | 12.834 | 1.00 | 60.92 |
| ATOM | 1263 | C  | ALA | 167 | 45.401 | 56.725 | 11.137 | 1.00 | 62.76 |
| ATOM | 1264 | O  | ALA | 167 | 45.147 | 55.967 | 10.197 | 1.00 | 63.38 |
| ATOM | 1265 | N  | SER | 168 | 46.066 | 57.872 | 10.999 | 1.00 | 63.98 |
| ATOM | 1266 | CA | SER | 168 | 46.556 | 58.345 | 9.704  | 1.00 | 64.43 |
| ATOM | 1267 | CB | SER | 168 | 47.636 | 59.414 | 9.903  | 1.00 | 64.96 |
| ATOM | 1268 | OG | SER | 168 | 47.130 | 60.546 | 10.594 | 1.00 | 65.76 |
| ATOM | 1269 | C  | SER | 168 | 47.115 | 57.216 | 8.846  | 1.00 | 64.59 |
| ATOM | 1270 | O  | SER | 168 | 47.805 | 56.322 | 9.347  | 1.00 | 64.35 |
| ATOM | 1271 | N  | GLY | 169 | 46.800 | 57.260 | 7.553  | 1.00 | 64.75 |
| ATOM | 1272 | CA | GLY | 169 | 47.280 | 56.245 | 6.632  | 1.00 | 65.55 |
| ATOM | 1273 | C  | GLY | 169 | 47.158 | 54.821 | 7.142  | 1.00 | 65.88 |
| ATOM | 1274 | O  | GLY | 169 | 48.151 | 54.097 | 7.255  | 1.00 | 65.72 |
| ATOM | 1275 | N  | ALA | 170 | 45.936 | 54.416 | 7.465  | 1.00 | 66.32 |
| ATOM | 1276 | CA | ALA | 170 | 45.699 | 53.065 | 7.947  | 1.00 | 66.82 |
| ATOM | 1277 | CB | ALA | 170 | 44.930 | 53.100 | 9.256  | 1.00 | 66.65 |
| ATOM | 1278 | C  | ALA | 170 | 44.890 | 52.346 | 6.879  | 1.00 | 67.02 |
| ATOM | 1279 | O  | ALA | 170 | 45.209 | 51.226 | 6.477  | 1.00 | 67.31 |
| ATOM | 1280 | N  | GLU | 171 | 43.847 | 53.017 | 6.410  | 1.00 | 66.85 |
| ATOM | 1281 | CA | GLU | 171 | 42.979 | 52.463 | 5.387  | 1.00 | 66.80 |
| ATOM | 1282 | CB | GLU | 171 | 41.705 | 53.292 | 5.287  | 1.00 | 67.90 |
| ATOM | 1283 | CG | GLU | 171 | 41.958 | 54.783 | 5.279  | 1.00 | 69.27 |
| ATOM | 1284 | CD | GLU | 171 | 40.850 | 55.552 | 4.590  | 1.00 | 70.17 |
| ATOM | 1285 | OE1| GLU | 171 | 40.789 | 55.506 | 3.340  | 1.00 | 70.45 |
| ATOM | 1286 | OE2| GLU | 171 | 40.038 | 56.191 | 5.296  | 1.00 | 70.67 |
| ATOM | 1287 | C  | GLU | 171 | 43.666 | 52.427 | 4.032  | 1.00 | 65.92 |
| ATOM | 1288 | O  | GLU | 171 | 44.469 | 53.301 | 3.711  | 1.00 | 66.22 |
| ATOM | 1289 | N  | GLY | 172 | 43.339 | 51.408 | 3.242  | 1.00 | 64.69 |
| ATOM | 1290 | CA | GLY | 172 | 43.922 | 51.265 | 1.925  | 1.00 | 62.79 |
| ATOM | 1291 | C  | GLY | 172 | 45.096 | 50.312 | 1.882  | 1.00 | 61.61 |
| ATOM | 1292 | O  | GLY | 172 | 45.493 | 49.884 | 0.805  | 1.00 | 61.59 |
| ATOM | 1293 | N  | ASN | 173 | 45.643 | 49.965 | 3.045  | 1.00 | 60.93 |
| ATOM | 1294 | CA | ASN | 173 | 46.800 | 49.065 | 3.115  | 1.00 | 60.42 |
| ATOM | 1295 | CB | ASN | 173 | 47.922 | 49.722 | 3.913  | 1.00 | 61.72 |
| ATOM | 1296 | CG | ASN | 173 | 48.035 | 51.201 | 3.631  | 1.00 | 62.78 |
| ATOM | 1297 | OD1| ASN | 173 | 48.367 | 51.605 | 2.515  | 1.00 | 63.29 |
| ATOM | 1298 | ND2| ASN | 173 | 47.741 | 52.024 | 4.637  | 1.00 | 63.06 |
| ATOM | 1299 | C  | ASN | 173 | 46.463 | 47.747 | 3.771  | 1.00 | 59.26 |
| ATOM | 1300 | O  | ASN | 173 | 45.440 | 47.624 | 4.430  | 1.00 | 59.57 |
| ATOM | 1301 | N  | ASN | 174 | 47.336 | 46.763 | 3.598  | 1.00 | 58.79 |
| ATOM | 1302 | CA | ASN | 174 | 47.126 | 45.447 | 4.196  | 1.00 | 58.46 |
| ATOM | 1303 | CB | ASN | 174 | 48.264 | 44.495 | 3.793  | 1.00 | 57.45 |
| ATOM | 1304 | CG | ASN | 174 | 48.104 | 43.093 | 4.375  | 1.00 | 57.22 |
| ATOM | 1305 | OD1| ASN | 174 | 48.757 | 42.144 | 3.924  | 1.00 | 56.21 |
| ATOM | 1306 | ND2| ASN | 174 | 47.245 | 42.957 | 5.382  | 1.00 | 56.76 |
| ATOM | 1307 | C  | ASN | 174 | 47.083 | 45.615 | 5.712  | 1.00 | 58.42 |

*FIG. 4W*

| ATOM | 1308 | O   | ASN | 174 | 47.927  | 46.302 | 6.281  | 1.00 | 59.03 |
|------|------|-----|-----|-----|---------|--------|--------|------|-------|
| ATOM | 1309 | N   | VAL | 175 | 46.091  | 45.008 | 6.359  | 1.00 | 58.23 |
| ATOM | 1310 | CA  | VAL | 175 | 45.966  | 45.106 | 7.809  | 1.00 | 57.79 |
| ATOM | 1311 | CB  | VAL | 175 | 44.544  | 44.765 | 8.295  | 1.00 | 57.69 |
| ATOM | 1312 | CG1 | VAL | 175 | 44.461  | 44.933 | 9.807  | 1.00 | 56.81 |
| ATOM | 1313 | CG2 | VAL | 175 | 43.531  | 45.665 | 7.603  | 1.00 | 57.69 |
| ATOM | 1314 | C   | VAL | 175 | 46.944  | 44.150 | 8.470  | 1.00 | 57.62 |
| ATOM | 1315 | O   | VAL | 175 | 47.734  | 44.560 | 9.319  | 1.00 | 57.89 |
| ATOM | 1316 | N   | VAL | 176 | 46.896  | 42.878 | 8.086  | 1.00 | 57.24 |
| ATOM | 1317 | CA  | VAL | 176 | 47.818  | 41.904 | 8.660  | 1.00 | 57.25 |
| ATOM | 1318 | CB  | VAL | 176 | 47.638  | 40.501 | 8.037  | 1.00 | 57.27 |
| ATOM | 1319 | CG1 | VAL | 176 | 48.597  | 39.511 | 8.701  | 1.00 | 56.21 |
| ATOM | 1320 | CG2 | VAL | 176 | 46.196  | 40.035 | 8.199  | 1.00 | 56.28 |
| ATOM | 1321 | C   | VAL | 176 | 49.232  | 42.396 | 8.362  | 1.00 | 57.38 |
| ATOM | 1322 | O   | VAL | 176 | 50.212  | 41.911 | 8.926  | 1.00 | 57.30 |
| ATOM | 1323 | N   | GLY | 177 | 49.319  | 43.374 | 7.467  | 1.00 | 57.41 |
| ATOM | 1324 | CA  | GLY | 177 | 50.605  | 43.939 | 7.103  | 1.00 | 57.60 |
| ATOM | 1325 | C   | GLY | 177 | 51.135  | 44.878 | 8.170  | 1.00 | 57.50 |
| ATOM | 1326 | O   | GLY | 177 | 52.171  | 44.605 | 8.781  | 1.00 | 58.09 |
| ATOM | 1327 | N   | LEU | 178 | 50.425  | 45.982 | 8.396  | 1.00 | 56.68 |
| ATOM | 1328 | CA  | LEU | 178 | 50.837  | 46.959 | 9.396  | 1.00 | 55.42 |
| ATOM | 1329 | CB  | LEU | 178 | 49.710  | 47.968 | 9.646  | 1.00 | 55.02 |
| ATOM | 1330 | CG  | LEU | 178 | 49.394  | 48.906 | 8.466  | 1.00 | 54.15 |
| ATOM | 1331 | CD1 | LEU | 178 | 48.158  | 49.743 | 8.766  | 1.00 | 53.80 |
| ATOM | 1332 | CD2 | LEU | 178 | 50.588  | 49.815 | 8.197  | 1.00 | 54.17 |
| ATOM | 1333 | C   | LEU | 178 | 51.247  | 46.279 | 10.701 | 1.00 | 54.84 |
| ATOM | 1334 | O   | LEU | 178 | 52.177  | 46.717 | 11.375 | 1.00 | 55.07 |
| ATOM | 1335 | N   | LEU | 179 | 50.575  | 45.192 | 11.050 | 1.00 | 53.85 |
| ATOM | 1336 | CA  | LEU | 179 | 50.917  | 44.491 | 12.274 | 1.00 | 53.57 |
| ATOM | 1337 | CB  | LEU | 179 | 49.882  | 43.409 | 12.582 | 1.00 | 52.75 |
| ATOM | 1338 | CG  | LEU | 179 | 50.099  | 42.671 | 13.907 | 1.00 | 52.23 |
| ATOM | 1339 | CD1 | LEU | 179 | 49.689  | 43.580 | 15.056 | 1.00 | 51.63 |
| ATOM | 1340 | CD2 | LEU | 179 | 49.286  | 41.381 | 13.935 | 1.00 | 51.34 |
| ATOM | 1341 | C   | LEU | 179 | 52.286  | 43.845 | 12.128 | 1.00 | 54.26 |
| ATOM | 1342 | O   | LEU | 179 | 53.070  | 43.796 | 13.075 | 1.00 | 54.60 |
| ATOM | 1343 | N   | ARG | 180 | 52.576  | 43.343 | 10.932 | 1.00 | 54.59 |
| ATOM | 1344 | CA  | ARG | 180 | 53.855  | 42.679 | 10.688 | 1.00 | 54.08 |
| ATOM | 1345 | CB  | ARG | 180 | 53.824  | 41.911 | 9.357  | 1.00 | 52.59 |
| ATOM | 1346 | CG  | ARG | 180 | 53.273  | 40.498 | 9.515  | 1.00 | 50.37 |
| ATOM | 1347 | CD  | ARG | 180 | 53.276  | 39.702 | 8.223  | 1.00 | 47.24 |
| ATOM | 1348 | NE  | ARG | 180 | 52.610  | 38.420 | 8.425  | 1.00 | 45.06 |
| ATOM | 1349 | CZ  | ARG | 180 | 51.979  | 37.754 | 7.462  | 1.00 | 43.97 |
| ATOM | 1350 | NH1 | ARG | 180 | 51.935  | 38.256 | 6.226  | 1.00 | 42.53 |
| ATOM | 1351 | NH2 | ARG | 180 | 51.366  | 36.601 | 7.735  | 1.00 | 42.95 |
| ATOM | 1352 | C   | ARG | 180 | 55.059  | 43.605 | 10.732 | 1.00 | 54.76 |
| ATOM | 1353 | O   | ARG | 180 | 56.009  | 43.343 | 11.473 | 1.00 | 54.65 |
| ATOM | 1354 | N   | ASP | 181 | 55.036  | 44.681 | 9.951  | 1.00 | 55.34 |
| ATOM | 1355 | CA  | ASP | 181 | 56.169  | 45.593 | 9.972  | 1.00 | 56.60 |
| ATOM | 1356 | CB  | ASP | 181 | 56.266  | 46.386 | 8.649  | 1.00 | 56.43 |
| ATOM | 1357 | CG  | ASP | 181 | 55.132  | 47.382 | 8.448  | 1.00 | 55.64 |
| ATOM | 1358 | OD1 | ASP | 181 | 54.658  | 47.483 | 7.294  | 1.00 | 55.20 |
| ATOM | 1359 | OD2 | ASP | 181 | 54.734  | 48.076 | 9.416  | 1.00 | 55.23 |
| ATOM | 1360 | C   | ASP | 181 | 56.115  | 46.514 | 11.199 | 1.00 | 57.64 |
| ATOM | 1361 | O   | ASP | 181 | 56.510  | 47.685 | 11.153 | 1.00 | 57.96 |
| ATOM | 1362 | N   | ALA | 182 | 55.634  | 45.947 | 12.303 | 1.00 | 57.87 |
| ATOM | 1363 | CA  | ALA | 182 | 55.524  | 46.646 | 13.577 | 1.00 | 57.84 |
| ATOM | 1364 | CB  | ALA | 182 | 54.078  | 47.048 | 13.836 | 1.00 | 58.19 |

*FIG. 4X*

| | | | | | | | | |
|---|---|---|---|---|---|---|---|---|
| ATOM | 1365 | C | ALA | 182 | 56.013 | 45.683 | 14.657 | 1.00 57.83 |
| ATOM | 1366 | O | ALA | 182 | 56.681 | 46.094 | 15.611 | 1.00 58.32 |
| ATOM | 1367 | N | ILE | 183 | 55.669 | 44.404 | 14.505 | 1.00 57.35 |
| ATOM | 1368 | CA | ILE | 183 | 56.109 | 43.381 | 15.448 | 1.00 57.40 |
| ATOM | 1369 | CB | ILE | 183 | 55.374 | 42.036 | 15.233 | 1.00 56.09 |
| ATOM | 1370 | CG2 | ILE | 183 | 56.025 | 40.932 | 16.074 | 1.00 55.25 |
| ATOM | 1371 | CG1 | ILE | 183 | 53.904 | 42.174 | 15.628 | 1.00 55.30 |
| ATOM | 1372 | CD1 | ILE | 183 | 53.115 | 40.881 | 15.505 | 1.00 54.14 |
| ATOM | 1373 | C | ILE | 183 | 57.600 | 43.164 | 15.199 | 1.00 58.51 |
| ATOM | 1374 | O | ILE | 183 | 58.294 | 42.531 | 16.002 | 1.00 59.24 |
| ATOM | 1375 | N | LYS | 184 | 58.093 | 43.689 | 14.077 | 1.00 59.04 |
| ATOM | 1376 | CA | LYS | 184 | 59.508 | 43.550 | 13.757 | 1.00 59.19 |
| ATOM | 1377 | CB | LYS | 184 | 59.719 | 43.243 | 12.268 | 1.00 59.15 |
| ATOM | 1378 | CG | LYS | 184 | 59.356 | 44.354 | 11.310 | 1.00 58.36 |
| ATOM | 1379 | CD | LYS | 184 | 59.566 | 43.897 | 9.868 | 1.00 58.59 |
| ATOM | 1380 | CE | LYS | 184 | 58.637 | 42.735 | 9.500 | 1.00 59.26 |
| ATOM | 1381 | NZ | LYS | 184 | 58.751 | 42.306 | 8.067 | 1.00 59.63 |
| ATOM | 1382 | C | LYS | 184 | 60.270 | 44.806 | 14.155 | 1.00 59.27 |
| ATOM | 1383 | O | LYS | 184 | 61.382 | 44.705 | 14.667 | 1.00 59.28 |
| ATOM | 1384 | N | ARG | 185 | 59.695 | 45.984 | 13.923 | 1.00 59.21 |
| ATOM | 1385 | CA | ARG | 185 | 60.383 | 47.211 | 14.331 | 1.00 59.69 |
| ATOM | 1386 | CB | ARG | 185 | 59.545 | 48.458 | 14.060 | 1.00 59.70 |
| ATOM | 1387 | CG | ARG | 185 | 59.278 | 48.772 | 12.610 | 1.00 60.85 |
| ATOM | 1388 | CD | ARG | 185 | 59.138 | 50.280 | 12.443 | 1.00 60.89 |
| ATOM | 1389 | NE | ARG | 185 | 58.121 | 50.628 | 11.459 | 1.00 62.26 |
| ATOM | 1390 | CZ | ARG | 185 | 56.819 | 50.403 | 11.620 | 1.00 61.84 |
| ATOM | 1391 | NH1 | ARG | 185 | 56.372 | 49.828 | 12.731 | 1.00 61.22 |
| ATOM | 1392 | NH2 | ARG | 185 | 55.966 | 50.754 | 10.666 | 1.00 62.23 |
| ATOM | 1393 | C | ARG | 185 | 60.574 | 47.104 | 15.836 | 1.00 60.41 |
| ATOM | 1394 | O | ARG | 185 | 61.630 | 47.430 | 16.384 | 1.00 60.45 |
| ATOM | 1395 | N | ARG | 186 | 59.518 | 46.633 | 16.489 | 1.00 61.07 |
| ATOM | 1396 | CA | ARG | 186 | 59.489 | 46.460 | 17.933 | 1.00 61.42 |
| ATOM | 1397 | CB | ARG | 186 | 58.066 | 46.055 | 18.358 | 1.00 61.16 |
| ATOM | 1398 | CG | ARG | 186 | 57.666 | 46.433 | 19.786 | 1.00 61.08 |
| ATOM | 1399 | CD | ARG | 186 | 57.666 | 45.473 | 20.828 | 1.00 60.87 |
| ATOM | 1400 | NE | ARG | 186 | 58.249 | 45.894 | 22.188 | 1.00 61.44 |
| ATOM | 1401 | CZ | ARG | 186 | 57.917 | 45.894 | 23.288 | 1.00 60.67 |
| ATOM | 1402 | NH1 | ARG | 186 | 58.294 | 45.246 | 23.201 | 1.00 60.28 |
| ATOM | 1403 | NH2 | ARG | 186 | 59.024 | 44.133 | 24.481 | 1.00 61.46 |
| ATOM | 1404 | C | ARG | 186 | 57.942 | 45.712 | 18.344 | 1.00 61.85 |
| ATOM | 1405 | O | ARG | 186 | 60.516 | 45.399 | 18.344 | 1.00 62.16 |
| ATOM | 1406 | N | GLY | 187 | 60.980 | 44.610 | 17.514 | 1.00 62.07 |
| ATOM | 1407 | CA | GLY | 187 | 60.873 | 45.401 | 19.628 | 1.00 62.22 |
| ATOM | 1408 | C | GLY | 187 | 61.843 | 44.455 | 20.157 | 1.00 62.50 |
| ATOM | 1409 | O | GLY | 187 | 61.591 | 43.017 | 19.754 | 1.00 62.37 |
| ATOM | 1410 | N | ASP | 188 | 60.541 | 42.692 | 19.202 | 1.00 63.08 |
| ATOM | 1411 | CA | ASP | 188 | 62.556 | 42.148 | 20.036 | 1.00 62.67 |
| ATOM | 1412 | CB | ASP | 188 | 62.414 | 40.746 | 19.684 | 1.00 61.80 |
| ATOM | 1413 | CG | ASP | 188 | 63.465 | 39.873 | 20.373 | 1.00 60.64 |
| ATOM | 1414 | OD1 | ASP | 188 | 63.027 | 38.409 | 20.468 | 1.00 60.77 |
| ATOM | 1415 | OD2 | ASP | 188 | 62.125 | 38.107 | 21.289 | 1.00 60.43 |
| ATOM | 1416 | C | ASP | 188 | 63.565 | 37.563 | 19.715 | 1.00 63.58 |
| ATOM | 1417 | O | ASP | 188 | 61.047 | 40.193 | 20.022 | 1.00 62.69 |
| ATOM | 1418 | N | PHE | 189 | 60.441 | 40.539 | 21.044 | 1.00 64.49 |
| ATOM | 1419 | CA | PHE | 189 | 60.599 | 39.309 | 19.138 | 1.00 64.75 |
| ATOM | 1420 | CB | PHE | 189 | 59.327 | 38.632 | 19.249 | 1.00 64.84 |
| ATOM | 1421 | CG | PHE | 189 | 58.233 | 39.629 | 19.598 | 1.00 65.46 |

*FIG. 4Y*

| ATOM | 1422 | CD1 | PHE | 189 | 56.707 | 37.824 | 20.402 | 1.00 | 65.54 |
| --- | --- | --- | --- | --- | --- | --- | --- | --- | --- |
| ATOM | 1423 | CD2 | PHE | 189 | 55.795 | 39.592 | 19.052 | 1.00 | 65.28 |
| ATOM | 1424 | CE1 | PHE | 189 | 55.455 | 37.224 | 20.481 | 1.00 | 65.61 |
| ATOM | 1425 | CE2 | PHE | 189 | 54.542 | 39.007 | 19.122 | 1.00 | 65.71 |
| ATOM | 1426 | CZ | PHE | 189 | 54.369 | 37.819 | 19.839 | 1.00 | 65.57 |
| ATOM | 1427 | C | PHE | 189 | 59.018 | 37.952 | 17.919 | 1.00 | 65.33 |
| ATOM | 1428 | O | PHE | 189 | 58.921 | 38.609 | 16.881 | 1.00 | 64.91 |
| ATOM | 1429 | N | GLU | 190 | 58.879 | 36.631 | 17.956 | 1.00 | 66.13 |
| ATOM | 1430 | CA | GLU | 190 | 58.584 | 35.854 | 16.752 | 1.00 | 66.57 |
| ATOM | 1431 | CB | GLU | 190 | 59.387 | 34.545 | 16.755 | 1.00 | 66.34 |
| ATOM | 1432 | CG | GLU | 190 | 60.778 | 34.649 | 17.389 | 1.00 | 64.66 |
| ATOM | 1433 | CD | GLU | 190 | 61.908 | 34.356 | 16.411 | 1.00 | 64.02 |
| ATOM | 1434 | OE1 | GLU | 190 | 63.054 | 34.161 | 16.874 | 1.00 | 63.09 |
| ATOM | 1435 | OE2 | GLU | 190 | 61.658 | 34.327 | 15.186 | 1.00 | 63.04 |
| ATOM | 1436 | C | GLU | 190 | 57.093 | 35.528 | 16.745 | 1.00 | 67.09 |
| ATOM | 1437 | O | GLU | 190 | 56.609 | 34.828 | 17.638 | 1.00 | 67.36 |
| ATOM | 1438 | N | MSE | 191 | 56.367 | 36.030 | 15.747 | 1.00 | 67.05 |
| ATOM | 1439 | CA | MSE | 191 | 54.928 | 35.775 | 15.666 | 1.00 | 66.65 |
| ATOM | 1440 | CB | MSE | 191 | 54.164 | 36.920 | 16.347 | 1.00 | 69.47 |
| ATOM | 1441 | CG | MSE | 191 | 52.867 | 36.492 | 17.037 | 1.00 | 72.30 |
| ATOM | 1442 | SE | MSE | 191 | 53.120 | 35.293 | 18.409 | 1.00 | 78.56 |
| ATOM | 1443 | CE | MSE | 191 | 51.941 | 35.893 | 19.581 | 1.00 | 75.88 |
| ATOM | 1444 | C | MSE | 191 | 54.412 | 35.590 | 14.230 | 1.00 | 64.85 |
| ATOM | 1445 | O | MSE | 191 | 54.399 | 36.538 | 13.435 | 1.00 | 64.30 |
| ATOM | 1446 | N | ASP | 192 | 53.977 | 34.368 | 13.910 | 1.00 | 62.82 |
| ATOM | 1447 | CA | ASP | 192 | 53.449 | 34.051 | 12.580 | 1.00 | 60.76 |
| ATOM | 1448 | CB | ASP | 192 | 53.774 | 32.607 | 12.207 | 1.00 | 61.24 |
| ATOM | 1449 | CG | ASP | 192 | 55.210 | 32.427 | 11.792 | 1.00 | 61.76 |
| ATOM | 1450 | OD1 | ASP | 192 | 55.684 | 33.219 | 10.947 | 1.00 | 62.45 |
| ATOM | 1451 | OD2 | ASP | 192 | 55.863 | 31.492 | 12.299 | 1.00 | 62.32 |
| ATOM | 1452 | C | ASP | 192 | 51.942 | 34.266 | 12.459 | 1.00 | 59.03 |
| ATOM | 1453 | O | ASP | 192 | 51.143 | 33.375 | 12.767 | 1.00 | 58.37 |
| ATOM | 1454 | N | VAL | 193 | 51.567 | 35.453 | 11.991 | 1.00 | 57.00 |
| ATOM | 1455 | CA | VAL | 193 | 50.167 | 35.818 | 11.818 | 1.00 | 54.85 |
| ATOM | 1456 | CB | VAL | 193 | 50.034 | 37.305 | 11.454 | 1.00 | 55.09 |
| ATOM | 1457 | CG1 | VAL | 193 | 48.568 | 37.712 | 11.448 | 1.00 | 54.84 |
| ATOM | 1458 | CG2 | VAL | 193 | 50.826 | 38.146 | 12.441 | 1.00 | 54.87 |
| ATOM | 1459 | C | VAL | 193 | 49.473 | 34.977 | 10.746 | 1.00 | 53.19 |
| ATOM | 1460 | O | VAL | 193 | 49.500 | 35.303 | 9.555 | 1.00 | 52.03 |
| ATOM | 1461 | N | VAL | 194 | 48.854 | 33.894 | 11.205 | 1.00 | 51.82 |
| ATOM | 1462 | CA | VAL | 194 | 48.126 | 32.949 | 10.367 | 1.00 | 50.66 |
| ATOM | 1463 | CB | VAL | 194 | 47.841 | 31.644 | 11.174 | 1.00 | 51.08 |
| ATOM | 1464 | CG1 | VAL | 194 | 46.686 | 30.860 | 10.554 | 1.00 | 52.09 |
| ATOM | 1465 | CG2 | VAL | 194 | 49.091 | 30.778 | 11.211 | 1.00 | 51.33 |
| ATOM | 1466 | C | VAL | 194 | 46.798 | 33.498 | 9.808 | 1.00 | 49.99 |
| ATOM | 1467 | O | VAL | 194 | 46.677 | 33.726 | 8.602 | 1.00 | 49.40 |
| ATOM | 1468 | N | ALA | 195 | 45.813 | 33.723 | 10.683 | 1.00 | 48.93 |
| ATOM | 1469 | CA | ALA | 195 | 44.499 | 34.193 | 10.251 | 1.00 | 47.60 |
| ATOM | 1470 | CB | ALA | 195 | 43.467 | 33.123 | 10.572 | 1.00 | 47.58 |
| ATOM | 1471 | C | ALA | 195 | 43.992 | 35.546 | 10.760 | 1.00 | 46.68 |
| ATOM | 1472 | O | ALA | 195 | 44.344 | 35.996 | 11.851 | 1.00 | 46.16 |
| ATOM | 1473 | N | MSE | 196 | 43.157 | 36.182 | 9.940 | 1.00 | 45.43 |
| ATOM | 1474 | CA | MSE | 196 | 42.521 | 37.459 | 10.279 | 1.00 | 44.60 |
| ATOM | 1475 | CB | MSE | 196 | 43.079 | 38.623 | 9.451 | 1.00 | 45.32 |
| ATOM | 1476 | CG | MSE | 196 | 42.329 | 39.925 | 9.716 | 1.00 | 47.29 |
| ATOM | 1477 | SE | MSE | 196 | 42.937 | 41.426 | 8.852 | 1.00 | 53.21 |
| ATOM | 1478 | CE | MSE | 196 | 44.264 | 41.920 | 9.982 | 1.00 | 51.44 |

*FIG. 4Z*

| ATOM | 1479 | C | MSE | 196 | 41.019 | 37.333 | 10.002 | 1.00 | 43.09 |
|---|---|---|---|---|---|---|---|---|---|
| ATOM | 1480 | O | MSE | 196 | 40.610 | 36.973 | 8.892 | 1.00 | 43.71 |
| ATOM | 1481 | N | VAL | 197 | 40.190 | 37.631 | 10.996 | 1.00 | 40.47 |
| ATOM | 1482 | CA | VAL | 197 | 38.751 | 37.514 | 10.799 | 1.00 | 37.00 |
| ATOM | 1483 | CB | VAL | 197 | 38.240 | 36.228 | 11.458 | 1.00 | 37.31 |
| ATOM | 1484 | CG1 | VAL | 197 | 38.840 | 35.004 | 10.766 | 1.00 | 36.64 |
| ATOM | 1485 | CG2 | VAL | 197 | 38.643 | 36.217 | 12.914 | 1.00 | 36.88 |
| ATOM | 1486 | C | VAL | 197 | 37.991 | 38.710 | 11.354 | 1.00 | 35.22 |
| ATOM | 1487 | O | VAL | 197 | 38.561 | 39.544 | 12.057 | 1.00 | 35.21 |
| ATOM | 1488 | N | ASN | 198 | 36.708 | 38.801 | 11.015 | 1.00 | 33.39 |
| ATOM | 1489 | CA | ASN | 198 | 35.830 | 39.883 | 11.491 | 1.00 | 30.23 |
| ATOM | 1490 | CB | ASN | 198 | 34.740 | 40.175 | 10.446 | 1.00 | 30.65 |
| ATOM | 1491 | CG | ASN | 198 | 33.801 | 41.309 | 10.852 | 1.00 | 31.35 |
| ATOM | 1492 | OD1 | ASN | 198 | 32.907 | 41.128 | 11.686 | 1.00 | 32.70 |
| ATOM | 1493 | ND2 | ASN | 198 | 33.997 | 42.486 | 10.251 | 1.00 | 30.53 |
| ATOM | 1494 | C | ASN | 198 | 35.217 | 39.356 | 12.780 | 1.00 | 28.41 |
| ATOM | 1495 | O | ASN | 198 | 35.052 | 38.143 | 12.937 | 1.00 | 26.14 |
| ATOM | 1496 | N | ASP | 199 | 34.892 | 40.252 | 13.711 | 1.00 | 27.77 |
| ATOM | 1497 | CA | ASP | 199 | 34.325 | 39.816 | 14.990 | 1.00 | 26.87 |
| ATOM | 1498 | CB | ASP | 199 | 34.156 | 41.007 | 15.945 | 1.00 | 26.75 |
| ATOM | 1499 | CG | ASP | 199 | 33.254 | 42.097 | 15.396 | 1.00 | 26.24 |
| ATOM | 1500 | OD1 | ASP | 199 | 33.221 | 42.292 | 14.167 | 1.00 | 26.90 |
| ATOM | 1501 | OD2 | ASP | 199 | 32.587 | 42.777 | 16.205 | 1.00 | 26.19 |
| ATOM | 1502 | C | ASP | 199 | 33.027 | 39.034 | 14.843 | 1.00 | 26.43 |
| ATOM | 1503 | O | ASP | 199 | 32.715 | 38.188 | 15.684 | 1.00 | 27.02 |
| ATOM | 1504 | N | THR | 200 | 32.291 | 39.292 | 13.763 | 1.00 | 25.45 |
| ATOM | 1505 | CA | THR | 200 | 31.050 | 38.585 | 13.510 | 1.00 | 25.65 |
| ATOM | 1506 | CB | THR | 200 | 30.261 | 39.193 | 12.339 | 1.00 | 25.75 |
| ATOM | 1507 | OG1 | THR | 200 | 31.008 | 39.044 | 11.130 | 1.00 | 26.04 |
| ATOM | 1508 | CG2 | THR | 200 | 30.002 | 40.672 | 12.573 | 1.00 | 26.48 |
| ATOM | 1509 | C | THR | 200 | 31.383 | 37.155 | 13.143 | 1.00 | 26.96 |
| ATOM | 1510 | O | THR | 200 | 30.832 | 36.211 | 13.712 | 1.00 | 27.62 |
| ATOM | 1511 | N | VAL | 201 | 32.295 | 36.990 | 12.189 | 1.00 | 28.07 |
| ATOM | 1512 | CA | VAL | 201 | 32.695 | 35.654 | 11.742 | 1.00 | 28.50 |
| ATOM | 1513 | CB | VAL | 201 | 33.785 | 35.726 | 10.665 | 1.00 | 29.26 |
| ATOM | 1514 | CG1 | VAL | 201 | 34.056 | 34.332 | 10.123 | 1.00 | 31.22 |
| ATOM | 1515 | CG2 | VAL | 201 | 33.370 | 36.684 | 9.546 | 1.00 | 27.90 |
| ATOM | 1516 | C | VAL | 201 | 33.231 | 34.818 | 12.901 | 1.00 | 29.16 |
| ATOM | 1517 | O | VAL | 201 | 32.816 | 33.676 | 13.101 | 1.00 | 29.44 |
| ATOM | 1518 | N | ALA | 202 | 34.156 | 35.395 | 13.663 | 1.00 | 30.31 |
| ATOM | 1519 | CA | ALA | 202 | 34.752 | 34.710 | 14.812 | 1.00 | 32.23 |
| ATOM | 1520 | CB | ALA | 202 | 35.591 | 35.705 | 15.643 | 1.00 | 31.72 |
| ATOM | 1521 | C | ALA | 202 | 33.688 | 34.070 | 15.696 | 1.00 | 33.37 |
| ATOM | 1522 | O | ALA | 202 | 33.789 | 32.894 | 16.073 | 1.00 | 34.14 |
| ATOM | 1523 | N | THR | 203 | 32.667 | 34.858 | 16.019 | 1.00 | 34.41 |
| ATOM | 1524 | CA | THR | 203 | 31.566 | 34.422 | 16.870 | 1.00 | 35.37 |
| ATOM | 1525 | CB | THR | 203 | 30.614 | 35.604 | 17.117 | 1.00 | 36.27 |
| ATOM | 1526 | OG1 | THR | 203 | 31.370 | 36.708 | 17.645 | 1.00 | 37.04 |
| ATOM | 1527 | CG2 | THR | 203 | 29.500 | 35.213 | 18.090 | 1.00 | 35.19 |
| ATOM | 1528 | C | THR | 203 | 30.800 | 33.260 | 16.242 | 1.00 | 36.08 |
| ATOM | 1529 | O | THR | 203 | 30.538 | 32.241 | 16.891 | 1.00 | 35.34 |
| ATOM | 1530 | N | MSE | 204 | 30.433 | 33.415 | 14.978 | 1.00 | 36.89 |
| ATOM | 1531 | CA | MSE | 204 | 29.722 | 32.348 | 14.299 | 1.00 | 37.94 |
| ATOM | 1532 | CB | MSE | 204 | 29.582 | 32.665 | 12.811 | 1.00 | 39.76 |
| ATOM | 1533 | CG | MSE | 204 | 29.065 | 31.504 | 11.954 | 1.00 | 40.74 |
| ATOM | 1534 | SE | MSE | 204 | 29.135 | 31.967 | 10.181 | 1.00 | 45.75 |
| ATOM | 1535 | CE | MSE | 204 | 30.643 | 31.057 | 9.627 | 1.00 | 45.26 |

*FIG. 4AA*

| ATOM | 1536 | C | MSE | 204 | 30.531 | 31.075 | 14.465 | 1.00 | 38.36 |
|------|------|------|-----|-----|--------|--------|--------|------|-------|
| ATOM | 1537 | O | MSE | 204 | 30.024 | 30.064 | 14.954 | 1.00 | 37.86 |
| ATOM | 1538 | N | ILE | 205 | 31.798 | 31.148 | 14.061 | 1.00 | 38.79 |
| ATOM | 1539 | CA | ILE | 205 | 32.696 | 30.008 | 14.137 | 1.00 | 40.09 |
| ATOM | 1540 | CB | ILE | 205 | 34.178 | 30.451 | 13.981 | 1.00 | 39.81 |
| ATOM | 1541 | CG2 | ILE | 205 | 35.098 | 29.240 | 14.072 | 1.00 | 39.47 |
| ATOM | 1542 | CG1 | ILE | 205 | 34.398 | 31.112 | 12.616 | 1.00 | 39.46 |
| ATOM | 1543 | CD1 | ILE | 205 | 34.250 | 30.158 | 11.425 | 1.00 | 39.34 |
| ATOM | 1544 | C | ILE | 205 | 32.527 | 29.215 | 15.440 | 1.00 | 41.34 |
| ATOM | 1545 | O | ILE | 205 | 32.121 | 28.050 | 15.408 | 1.00 | 41.41 |
| ATOM | 1546 | N | SER | 206 | 32.812 | 29.830 | 16.584 | 1.00 | 42.01 |
| ATOM | 1547 | CA | SER | 206 | 32.683 | 29.112 | 17.849 | 1.00 | 43.71 |
| ATOM | 1548 | CB | SER | 206 | 32.999 | 30.038 | 19.013 | 1.00 | 43.57 |
| ATOM | 1549 | OG | SER | 206 | 32.149 | 31.163 | 18.971 | 1.00 | 44.54 |
| ATOM | 1550 | C | SER | 206 | 31.306 | 28.494 | 18.056 | 1.00 | 44.83 |
| ATOM | 1551 | O | SER | 206 | 31.185 | 27.304 | 18.364 | 1.00 | 45.40 |
| ATOM | 1552 | N | CYS | 207 | 30.260 | 29.291 | 17.894 | 1.00 | 46.32 |
| ATOM | 1553 | CA | CYS | 207 | 28.912 | 28.764 | 18.079 | 1.00 | 48.14 |
| ATOM | 1554 | CB | CYS | 207 | 27.869 | 29.842 | 17.780 | 1.00 | 46.74 |
| ATOM | 1555 | SG | CYS | 207 | 27.946 | 31.264 | 18.883 | 1.00 | 42.50 |
| ATOM | 1556 | C | CYS | 207 | 28.666 | 27.551 | 17.186 | 1.00 | 50.79 |
| ATOM | 1557 | O | CYS | 207 | 27.715 | 26.799 | 17.403 | 1.00 | 50.97 |
| ATOM | 1558 | N | TYR | 208 | 29.533 | 27.361 | 16.190 | 1.00 | 53.91 |
| ATOM | 1559 | CA | TYR | 208 | 29.418 | 26.243 | 15.247 | 1.00 | 56.61 |
| ATOM | 1560 | CB | TYR | 208 | 30.350 | 26.458 | 14.045 | 1.00 | 56.96 |
| ATOM | 1561 | CG | TYR | 208 | 30.370 | 25.303 | 13.062 | 1.00 | 57.29 |
| ATOM | 1562 | CD1 | TYR | 208 | 29.307 | 25.090 | 12.182 | 1.00 | 57.54 |
| ATOM | 1563 | CE1 | TYR | 208 | 29.319 | 24.026 | 11.280 | 1.00 | 57.47 |
| ATOM | 1564 | CD2 | TYR | 208 | 31.448 | 24.418 | 13.019 | 1.00 | 57.54 |
| ATOM | 1565 | CE2 | TYR | 208 | 31.468 | 23.350 | 12.125 | 1.00 | 57.60 |
| ATOM | 1566 | CZ | TYR | 208 | 30.404 | 23.163 | 11.258 | 1.00 | 57.47 |
| ATOM | 1567 | OH | TYR | 208 | 30.435 | 22.126 | 10.360 | 1.00 | 57.71 |
| ATOM | 1568 | C | TYR | 208 | 29.705 | 24.867 | 15.854 | 1.00 | 58.12 |
| ATOM | 1569 | O | TYR | 208 | 28.874 | 23.960 | 15.773 | 1.00 | 58.61 |
| ATOM | 1570 | N | TYR | 209 | 30.876 | 24.699 | 16.459 | 1.00 | 59.77 |
| ATOM | 1571 | CA | TYR | 209 | 31.198 | 23.399 | 17.028 | 1.00 | 61.36 |
| ATOM | 1572 | CB | TYR | 209 | 32.619 | 23.394 | 17.581 | 1.00 | 63.23 |
| ATOM | 1573 | CG | TYR | 209 | 33.648 | 23.401 | 16.472 | 1.00 | 65.26 |
| ATOM | 1574 | CD1 | TYR | 209 | 34.058 | 24.595 | 15.876 | 1.00 | 66.13 |
| ATOM | 1575 | CE1 | TYR | 209 | 34.959 | 24.594 | 14.807 | 1.00 | 67.31 |
| ATOM | 1576 | CD2 | TYR | 209 | 34.165 | 22.206 | 15.973 | 1.00 | 65.88 |
| ATOM | 1577 | CE2 | TYR | 209 | 35.062 | 22.193 | 14.906 | 1.00 | 66.79 |
| ATOM | 1578 | CZ | TYR | 209 | 35.457 | 23.386 | 14.328 | 1.00 | 67.37 |
| ATOM | 1579 | OH | TYR | 209 | 36.350 | 23.370 | 13.277 | 1.00 | 67.62 |
| ATOM | 1580 | C | TYR | 209 | 30.206 | 22.965 | 18.083 | 1.00 | 61.32 |
| ATOM | 1581 | O | TYR | 209 | 30.048 | 21.771 | 18.336 | 1.00 | 61.19 |
| ATOM | 1582 | N | GLU | 210 | 29.523 | 23.938 | 18.680 | 1.00 | 61.63 |
| ATOM | 1583 | CA | GLU | 210 | 28.524 | 23.658 | 19.701 | 1.00 | 61.05 |
| ATOM | 1584 | CB | GLU | 210 | 28.444 | 24.808 | 20.706 | 1.00 | 62.29 |
| ATOM | 1585 | CG | GLU | 210 | 27.539 | 24.499 | 21.884 | 1.00 | 65.45 |
| ATOM | 1586 | CD | GLU | 210 | 27.716 | 25.463 | 23.050 | 1.00 | 67.38 |
| ATOM | 1587 | OE1 | GLU | 210 | 28.865 | 25.609 | 23.535 | 1.00 | 68.93 |
| ATOM | 1588 | OE2 | GLU | 210 | 26.707 | 26.065 | 23.488 | 1.00 | 67.92 |
| ATOM | 1589 | C | GLU | 210 | 27.175 | 23.459 | 19.026 | 1.00 | 60.04 |
| ATOM | 1590 | O | GLU | 210 | 26.255 | 22.901 | 19.618 | 1.00 | 59.93 |
| ATOM | 1591 | N | ASP | 211 | 27.073 | 23.920 | 17.780 | 1.00 | 58.82 |
| ATOM | 1592 | CA | ASP | 211 | 25.849 | 23.797 | 16.984 | 1.00 | 57.80 |

*FIG. 4BB*

| ATOM | 1593 | CB  | ASP | 211 | 24.804 | 24.824 | 17.441 | 1.00 | 58.16 |
| ATOM | 1594 | CG  | ASP | 211 | 23.504 | 24.730 | 16.653 | 1.00 | 58.25 |
| ATOM | 1595 | OD1 | ASP | 211 | 22.490 | 25.299 | 17.111 | 1.00 | 57.88 |
| ATOM | 1596 | OD2 | ASP | 211 | 23.495 | 24.096 | 15.572 | 1.00 | 58.65 |
| ATOM | 1597 | C   | ASP | 211 | 26.173 | 23.993 | 15.503 | 1.00 | 56.54 |
| ATOM | 1598 | O   | ASP | 211 | 26.351 | 25.116 | 15.037 | 1.00 | 56.17 |
| ATOM | 1599 | N   | HIS | 212 | 26.234 | 22.884 | 14.773 | 1.00 | 55.81 |
| ATOM | 1600 | CA  | HIS | 212 | 26.577 | 22.884 | 13.351 | 1.00 | 55.26 |
| ATOM | 1601 | CB  | HIS | 212 | 26.699 | 21.442 | 12.852 | 1.00 | 57.87 |
| ATOM | 1602 | CG  | HIS | 212 | 27.816 | 20.678 | 13.493 | 1.00 | 61.52 |
| ATOM | 1603 | CD2 | HIS | 212 | 27.815 | 19.527 | 14.205 | 1.00 | 62.63 |
| ATOM | 1604 | ND1 | HIS | 212 | 29.127 | 21.110 | 13.460 | 1.00 | 62.80 |
| ATOM | 1605 | CE1 | HIS | 212 | 29.884 | 20.258 | 14.127 | 1.00 | 63.70 |
| ATOM | 1606 | NE2 | HIS | 212 | 29.114 | 19.288 | 14.590 | 1.00 | 63.71 |
| ATOM | 1607 | C   | HIS | 212 | 25.665 | 23.656 | 12.412 | 1.00 | 53.29 |
| ATOM | 1608 | O   | HIS | 212 | 26.014 | 23.883 | 11.251 | 1.00 | 52.77 |
| ATOM | 1609 | N   | GLN | 213 | 24.496 | 24.058 | 12.895 | 1.00 | 51.08 |
| ATOM | 1610 | CA  | GLN | 213 | 23.579 | 24.790 | 12.037 | 1.00 | 48.22 |
| ATOM | 1611 | CB  | GLN | 213 | 22.135 | 24.347 | 12.298 | 1.00 | 49.39 |
| ATOM | 1612 | CG  | GLN | 213 | 21.957 | 22.839 | 12.130 | 1.00 | 50.76 |
| ATOM | 1613 | CD  | GLN | 213 | 20.507 | 22.410 | 11.965 | 1.00 | 51.82 |
| ATOM | 1614 | OE1 | GLN | 213 | 19.653 | 22.721 | 12.803 | 1.00 | 52.48 |
| ATOM | 1615 | NE2 | GLN | 213 | 20.223 | 21.679 | 10.883 | 1.00 | 51.72 |
| ATOM | 1616 | C   | GLN | 213 | 23.746 | 26.289 | 12.202 | 1.00 | 45.19 |
| ATOM | 1617 | O   | GLN | 213 | 22.978 | 27.077 | 11.654 | 1.00 | 45.00 |
| ATOM | 1618 | N   | CYS | 214 | 24.759 | 26.686 | 12.957 | 1.00 | 41.87 |
| ATOM | 1619 | CA  | CYS | 214 | 25.015 | 28.105 | 13.122 | 1.00 | 39.08 |
| ATOM | 1620 | CB  | CYS | 214 | 25.907 | 28.386 | 14.332 | 1.00 | 39.18 |
| ATOM | 1621 | SG  | CYS | 214 | 26.281 | 30.175 | 14.542 | 1.00 | 40.32 |
| ATOM | 1622 | C   | CYS | 214 | 25.743 | 28.530 | 11.859 | 1.00 | 36.43 |
| ATOM | 1623 | O   | CYS | 214 | 26.915 | 28.214 | 11.689 | 1.00 | 36.06 |
| ATOM | 1624 | N   | GLU | 215 | 25.046 | 29.223 | 10.967 | 1.00 | 33.00 |
| ATOM | 1625 | CA  | GLU | 215 | 25.664 | 29.672 |  9.736 | 1.00 | 30.60 |
| ATOM | 1626 | CB  | GLU | 215 | 25.056 | 28.960 |  8.541 | 1.00 | 31.95 |
| ATOM | 1627 | CG  | GLU | 215 | 25.289 | 27.466 |  8.561 | 1.00 | 33.57 |
| ATOM | 1628 | CD  | GLU | 215 | 24.973 | 26.827 |  7.233 | 1.00 | 35.80 |
| ATOM | 1629 | OE1 | GLU | 215 | 25.719 | 27.094 |  6.264 | 1.00 | 37.32 |
| ATOM | 1630 | OE2 | GLU | 215 | 23.978 | 26.064 |  7.156 | 1.00 | 37.21 |
| ATOM | 1631 | C   | GLU | 215 | 25.518 | 31.162 |  9.563 | 1.00 | 28.84 |
| ATOM | 1632 | O   | GLU | 215 | 25.665 | 31.687 |  8.459 | 1.00 | 28.39 |
| ATOM | 1633 | N   | VAL | 216 | 25.243 | 31.847 | 10.669 | 1.00 | 26.45 |
| ATOM | 1634 | CA  | VAL | 216 | 25.083 | 33.291 | 10.648 | 1.00 | 23.67 |
| ATOM | 1635 | CB  | VAL | 216 | 23.589 | 33.706 | 10.607 | 1.00 | 23.44 |
| ATOM | 1636 | CG1 | VAL | 216 | 23.485 | 35.214 | 10.492 | 1.00 | 22.72 |
| ATOM | 1637 | CG2 | VAL | 216 | 22.875 | 33.031 |  9.449 | 1.00 | 22.30 |
| ATOM | 1638 | C   | VAL | 216 | 25.671 | 33.858 | 11.921 | 1.00 | 22.20 |
| ATOM | 1639 | O   | VAL | 216 | 25.444 | 33.328 | 13.006 | 1.00 | 22.86 |
| ATOM | 1640 | N   | GLY | 217 | 26.423 | 34.939 | 11.793 | 1.00 | 21.40 |
| ATOM | 1641 | CA  | GLY | 217 | 26.997 | 35.554 | 12.965 | 1.00 | 21.14 |
| ATOM | 1642 | C   | GLY | 217 | 26.524 | 36.994 | 13.022 | 1.00 | 22.30 |
| ATOM | 1643 | O   | GLY | 217 | 26.432 | 37.677 | 11.983 | 1.00 | 22.05 |
| ATOM | 1644 | N   | MSE | 218 | 26.201 | 37.454 | 14.228 | 1.00 | 23.03 |
| ATOM | 1645 | CA  | MSE | 218 | 25.748 | 38.815 | 14.414 | 1.00 | 23.03 |
| ATOM | 1646 | CB  | MSE | 218 | 24.208 | 38.880 | 14.445 | 1.00 | 25.98 |
| ATOM | 1647 | CG  | MSE | 218 | 23.647 | 40.306 | 14.646 | 1.00 | 28.99 |
| ATOM | 1648 | SE  | MSE | 218 | 21.806 | 40.486 | 14.543 | 1.00 | 35.34 |
| ATOM | 1649 | CE  | MSE | 218 | 21.273 | 39.804 | 16.207 | 1.00 | 31.95 |

*FIG. 4CC*

| ATOM | 1650 | C | MSE | 218 | 26.320 | 39.405 | 15.694 | 1.00 | 21.99 |
|---|---|---|---|---|---|---|---|---|---|
| ATOM | 1651 | O | MSE | 218 | 26.425 | 38.738 | 16.724 | 1.00 | 22.34 |
| ATOM | 1652 | N | ILE | 219 | 26.694 | 40.670 | 15.606 | 1.00 | 21.28 |
| ATOM | 1653 | CA | ILE | 219 | 27.240 | 41.402 | 16.720 | 1.00 | 20.85 |
| ATOM | 1654 | CB | ILE | 219 | 28.702 | 41.840 | 16.449 | 1.00 | 20.74 |
| ATOM | 1655 | CG2 | ILE | 219 | 29.164 | 42.757 | 17.558 | 1.00 | 19.65 |
| ATOM | 1656 | CG1 | ILE | 219 | 29.623 | 40.627 | 16.335 | 1.00 | 19.32 |
| ATOM | 1657 | CD1 | ILE | 219 | 29.656 | 39.770 | 17.596 | 1.00 | 20.63 |
| ATOM | 1658 | C | ILE | 219 | 26.413 | 42.676 | 16.838 | 1.00 | 21.47 |
| ATOM | 1659 | O | ILE | 219 | 26.297 | 43.431 | 15.868 | 1.00 | 21.30 |
| ATOM | 1660 | N | VAL | 220 | 25.823 | 42.908 | 18.003 | 1.00 | 21.91 |
| ATOM | 1661 | CA | VAL | 220 | 25.059 | 44.135 | 18.224 | 1.00 | 22.49 |
| ATOM | 1662 | CB | VAL | 220 | 23.563 | 43.873 | 18.479 | 1.00 | 22.04 |
| ATOM | 1663 | CG1 | VAL | 220 | 22.815 | 45.183 | 18.425 | 1.00 | 21.50 |
| ATOM | 1664 | CG2 | VAL | 220 | 23.007 | 42.901 | 17.463 | 1.00 | 22.03 |
| ATOM | 1665 | C | VAL | 220 | 25.650 | 44.775 | 19.477 | 1.00 | 23.27 |
| ATOM | 1666 | O | VAL | 220 | 25.095 | 44.642 | 20.575 | 1.00 | 23.94 |
| ATOM | 1667 | N | GLY | 221 | 26.795 | 45.436 | 19.312 | 1.00 | 22.78 |
| ATOM | 1668 | CA | GLY | 221 | 27.448 | 46.063 | 20.443 | 1.00 | 22.86 |
| ATOM | 1669 | C | GLY | 221 | 27.728 | 47.509 | 20.138 | 1.00 | 23.75 |
| ATOM | 1670 | O | GLY | 221 | 26.816 | 48.264 | 19.828 | 1.00 | 25.09 |
| ATOM | 1671 | N | THR | 222 | 28.988 | 47.906 | 20.233 | 1.00 | 24.06 |
| ATOM | 1672 | CA | THR | 222 | 29.375 | 49.277 | 19.939 | 1.00 | 24.06 |
| ATOM | 1673 | CB | THR | 222 | 30.893 | 49.423 | 19.960 | 1.00 | 24.59 |
| ATOM | 1674 | OG1 | THR | 222 | 31.377 | 49.051 | 21.258 | 1.00 | 26.00 |
| ATOM | 1675 | CG2 | THR | 222 | 31.299 | 50.860 | 19.640 | 1.00 | 24.67 |
| ATOM | 1676 | C | THR | 222 | 28.888 | 49.530 | 18.533 | 1.00 | 24.09 |
| ATOM | 1677 | O | THR | 222 | 28.248 | 50.530 | 18.259 | 1.00 | 24.72 |
| ATOM | 1678 | N | GLY | 223 | 29.211 | 48.597 | 17.646 | 1.00 | 24.40 |
| ATOM | 1679 | CA | GLY | 223 | 28.790 | 48.686 | 16.262 | 1.00 | 24.65 |
| ATOM | 1680 | C | GLY | 223 | 27.797 | 47.560 | 16.020 | 1.00 | 25.05 |
| ATOM | 1681 | O | GLY | 223 | 27.478 | 46.779 | 16.936 | 1.00 | 25.80 |
| ATOM | 1682 | N | CYS | 224 | 27.298 | 47.453 | 14.798 | 1.00 | 24.73 |
| ATOM | 1683 | CA | CYS | 224 | 26.338 | 46.405 | 14.504 | 1.00 | 24.18 |
| ATOM | 1684 | CB | CYS | 224 | 24.928 | 46.958 | 14.682 | 1.00 | 24.47 |
| ATOM | 1685 | SG | CYS | 224 | 23.640 | 45.925 | 13.998 | 1.00 | 25.11 |
| ATOM | 1686 | C | CYS | 224 | 26.550 | 45.895 | 13.085 | 1.00 | 23.65 |
| ATOM | 1687 | O | CYS | 224 | 26.618 | 46.683 | 12.144 | 1.00 | 24.07 |
| ATOM | 1688 | N | ASN | 225 | 26.650 | 44.578 | 12.941 | 1.00 | 23.06 |
| ATOM | 1689 | CA | ASN | 225 | 26.883 | 43.963 | 11.638 | 1.00 | 23.27 |
| ATOM | 1690 | CB | ASN | 225 | 28.346 | 44.230 | 11.210 | 1.00 | 26.15 |
| ATOM | 1691 | CG | ASN | 225 | 28.831 | 43.296 | 10.098 | 1.00 | 27.94 |
| ATOM | 1692 | OD1 | ASN | 225 | 28.271 | 43.265 | 8.997 | 1.00 | 29.23 |
| ATOM | 1693 | ND2 | ASN | 225 | 29.878 | 42.524 | 10.393 | 1.00 | 28.62 |
| ATOM | 1694 | C | ASN | 225 | 26.603 | 42.459 | 11.740 | 1.00 | 21.80 |
| ATOM | 1695 | O | ASN | 225 | 26.291 | 41.954 | 12.827 | 1.00 | 20.54 |
| ATOM | 1696 | N | ALA | 226 | 26.709 | 41.759 | 10.610 | 1.00 | 19.99 |
| ATOM | 1697 | CA | ALA | 226 | 26.478 | 40.322 | 10.566 | 1.00 | 19.47 |
| ATOM | 1698 | CB | ALA | 226 | 24.994 | 40.032 | 10.443 | 1.00 | 20.99 |
| ATOM | 1699 | C | ALA | 226 | 27.194 | 39.723 | 9.378 | 1.00 | 18.72 |
| ATOM | 1700 | O | ALA | 226 | 27.529 | 40.428 | 8.415 | 1.00 | 17.97 |
| ATOM | 1701 | N | CYS | 227 | 27.404 | 38.415 | 9.439 | 1.00 | 18.36 |
| ATOM | 1702 | CA | CYS | 227 | 28.077 | 37.675 | 8.368 | 1.00 | 19.35 |
| ATOM | 1703 | CB | CYS | 227 | 29.523 | 37.396 | 8.751 | 1.00 | 18.42 |
| ATOM | 1704 | SG | CYS | 227 | 29.556 | 36.326 | 10.207 | 1.00 | 20.13 |
| ATOM | 1705 | C | CYS | 227 | 27.331 | 36.352 | 8.291 | 1.00 | 19.81 |
| ATOM | 1706 | O | CYS | 227 | 26.702 | 35.951 | 9.280 | 1.00 | 20.62 |

*FIG. 4DD*

| ATOM | 1707 | N   | TYR | 228 | 27.402 | 35.668 | 7.148  | 1.00 | 20.49 |
| ATOM | 1708 | CA  | TYR | 228 | 26.705 | 34.384 | 6.989  | 1.00 | 20.56 |
| ATOM | 1709 | CB  | TYR | 228 | 25.242 | 34.633 | 6.624  | 1.00 | 17.90 |
| ATOM | 1710 | CG  | TYR | 228 | 25.096 | 35.134 | 5.204  | 1.00 | 15.65 |
| ATOM | 1711 | CD1 | TYR | 228 | 24.922 | 34.249 | 4.145  | 1.00 | 15.81 |
| ATOM | 1712 | CE1 | TYR | 228 | 24.885 | 34.701 | 2.823  | 1.00 | 15.89 |
| ATOM | 1713 | CD2 | TYR | 228 | 25.221 | 36.483 | 4.913  | 1.00 | 15.28 |
| ATOM | 1714 | CE2 | TYR | 228 | 25.186 | 36.949 | 3.601  | 1.00 | 16.08 |
| ATOM | 1715 | CZ  | TYR | 228 | 25.022 | 36.051 | 2.564  | 1.00 | 16.76 |
| ATOM | 1716 | OH  | TYR | 228 | 25.033 | 36.505 | 1.263  | 1.00 | 18.93 |
| ATOM | 1717 | C   | TYR | 228 | 27.345 | 33.539 | 5.887  | 1.00 | 22.19 |
| ATOM | 1718 | O   | TYR | 228 | 28.174 | 34.024 | 5.112  | 1.00 | 21.49 |
| ATOM | 1719 | N   | MSE | 229 | 26.928 | 32.278 | 5.808  | 1.00 | 24.74 |
| ATOM | 1720 | CA  | MSE | 229 | 27.438 | 31.349 | 4.808  | 1.00 | 26.69 |
| ATOM | 1721 | CB  | MSE | 229 | 27.342 | 29.918 | 5.339  | 1.00 | 28.61 |
| ATOM | 1722 | CG  | MSE | 229 | 28.167 | 29.637 | 6.598  | 1.00 | 32.37 |
| ATOM | 1723 | SE  | MSE | 229 | 29.987 | 30.056 | 6.460  | 1.00 | 41.17 |
| ATOM | 1724 | CE  | MSE | 229 | 30.544 | 28.874 | 5.098  | 1.00 | 36.30 |
| ATOM | 1725 | C   | MSE | 229 | 26.663 | 31.470 | 3.481  | 1.00 | 27.83 |
| ATOM | 1726 | O   | MSE | 229 | 25.535 | 30.994 | 3.363  | 1.00 | 28.02 |
| ATOM | 1727 | N   | GLU | 230 | 27.282 | 32.109 | 2.492  | 1.00 | 29.19 |
| ATOM | 1728 | CA  | GLU | 230 | 26.688 | 32.296 | 1.172  | 1.00 | 29.81 |
| ATOM | 1729 | CB  | GLU | 230 | 27.165 | 33.623 | 0.577  | 1.00 | 30.83 |
| ATOM | 1730 | CG  | GLU | 230 | 26.685 | 33.922 | -0.843 | 1.00 | 32.33 |
| ATOM | 1731 | CD  | GLU | 230 | 25.173 | 33.825 | -0.989 | 1.00 | 34.04 |
| ATOM | 1732 | OE1 | GLU | 230 | 24.663 | 32.698 | -1.222 | 1.00 | 34.43 |
| ATOM | 1733 | OE2 | GLU | 230 | 24.497 | 34.878 | -0.858 | 1.00 | 33.65 |
| ATOM | 1734 | C   | GLU | 230 | 27.127 | 31.143 | 0.282  | 1.00 | 30.91 |
| ATOM | 1735 | O   | GLU | 230 | 27.958 | 30.319 | 0.685  | 1.00 | 30.80 |
| ATOM | 1736 | N   | GLU | 231 | 26.562 | 31.078 | -0.923 | 1.00 | 32.47 |
| ATOM | 1737 | CA  | GLU | 231 | 26.885 | 30.024 | -1.883 | 1.00 | 34.04 |
| ATOM | 1738 | CB  | GLU | 231 | 25.668 | 29.696 | -2.745 | 1.00 | 34.21 |
| ATOM | 1739 | CG  | GLU | 231 | 24.408 | 29.396 | -1.979 | 1.00 | 34.89 |
| ATOM | 1740 | CD  | GLU | 231 | 24.452 | 28.054 | -1.296 | 1.00 | 36.36 |
| ATOM | 1741 | OE1 | GLU | 231 | 24.745 | 27.064 | -2.002 | 1.00 | 36.80 |
| ATOM | 1742 | OE2 | GLU | 231 | 24.182 | 27.981 | -0.067 | 1.00 | 36.72 |
| ATOM | 1743 | C   | GLU | 231 | 27.997 | 30.550 | -2.777 | 1.00 | 35.65 |
| ATOM | 1744 | O   | GLU | 231 | 27.889 | 31.663 | -3.304 | 1.00 | 35.42 |
| ATOM | 1745 | N   | MSE | 232 | 29.060 | 29.758 | -2.952 | 1.00 | 37.13 |
| ATOM | 1746 | CA  | MSE | 232 | 30.188 | 30.181 | -3.780 | 1.00 | 38.19 |
| ATOM | 1747 | CB  | MSE | 232 | 31.191 | 29.036 | -3.935 | 1.00 | 41.27 |
| ATOM | 1748 | CG  | MSE | 232 | 32.195 | 28.912 | -2.765 | 1.00 | 45.40 |
| ATOM | 1749 | SE  | MSE | 232 | 33.237 | 30.431 | -2.467 | 1.00 | 52.07 |
| ATOM | 1750 | CE  | MSE | 232 | 34.286 | 30.483 | -3.969 | 1.00 | 48.20 |
| ATOM | 1751 | C   | MSE | 232 | 29.694 | 30.664 | -5.137 | 1.00 | 38.02 |
| ATOM | 1752 | O   | MSE | 232 | 30.179 | 31.656 | -5.678 | 1.00 | 36.84 |
| ATOM | 1753 | N   | GLN | 233 | 28.698 | 29.970 | -5.668 | 1.00 | 38.35 |
| ATOM | 1754 | CA  | GLN | 233 | 28.110 | 30.331 | -6.948 | 1.00 | 38.79 |
| ATOM | 1755 | CB  | GLN | 233 | 26.954 | 29.373 | -7.257 | 1.00 | 40.19 |
| ATOM | 1756 | CG  | GLN | 233 | 25.658 | 30.041 | -7.672 | 1.00 | 41.80 |
| ATOM | 1757 | CD  | GLN | 233 | 24.460 | 29.119 | -7.510 | 1.00 | 43.22 |
| ATOM | 1758 | OE1 | GLN | 233 | 24.226 | 28.582 | -6.424 | 1.00 | 44.27 |
| ATOM | 1759 | NE2 | GLN | 233 | 23.688 | 28.936 | -8.586 | 1.00 | 43.87 |
| ATOM | 1760 | C   | GLN | 233 | 27.615 | 31.777 | -6.936 | 1.00 | 38.45 |
| ATOM | 1761 | O   | GLN | 233 | 27.495 | 32.407 | -7.984 | 1.00 | 39.07 |
| ATOM | 1762 | N   | ASN | 234 | 27.329 | 32.313 | -5.753 | 1.00 | 37.79 |
| ATOM | 1763 | CA  | ASN | 234 | 26.840 | 33.687 | -5.668 | 1.00 | 36.56 |

*FIG. 4EE*

| ATOM | 1764 | CB | ASN | 234 | 25.657 | 33.771 | -4.706 | 1.00 | 37.03 |
| --- | --- | --- | --- | --- | --- | --- | --- | --- | --- |
| ATOM | 1765 | CG | ASN | 234 | 24.505 | 32.864 | -5.119 | 1.00 | 36.83 |
| ATOM | 1766 | OD1 | ASN | 234 | 24.152 | 32.793 | -6.299 | 1.00 | 36.50 |
| ATOM | 1767 | ND2 | ASN | 234 | 23.910 | 32.173 | -4.146 | 1.00 | 36.25 |
| ATOM | 1768 | C | ASN | 234 | 27.919 | 34.676 | -5.250 | 1.00 | 35.71 |
| ATOM | 1769 | O | ASN | 234 | 27.712 | 35.890 | -5.301 | 1.00 | 35.11 |
| ATOM | 1770 | N | VAL | 235 | 29.069 | 34.156 | -4.837 | 1.00 | 35.22 |
| ATOM | 1771 | CA | VAL | 235 | 30.177 | 35.009 | -4.439 | 1.00 | 34.85 |
| ATOM | 1772 | CB | VAL | 235 | 31.056 | 34.321 | -3.384 | 1.00 | 34.01 |
| ATOM | 1773 | CG1 | VAL | 235 | 31.949 | 35.343 | -2.717 | 1.00 | 32.35 |
| ATOM | 1774 | CG2 | VAL | 235 | 30.185 | 33.576 | -2.376 | 1.00 | 32.63 |
| ATOM | 1775 | C | VAL | 235 | 30.999 | 35.209 | -5.706 | 1.00 | 35.79 |
| ATOM | 1776 | O | VAL | 235 | 32.011 | 34.548 | -5.910 | 1.00 | 35.65 |
| ATOM | 1777 | N | GLU | 236 | 30.556 | 36.125 | -6.556 | 1.00 | 37.55 |
| ATOM | 1778 | CA | GLU | 236 | 31.220 | 36.383 | -7.830 | 1.00 | 39.52 |
| ATOM | 1779 | CB | GLU | 236 | 30.337 | 37.284 | -8.701 | 1.00 | 39.67 |
| ATOM | 1780 | CG | GLU | 236 | 29.242 | 36.539 | -9.448 | 1.00 | 41.02 |
| ATOM | 1781 | CD | GLU | 236 | 28.214 | 37.467 | -10.072 | 1.00 | 42.58 |
| ATOM | 1782 | OE1 | GLU | 236 | 28.607 | 38.529 | -10.630 | 1.00 | 42.67 |
| ATOM | 1783 | OE2 | GLU | 236 | 27.009 | 37.121 | -10.011 | 1.00 | 43.02 |
| ATOM | 1784 | C | GLU | 236 | 32.631 | 36.961 | -7.782 | 1.00 | 40.97 |
| ATOM | 1785 | O | GLU | 236 | 33.328 | 36.967 | -8.803 | 1.00 | 42.27 |
| ATOM | 1786 | N | LEU | 237 | 33.064 | 37.457 | -6.628 | 1.00 | 41.32 |
| ATOM | 1787 | CA | LEU | 237 | 34.408 | 38.017 | -6.538 | 1.00 | 41.63 |
| ATOM | 1788 | CB | LEU | 237 | 34.438 | 39.163 | -5.537 | 1.00 | 41.68 |
| ATOM | 1789 | CG | LEU | 237 | 33.545 | 40.367 | -5.820 | 1.00 | 42.50 |
| ATOM | 1790 | CD1 | LEU | 237 | 33.630 | 41.301 | -4.623 | 1.00 | 44.17 |
| ATOM | 1791 | CD2 | LEU | 237 | 33.984 | 41.101 | -7.085 | 1.00 | 42.46 |
| ATOM | 1792 | C | LEU | 237 | 35.454 | 36.970 | -6.148 | 1.00 | 42.43 |
| ATOM | 1793 | O | LEU | 237 | 36.636 | 37.294 | -6.010 | 1.00 | 42.30 |
| ATOM | 1794 | N | VAL | 238 | 35.019 | 35.724 | -5.967 | 1.00 | 42.96 |
| ATOM | 1795 | CA | VAL | 238 | 35.922 | 34.629 | -5.606 | 1.00 | 43.89 |
| ATOM | 1796 | CB | VAL | 238 | 35.917 | 34.380 | -4.097 | 1.00 | 42.33 |
| ATOM | 1797 | CG1 | VAL | 238 | 36.722 | 33.136 | -3.769 | 1.00 | 41.32 |
| ATOM | 1798 | CG2 | VAL | 238 | 36.503 | 35.578 | -3.385 | 1.00 | 42.74 |
| ATOM | 1799 | C | VAL | 238 | 35.520 | 33.337 | -6.313 | 1.00 | 45.65 |
| ATOM | 1800 | O | VAL | 238 | 34.755 | 32.555 | -5.770 | 1.00 | 46.15 |
| ATOM | 1801 | N | GLU | 239 | 36.069 | 33.116 | -7.510 | 1.00 | 47.60 |
| ATOM | 1802 | CA | GLU | 239 | 35.769 | 31.947 | -8.346 | 1.00 | 48.96 |
| ATOM | 1803 | CB | GLU | 239 | 36.819 | 31.793 | -9.448 | 1.00 | 51.17 |
| ATOM | 1804 | CG | GLU | 239 | 37.000 | 33.026 | -10.290 | 1.00 | 53.95 |
| ATOM | 1805 | CD | GLU | 239 | 37.817 | 34.066 | -9.570 | 1.00 | 56.27 |
| ATOM | 1806 | OE1 | GLU | 239 | 39.070 | 33.982 | -9.637 | 1.00 | 58.40 |
| ATOM | 1807 | OE2 | GLU | 239 | 37.211 | 34.950 | -8.918 | 1.00 | 57.25 |
| ATOM | 1808 | C | GLU | 239 | 35.599 | 30.594 | -7.675 | 1.00 | 48.87 |
| ATOM | 1809 | O | GLU | 239 | 36.272 | 30.274 | -6.701 | 1.00 | 48.25 |
| ATOM | 1810 | N | GLY | 240 | 34.705 | 29.797 | -8.252 | 1.00 | 49.09 |
| ATOM | 1811 | CA | GLY | 240 | 34.412 | 28.469 | -7.750 | 1.00 | 50.05 |
| ATOM | 1812 | C | GLY | 240 | 32.967 | 28.418 | -7.296 | 1.00 | 51.04 |
| ATOM | 1813 | O | GLY | 240 | 32.482 | 29.379 | -6.712 | 1.00 | 52.00 |
| ATOM | 1814 | N | ASP | 241 | 32.259 | 27.332 | -7.580 | 1.00 | 51.38 |
| ATOM | 1815 | CA | ASP | 241 | 30.882 | 27.214 | -7.127 | 1.00 | 52.10 |
| ATOM | 1816 | CB | ASP | 241 | 29.963 | 26.766 | -8.252 | 1.00 | 52.95 |
| ATOM | 1817 | CG | ASP | 241 | 30.186 | 27.534 | -9.529 | 1.00 | 53.84 |
| ATOM | 1818 | OD1 | ASP | 241 | 30.046 | 28.779 | -9.522 | 1.00 | 53.20 |
| ATOM | 1819 | OD2 | ASP | 241 | 30.496 | 26.875 | -10.546 | 1.00 | 53.97 |
| ATOM | 1820 | C | ASP | 241 | 30.924 | 26.122 | -6.083 | 1.00 | 52.90 |

*FIG. 4FF*

```
ATOM   1821  O    ASP   241     29.898  25.563  -5.701  1.00  53.59
ATOM   1822  N    GLU   242     32.131  25.816  -5.626  1.00  53.45
ATOM   1823  CA   GLU   242     32.325  24.760  -4.646  1.00  53.65
ATOM   1824  CB   GLU   242     33.785  24.299  -4.670  1.00  55.19
ATOM   1825  CG   GLU   242     34.056  23.062  -3.826  1.00  57.57
ATOM   1826  CD   GLU   242     35.527  22.672  -3.811  1.00  58.85
ATOM   1827  OE1  GLU   242     36.063  22.340  -4.893  1.00  59.63
ATOM   1828  OE2  GLU   242     36.143  22.701  -2.717  1.00  59.85
ATOM   1829  C    GLU   242     31.933  25.159  -3.229  1.00  52.66
ATOM   1830  O    GLU   242     32.469  26.113  -2.661  1.00  53.15
ATOM   1831  N    GLY   243     30.987  24.418  -2.665  1.00  51.11
ATOM   1832  CA   GLY   243     30.545  24.673  -1.305  1.00  48.74
ATOM   1833  C    GLY   243     30.200  26.110  -0.967  1.00  46.87
ATOM   1834  O    GLY   243     29.879  26.917  -1.850  1.00  46.49
ATOM   1835  N    ARG   244     30.288  26.421   0.326  1.00  44.89
ATOM   1836  CA   ARG   244     29.967  27.748   0.838  1.00  43.27
ATOM   1837  CB   ARG   244     28.852  27.639   1.873  1.00  42.24
ATOM   1838  CG   ARG   244     27.571  27.040   1.339  1.00  42.16
ATOM   1839  CD   ARG   244     26.442  27.153   2.356  1.00  41.35
ATOM   1840  NE   ARG   244     25.254  26.425   1.925  1.00  39.30
ATOM   1841  CZ   ARG   244     24.702  25.446   2.630  1.00  39.15
ATOM   1842  NH1  ARG   244     25.236  25.085   3.794  1.00  38.10
ATOM   1843  NH2  ARG   244     23.627  24.821   2.168  1.00  38.77
ATOM   1844  C    ARG   244     31.121  28.524   1.465  1.00  42.34
ATOM   1845  O    ARG   244     32.089  27.945   1.958  1.00  41.77
ATOM   1846  N    MSE   245     30.990  29.849   1.446  1.00  42.07
ATOM   1847  CA   MSE   245     31.977  30.745   2.042  1.00  41.32
ATOM   1848  CB   MSE   245     32.846  31.391   0.974  1.00  42.25
ATOM   1849  CG   MSE   245     33.870  32.345   1.566  1.00  44.07
ATOM   1850  SE   MSE   245     34.884  33.206   0.332  1.00  47.16
ATOM   1851  CE   MSE   245     36.149  31.909  -0.005  1.00  44.40
ATOM   1852  C    MSE   245     31.324  31.863   2.863  1.00  40.37
ATOM   1853  O    MSE   245     30.525  32.644   2.338  1.00  40.13
ATOM   1854  N    CYS   246     31.664  31.940   4.148  1.00  38.95
ATOM   1855  CA   CYS   246     31.125  32.990   5.001  1.00  37.00
ATOM   1856  CB   CYS   246     31.794  32.953   6.376  1.00  37.69
ATOM   1857  SG   CYS   246     31.231  34.229   7.567  1.00  38.96
ATOM   1858  C    CYS   246     31.422  34.320   4.311  1.00  35.82
ATOM   1859  O    CYS   246     32.484  34.497   3.706  1.00  34.54
ATOM   1860  N    VAL   247     30.466  35.240   4.388  1.00  34.51
ATOM   1861  CA   VAL   247     30.591  36.566   3.782  1.00  32.46
ATOM   1862  CB   VAL   247     29.609  36.751   2.588  1.00  32.34
ATOM   1863  CG1  VAL   247     29.709  38.170   2.038  1.00  31.78
ATOM   1864  CG2  VAL   247     29.930  35.750   1.486  1.00  32.04
ATOM   1865  C    VAL   247     30.239  37.580   4.863  1.00  32.03
ATOM   1866  O    VAL   247     29.291  37.377   5.628  1.00  33.28
ATOM   1867  N    ASN   248     31.011  38.657   4.931  1.00  29.34
ATOM   1868  CA   ASN   248     30.792  39.699   5.917  1.00  27.36
ATOM   1869  CB   ASN   248     32.147  40.219   6.401  1.00  28.42
ATOM   1870  CG   ASN   248     32.031  41.471   7.253  1.00  29.34
ATOM   1871  OD1  ASN   248     30.975  41.774   7.816  1.00  29.82
ATOM   1872  ND2  ASN   248     33.141  42.201   7.374  1.00  29.54
ATOM   1873  C    ASN   248     29.983  40.798   5.257  1.00  27.10
ATOM   1874  O    ASN   248     30.531  41.618   4.503  1.00  26.98
ATOM   1875  N    THR   249     28.679  40.823   5.544  1.00  26.01
ATOM   1876  CA   THR   249     27.778  41.809   4.937  1.00  23.85
ATOM   1877  CB   THR   249     26.325  41.634   5.424  1.00  23.81
```

*FIG. 4GG*

| ATOM | 1878 | OG1 | THR | 249 | 26.228 | 42.100 | 6.775 | 1.00 | 25.10 |
|---|---|---|---|---|---|---|---|---|---|
| ATOM | 1879 | CG2 | THR | 249 | 25.899 | 40.156 | 5.380 | 1.00 | 22.15 |
| ATOM | 1880 | C | THR | 249 | 28.208 | 43.226 | 5.270 | 1.00 | 24.20 |
| ATOM | 1881 | O | THR | 249 | 28.023 | 44.143 | 4.467 | 1.00 | 23.38 |
| ATOM | 1882 | N | GLU | 250 | 28.777 | 43.406 | 6.462 | 1.00 | 24.31 |
| ATOM | 1883 | CA | GLU | 250 | 29.219 | 44.733 | 6.891 | 1.00 | 23.61 |
| ATOM | 1884 | CB | GLU | 250 | 30.446 | 45.145 | 6.060 | 1.00 | 23.87 |
| ATOM | 1885 | CG | GLU | 250 | 31.242 | 46.362 | 6.571 | 1.00 | 25.94 |
| ATOM | 1886 | CD | GLU | 250 | 32.237 | 46.041 | 7.700 | 1.00 | 25.83 |
| ATOM | 1887 | OE1 | GLU | 250 | 32.728 | 44.893 | 7.813 | 1.00 | 25.67 |
| ATOM | 1888 | OE2 | GLU | 250 | 32.552 | 46.960 | 8.473 | 1.00 | 26.46 |
| ATOM | 1889 | C | GLU | 250 | 28.003 | 45.624 | 6.589 | 1.00 | 23.30 |
| ATOM | 1890 | O | GLU | 250 | 28.110 | 46.648 | 5.896 | 1.00 | 23.33 |
| ATOM | 1891 | N | TRP | 251 | 26.841 | 45.208 | 7.096 | 1.00 | 22.28 |
| ATOM | 1892 | CA | TRP | 251 | 25.609 | 45.940 | 6.840 | 1.00 | 22.36 |
| ATOM | 1893 | CB | TRP | 251 | 24.376 | 45.077 | 7.133 | 1.00 | 20.65 |
| ATOM | 1894 | CG | TRP | 251 | 24.133 | 44.726 | 8.543 | 1.00 | 18.29 |
| ATOM | 1895 | CD2 | TRP | 251 | 23.308 | 43.648 | 9.016 | 1.00 | 16.51 |
| ATOM | 1896 | CE2 | TRP | 251 | 23.279 | 43.725 | 10.424 | 1.00 | 15.08 |
| ATOM | 1897 | CE3 | TRP | 251 | 22.589 | 42.635 | 8.384 | 1.00 | 16.17 |
| ATOM | 1898 | CD1 | TRP | 251 | 24.565 | 45.395 | 9.652 | 1.00 | 17.71 |
| ATOM | 1899 | NE1 | TRP | 251 | 24.051 | 44.795 | 10.795 | 1.00 | 17.10 |
| ATOM | 1900 | CZ2 | TRP | 251 | 22.567 | 42.830 | 11.201 | 1.00 | 14.23 |
| ATOM | 1901 | CZ3 | TRP | 251 | 21.872 | 41.737 | 9.171 | 1.00 | 15.72 |
| ATOM | 1902 | CH2 | TRP | 251 | 21.869 | 41.842 | 10.559 | 1.00 | 14.23 |
| ATOM | 1903 | C | TRP | 251 | 25.445 | 47.283 | 7.523 | 1.00 | 23.49 |
| ATOM | 1904 | O | TRP | 251 | 24.541 | 48.044 | 7.167 | 1.00 | 23.95 |
| ATOM | 1905 | N | GLY | 252 | 26.302 | 47.579 | 8.500 | 1.00 | 24.44 |
| ATOM | 1906 | CA | GLY | 252 | 26.214 | 48.857 | 9.179 | 1.00 | 25.17 |
| ATOM | 1907 | C | GLY | 252 | 26.195 | 49.979 | 8.152 | 1.00 | 26.19 |
| ATOM | 1908 | O | GLY | 252 | 25.715 | 51.086 | 8.429 | 1.00 | 26.19 |
| ATOM | 1909 | N | ALA | 253 | 26.714 | 49.675 | 6.960 | 1.00 | 26.83 |
| ATOM | 1910 | CA | ALA | 253 | 26.791 | 50.622 | 5.851 | 1.00 | 27.86 |
| ATOM | 1911 | CB | ALA | 253 | 27.822 | 50.148 | 4.851 | 1.00 | 27.90 |
| ATOM | 1912 | C | ALA | 253 | 25.448 | 50.834 | 5.144 | 1.00 | 28.52 |
| ATOM | 1913 | O | ALA | 253 | 25.249 | 51.834 | 4.448 | 1.00 | 27.73 |
| ATOM | 1914 | N | PHE | 254 | 24.536 | 49.884 | 5.314 | 1.00 | 30.23 |
| ATOM | 1915 | CA | PHE | 254 | 23.224 | 49.974 | 4.696 | 1.00 | 31.42 |
| ATOM | 1916 | CB | PHE | 254 | 22.289 | 48.947 | 5.314 | 1.00 | 31.71 |
| ATOM | 1917 | CG | PHE | 254 | 20.899 | 48.995 | 4.768 | 1.00 | 31.90 |
| ATOM | 1918 | CD1 | PHE | 254 | 20.655 | 48.736 | 3.429 | 1.00 | 31.47 |
| ATOM | 1919 | CD2 | PHE | 254 | 19.824 | 49.273 | 5.600 | 1.00 | 32.95 |
| ATOM | 1920 | CE1 | PHE | 254 | 19.367 | 48.746 | 2.927 | 1.00 | 31.38 |
| ATOM | 1921 | CE2 | PHE | 254 | 18.518 | 49.285 | 5.096 | 1.00 | 32.69 |
| ATOM | 1922 | CZ | PHE | 254 | 18.295 | 49.021 | 3.763 | 1.00 | 31.47 |
| ATOM | 1923 | C | PHE | 254 | 22.664 | 51.367 | 4.928 | 1.00 | 32.56 |
| ATOM | 1924 | O | PHE | 254 | 22.638 | 51.839 | 6.064 | 1.00 | 33.19 |
| ATOM | 1925 | N | GLY | 255 | 22.227 | 52.017 | 3.849 | 1.00 | 33.62 |
| ATOM | 1926 | CA | GLY | 255 | 21.674 | 53.354 | 3.947 | 1.00 | 34.98 |
| ATOM | 1927 | C | GLY | 255 | 22.673 | 54.429 | 3.565 | 1.00 | 36.85 |
| ATOM | 1928 | O | GLY | 255 | 22.317 | 55.604 | 3.424 | 1.00 | 36.70 |
| ATOM | 1929 | N | ASP | 256 | 23.932 | 54.038 | 3.395 | 1.00 | 38.95 |
| ATOM | 1930 | CA | ASP | 256 | 24.966 | 55.000 | 3.038 | 1.00 | 41.47 |
| ATOM | 1931 | CB | ASP | 256 | 26.349 | 54.347 | 3.088 | 1.00 | 41.77 |
| ATOM | 1932 | CG | ASP | 256 | 26.880 | 54.224 | 4.502 | 1.00 | 42.36 |
| ATOM | 1933 | OD1 | ASP | 256 | 26.573 | 55.120 | 5.322 | 1.00 | 43.08 |
| ATOM | 1934 | OD2 | ASP | 256 | 27.617 | 53.251 | 4.791 | 1.00 | 42.28 |

*FIG. 4HH*

| | | | | | | | | |
|---|---|---|---|---|---|---|---|---|
| ATOM | 1935 | C | ASP | 256 | 24.744 | 55.636 | 1.666 | 1.00 43.10 |
| ATOM | 1936 | O | ASP | 256 | 25.489 | 56.533 | 1.261 | 1.00 44.08 |
| ATOM | 1937 | N | SER | 257 | 23.729 | 55.171 | 0.946 | 1.00 44.19 |
| ATOM | 1938 | CA | SER | 257 | 23.427 | 55.738 | -0.363 | 1.00 45.32 |
| ATOM | 1939 | CB | SER | 257 | 23.714 | 54.713 | -1.467 | 1.00 45.78 |
| ATOM | 1940 | OG | SER | 257 | 22.845 | 53.601 | -1.375 | 1.00 46.48 |
| ATOM | 1941 | C | SER | 257 | 21.967 | 56.204 | -0.423 | 1.00 45.41 |
| ATOM | 1942 | O | SER | 257 | 21.378 | 56.316 | -1.501 | 1.00 46.14 |
| ATOM | 1943 | N | GLY | 258 | 21.393 | 56.466 | 0.751 | 1.00 45.52 |
| ATOM | 1944 | CA | GLY | 258 | 20.018 | 56.933 | 0.835 | 1.00 45.22 |
| ATOM | 1945 | C | GLY | 258 | 18.922 | 55.896 | 1.042 | 1.00 45.11 |
| ATOM | 1946 | O | GLY | 258 | 17.745 | 56.253 | 1.068 | 1.00 45.45 |
| ATOM | 1947 | N | GLU | 259 | 19.284 | 54.627 | 1.205 | 1.00 44.67 |
| ATOM | 1948 | CA | GLU | 259 | 18.288 | 53.572 | 1.380 | 1.00 44.04 |
| ATOM | 1949 | CB | GLU | 259 | 18.954 | 52.187 | 1.415 | 1.00 44.23 |
| ATOM | 1950 | CG | GLU | 259 | 19.952 | 51.916 | 0.295 | 1.00 44.88 |
| ATOM | 1951 | CD | GLU | 259 | 21.318 | 52.552 | 0.548 | 1.00 45.53 |
| ATOM | 1952 | OE1 | GLU | 259 | 21.381 | 53.785 | 0.753 | 1.00 44.98 |
| ATOM | 1953 | OE2 | GLU | 259 | 22.335 | 51.817 | 0.537 | 1.00 45.95 |
| ATOM | 1954 | C | GLU | 259 | 17.462 | 53.749 | 2.647 | 1.00 43.91 |
| ATOM | 1955 | O | GLU | 259 | 16.461 | 53.061 | 2.836 | 1.00 43.49 |
| ATOM | 1956 | N | LEU | 260 | 17.875 | 54.661 | 3.520 | 1.00 43.87 |
| ATOM | 1957 | CA | LEU | 260 | 17.143 | 54.865 | 4.765 | 1.00 44.40 |
| ATOM | 1958 | CB | LEU | 260 | 18.023 | 54.513 | 5.967 | 1.00 44.36 |
| ATOM | 1959 | CG | LEU | 260 | 18.398 | 53.041 | 6.153 | 1.00 44.87 |
| ATOM | 1960 | CD1 | LEU | 260 | 19.315 | 52.879 | 7.369 | 1.00 44.30 |
| ATOM | 1961 | CD2 | LEU | 260 | 17.127 | 52.216 | 6.307 | 1.00 44.88 |
| ATOM | 1962 | C | LEU | 260 | 16.632 | 56.282 | 4.932 | 1.00 44.59 |
| ATOM | 1963 | O | LEU | 260 | 15.744 | 56.534 | 5.749 | 1.00 44.72 |
| ATOM | 1964 | N | ASP | 261 | 17.200 | 57.202 | 4.161 | 1.00 44.48 |
| ATOM | 1965 | CA | ASP | 261 | 16.821 | 58.608 | 4.234 | 1.00 44.18 |
| ATOM | 1966 | CB | ASP | 261 | 16.813 | 59.224 | 2.841 | 1.00 44.99 |
| ATOM | 1967 | CG | ASP | 261 | 18.192 | 59.310 | 2.247 | 1.00 46.23 |
| ATOM | 1968 | OD1 | ASP | 261 | 19.165 | 58.994 | 2.980 | 1.00 46.42 |
| ATOM | 1969 | OD2 | ASP | 261 | 18.296 | 59.697 | 1.055 | 1.00 46.79 |
| ATOM | 1970 | C | ASP | 261 | 15.482 | 58.885 | 4.892 | 1.00 43.00 |
| ATOM | 1971 | O | ASP | 261 | 15.415 | 59.592 | 5.898 | 1.00 42.63 |
| ATOM | 1972 | N | GLU | 262 | 14.424 | 58.317 | 4.320 | 1.00 41.88 |
| ATOM | 1973 | CA | GLU | 262 | 13.070 | 58.525 | 4.810 | 1.00 41.00 |
| ATOM | 1974 | CB | GLU | 262 | 12.088 | 57.744 | 3.940 | 1.00 41.65 |
| ATOM | 1975 | CG | GLU | 262 | 12.249 | 56.254 | 3.999 | 1.00 43.54 |
| ATOM | 1976 | CD | GLU | 262 | 11.359 | 55.562 | 2.996 | 1.00 45.44 |
| ATOM | 1977 | OE1 | GLU | 262 | 11.715 | 55.561 | 1.800 | 1.00 47.21 |
| ATOM | 1978 | OE2 | GLU | 262 | 10.296 | 55.031 | 3.391 | 1.00 47.29 |
| ATOM | 1979 | C | GLU | 262 | 12.830 | 58.211 | 6.286 | 1.00 39.99 |
| ATOM | 1980 | O | GLU | 262 | 11.997 | 58.852 | 6.918 | 1.00 40.22 |
| ATOM | 1981 | N | PHE | 263 | 13.545 | 57.238 | 6.845 | 1.00 38.83 |
| ATOM | 1982 | CA | PHE | 263 | 13.360 | 56.908 | 8.258 | 1.00 37.00 |
| ATOM | 1983 | CB | PHE | 263 | 13.684 | 55.430 | 8.512 | 1.00 34.37 |
| ATOM | 1984 | CG | PHE | 263 | 12.828 | 54.476 | 7.717 | 1.00 32.41 |
| ATOM | 1985 | CD1 | PHE | 263 | 13.366 | 53.753 | 6.660 | 1.00 30.67 |
| ATOM | 1986 | CD2 | PHE | 263 | 11.474 | 54.317 | 8.012 | 1.00 30.95 |
| ATOM | 1987 | CE1 | PHE | 263 | 12.567 | 52.886 | 5.909 | 1.00 29.82 |
| ATOM | 1988 | CE2 | PHE | 263 | 10.667 | 53.450 | 7.261 | 1.00 28.87 |
| ATOM | 1989 | CZ | PHE | 263 | 11.214 | 52.737 | 6.213 | 1.00 29.09 |
| ATOM | 1990 | C | PHE | 263 | 14.197 | 57.797 | 9.190 | 1.00 36.78 |
| ATOM | 1991 | O | PHE | 263 | 13.809 | 58.041 | 10.327 | 1.00 37.58 |

*FIG. 4II*

| ATOM | 1992 | N | LEU | 264 | 15.328 | 58.301 | 8.712 | 1.00 | 36.72 |
| ATOM | 1993 | CA | LEU | 264 | 16.193 | 59.142 | 9.542 | 1.00 | 37.11 |
| ATOM | 1994 | CB | LEU | 264 | 17.389 | 59.638 | 8.725 | 1.00 | 36.98 |
| ATOM | 1995 | CG | LEU | 264 | 18.131 | 58.621 | 7.852 | 1.00 | 36.59 |
| ATOM | 1996 | CD1 | LEU | 264 | 19.233 | 59.346 | 7.077 | 1.00 | 35.39 |
| ATOM | 1997 | CD2 | LEU | 264 | 18.701 | 57.503 | 8.717 | 1.00 | 35.46 |
| ATOM | 1998 | C | LEU | 264 | 15.482 | 60.350 | 10.158 | 1.00 | 37.28 |
| ATOM | 1999 | O | LEU | 264 | 14.879 | 61.148 | 9.451 | 1.00 | 38.03 |
| ATOM | 2000 | N | LEU | 265 | 15.574 | 60.480 | 11.479 | 1.00 | 37.63 |
| ATOM | 2001 | CA | LEU | 265 | 14.965 | 61.585 | 12.215 | 1.00 | 37.33 |
| ATOM | 2002 | CB | LEU | 265 | 14.380 | 61.070 | 13.527 | 1.00 | 36.25 |
| ATOM | 2003 | CG | LEU | 265 | 13.529 | 59.807 | 13.417 | 1.00 | 35.76 |
| ATOM | 2004 | CD1 | LEU | 265 | 13.157 | 59.295 | 14.808 | 1.00 | 35.17 |
| ATOM | 2005 | CD2 | LEU | 265 | 12.292 | 60.120 | 12.598 | 1.00 | 35.59 |
| ATOM | 2006 | C | LEU | 265 | 16.054 | 62.613 | 12.521 | 1.00 | 38.22 |
| ATOM | 2007 | O | LEU | 265 | 17.239 | 62.285 | 12.486 | 1.00 | 38.34 |
| ATOM | 2008 | N | GLU | 266 | 15.653 | 63.844 | 12.832 | 1.00 | 39.22 |
| ATOM | 2009 | CA | GLU | 266 | 16.599 | 64.922 | 13.137 | 1.00 | 40.56 |
| ATOM | 2010 | CB | GLU | 266 | 15.874 | 66.101 | 13.813 | 1.00 | 41.82 |
| ATOM | 2011 | CG | GLU | 266 | 15.277 | 65.777 | 15.196 | 1.00 | 44.28 |
| ATOM | 2012 | CD | GLU | 266 | 14.612 | 66.974 | 15.886 | 1.00 | 44.95 |
| ATOM | 2013 | OE1 | GLU | 266 | 13.543 | 67.432 | 15.410 | 1.00 | 45.08 |
| ATOM | 2014 | OE2 | GLU | 266 | 15.163 | 67.452 | 16.910 | 1.00 | 45.53 |
| ATOM | 2015 | C | GLU | 266 | 17.733 | 64.435 | 14.036 | 1.00 | 40.54 |
| ATOM | 2016 | O | GLU | 266 | 18.910 | 64.657 | 13.750 | 1.00 | 40.69 |
| ATOM | 2017 | N | TYR | 267 | 17.366 | 63.760 | 15.121 | 1.00 | 40.61 |
| ATOM | 2018 | CA | TYR | 267 | 18.342 | 63.234 | 16.062 | 1.00 | 40.30 |
| ATOM | 2019 | CB | TYR | 267 | 17.639 | 62.364 | 17.110 | 1.00 | 39.44 |
| ATOM | 2020 | CG | TYR | 267 | 16.216 | 62.784 | 17.423 | 1.00 | 38.98 |
| ATOM | 2021 | CD1 | TYR | 267 | 15.134 | 61.967 | 17.066 | 1.00 | 38.66 |
| ATOM | 2022 | CE1 | TYR | 267 | 13.813 | 62.342 | 17.349 | 1.00 | 38.28 |
| ATOM | 2023 | CD2 | TYR | 267 | 15.943 | 63.995 | 18.075 | 1.00 | 38.72 |
| ATOM | 2024 | CE2 | TYR | 267 | 14.619 | 64.381 | 18.364 | 1.00 | 38.45 |
| ATOM | 2025 | CZ | TYR | 267 | 13.564 | 63.548 | 17.996 | 1.00 | 38.30 |
| ATOM | 2026 | OH | TYR | 267 | 12.267 | 63.923 | 18.251 | 1.00 | 37.22 |
| ATOM | 2027 | C | TYR | 267 | 19.381 | 62.403 | 15.296 | 1.00 | 40.27 |
| ATOM | 2028 | O | TYR | 267 | 20.580 | 62.469 | 15.579 | 1.00 | 40.14 |
| ATOM | 2029 | N | ASP | 268 | 18.909 | 61.626 | 14.324 | 1.00 | 40.61 |
| ATOM | 2030 | CA | ASP | 268 | 19.781 | 60.790 | 13.511 | 1.00 | 40.87 |
| ATOM | 2031 | CB | ASP | 268 | 18.946 | 59.920 | 12.566 | 1.00 | 39.36 |
| ATOM | 2032 | CG | ASP | 268 | 18.183 | 58.843 | 13.301 | 1.00 | 38.52 |
| ATOM | 2033 | OD1 | ASP | 268 | 18.819 | 58.118 | 14.082 | 1.00 | 39.79 |
| ATOM | 2034 | OD2 | ASP | 268 | 16.961 | 58.711 | 13.110 | 1.00 | 36.13 |
| ATOM | 2035 | C | ASP | 268 | 20.764 | 61.643 | 12.712 | 1.00 | 41.97 |
| ATOM | 2036 | O | ASP | 268 | 21.956 | 61.339 | 12.667 | 1.00 | 42.91 |
| ATOM | 2037 | N | ARG | 269 | 20.266 | 62.710 | 12.090 | 1.00 | 42.73 |
| ATOM | 2038 | CA | ARG | 269 | 21.113 | 63.606 | 11.310 | 1.00 | 43.23 |
| ATOM | 2039 | CB | ARG | 269 | 20.302 | 64.793 | 10.786 | 1.00 | 45.34 |
| ATOM | 2040 | CG | ARG | 269 | 18.923 | 64.464 | 10.223 | 1.00 | 47.46 |
| ATOM | 2041 | CD | ARG | 269 | 19.000 | 63.819 | 8.864 | 1.00 | 49.22 |
| ATOM | 2042 | NE | ARG | 269 | 17.667 | 63.552 | 8.337 | 1.00 | 52.67 |
| ATOM | 2043 | CZ | ARG | 269 | 17.426 | 62.969 | 7.165 | 1.00 | 54.63 |
| ATOM | 2044 | NH1 | ARG | 269 | 18.436 | 62.591 | 6.386 | 1.00 | 55.41 |
| ATOM | 2045 | NH2 | ARG | 269 | 16.173 | 62.747 | 6.775 | 1.00 | 55.38 |
| ATOM | 2046 | C | ARG | 269 | 22.204 | 64.150 | 12.231 | 1.00 | 42.99 |
| ATOM | 2047 | O | ARG | 269 | 23.400 | 63.999 | 11.977 | 1.00 | 43.63 |
| ATOM | 2048 | N | LEU | 270 | 21.777 | 64.796 | 13.305 | 1.00 | 41.99 |

*FIG. 4JJ*

| | | | | | | | |
|---|---|---|---|---|---|---|---|
| ATOM | 2049 | CA | LEU | 270 | 22.702 | 65.372 | 14.261 | 1.00 | 41.33 |
| ATOM | 2050 | CB | LEU | 270 | 21.924 | 65.812 | 15.502 | 1.00 | 41.15 |
| ATOM | 2051 | CG | LEU | 270 | 21.004 | 67.002 | 15.217 | 1.00 | 40.34 |
| ATOM | 2052 | CD1 | LEU | 270 | 19.964 | 67.182 | 16.307 | 1.00 | 39.94 |
| ATOM | 2053 | CD2 | LEU | 270 | 21.879 | 68.237 | 15.084 | 1.00 | 40.26 |
| ATOM | 2054 | C | LEU | 270 | 23.828 | 64.406 | 14.635 | 1.00 | 41.26 |
| ATOM | 2055 | O | LEU | 270 | 25.009 | 64.762 | 14.553 | 1.00 | 41.76 |
| ATOM | 2056 | N | VAL | 271 | 23.462 | 63.188 | 15.030 | 1.00 | 40.24 |
| ATOM | 2057 | CA | VAL | 271 | 24.443 | 62.177 | 15.415 | 1.00 | 40.08 |
| ATOM | 2058 | CB | VAL | 271 | 23.776 | 60.838 | 15.730 | 1.00 | 40.42 |
| ATOM | 2059 | CG1 | VAL | 271 | 24.846 | 59.800 | 16.050 | 1.00 | 39.86 |
| ATOM | 2060 | CG2 | VAL | 271 | 22.796 | 61.000 | 16.891 | 1.00 | 40.86 |
| ATOM | 2061 | C | VAL | 271 | 25.477 | 61.903 | 14.329 | 1.00 | 40.51 |
| ATOM | 2062 | O | VAL | 271 | 26.676 | 61.832 | 14.595 | 1.00 | 40.15 |
| ATOM | 2063 | N | ASP | 272 | 24.998 | 61.730 | 13.103 | 1.00 | 40.78 |
| ATOM | 2064 | CA | ASP | 272 | 25.866 | 61.447 | 11.977 | 1.00 | 40.36 |
| ATOM | 2065 | CB | ASP | 272 | 25.038 | 61.344 | 10.695 | 1.00 | 39.16 |
| ATOM | 2066 | CG | ASP | 272 | 25.792 | 60.670 | 9.553 | 1.00 | 38.09 |
| ATOM | 2067 | OD1 | ASP | 272 | 26.821 | 60.000 | 9.807 | 1.00 | 36.54 |
| ATOM | 2068 | OD2 | ASP | 272 | 25.335 | 60.798 | 8.394 | 1.00 | 37.12 |
| ATOM | 2069 | C | ASP | 272 | 26.901 | 62.544 | 11.849 | 1.00 | 40.88 |
| ATOM | 2070 | O | ASP | 272 | 28.099 | 62.297 | 11.953 | 1.00 | 40.75 |
| ATOM | 2071 | N | GLU | 273 | 26.429 | 63.763 | 11.638 | 1.00 | 41.96 |
| ATOM | 2072 | CA | GLU | 273 | 27.321 | 64.896 | 11.477 | 1.00 | 43.14 |
| ATOM | 2073 | CB | GLU | 273 | 26.501 | 66.170 | 11.470 | 1.00 | 44.13 |
| ATOM | 2074 | CG | GLU | 273 | 25.576 | 66.214 | 10.272 | 1.00 | 46.73 |
| ATOM | 2075 | CD | GLU | 273 | 24.629 | 67.388 | 10.308 | 1.00 | 48.40 |
| ATOM | 2076 | OE1 | GLU | 273 | 25.047 | 68.455 | 10.828 | 1.00 | 49.15 |
| ATOM | 2077 | OE2 | GLU | 273 | 23.482 | 67.241 | 9.811 | 1.00 | 48.64 |
| ATOM | 2078 | C | GLU | 273 | 28.428 | 64.968 | 12.517 | 1.00 | 43.48 |
| ATOM | 2079 | O | GLU | 273 | 29.575 | 65.279 | 12.187 | 1.00 | 43.59 |
| ATOM | 2080 | N | SER | 274 | 28.095 | 64.666 | 13.767 | 1.00 | 44.05 |
| ATOM | 2081 | CA | SER | 274 | 29.089 | 64.702 | 14.837 | 1.00 | 44.54 |
| ATOM | 2082 | CB | SER | 274 | 28.421 | 64.568 | 16.205 | 1.00 | 45.39 |
| ATOM | 2083 | OG | SER | 274 | 27.496 | 65.611 | 16.424 | 1.00 | 48.14 |
| ATOM | 2084 | C | SER | 274 | 30.106 | 63.582 | 14.694 | 1.00 | 44.23 |
| ATOM | 2085 | O | SER | 274 | 31.292 | 63.783 | 14.931 | 1.00 | 44.76 |
| ATOM | 2086 | N | SER | 275 | 29.632 | 62.400 | 14.318 | 1.00 | 43.84 |
| ATOM | 2087 | CA | SER | 275 | 30.489 | 61.227 | 14.162 | 1.00 | 43.42 |
| ATOM | 2088 | CB | SER | 275 | 29.754 | 60.139 | 13.392 | 1.00 | 43.28 |
| ATOM | 2089 | OG | SER | 275 | 29.758 | 60.444 | 12.010 | 1.00 | 42.94 |
| ATOM | 2090 | C | SER | 275 | 31.789 | 61.535 | 13.426 | 1.00 | 43.34 |
| ATOM | 2091 | O | SER | 275 | 31.914 | 62.552 | 12.738 | 1.00 | 43.76 |
| ATOM | 2092 | N | ALA | 276 | 32.756 | 60.639 | 13.570 | 1.00 | 42.68 |
| ATOM | 2093 | CA | ALA | 276 | 34.034 | 60.805 | 12.906 | 1.00 | 42.98 |
| ATOM | 2094 | CB | ALA | 276 | 35.108 | 60.015 | 13.639 | 1.00 | 42.92 |
| ATOM | 2095 | C | ALA | 276 | 33.930 | 60.319 | 11.465 | 1.00 | 43.23 |
| ATOM | 2096 | O | ALA | 276 | 34.936 | 60.277 | 10.751 | 1.00 | 44.60 |
| ATOM | 2097 | N | ASN | 277 | 32.722 | 59.949 | 11.039 | 1.00 | 42.10 |
| ATOM | 2098 | CA | ASN | 277 | 32.517 | 59.447 | 9.691 | 1.00 | 40.87 |
| ATOM | 2099 | CB | ASN | 277 | 32.615 | 57.927 | 9.685 | 1.00 | 41.63 |
| ATOM | 2100 | CG | ASN | 277 | 31.654 | 57.283 | 10.659 | 1.00 | 42.64 |
| ATOM | 2101 | OD1 | ASN | 277 | 30.670 | 57.898 | 11.067 | 1.00 | 43.50 |
| ATOM | 2102 | ND2 | ASN | 277 | 31.925 | 56.033 | 11.029 | 1.00 | 42.98 |
| ATOM | 2103 | C | ASN | 277 | 31.178 | 59.865 | 9.104 | 1.00 | 40.57 |
| ATOM | 2104 | O | ASN | 277 | 30.430 | 59.039 | 8.579 | 1.00 | 39.89 |
| ATOM | 2105 | N | PRO | 278 | 30.868 | 61.163 | 9.163 | 1.00 | 40.83 |

*FIG. 4KK*

| | | | | | | | | |
|---|---|---|---|---|---|---|---|---|
| ATOM | 2106 | CD | PRO | 278 | 31.783 | 62.282 | 9.451 | 1.00 40.90 |
| ATOM | 2107 | CA | PRO | 278 | 29.600 | 61.657 | 8.623 | 1.00 40.71 |
| ATOM | 2108 | CB | PRO | 278 | 29.807 | 63.175 | 8.579 | 1.00 40.88 |
| ATOM | 2109 | CG | PRO | 278 | 31.303 | 63.326 | 8.474 | 1.00 41.27 |
| ATOM | 2110 | C | PRO | 278 | 29.239 | 61.074 | 7.258 | 1.00 40.60 |
| ATOM | 2111 | O | PRO | 278 | 29.949 | 61.284 | 6.270 | 1.00 40.71 |
| ATOM | 2112 | N | GLY | 279 | 28.131 | 60.338 | 7.216 | 1.00 40.34 |
| ATOM | 2113 | CA | GLY | 279 | 27.676 | 59.747 | 5.971 | 1.00 39.10 |
| ATOM | 2114 | C | GLY | 279 | 27.904 | 58.252 | 5.828 | 1.00 38.94 |
| ATOM | 2115 | O | GLY | 279 | 27.315 | 57.635 | 4.952 | 1.00 39.74 |
| ATOM | 2116 | N | GLN | 280 | 28.735 | 57.660 | 6.683 | 1.00 38.66 |
| ATOM | 2117 | CA | GLN | 280 | 29.049 | 56.230 | 6.605 | 1.00 37.75 |
| ATOM | 2118 | CB | GLN | 280 | 30.563 | 56.043 | 6.513 | 1.00 37.97 |
| ATOM | 2119 | CG | GLN | 280 | 31.243 | 56.954 | 5.509 | 1.00 39.85 |
| ATOM | 2120 | CD | GLN | 280 | 32.743 | 57.046 | 5.730 | 1.00 40.76 |
| ATOM | 2121 | OE1 | GLN | 280 | 33.465 | 56.058 | 5.587 | 1.00 41.39 |
| ATOM | 2122 | NE2 | GLN | 280 | 33.220 | 58.240 | 6.083 | 1.00 41.57 |
| ATOM | 2123 | C | GLN | 280 | 28.553 | 55.455 | 7.817 | 1.00 36.99 |
| ATOM | 2124 | O | GLN | 280 | 28.645 | 55.939 | 8.941 | 1.00 37.89 |
| ATOM | 2125 | N | GLN | 281 | 28.054 | 54.242 | 7.592 | 1.00 35.75 |
| ATOM | 2126 | CA | GLN | 281 | 27.572 | 53.401 | 8.681 | 1.00 34.04 |
| ATOM | 2127 | CB | GLN | 281 | 28.590 | 53.404 | 9.829 | 1.00 33.35 |
| ATOM | 2128 | CG | GLN | 281 | 29.971 | 52.951 | 9.447 | 1.00 33.09 |
| ATOM | 2129 | CD | GLN | 281 | 29.967 | 51.576 | 8.800 | 1.00 34.44 |
| ATOM | 2130 | OE1 | GLN | 281 | 29.917 | 51.451 | 7.572 | 1.00 33.95 |
| ATOM | 2131 | NE2 | GLN | 281 | 30.000 | 50.529 | 9.630 | 1.00 34.63 |
| ATOM | 2132 | C | GLN | 281 | 26.210 | 53.831 | 9.237 | 1.00 33.42 |
| ATOM | 2133 | O | GLN | 281 | 25.895 | 53.530 | 10.390 | 1.00 34.87 |
| ATOM | 2134 | N | LEU | 282 | 25.395 | 54.511 | 8.436 | 1.00 31.53 |
| ATOM | 2135 | CA | LEU | 282 | 24.098 | 54.992 | 8.913 | 1.00 29.87 |
| ATOM | 2136 | CB | LEU | 282 | 23.345 | 55.685 | 7.777 | 1.00 30.15 |
| ATOM | 2137 | CG | LEU | 282 | 24.030 | 56.871 | 7.085 | 1.00 30.41 |
| ATOM | 2138 | CD1 | LEU | 282 | 22.963 | 57.741 | 6.435 | 1.00 29.82 |
| ATOM | 2139 | CD2 | LEU | 282 | 24.815 | 57.699 | 8.097 | 1.00 30.66 |
| ATOM | 2140 | C | LEU | 282 | 23.191 | 53.949 | 9.578 | 1.00 28.70 |
| ATOM | 2141 | O | LEU | 282 | 22.716 | 54.153 | 10.698 | 1.00 28.78 |
| ATOM | 2142 | N | TYR | 283 | 22.935 | 52.841 | 8.894 | 1.00 27.35 |
| ATOM | 2143 | CA | TYR | 283 | 22.095 | 51.793 | 9.461 | 1.00 26.53 |
| ATOM | 2144 | CB | TYR | 283 | 22.233 | 50.511 | 8.633 | 1.00 24.41 |
| ATOM | 2145 | CG | TYR | 283 | 21.420 | 49.338 | 9.143 | 1.00 22.90 |
| ATOM | 2146 | CD1 | TYR | 283 | 20.021 | 49.413 | 9.210 | 1.00 21.94 |
| ATOM | 2147 | CE1 | TYR | 283 | 19.257 | 48.318 | 9.609 | 1.00 20.96 |
| ATOM | 2148 | CD2 | TYR | 283 | 22.038 | 48.129 | 9.503 | 1.00 21.53 |
| ATOM | 2149 | CE2 | TYR | 283 | 21.279 | 47.030 | 9.907 | 1.00 20.87 |
| ATOM | 2150 | CZ | TYR | 283 | 19.886 | 47.140 | 9.950 | 1.00 21.33 |
| ATOM | 2151 | OH | TYR | 283 | 19.105 | 46.068 | 10.310 | 1.00 23.85 |
| ATOM | 2152 | C | TYR | 283 | 22.567 | 51.532 | 10.891 | 1.00 27.12 |
| ATOM | 2153 | O | TYR | 283 | 21.783 | 51.521 | 11.841 | 1.00 28.95 |
| ATOM | 2154 | N | GLU | 284 | 23.869 | 51.352 | 11.035 | 1.00 26.60 |
| ATOM | 2155 | CA | GLU | 284 | 24.486 | 51.072 | 12.317 | 1.00 26.43 |
| ATOM | 2156 | CB | GLU | 284 | 25.982 | 50.905 | 12.108 | 1.00 27.03 |
| ATOM | 2157 | CG | GLU | 284 | 26.763 | 50.680 | 13.375 | 1.00 27.21 |
| ATOM | 2158 | CD | GLU | 284 | 28.224 | 50.492 | 13.082 | 1.00 27.57 |
| ATOM | 2159 | OE1 | GLU | 284 | 28.897 | 51.506 | 12.734 | 1.00 27.02 |
| ATOM | 2160 | OE2 | GLU | 284 | 28.670 | 49.319 | 13.185 | 1.00 26.30 |
| ATOM | 2161 | C | GLU | 284 | 24.249 | 52.133 | 13.381 | 1.00 26.81 |
| ATOM | 2162 | O | GLU | 284 | 24.197 | 51.826 | 14.582 | 1.00 26.06 |

*FIG. 4LL*

| | | | | | | | | |
|---|---|---|---|---|---|---|---|---|
| ATOM | 2163 | N | LYS | 285 | 24.134 | 53.384 | 12.940 | 1.00 27.07 |
| ATOM | 2164 | CA | LYS | 285 | 23.926 | 54.502 | 13.860 | 1.00 27.39 |
| ATOM | 2165 | CB | LYS | 285 | 24.339 | 55.825 | 13.186 | 1.00 25.99 |
| ATOM | 2166 | CG | LYS | 285 | 25.840 | 56.012 | 13.132 | 1.00 24.13 |
| ATOM | 2167 | CD | LYS | 285 | 26.235 | 57.110 | 12.179 | 1.00 23.29 |
| ATOM | 2168 | CE | LYS | 285 | 27.755 | 57.193 | 12.052 | 1.00 22.03 |
| ATOM | 2169 | NZ | LYS | 285 | 28.142 | 58.198 | 11.027 | 1.00 21.72 |
| ATOM | 2170 | C | LYS | 285 | 22.488 | 54.595 | 14.368 | 1.00 28.05 |
| ATOM | 2171 | O | LYS | 285 | 22.086 | 55.615 | 14.941 | 1.00 28.61 |
| ATOM | 2172 | N | LEU | 286 | 21.717 | 53.535 | 14.144 | 1.00 27.60 |
| ATOM | 2173 | CA | LEU | 286 | 20.335 | 53.488 | 14.599 | 1.00 27.30 |
| ATOM | 2174 | CB | LEU | 286 | 19.399 | 53.157 | 13.435 | 1.00 28.57 |
| ATOM | 2175 | CG | LEU | 286 | 19.375 | 54.167 | 12.279 | 1.00 30.25 |
| ATOM | 2176 | CD1 | LEU | 286 | 18.480 | 53.647 | 11.139 | 1.00 29.98 |
| ATOM | 2177 | CD2 | LEU | 286 | 18.863 | 55.507 | 12.780 | 1.00 29.35 |
| ATOM | 2178 | C | LEU | 286 | 20.260 | 52.381 | 15.632 | 1.00 27.01 |
| ATOM | 2179 | O | LEU | 286 | 19.296 | 52.294 | 16.399 | 1.00 27.55 |
| ATOM | 2180 | N | ILE | 287 | 21.306 | 51.554 | 15.645 | 1.00 26.00 |
| ATOM | 2181 | CA | ILE | 287 | 21.415 | 50.399 | 16.532 | 1.00 24.38 |
| ATOM | 2182 | CB | ILE | 287 | 21.551 | 49.141 | 15.715 | 1.00 23.92 |
| ATOM | 2183 | CG2 | ILE | 287 | 21.470 | 47.919 | 16.628 | 1.00 22.70 |
| ATOM | 2184 | CG1 | ILE | 287 | 20.510 | 49.158 | 14.597 | 1.00 22.87 |
| ATOM | 2185 | CD1 | ILE | 287 | 20.676 | 48.042 | 13.607 | 1.00 22.79 |
| ATOM | 2186 | C | ILE | 287 | 22.639 | 50.444 | 17.433 | 1.00 24.65 |
| ATOM | 2187 | O | ILE | 287 | 22.550 | 50.255 | 18.644 | 1.00 23.54 |
| ATOM | 2188 | N | GLY | 288 | 23.791 | 50.668 | 16.810 | 1.00 25.94 |
| ATOM | 2189 | CA | GLY | 288 | 25.060 | 50.714 | 17.519 | 1.00 26.86 |
| ATOM | 2190 | C | GLY | 288 | 25.081 | 51.266 | 18.927 | 1.00 27.76 |
| ATOM | 2191 | O | GLY | 288 | 24.697 | 52.412 | 19.164 | 1.00 28.19 |
| ATOM | 2192 | N | GLY | 289 | 25.554 | 50.445 | 19.860 | 1.00 28.95 |
| ATOM | 2193 | CA | GLY | 289 | 25.656 | 50.856 | 21.249 | 1.00 30.64 |
| ATOM | 2194 | C | GLY | 289 | 26.632 | 52.007 | 21.407 | 1.00 31.92 |
| ATOM | 2195 | O | GLY | 289 | 26.930 | 52.442 | 22.509 | 1.00 32.56 |
| ATOM | 2196 | N | LYS | 290 | 27.133 | 52.504 | 20.291 | 1.00 32.83 |
| ATOM | 2197 | CA | LYS | 290 | 28.067 | 53.607 | 20.296 | 1.00 33.99 |
| ATOM | 2198 | CB | LYS | 290 | 29.104 | 53.373 | 19.191 | 1.00 35.04 |
| ATOM | 2199 | CG | LYS | 290 | 29.858 | 54.598 | 18.665 | 1.00 36.71 |
| ATOM | 2200 | CD | LYS | 290 | 31.032 | 54.996 | 19.551 | 1.00 38.80 |
| ATOM | 2201 | CE | LYS | 290 | 31.936 | 56.011 | 18.839 | 1.00 39.77 |
| ATOM | 2202 | NZ | LYS | 290 | 32.864 | 56.707 | 19.787 | 1.00 41.04 |
| ATOM | 2203 | C | LYS | 290 | 27.278 | 54.880 | 20.035 | 1.00 34.58 |
| ATOM | 2204 | O | LYS | 290 | 27.810 | 55.984 | 20.138 | 1.00 35.79 |
| ATOM | 2205 | N | TYR | 291 | 26.001 | 54.734 | 19.708 | 1.00 33.80 |
| ATOM | 2206 | CA | TYR | 291 | 25.196 | 55.907 | 19.406 | 1.00 33.61 |
| ATOM | 2207 | CB | TYR | 291 | 25.010 | 56.046 | 17.892 | 1.00 33.22 |
| ATOM | 2208 | CG | TYR | 291 | 26.256 | 55.752 | 17.084 | 1.00 33.77 |
| ATOM | 2209 | CD1 | TYR | 291 | 26.659 | 54.435 | 16.838 | 1.00 34.23 |
| ATOM | 2210 | CE1 | TYR | 291 | 27.789 | 54.155 | 16.065 | 1.00 34.17 |
| ATOM | 2211 | CD2 | TYR | 291 | 27.021 | 56.783 | 16.542 | 1.00 33.61 |
| ATOM | 2212 | CE2 | TYR | 291 | 28.150 | 56.515 | 15.773 | 1.00 33.54 |
| ATOM | 2213 | CZ | TYR | 291 | 28.528 | 55.200 | 15.532 | 1.00 33.76 |
| ATOM | 2214 | OH | TYR | 291 | 29.620 | 54.928 | 14.729 | 1.00 34.36 |
| ATOM | 2215 | C | TYR | 291 | 23.836 | 55.874 | 20.070 | 1.00 33.11 |
| ATOM | 2216 | O | TYR | 291 | 23.069 | 56.828 | 19.975 | 1.00 32.86 |
| ATOM | 2217 | N | MSE | 292 | 23.521 | 54.778 | 20.737 | 1.00 33.27 |
| ATOM | 2218 | CA | MSE | 292 | 22.230 | 54.699 | 21.389 | 1.00 33.18 |
| ATOM | 2219 | CB | MSE | 292 | 22.066 | 53.349 | 22.062 | 1.00 33.77 |

*FIG. 4MM*

```
ATOM   2220  CG  MSE  292      20.639  52.975  22.314  1.00  35.15
ATOM   2221  SE  MSE  292      20.564  51.230  22.803  1.00  41.54
ATOM   2222  CE  MSE  292      20.269  50.385  21.171  1.00  35.91
ATOM   2223  C   MSE  292      22.148  55.818  22.423  1.00  32.97
ATOM   2224  O   MSE  292      21.227  56.637  22.400  1.00  33.49
ATOM   2225  N   GLY  293      23.131  55.861  23.315  1.00  32.96
ATOM   2226  CA  GLY  293      23.151  56.892  24.334  1.00  32.25
ATOM   2227  C   GLY  293      23.067  58.290  23.750  1.00  32.18
ATOM   2228  O   GLY  293      22.307  59.126  24.241  1.00  33.24
ATOM   2229  N   GLU  294      23.835  58.560  22.702  1.00  31.47
ATOM   2230  CA  GLU  294      23.809  59.883  22.096  1.00  31.38
ATOM   2231  CB  GLU  294      24.875  59.971  21.008  1.00  33.29
ATOM   2232  CG  GLU  294      24.986  61.321  20.304  1.00  34.67
ATOM   2233  CD  GLU  294      25.227  62.474  21.257  1.00  35.80
ATOM   2234  OE1 GLU  294      25.708  62.244  22.389  1.00  36.49
ATOM   2235  OE2 GLU  294      24.946  63.623  20.858  1.00  37.16
ATOM   2236  C   GLU  294      22.428  60.192  21.521  1.00  30.62
ATOM   2237  O   GLU  294      21.919  61.305  21.664  1.00  30.94
ATOM   2238  N   LEU  295      21.818  59.204  20.878  1.00  29.56
ATOM   2239  CA  LEU  295      20.495  59.392  20.303  1.00  29.24
ATOM   2240  CB  LEU  295      20.030  58.112  19.589  1.00  27.27
ATOM   2241  CG  LEU  295      20.389  58.007  18.099  1.00  25.46
ATOM   2242  CD1 LEU  295      19.979  56.668  17.522  1.00  21.87
ATOM   2243  CD2 LEU  295      19.677  59.136  17.352  1.00  25.71
ATOM   2244  C   LEU  295      19.497  59.787  21.388  1.00  29.98
ATOM   2245  O   LEU  295      18.587  60.573  21.156  1.00  30.19
ATOM   2246  N   VAL  296      19.665  59.250  22.585  1.00  31.23
ATOM   2247  CA  VAL  296      18.745  59.590  23.657  1.00  32.87
ATOM   2248  CB  VAL  296      18.890  58.623  24.831  1.00  32.48
ATOM   2249  CG1 VAL  296      17.827  58.899  25.868  1.00  32.99
ATOM   2250  CG2 VAL  296      18.762  57.198  24.323  1.00  33.56
ATOM   2251  C   VAL  296      19.020  61.025  24.122  1.00  33.74
ATOM   2252  O   VAL  296      18.086  61.778  24.431  1.00  33.68
ATOM   2253  N   ARG  297      20.296  61.409  24.145  1.00  34.02
ATOM   2254  CA  ARG  297      20.659  62.757  24.563  1.00  35.34
ATOM   2255  CB  ARG  297      22.147  63.008  24.342  1.00  34.89
ATOM   2256  CG  ARG  297      22.940  63.279  25.609  1.00  35.27
ATOM   2257  CD  ARG  297      23.791  64.525  25.454  1.00  35.98
ATOM   2258  NE  ARG  297      24.226  64.700  24.074  1.00  37.11
ATOM   2259  CZ  ARG  297      24.476  65.878  23.513  1.00  37.43
ATOM   2260  NH1 ARG  297      24.348  66.994  24.226  1.00  38.45
ATOM   2261  NH2 ARG  297      24.809  65.944  22.229  1.00  36.61
ATOM   2262  C   ARG  297      19.870  63.766  23.747  1.00  36.07
ATOM   2263  O   ARG  297      19.103  64.574  24.285  1.00  36.76
ATOM   2264  N   LEU  298      20.063  63.699  22.437  1.00  36.93
ATOM   2265  CA  LEU  298      19.407  64.596  21.500  1.00  37.55
ATOM   2266  CB  LEU  298      19.768  64.178  20.077  1.00  37.28
ATOM   2267  CG  LEU  298      21.272  64.065  19.816  1.00  36.13
ATOM   2268  CD1 LEU  298      21.478  63.784  18.341  1.00  36.85
ATOM   2269  CD2 LEU  298      21.991  65.356  20.218  1.00  35.02
ATOM   2270  C   LEU  298      17.892  64.633  21.670  1.00  38.53
ATOM   2271  O   LEU  298      17.276  65.708  21.618  1.00  38.44
ATOM   2272  N   VAL  299      17.289  63.462  21.866  1.00  39.23
ATOM   2273  CA  VAL  299      15.839  63.389  22.054  1.00  40.08
ATOM   2274  CB  VAL  299      15.349  61.932  22.110  1.00  39.44
ATOM   2275  CG1 VAL  299      13.844  61.892  22.385  1.00  37.91
ATOM   2276  CG2 VAL  299      15.676  61.240  20.802  1.00  38.72
```

*FIG. 4NN*

| ATOM | 2277 | C   | VAL | 299 | 15.435 | 64.087 | 23.350 | 1.00 | 40.94 |
|------|------|-----|-----|-----|--------|--------|--------|------|-------|
| ATOM | 2278 | O   | VAL | 299 | 14.321 | 64.612 | 23.461 | 1.00 | 41.66 |
| ATOM | 2279 | N   | LEU | 300 | 16.337 | 64.091 | 24.328 | 1.00 | 41.41 |
| ATOM | 2280 | CA  | LEU | 300 | 16.043 | 64.737 | 25.600 | 1.00 | 42.31 |
| ATOM | 2281 | CB  | LEU | 300 | 16.973 | 64.224 | 26.713 | 1.00 | 41.48 |
| ATOM | 2282 | CG  | LEU | 300 | 16.943 | 62.766 | 27.206 | 1.00 | 40.38 |
| ATOM | 2283 | CD1 | LEU | 300 | 17.677 | 62.711 | 28.545 | 1.00 | 40.14 |
| ATOM | 2284 | CD2 | LEU | 300 | 15.517 | 62.251 | 27.380 | 1.00 | 38.74 |
| ATOM | 2285 | C   | LEU | 300 | 16.204 | 66.251 | 25.444 | 1.00 | 43.44 |
| ATOM | 2286 | O   | LEU | 300 | 15.304 | 67.020 | 25.806 | 1.00 | 43.84 |
| ATOM | 2287 | N   | LEU | 301 | 17.346 | 66.675 | 24.898 | 1.00 | 43.90 |
| ATOM | 2288 | CA  | LEU | 301 | 17.603 | 68.100 | 24.707 | 1.00 | 43.85 |
| ATOM | 2289 | CB  | LEU | 301 | 18.895 | 68.335 | 23.919 | 1.00 | 43.20 |
| ATOM | 2290 | CG  | LEU | 301 | 20.211 | 67.969 | 24.613 | 1.00 | 43.48 |
| ATOM | 2291 | CD1 | LEU | 301 | 21.385 | 68.372 | 23.730 | 1.00 | 43.37 |
| ATOM | 2292 | CD2 | LEU | 301 | 20.307 | 68.675 | 25.955 | 1.00 | 43.71 |
| ATOM | 2293 | C   | LEU | 301 | 16.444 | 68.738 | 23.969 | 1.00 | 44.11 |
| ATOM | 2294 | O   | LEU | 301 | 16.068 | 69.875 | 24.254 | 1.00 | 44.38 |
| ATOM | 2295 | N   | ARG | 302 | 15.863 | 68.007 | 23.025 | 1.00 | 44.45 |
| ATOM | 2296 | CA  | ARG | 302 | 14.753 | 68.571 | 22.280 | 1.00 | 45.04 |
| ATOM | 2297 | CB  | ARG | 302 | 14.296 | 67.660 | 21.148 | 1.00 | 45.49 |
| ATOM | 2298 | CG  | ARG | 302 | 13.082 | 68.256 | 20.468 | 1.00 | 45.91 |
| ATOM | 2299 | CD  | ARG | 302 | 12.391 | 67.327 | 19.514 | 1.00 | 46.45 |
| ATOM | 2300 | NE  | ARG | 302 | 11.194 | 67.985 | 19.007 | 1.00 | 47.37 |
| ATOM | 2301 | CZ  | ARG | 302 | 10.423 | 67.503 | 18.043 | 1.00 | 48.12 |
| ATOM | 2302 | NH1 | ARG | 302 | 10.719 | 66.344 | 17.466 | 1.00 | 48.80 |
| ATOM | 2303 | NH2 | ARG | 302 | 9.357  | 68.190 | 17.657 | 1.00 | 47.77 |
| ATOM | 2304 | C   | ARG | 302 | 13.577 | 68.807 | 23.196 | 1.00 | 45.13 |
| ATOM | 2305 | O   | ARG | 302 | 12.982 | 69.885 | 23.198 | 1.00 | 45.57 |
| ATOM | 2306 | N   | LEU | 303 | 13.228 | 67.787 | 23.966 | 1.00 | 45.14 |
| ATOM | 2307 | CA  | LEU | 303 | 12.113 | 67.918 | 24.883 | 1.00 | 45.18 |
| ATOM | 2308 | CB  | LEU | 303 | 11.952 | 66.624 | 25.695 | 1.00 | 44.02 |
| ATOM | 2309 | CG  | LEU | 303 | 11.495 | 65.427 | 24.846 | 1.00 | 42.43 |
| ATOM | 2310 | CD1 | LEU | 303 | 11.365 | 64.162 | 25.690 | 1.00 | 41.06 |
| ATOM | 2311 | CD2 | LEU | 303 | 10.154 | 65.784 | 24.207 | 1.00 | 41.96 |
| ATOM | 2312 | C   | LEU | 303 | 12.359 | 69.133 | 25.783 | 1.00 | 45.83 |
| ATOM | 2313 | O   | LEU | 303 | 11.444 | 69.919 | 26.044 | 1.00 | 45.85 |
| ATOM | 2314 | N   | VAL | 304 | 13.599 | 69.302 | 26.232 | 1.00 | 46.44 |
| ATOM | 2315 | CA  | VAL | 304 | 13.943 | 70.440 | 27.085 | 1.00 | 47.76 |
| ATOM | 2316 | CB  | VAL | 304 | 15.443 | 70.426 | 27.496 | 1.00 | 47.79 |
| ATOM | 2317 | CG1 | VAL | 304 | 15.866 | 71.815 | 27.996 | 1.00 | 46.89 |
| ATOM | 2318 | CG2 | VAL | 304 | 15.678 | 69.386 | 28.581 | 1.00 | 47.81 |
| ATOM | 2319 | C   | VAL | 304 | 13.666 | 71.764 | 26.371 | 1.00 | 48.44 |
| ATOM | 2320 | O   | VAL | 304 | 12.899 | 72.596 | 26.861 | 1.00 | 48.95 |
| ATOM | 2321 | N   | ASP | 305 | 14.297 | 71.946 | 25.212 | 1.00 | 48.52 |
| ATOM | 2322 | CA  | ASP | 305 | 14.143 | 73.165 | 24.432 | 1.00 | 48.31 |
| ATOM | 2323 | CB  | ASP | 305 | 14.968 | 73.067 | 23.143 | 1.00 | 49.45 |
| ATOM | 2324 | CG  | ASP | 305 | 16.441 | 72.715 | 23.412 | 1.00 | 51.00 |
| ATOM | 2325 | OD1 | ASP | 305 | 17.056 | 73.323 | 24.317 | 1.00 | 50.99 |
| ATOM | 2326 | OD2 | ASP | 305 | 16.994 | 71.834 | 22.715 | 1.00 | 51.84 |
| ATOM | 2327 | C   | ASP | 305 | 12.677 | 73.460 | 24.122 | 1.00 | 47.77 |
| ATOM | 2328 | O   | ASP | 305 | 12.341 | 74.541 | 23.641 | 1.00 | 48.22 |
| ATOM | 2329 | N   | GLU | 306 | 11.799 | 72.505 | 24.407 | 1.00 | 46.84 |
| ATOM | 2330 | CA  | GLU | 306 | 10.378 | 72.713 | 24.176 | 1.00 | 46.34 |
| ATOM | 2331 | CB  | GLU | 306 | 9.831  | 71.683 | 23.184 | 1.00 | 46.20 |
| ATOM | 2332 | CG  | GLU | 306 | 9.866  | 72.216 | 21.761 | 1.00 | 48.15 |
| ATOM | 2333 | CD  | GLU | 306 | 9.571  | 71.175 | 20.692 | 1.00 | 49.26 |

*FIG. 40O*

| | | | | | | | | |
|---|---|---|---|---|---|---|---|---|
| ATOM | 2334 | OE1 | GLU | 306 | 8.514 | 70.499 | 20.768 | 1.00 50.03 |
| ATOM | 2335 | OE2 | GLU | 306 | 10.398 | 71.049 | 19.759 | 1.00 49.62 |
| ATOM | 2336 | C | GLU | 306 | 9.635 | 72.661 | 25.493 | 1.00 45.99 |
| ATOM | 2337 | O | GLU | 306 | 8.459 | 72.331 | 25.550 | 1.00 45.90 |
| ATOM | 2338 | N | ASN | 307 | 10.350 | 72.997 | 26.560 | 1.00 46.00 |
| ATOM | 2339 | CA | ASN | 307 | 9.787 | 73.029 | 27.902 | 1.00 45.60 |
| ATOM | 2340 | CB | ASN | 307 | 9.033 | 74.342 | 28.094 | 1.00 46.42 |
| ATOM | 2341 | CG | ASN | 307 | 9.971 | 75.531 | 28.224 | 1.00 46.98 |
| ATOM | 2342 | OD1 | ASN | 307 | 10.435 | 75.849 | 29.321 | 1.00 47.63 |
| ATOM | 2343 | ND2 | ASN | 307 | 10.273 | 76.181 | 27.102 | 1.00 46.93 |
| ATOM | 2344 | C | ASN | 307 | 8.886 | 71.853 | 28.246 | 1.00 45.05 |
| ATOM | 2345 | O | ASN | 307 | 7.812 | 72.029 | 28.829 | 1.00 45.19 |
| ATOM | 2346 | N | LEU | 308 | 9.336 | 70.650 | 27.900 | 1.00 44.24 |
| ATOM | 2347 | CA | LEU | 308 | 8.575 | 69.439 | 28.180 | 1.00 43.28 |
| ATOM | 2348 | CB | LEU | 308 | 8.376 | 68.637 | 26.893 | 1.00 43.27 |
| ATOM | 2349 | CG | LEU | 308 | 7.070 | 68.825 | 26.115 | 1.00 44.09 |
| ATOM | 2350 | CD1 | LEU | 308 | 6.765 | 70.294 | 25.935 | 1.00 44.22 |
| ATOM | 2351 | CD2 | LEU | 308 | 7.182 | 68.139 | 24.760 | 1.00 43.94 |
| ATOM | 2352 | C | LEU | 308 | 9.287 | 68.570 | 29.205 | 1.00 42.96 |
| ATOM | 2353 | O | LEU | 308 | 8.688 | 67.660 | 29.775 | 1.00 42.27 |
| ATOM | 2354 | N | LEU | 309 | 10.560 | 68.868 | 29.448 | 1.00 43.49 |
| ATOM | 2355 | CA | LEU | 309 | 11.368 | 68.077 | 30.371 | 1.00 44.85 |
| ATOM | 2356 | CB | LEU | 309 | 12.030 | 66.936 | 29.581 | 1.00 43.53 |
| ATOM | 2357 | CG | LEU | 309 | 12.958 | 65.925 | 30.254 | 1.00 42.07 |
| ATOM | 2358 | CD1 | LEU | 309 | 12.235 | 65.226 | 31.390 | 1.00 40.83 |
| ATOM | 2359 | CD2 | LEU | 309 | 13.416 | 64.913 | 29.212 | 1.00 42.11 |
| ATOM | 2360 | C | LEU | 309 | 12.436 | 68.900 | 31.108 | 1.00 46.21 |
| ATOM | 2361 | O | LEU | 309 | 13.074 | 69.777 | 30.518 | 1.00 46.04 |
| ATOM | 2362 | N | PHE | 310 | 12.625 | 68.601 | 32.397 | 1.00 47.92 |
| ATOM | 2363 | CA | PHE | 310 | 13.608 | 69.293 | 33.238 | 1.00 49.25 |
| ATOM | 2364 | CB | PHE | 310 | 15.013 | 69.093 | 32.666 | 1.00 48.20 |
| ATOM | 2365 | CG | PHE | 310 | 15.438 | 67.650 | 32.590 | 1.00 47.06 |
| ATOM | 2366 | CD1 | PHE | 310 | 16.338 | 67.228 | 31.615 | 1.00 46.24 |
| ATOM | 2367 | CD2 | PHE | 310 | 14.947 | 66.715 | 33.497 | 1.00 46.63 |
| ATOM | 2368 | CE1 | PHE | 310 | 16.740 | 65.903 | 31.540 | 1.00 45.74 |
| ATOM | 2369 | CE2 | PHE | 310 | 15.344 | 65.385 | 33.433 | 1.00 46.27 |
| ATOM | 2370 | CZ | PHE | 310 | 16.243 | 64.978 | 32.451 | 1.00 45.93 |
| ATOM | 2371 | C | PHE | 310 | 13.292 | 70.785 | 33.345 | 1.00 51.16 |
| ATOM | 2372 | O | PHE | 310 | 14.185 | 71.616 | 33.561 | 1.00 50.84 |
| ATOM | 2373 | N | HIS | 311 | 12.009 | 71.109 | 33.183 | 1.00 53.40 |
| ATOM | 2374 | CA | HIS | 311 | 11.529 | 72.482 | 33.262 | 1.00 55.80 |
| ATOM | 2375 | CB | HIS | 311 | 11.744 | 73.012 | 34.683 | 1.00 57.57 |
| ATOM | 2376 | CG | HIS | 311 | 11.212 | 72.098 | 35.745 | 1.00 59.78 |
| ATOM | 2377 | CD2 | HIS | 311 | 11.848 | 71.363 | 36.689 | 1.00 60.29 |
| ATOM | 2378 | ND1 | HIS | 311 | 9.867 | 71.815 | 35.879 | 1.00 60.36 |
| ATOM | 2379 | CE1 | HIS | 311 | 9.699 | 70.944 | 36.860 | 1.00 60.99 |
| ATOM | 2380 | NE2 | HIS | 311 | 10.885 | 70.654 | 37.368 | 1.00 60.85 |
| ATOM | 2381 | C | HIS | 311 | 12.214 | 73.384 | 32.236 | 1.00 56.24 |
| ATOM | 2382 | O | HIS | 311 | 12.288 | 74.608 | 32.415 | 1.00 56.87 |
| ATOM | 2383 | N | GLY | 312 | 12.705 | 72.772 | 31.159 | 1.00 55.96 |
| ATOM | 2384 | CA | GLY | 312 | 13.366 | 73.522 | 30.109 | 1.00 55.87 |
| ATOM | 2385 | C | GLY | 312 | 14.820 | 73.804 | 30.420 | 1.00 56.16 |
| ATOM | 2386 | O | GLY | 312 | 15.563 | 74.264 | 29.562 | 1.00 56.58 |
| ATOM | 2387 | N | GLU | 313 | 15.235 | 73.519 | 31.646 | 1.00 56.52 |
| ATOM | 2388 | CA | GLU | 313 | 16.612 | 73.765 | 32.048 | 1.00 57.69 |
| ATOM | 2389 | CB | GLU | 313 | 16.621 | 74.379 | 33.447 | 1.00 59.84 |
| ATOM | 2390 | CG | GLU | 313 | 15.849 | 75.698 | 33.515 | 1.00 63.16 |

*FIG. 4PP*

| | | | | | | | | |
|---|---|---|---|---|---|---|---|---|
| ATOM | 2391 | CD | GLU | 313 | 15.388 | 76.061 | 34.925 | 1.00 65.16 |
| ATOM | 2392 | OE1 | GLU | 313 | 14.554 | 75.315 | 35.503 | 1.00 66.01 |
| ATOM | 2393 | OE2 | GLU | 313 | 15.858 | 77.096 | 35.455 | 1.00 66.34 |
| ATOM | 2394 | C | GLU | 313 | 17.439 | 72.484 | 32.011 | 1.00 57.06 |
| ATOM | 2395 | O | GLU | 313 | 17.155 | 71.529 | 32.728 | 1.00 57.01 |
| ATOM | 2396 | N | ALA | 314 | 18.463 | 72.472 | 31.169 | 1.00 56.56 |
| ATOM | 2397 | CA | ALA | 314 | 19.316 | 71.305 | 31.029 | 1.00 56.76 |
| ATOM | 2398 | CB | ALA | 314 | 19.454 | 70.939 | 29.557 | 1.00 56.47 |
| ATOM | 2399 | C | ALA | 314 | 20.699 | 71.490 | 31.643 | 1.00 56.94 |
| ATOM | 2400 | O | ALA | 314 | 21.310 | 72.558 | 31.527 | 1.00 57.46 |
| ATOM | 2401 | N | SER | 315 | 21.183 | 70.422 | 32.276 | 1.00 56.73 |
| ATOM | 2402 | CA | SER | 315 | 22.487 | 70.383 | 32.932 | 1.00 56.15 |
| ATOM | 2403 | CB | SER | 315 | 22.666 | 69.029 | 33.624 | 1.00 56.44 |
| ATOM | 2404 | OG | SER | 315 | 23.981 | 68.868 | 34.130 | 1.00 57.39 |
| ATOM | 2405 | C | SER | 315 | 23.673 | 70.627 | 32.003 | 1.00 56.00 |
| ATOM | 2406 | O | SER | 315 | 23.595 | 70.416 | 30.793 | 1.00 55.42 |
| ATOM | 2407 | N | GLU | 316 | 24.776 | 71.070 | 32.598 | 1.00 56.67 |
| ATOM | 2408 | CA | GLU | 316 | 26.012 | 71.346 | 31.875 | 1.00 57.46 |
| ATOM | 2409 | CB | GLU | 316 | 27.111 | 71.754 | 32.860 | 1.00 58.71 |
| ATOM | 2410 | CG | GLU | 316 | 28.458 | 72.050 | 32.206 | 1.00 60.34 |
| ATOM | 2411 | CD | GLU | 316 | 28.442 | 73.343 | 31.406 | 1.00 61.64 |
| ATOM | 2412 | OE1 | GLU | 316 | 28.288 | 74.420 | 32.031 | 1.00 62.41 |
| ATOM | 2413 | OE2 | GLU | 316 | 28.574 | 73.280 | 30.160 | 1.00 61.76 |
| ATOM | 2414 | C | GLU | 316 | 26.442 | 70.078 | 31.161 | 1.00 57.35 |
| ATOM | 2415 | O | GLU | 316 | 26.770 | 70.088 | 29.972 | 1.00 57.68 |
| ATOM | 2416 | N | GLN | 317 | 26.439 | 68.988 | 31.920 | 1.00 56.84 |
| ATOM | 2417 | CA | GLN | 317 | 26.817 | 67.677 | 31.427 | 1.00 56.23 |
| ATOM | 2418 | CB | GLN | 317 | 26.760 | 66.669 | 32.580 | 1.00 55.93 |
| ATOM | 2419 | CG | GLN | 317 | 27.504 | 67.113 | 33.840 | 1.00 55.46 |
| ATOM | 2420 | CD | GLN | 317 | 27.063 | 66.355 | 35.085 | 1.00 55.01 |
| ATOM | 2421 | OE1 | GLN | 317 | 27.246 | 65.140 | 35.194 | 1.00 54.83 |
| ATOM | 2422 | NE2 | GLN | 317 | 26.468 | 67.074 | 36.029 | 1.00 54.68 |
| ATOM | 2423 | C | GLN | 317 | 25.902 | 67.210 | 30.290 | 1.00 56.37 |
| ATOM | 2424 | O | GLN | 317 | 26.376 | 66.634 | 29.312 | 1.00 56.16 |
| ATOM | 2425 | N | LEU | 318 | 24.599 | 67.476 | 30.412 | 1.00 56.41 |
| ATOM | 2426 | CA | LEU | 318 | 23.616 | 67.043 | 29.413 | 1.00 56.48 |
| ATOM | 2427 | CB | LEU | 318 | 22.190 | 67.333 | 29.890 | 1.00 55.59 |
| ATOM | 2428 | CG | LEU | 318 | 21.084 | 66.700 | 29.034 | 1.00 54.71 |
| ATOM | 2429 | CD1 | LEU | 318 | 21.090 | 65.191 | 29.231 | 1.00 53.88 |
| ATOM | 2430 | CD2 | LEU | 318 | 19.731 | 67.268 | 29.422 | 1.00 54.28 |
| ATOM | 2431 | C | LEU | 318 | 23.784 | 67.621 | 28.017 | 1.00 56.99 |
| ATOM | 2432 | O | LEU | 318 | 23.692 | 66.893 | 27.029 | 1.00 57.21 |
| ATOM | 2433 | N | ARG | 319 | 24.011 | 68.924 | 27.919 | 1.00 57.16 |
| ATOM | 2434 | CA | ARG | 319 | 24.177 | 69.530 | 26.606 | 1.00 57.68 |
| ATOM | 2435 | CB | ARG | 319 | 23.870 | 71.026 | 26.690 | 1.00 59.32 |
| ATOM | 2436 | CG | ARG | 319 | 22.420 | 71.284 | 27.105 | 1.00 62.20 |
| ATOM | 2437 | CD | ARG | 319 | 22.125 | 72.743 | 27.401 | 1.00 64.53 |
| ATOM | 2438 | NE | ARG | 319 | 20.758 | 72.927 | 27.892 | 1.00 66.89 |
| ATOM | 2439 | CZ | ARG | 319 | 20.297 | 74.055 | 28.433 | 1.00 68.29 |
| ATOM | 2440 | NH1 | ARG | 319 | 21.096 | 75.112 | 28.555 | 1.00 68.30 |
| ATOM | 2441 | NH2 | ARG | 319 | 19.034 | 74.127 | 28.851 | 1.00 68.25 |
| ATOM | 2442 | C | ARG | 319 | 25.587 | 69.278 | 26.081 | 1.00 57.09 |
| ATOM | 2443 | O | ARG | 319 | 26.049 | 69.951 | 25.160 | 1.00 57.05 |
| ATOM | 2444 | N | THR | 320 | 26.246 | 68.277 | 26.667 | 1.00 56.25 |
| ATOM | 2445 | CA | THR | 320 | 27.612 | 67.888 | 26.318 | 1.00 55.15 |
| ATOM | 2446 | CB | THR | 320 | 28.478 | 67.836 | 27.589 | 1.00 54.85 |
| ATOM | 2447 | OG1 | THR | 320 | 28.601 | 69.158 | 28.133 | 1.00 54.94 |

*FIG. 4QQ*

```
ATOM   2448  CG2 THR   320      29.854  67.262  27.287  1.00 54.63
ATOM   2449  C   THR   320      27.689  66.524  25.613  1.00 55.04
ATOM   2450  O   THR   320      27.476  65.480  26.229  1.00 55.13
ATOM   2451  N   ARG   321      28.017  66.536  24.326  1.00 54.38
ATOM   2452  CA  ARG   321      28.106  65.304  23.545  1.00 54.36
ATOM   2453  CB  ARG   321      28.841  65.586  22.236  1.00 56.05
ATOM   2454  CG  ARG   321      28.153  66.651  21.402  1.00 59.03
ATOM   2455  CD  ARG   321      28.943  67.013  20.156  1.00 61.60
ATOM   2456  NE  ARG   321      28.331  68.123  19.426  1.00 63.68
ATOM   2457  CZ  ARG   321      28.909  68.753  18.406  1.00 65.43
ATOM   2458  NH1 ARG   321      30.119  68.381  17.997  1.00 65.83
ATOM   2459  NH2 ARG   321      28.280  69.750  17.792  1.00 65.76
ATOM   2460  C   ARG   321      28.765  64.123  24.262  1.00 52.97
ATOM   2461  O   ARG   321      29.885  64.234  24.758  1.00 53.13
ATOM   2462  N   GLY   322      28.056  62.996  24.316  1.00 51.39
ATOM   2463  CA  GLY   322      28.592  61.802  24.950  1.00 49.22
ATOM   2464  C   GLY   322      28.198  61.609  26.402  1.00 48.17
ATOM   2465  O   GLY   322      28.450  60.550  26.986  1.00 48.17
ATOM   2466  N   ALA   323      27.574  62.627  26.988  1.00 46.66
ATOM   2467  CA  ALA   323      27.150  62.573  28.385  1.00 44.99
ATOM   2468  CB  ALA   323      26.462  63.861  28.761  1.00 45.87
ATOM   2469  C   ALA   323      26.224  61.403  28.676  1.00 43.43
ATOM   2470  O   ALA   323      26.514  60.562  29.530  1.00 43.02
ATOM   2471  N   PHE   324      25.094  61.361  27.981  1.00 41.61
ATOM   2472  CA  PHE   324      24.147  60.282  28.185  1.00 40.44
ATOM   2473  CB  PHE   324      22.797  60.631  27.564  1.00 38.94
ATOM   2474  CG  PHE   324      21.644  59.988  28.262  1.00 38.08
ATOM   2475  CD1 PHE   324      21.047  60.613  29.360  1.00 37.48
ATOM   2476  CD2 PHE   324      21.185  58.733  27.860  1.00 36.96
ATOM   2477  CE1 PHE   324      20.010  59.998  30.050  1.00 37.11
ATOM   2478  CE2 PHE   324      20.146  58.105  28.542  1.00 37.79
ATOM   2479  CZ  PHE   324      19.555  58.739  29.643  1.00 37.73
ATOM   2480  C   PHE   324      24.721  59.033  27.525  1.00 40.11
ATOM   2481  O   PHE   324      24.785  58.937  26.289  1.00 40.76
ATOM   2482  N   GLU   325      25.129  58.072  28.350  1.00 39.06
ATOM   2483  CA  GLU   325      25.740  56.851  27.844  1.00 37.85
ATOM   2484  CB  GLU   325      26.846  56.418  28.781  1.00 38.17
ATOM   2485  CG  GLU   325      27.790  57.528  29.085  1.00 40.68
ATOM   2486  CD  GLU   325      28.922  57.075  29.951  1.00 42.47
ATOM   2487  OE1 GLU   325      28.653  56.608  31.086  1.00 44.06
ATOM   2488  OE2 GLU   325      30.080  57.181  29.490  1.00 44.51
ATOM   2489  C   GLU   325      24.799  55.693  27.641  1.00 36.60
ATOM   2490  O   GLU   325      23.903  55.445  28.447  1.00 37.31
ATOM   2491  N   THR   326      25.019  54.968  26.554  1.00 35.30
ATOM   2492  CA  THR   326      24.193  53.816  26.245  1.00 33.37
ATOM   2493  CB  THR   326      24.875  52.921  25.207  1.00 31.58
ATOM   2494  OG1 THR   326      24.934  53.617  23.956  1.00 29.82
ATOM   2495  CG2 THR   326      24.113  51.619  25.041  1.00 29.94
ATOM   2496  C   THR   326      23.951  53.016  27.515  1.00 33.05
ATOM   2497  O   THR   326      22.846  52.528  27.742  1.00 33.99
ATOM   2498  N   ARG   327      24.981  52.902  28.349  1.00 32.29
ATOM   2499  CA  ARG   327      24.859  52.148  29.588  1.00 31.76
ATOM   2500  CB  ARG   327      26.146  52.245  30.417  1.00 33.30
ATOM   2501  CG  ARG   327      26.226  51.162  31.485  1.00 36.71
ATOM   2502  CD  ARG   327      27.596  51.043  32.177  1.00 38.88
ATOM   2503  NE  ARG   327      27.795  52.024  33.249  1.00 40.62
ATOM   2504  CZ  ARG   327      28.274  53.255  33.069  1.00 41.13
```

*FIG. 4RR*

| | | | | | | | |
|---|---|---|---|---|---|---|---|
| ATOM | 2505 | NH1 ARG | 327 | 28.615 | 53.670 | 31.846 | 1.00 40.49 |
| ATOM | 2506 | NH2 ARG | 327 | 28.393 | 54.078 | 34.113 | 1.00 40.82 |
| ATOM | 2507 | C   ARG | 327 | 23.681 | 52.691 | 30.387 | 1.00 30.62 |
| ATOM | 2508 | O   ARG | 327 | 22.888 | 51.930 | 30.940 | 1.00 29.96 |
| ATOM | 2509 | N   PHE | 328 | 23.559 | 54.014 | 30.425 | 1.00 29.60 |
| ATOM | 2510 | CA  PHE | 328 | 22.479 | 54.660 | 31.154 | 1.00 28.70 |
| ATOM | 2511 | CB  PHE | 328 | 22.632 | 56.176 | 31.069 | 1.00 28.03 |
| ATOM | 2512 | CG  PHE | 328 | 23.903 | 56.684 | 31.686 | 1.00 27.73 |
| ATOM | 2513 | CD1 PHE | 328 | 24.337 | 57.975 | 31.439 | 1.00 27.37 |
| ATOM | 2514 | CD2 PHE | 328 | 24.678 | 55.857 | 32.505 | 1.00 28.92 |
| ATOM | 2515 | CE1 PHE | 328 | 25.526 | 58.437 | 31.992 | 1.00 28.75 |
| ATOM | 2516 | CE2 PHE | 328 | 25.871 | 56.305 | 33.069 | 1.00 28.74 |
| ATOM | 2517 | CZ  PHE | 328 | 26.298 | 57.599 | 32.812 | 1.00 28.68 |
| ATOM | 2518 | C   PHE | 328 | 21.135 | 54.226 | 30.590 | 1.00 29.06 |
| ATOM | 2519 | O   PHE | 328 | 20.189 | 53.953 | 31.351 | 1.00 29.59 |
| ATOM | 2520 | N   VAL | 329 | 21.057 | 54.154 | 29.257 | 1.00 28.40 |
| ATOM | 2521 | CA  VAL | 329 | 19.830 | 53.735 | 28.587 | 1.00 26.44 |
| ATOM | 2522 | CB  VAL | 329 | 20.040 | 53.552 | 27.059 | 1.00 25.14 |
| ATOM | 2523 | CG1 VAL | 329 | 18.737 | 53.107 | 26.387 | 1.00 22.55 |
| ATOM | 2524 | CG2 VAL | 329 | 20.542 | 54.841 | 26.444 | 1.00 23.05 |
| ATOM | 2525 | C   VAL | 329 | 19.388 | 52.399 | 29.166 | 1.00 27.98 |
| ATOM | 2526 | O   VAL | 329 | 18.240 | 52.239 | 29.576 | 1.00 27.88 |
| ATOM | 2527 | N   SER | 330 | 20.308 | 51.442 | 29.219 | 1.00 28.76 |
| ATOM | 2528 | CA  SER | 330 | 19.966 | 50.117 | 29.718 | 1.00 30.08 |
| ATOM | 2529 | CB  SER | 330 | 21.136 | 49.171 | 29.534 | 1.00 30.45 |
| ATOM | 2530 | OG  SER | 330 | 20.720 | 47.852 | 29.822 | 1.00 31.92 |
| ATOM | 2531 | C   SER | 330 | 19.534 | 50.107 | 31.172 | 1.00 31.40 |
| ATOM | 2532 | O   SER | 330 | 18.690 | 49.298 | 31.577 | 1.00 31.74 |
| ATOM | 2533 | N   GLN | 331 | 20.118 | 50.993 | 31.972 | 1.00 32.45 |
| ATOM | 2534 | CA  GLN | 331 | 19.745 | 51.061 | 33.381 | 1.00 33.16 |
| ATOM | 2535 | CB  GLN | 331 | 20.668 | 51.992 | 34.151 | 1.00 33.58 |
| ATOM | 2536 | CG  GLN | 331 | 22.093 | 51.540 | 34.194 | 1.00 35.83 |
| ATOM | 2537 | CD  GLN | 331 | 22.947 | 52.534 | 34.919 | 1.00 37.72 |
| ATOM | 2538 | OE1 GLN | 331 | 22.626 | 52.927 | 36.043 | 1.00 39.62 |
| ATOM | 2539 | NE2 GLN | 331 | 24.042 | 52.958 | 34.291 | 1.00 38.98 |
| ATOM | 2540 | C   GLN | 331 | 18.327 | 51.591 | 33.482 | 1.00 33.78 |
| ATOM | 2541 | O   GLN | 331 | 17.428 | 50.881 | 33.938 | 1.00 34.06 |
| ATOM | 2542 | N   VAL | 332 | 18.129 | 52.835 | 33.038 | 1.00 33.77 |
| ATOM | 2543 | CA  VAL | 332 | 16.808 | 53.457 | 33.097 | 1.00 33.65 |
| ATOM | 2544 | CB  VAL | 332 | 16.760 | 54.791 | 32.282 | 1.00 32.19 |
| ATOM | 2545 | CG1 VAL | 332 | 17.279 | 54.584 | 30.905 | 1.00 33.04 |
| ATOM | 2546 | CG2 VAL | 332 | 15.340 | 55.312 | 32.215 | 1.00 31.67 |
| ATOM | 2547 | C   VAL | 332 | 15.695 | 52.505 | 32.638 | 1.00 34.20 |
| ATOM | 2548 | O   VAL | 332 | 14.571 | 52.566 | 33.139 | 1.00 34.51 |
| ATOM | 2549 | N   GLU | 333 | 16.001 | 51.607 | 31.711 | 1.00 34.30 |
| ATOM | 2550 | CA  GLU | 333 | 14.981 | 50.676 | 31.258 | 1.00 34.92 |
| ATOM | 2551 | CB  GLU | 333 | 15.210 | 50.289 | 29.795 | 1.00 34.40 |
| ATOM | 2552 | CG  GLU | 333 | 14.893 | 51.413 | 28.837 | 1.00 33.07 |
| ATOM | 2553 | CD  GLU | 333 | 14.806 | 50.956 | 27.409 | 1.00 31.80 |
| ATOM | 2554 | OE1 GLU | 333 | 13.983 | 50.060 | 27.114 | 1.00 31.65 |
| ATOM | 2555 | OE2 GLU | 333 | 15.561 | 51.504 | 26.581 | 1.00 31.72 |
| ATOM | 2556 | C   GLU | 333 | 14.949 | 49.438 | 32.135 | 1.00 35.76 |
| ATOM | 2557 | O   GLU | 333 | 14.163 | 48.520 | 31.911 | 1.00 35.73 |
| ATOM | 2558 | N   SER | 334 | 15.814 | 49.419 | 33.138 | 1.00 36.91 |
| ATOM | 2559 | CA  SER | 334 | 15.876 | 48.307 | 34.071 | 1.00 38.13 |
| ATOM | 2560 | CB  SER | 334 | 17.328 | 47.934 | 34.346 | 1.00 39.38 |
| ATOM | 2561 | OG  SER | 334 | 17.460 | 46.524 | 34.468 | 1.00 41.52 |

*FIG. 4SS*

| ATOM | 2562 | C | SER | 334 | 15.201 | 48.747 | 35.362 | 1.00 | 37.93 |
|------|------|-----|-----|-----|--------|--------|--------|------|-------|
| ATOM | 2563 | O | SER | 334 | 15.053 | 47.973 | 36.306 | 1.00 | 38.63 |
| ATOM | 2564 | N | ASP | 335 | 14.807 | 50.014 | 35.385 | 1.00 | 38.51 |
| ATOM | 2565 | CA | ASP | 335 | 14.133 | 50.619 | 36.521 | 1.00 | 38.59 |
| ATOM | 2566 | CB | ASP | 335 | 13.776 | 52.061 | 36.173 | 1.00 | 39.10 |
| ATOM | 2567 | CG | ASP | 335 | 13.346 | 52.864 | 37.373 | 1.00 | 39.89 |
| ATOM | 2568 | OD1 | ASP | 335 | 12.278 | 52.547 | 37.950 | 1.00 | 40.30 |
| ATOM | 2569 | OD2 | ASP | 335 | 14.079 | 53.816 | 37.737 | 1.00 | 39.90 |
| ATOM | 2570 | C | ASP | 335 | 12.876 | 49.809 | 36.840 | 1.00 | 39.11 |
| ATOM | 2571 | O | ASP | 335 | 12.241 | 49.249 | 35.945 | 1.00 | 39.03 |
| ATOM | 2572 | N | THR | 336 | 12.517 | 49.768 | 38.119 | 1.00 | 39.68 |
| ATOM | 2573 | CA | THR | 336 | 11.372 | 48.999 | 38.605 | 1.00 | 39.94 |
| ATOM | 2574 | CB | THR | 336 | 11.773 | 48.297 | 39.896 | 1.00 | 39.68 |
| ATOM | 2575 | OG1 | THR | 336 | 12.901 | 47.464 | 39.630 | 1.00 | 40.95 |
| ATOM | 2576 | CG2 | THR | 336 | 10.650 | 47.452 | 40.426 | 1.00 | 39.84 |
| ATOM | 2577 | C | THR | 336 | 10.043 | 49.735 | 38.853 | 1.00 | 40.52 |
| ATOM | 2578 | O | THR | 336 | 8.984 | 49.108 | 38.931 | 1.00 | 40.91 |
| ATOM | 2579 | N | GLY | 337 | 10.085 | 51.054 | 38.970 | 1.00 | 40.80 |
| ATOM | 2580 | CA | GLY | 337 | 8.870 | 51.804 | 39.234 | 1.00 | 41.83 |
| ATOM | 2581 | C | GLY | 337 | 9.307 | 52.948 | 40.112 | 1.00 | 42.60 |
| ATOM | 2582 | O | GLY | 337 | 8.990 | 54.105 | 39.865 | 1.00 | 43.33 |
| ATOM | 2583 | N | ASP | 338 | 10.043 | 52.604 | 41.156 | 1.00 | 43.47 |
| ATOM | 2584 | CA | ASP | 338 | 10.606 | 53.589 | 42.059 | 1.00 | 44.40 |
| ATOM | 2585 | CB | ASP | 338 | 11.354 | 52.868 | 43.175 | 1.00 | 44.83 |
| ATOM | 2586 | CG | ASP | 338 | 12.303 | 51.808 | 42.637 | 1.00 | 45.34 |
| ATOM | 2587 | OD1 | ASP | 338 | 11.879 | 51.032 | 41.751 | 1.00 | 46.12 |
| ATOM | 2588 | OD2 | ASP | 338 | 13.465 | 51.742 | 43.087 | 1.00 | 45.59 |
| ATOM | 2589 | C | ASP | 338 | 11.597 | 54.296 | 41.142 | 1.00 | 44.84 |
| ATOM | 2590 | O | ASP | 338 | 12.605 | 53.709 | 40.756 | 1.00 | 45.53 |
| ATOM | 2591 | N | ARG | 339 | 11.310 | 55.533 | 40.763 | 1.00 | 44.81 |
| ATOM | 2592 | CA | ARG | 339 | 12.208 | 56.256 | 39.874 | 1.00 | 45.11 |
| ATOM | 2593 | CB | ARG | 339 | 11.702 | 57.687 | 39.654 | 1.00 | 45.72 |
| ATOM | 2594 | CG | ARG | 339 | 10.466 | 57.799 | 38.783 | 1.00 | 46.11 |
| ATOM | 2595 | CD | ARG | 339 | 9.201 | 57.413 | 39.521 | 1.00 | 46.99 |
| ATOM | 2596 | NE | ARG | 339 | 8.041 | 57.492 | 38.633 | 1.00 | 47.58 |
| ATOM | 2597 | CZ | ARG | 339 | 6.780 | 57.326 | 39.017 | 1.00 | 47.30 |
| ATOM | 2598 | NH1 | ARG | 339 | 6.492 | 57.068 | 40.287 | 1.00 | 47.38 |
| ATOM | 2599 | NH2 | ARG | 339 | 5.806 | 57.413 | 38.123 | 1.00 | 47.44 |
| ATOM | 2600 | C | ARG | 339 | 13.637 | 56.295 | 40.419 | 1.00 | 44.98 |
| ATOM | 2601 | O | ARG | 339 | 14.466 | 57.084 | 39.960 | 1.00 | 44.83 |
| ATOM | 2602 | N | LYS | 340 | 13.922 | 55.441 | 41.394 | 1.00 | 44.75 |
| ATOM | 2603 | CA | LYS | 340 | 15.238 | 55.394 | 42.001 | 1.00 | 45.05 |
| ATOM | 2604 | CB | LYS | 340 | 15.341 | 54.179 | 42.917 | 1.00 | 46.19 |
| ATOM | 2605 | CG | LYS | 340 | 14.358 | 54.250 | 44.081 | 1.00 | 47.87 |
| ATOM | 2606 | CD | LYS | 340 | 14.598 | 53.154 | 45.094 | 1.00 | 49.25 |
| ATOM | 2607 | CE | LYS | 340 | 13.365 | 52.949 | 45.957 | 1.00 | 50.44 |
| ATOM | 2608 | NZ | LYS | 340 | 13.353 | 51.589 | 46.598 | 1.00 | 51.78 |
| ATOM | 2609 | C | LYS | 340 | 16.398 | 55.422 | 41.014 | 1.00 | 44.66 |
| ATOM | 2610 | O | LYS | 340 | 17.186 | 56.372 | 41.026 | 1.00 | 44.90 |
| ATOM | 2611 | N | GLN | 341 | 16.509 | 54.408 | 40.155 | 1.00 | 43.94 |
| ATOM | 2612 | CA | GLN | 341 | 17.603 | 54.362 | 39.174 | 1.00 | 42.93 |
| ATOM | 2613 | CB | GLN | 341 | 17.598 | 53.028 | 38.435 | 1.00 | 45.04 |
| ATOM | 2614 | CG | GLN | 341 | 18.035 | 51.860 | 39.289 | 1.00 | 48.03 |
| ATOM | 2615 | CD | GLN | 341 | 18.758 | 50.801 | 38.482 | 1.00 | 49.69 |
| ATOM | 2616 | OE1 | GLN | 341 | 19.731 | 51.101 | 37.779 | 1.00 | 50.67 |
| ATOM | 2617 | NE2 | GLN | 341 | 18.297 | 49.556 | 38.581 | 1.00 | 50.43 |
| ATOM | 2618 | C | GLN | 341 | 17.616 | 55.497 | 38.146 | 1.00 | 40.93 |

*FIG. 4TT*

```
ATOM   2619  O    GLN  341      18.672  56.057  37.839  1.00  38.85
ATOM   2620  N    ILE  342      16.449  55.824  37.600  1.00  39.61
ATOM   2621  CA   ILE  342      16.364  56.905  36.624  1.00  39.07
ATOM   2622  CB   ILE  342      14.920  57.110  36.130  1.00  39.24
ATOM   2623  CG2  ILE  342      14.880  58.226  35.107  1.00  39.19
ATOM   2624  CG1  ILE  342      14.392  55.817  35.501  1.00  39.87
ATOM   2625  CD1  ILE  342      12.945  55.902  35.070  1.00  40.76
ATOM   2626  C    ILE  342      16.832  58.185  37.301  1.00  38.43
ATOM   2627  O    ILE  342      17.704  58.892  36.795  1.00  37.48
ATOM   2628  N    TYR  343      16.240  58.466  38.456  1.00  38.93
ATOM   2629  CA   TYR  343      16.580  59.647  39.236  1.00  39.71
ATOM   2630  CB   TYR  343      15.813  59.656  40.567  1.00  40.97
ATOM   2631  CG   TYR  343      16.173  60.835  41.448  1.00  42.53
ATOM   2632  CD1  TYR  343      15.344  61.954  41.521  1.00  43.30
ATOM   2633  CE1  TYR  343      15.730  63.092  42.228  1.00  44.58
ATOM   2634  CD2  TYR  343      17.397  60.880  42.119  1.00  43.04
ATOM   2635  CE2  TYR  343      17.791  62.014  42.826  1.00  43.55
ATOM   2636  CZ   TYR  343      16.958  63.117  42.872  1.00  44.31
ATOM   2637  OH   TYR  343      17.369  64.260  43.523  1.00  45.74
ATOM   2638  C    TYR  343      18.070  59.635  39.532  1.00  39.93
ATOM   2639  O    TYR  343      18.789  60.598  39.262  1.00  40.28
ATOM   2640  N    ASN  344      18.525  58.529  40.098  1.00  40.14
ATOM   2641  CA   ASN  344      19.924  58.371  40.460  1.00  40.97
ATOM   2642  CB   ASN  344      20.146  56.958  40.989  1.00  42.94
ATOM   2643  CG   ASN  344      21.287  56.880  41.977  1.00  44.68
ATOM   2644  OD1  ASN  344      22.448  57.137  41.628  1.00  46.05
ATOM   2645  ND2  ASN  344      20.965  56.531  43.225  1.00  44.93
ATOM   2646  C    ASN  344      20.869  58.649  39.292  1.00  40.46
ATOM   2647  O    ASN  344      21.946  59.208  39.483  1.00  40.33
ATOM   2648  N    ILE  345      20.460  58.262  38.085  1.00  40.50
ATOM   2649  CA   ILE  345      21.280  58.467  36.890  1.00  39.89
ATOM   2650  CB   ILE  345      20.803  57.555  35.720  1.00  39.76
ATOM   2651  CG2  ILE  345      21.597  57.849  34.448  1.00  38.62
ATOM   2652  CG1  ILE  345      20.966  56.090  36.114  1.00  38.74
ATOM   2653  CD1  ILE  345      20.201  55.151  35.242  1.00  38.61
ATOM   2654  C    ILE  345      21.247  59.924  36.434  1.00  39.80
ATOM   2655  O    ILE  345      22.281  60.490  36.074  1.00  39.67
ATOM   2656  N    LEU  346      20.062  60.529  36.449  1.00  39.59
ATOM   2657  CA   LEU  346      19.912  61.923  36.029  1.00  39.58
ATOM   2658  CB   LEU  346      18.434  62.255  35.818  1.00  37.79
ATOM   2659  CG   LEU  346      17.809  61.528  34.625  1.00  36.58
ATOM   2660  CD1  LEU  346      16.277  61.599  34.684  1.00  35.18
ATOM   2661  CD2  LEU  346      18.363  62.145  33.337  1.00  35.05
ATOM   2662  C    LEU  346      20.519  62.892  37.034  1.00  40.82
ATOM   2663  O    LEU  346      21.177  63.857  36.654  1.00  41.02
ATOM   2664  N    SER  347      20.298  62.646  38.322  1.00  42.34
ATOM   2665  CA   SER  347      20.859  63.530  39.339  1.00  43.44
ATOM   2666  CB   SER  347      20.491  63.042  40.745  1.00  43.90
ATOM   2667  OG   SER  347      20.665  61.639  40.868  1.00  45.32
ATOM   2668  C    SER  347      22.368  63.556  39.156  1.00  43.44
ATOM   2669  O    SER  347      22.974  64.624  39.051  1.00  44.11
ATOM   2670  N    THR  348      22.969  62.374  39.096  1.00  43.10
ATOM   2671  CA   THR  348      24.407  62.285  38.909  1.00  42.97
ATOM   2672  CB   THR  348      24.853  60.830  38.700  1.00  42.31
ATOM   2673  OG1  THR  348      24.666  60.096  39.918  1.00  42.08
ATOM   2674  CG2  THR  348      26.322  60.780  38.282  1.00  40.85
ATOM   2675  C    THR  348      24.798  63.093  37.683  1.00  43.25
```

*FIG. 4UU*

| ATOM | 2676 | O   | THR | 348 | 25.796 | 63.813 | 37.680 | 1.00 | 43.52 |
|------|------|-----|-----|-----|--------|--------|--------|------|-------|
| ATOM | 2677 | N   | LEU | 349 | 23.990 | 62.982 | 36.640 | 1.00 | 43.57 |
| ATOM | 2678 | CA  | LEU | 349 | 24.271 | 63.697 | 35.412 | 1.00 | 44.17 |
| ATOM | 2679 | CB  | LEU | 349 | 23.343 | 63.180 | 34.311 | 1.00 | 44.43 |
| ATOM | 2680 | CG  | LEU | 349 | 23.787 | 63.204 | 32.847 | 1.00 | 44.86 |
| ATOM | 2681 | CD1 | LEU | 349 | 25.198 | 62.658 | 32.688 | 1.00 | 44.59 |
| ATOM | 2682 | CD2 | LEU | 349 | 22.790 | 62.375 | 32.046 | 1.00 | 44.64 |
| ATOM | 2683 | C   | LEU | 349 | 24.102 | 65.201 | 35.638 | 1.00 | 44.32 |
| ATOM | 2684 | O   | LEU | 349 | 24.317 | 66.003 | 34.726 | 1.00 | 45.33 |
| ATOM | 2685 | N   | GLY | 350 | 23.722 | 65.574 | 36.862 | 1.00 | 43.94 |
| ATOM | 2686 | CA  | GLY | 350 | 23.559 | 66.981 | 37.210 | 1.00 | 43.15 |
| ATOM | 2687 | C   | GLY | 350 | 22.167 | 67.570 | 37.038 | 1.00 | 42.49 |
| ATOM | 2688 | O   | GLY | 350 | 22.024 | 68.752 | 36.703 | 1.00 | 41.70 |
| ATOM | 2689 | N   | LEU | 351 | 21.143 | 66.758 | 37.288 | 1.00 | 41.97 |
| ATOM | 2690 | CA  | LEU | 351 | 19.758 | 67.197 | 37.132 | 1.00 | 41.45 |
| ATOM | 2691 | CB  | LEU | 351 | 19.194 | 66.676 | 35.812 | 1.00 | 40.99 |
| ATOM | 2692 | CG  | LEU | 351 | 19.875 | 67.115 | 34.522 | 1.00 | 40.66 |
| ATOM | 2693 | CD1 | LEU | 351 | 19.516 | 66.144 | 33.416 | 1.00 | 41.63 |
| ATOM | 2694 | CD2 | LEU | 351 | 19.453 | 68.533 | 34.172 | 1.00 | 40.77 |
| ATOM | 2695 | C   | LEU | 351 | 18.858 | 66.718 | 38.262 | 1.00 | 41.15 |
| ATOM | 2696 | O   | LEU | 351 | 19.170 | 65.760 | 38.973 | 1.00 | 40.88 |
| ATOM | 2697 | N   | ARG | 352 | 17.720 | 67.379 | 38.410 | 1.00 | 41.10 |
| ATOM | 2698 | CA  | ARG | 352 | 16.782 | 67.007 | 39.457 | 1.00 | 41.25 |
| ATOM | 2699 | CB  | ARG | 352 | 16.614 | 68.173 | 40.431 | 1.00 | 42.65 |
| ATOM | 2700 | CG  | ARG | 352 | 17.929 | 68.581 | 41.070 | 1.00 | 43.68 |
| ATOM | 2701 | CD  | ARG | 352 | 18.504 | 67.421 | 41.851 | 1.00 | 45.59 |
| ATOM | 2702 | NE  | ARG | 352 | 19.960 | 67.478 | 41.917 | 1.00 | 47.73 |
| ATOM | 2703 | CZ  | ARG | 352 | 20.715 | 66.567 | 42.521 | 1.00 | 48.77 |
| ATOM | 2704 | NH1 | ARG | 352 | 20.143 | 65.524 | 43.119 | 1.00 | 49.05 |
| ATOM | 2705 | NH2 | ARG | 352 | 22.038 | 66.700 | 42.519 | 1.00 | 49.14 |
| ATOM | 2706 | C   | ARG | 352 | 15.458 | 66.621 | 38.827 | 1.00 | 39.59 |
| ATOM | 2707 | O   | ARG | 352 | 14.512 | 67.399 | 38.793 | 1.00 | 40.34 |
| ATOM | 2708 | N   | PRO | 353 | 15.378 | 65.388 | 38.324 | 1.00 | 38.06 |
| ATOM | 2709 | CD  | PRO | 353 | 16.325 | 64.285 | 38.555 | 1.00 | 37.28 |
| ATOM | 2710 | CA  | PRO | 353 | 14.159 | 64.901 | 37.683 | 1.00 | 37.45 |
| ATOM | 2711 | CB  | PRO | 353 | 14.595 | 63.552 | 37.134 | 1.00 | 37.27 |
| ATOM | 2712 | CG  | PRO | 353 | 15.491 | 63.064 | 38.232 | 1.00 | 36.92 |
| ATOM | 2713 | C   | PRO | 353 | 12.998 | 64.763 | 38.650 | 1.00 | 36.35 |
| ATOM | 2714 | O   | PRO | 353 | 13.180 | 64.360 | 39.791 | 1.00 | 36.28 |
| ATOM | 2715 | N   | SER | 354 | 11.805 | 65.110 | 38.194 | 1.00 | 35.82 |
| ATOM | 2716 | CA  | SER | 354 | 10.625 | 64.951 | 39.028 | 1.00 | 36.40 |
| ATOM | 2717 | CB  | SER | 354 | 9.570  | 66.010 | 38.698 | 1.00 | 35.94 |
| ATOM | 2718 | OG  | SER | 354 | 8.944  | 65.725 | 37.459 | 1.00 | 35.63 |
| ATOM | 2719 | C   | SER | 354 | 10.091 | 63.570 | 38.653 | 1.00 | 36.41 |
| ATOM | 2720 | O   | SER | 354 | 10.592 | 62.948 | 37.716 | 1.00 | 37.42 |
| ATOM | 2721 | N   | THR | 355 | 9.087  | 63.091 | 39.375 | 1.00 | 36.02 |
| ATOM | 2722 | CA  | THR | 355 | 8.493  | 61.790 | 39.099 | 1.00 | 35.68 |
| ATOM | 2723 | CB  | THR | 355 | 7.200  | 61.615 | 39.923 | 1.00 | 36.38 |
| ATOM | 2724 | OG1 | THR | 355 | 7.525  | 61.645 | 41.316 | 1.00 | 37.75 |
| ATOM | 2725 | CG2 | THR | 355 | 6.510  | 60.293 | 39.598 | 1.00 | 36.44 |
| ATOM | 2726 | C   | THR | 355 | 8.161  | 61.633 | 37.609 | 1.00 | 35.80 |
| ATOM | 2727 | O   | THR | 355 | 8.319  | 60.548 | 37.029 | 1.00 | 34.73 |
| ATOM | 2728 | N   | THR | 356 | 7.698  | 62.720 | 36.994 | 1.00 | 35.28 |
| ATOM | 2729 | CA  | THR | 356 | 7.336  | 62.690 | 35.586 | 1.00 | 35.39 |
| ATOM | 2730 | CB  | THR | 356 | 6.287  | 63.774 | 35.263 | 1.00 | 35.59 |
| ATOM | 2731 | OG1 | THR | 356 | 6.651  | 64.990 | 35.925 | 1.00 | 35.39 |
| ATOM | 2732 | CG2 | THR | 356 | 4.892  | 63.331 | 35.719 | 1.00 | 34.33 |

*FIG. 4VV*

| | | | | | | | | |
|---|---|---|---|---|---|---|---|---|
| ATOM | 2733 | C | THR | 356 | 8.542 | 62.848 | 34.662 | 1.00 35.30 |
| ATOM | 2734 | O | THR | 356 | 8.560 | 62.285 | 33.559 | 1.00 34.91 |
| ATOM | 2735 | N | ASP | 357 | 9.537 | 63.624 | 35.089 | 1.00 35.07 |
| ATOM | 2736 | CA | ASP | 357 | 10.740 | 63.782 | 34.277 | 1.00 35.80 |
| ATOM | 2737 | CB | ASP | 357 | 11.804 | 64.598 | 35.012 | 1.00 36.76 |
| ATOM | 2738 | CG | ASP | 357 | 11.451 | 66.077 | 35.116 | 1.00 38.19 |
| ATOM | 2739 | OD1 | ASP | 357 | 11.475 | 66.778 | 34.071 | 1.00 37.60 |
| ATOM | 2740 | OD2 | ASP | 357 | 11.158 | 66.538 | 36.249 | 1.00 38.76 |
| ATOM | 2741 | C | ASP | 357 | 11.277 | 62.373 | 34.039 | 1.00 35.97 |
| ATOM | 2742 | O | ASP | 357 | 11.460 | 61.942 | 32.901 | 1.00 36.94 |
| ATOM | 2743 | N | CYS | 358 | 11.498 | 61.649 | 35.131 | 1.00 35.67 |
| ATOM | 2744 | CA | CYS | 358 | 12.013 | 60.293 | 35.057 | 1.00 35.44 |
| ATOM | 2745 | CB | CYS | 358 | 12.051 | 59.658 | 36.447 | 1.00 35.93 |
| ATOM | 2746 | SG | CYS | 358 | 13.247 | 60.410 | 37.575 | 1.00 35.81 |
| ATOM | 2747 | C | CYS | 358 | 11.177 | 59.433 | 34.138 | 1.00 34.88 |
| ATOM | 2748 | O | CYS | 358 | 11.711 | 58.698 | 33.308 | 1.00 35.87 |
| ATOM | 2749 | N | ASP | 359 | 9.863 | 59.517 | 34.290 | 1.00 34.10 |
| ATOM | 2750 | CA | ASP | 359 | 8.960 | 58.729 | 33.464 | 1.00 33.10 |
| ATOM | 2751 | CB | ASP | 359 | 7.519 | 58.964 | 33.910 | 1.00 35.03 |
| ATOM | 2752 | CG | ASP | 359 | 7.118 | 58.058 | 35.062 | 1.00 36.65 |
| ATOM | 2753 | OD1 | ASP | 359 | 7.950 | 57.850 | 35.975 | 1.00 38.15 |
| ATOM | 2754 | OD2 | ASP | 359 | 5.969 | 57.561 | 35.055 | 1.00 37.12 |
| ATOM | 2755 | C | ASP | 359 | 9.130 | 59.058 | 31.985 | 1.00 31.16 |
| ATOM | 2756 | O | ASP | 359 | 9.090 | 58.170 | 31.133 | 1.00 30.01 |
| ATOM | 2757 | N | ILE | 360 | 9.325 | 60.334 | 31.682 | 1.00 29.54 |
| ATOM | 2758 | CA | ILE | 360 | 9.524 | 60.741 | 30.300 | 1.00 28.61 |
| ATOM | 2759 | CB | ILE | 360 | 9.546 | 62.273 | 30.162 | 1.00 27.75 |
| ATOM | 2760 | CG2 | ILE | 360 | 10.255 | 62.668 | 28.874 | 1.00 27.01 |
| ATOM | 2761 | CG1 | ILE | 360 | 8.112 | 62.818 | 30.235 | 1.00 26.18 |
| ATOM | 2762 | CD1 | ILE | 360 | 8.024 | 64.322 | 30.190 | 1.00 23.23 |
| ATOM | 2763 | C | ILE | 360 | 10.857 | 60.176 | 29.825 | 1.00 29.21 |
| ATOM | 2764 | O | ILE | 360 | 10.919 | 59.480 | 28.805 | 1.00 29.88 |
| ATOM | 2765 | N | VAL | 361 | 11.923 | 60.466 | 30.569 | 1.00 28.39 |
| ATOM | 2766 | CA | VAL | 361 | 13.248 | 59.971 | 30.219 | 1.00 28.01 |
| ATOM | 2767 | CB | VAL | 361 | 14.258 | 60.256 | 31.342 | 1.00 27.73 |
| ATOM | 2768 | CG1 | VAL | 361 | 15.575 | 59.551 | 31.055 | 1.00 27.43 |
| ATOM | 2769 | CG2 | VAL | 361 | 14.492 | 61.759 | 31.453 | 1.00 27.76 |
| ATOM | 2770 | C | VAL | 361 | 13.245 | 58.464 | 29.919 | 1.00 27.74 |
| ATOM | 2771 | O | VAL | 361 | 14.055 | 57.982 | 29.107 | 1.00 27.40 |
| ATOM | 2772 | N | ARG | 362 | 12.341 | 57.719 | 30.556 | 1.00 27.72 |
| ATOM | 2773 | CA | ARG | 362 | 12.277 | 56.275 | 30.325 | 1.00 27.95 |
| ATOM | 2774 | CB | ARG | 362 | 11.523 | 55.571 | 31.455 | 1.00 29.48 |
| ATOM | 2775 | CG | ARG | 362 | 11.137 | 54.147 | 31.101 | 1.00 31.97 |
| ATOM | 2776 | CD | ARG | 362 | 10.900 | 53.266 | 32.308 | 1.00 33.93 |
| ATOM | 2777 | NE | ARG | 362 | 10.930 | 51.859 | 31.893 | 1.00 37.37 |
| ATOM | 2778 | CZ | ARG | 362 | 10.938 | 50.817 | 32.725 | 1.00 37.52 |
| ATOM | 2779 | NH1 | ARG | 362 | 10.920 | 51.010 | 34.043 | 1.00 38.72 |
| ATOM | 2780 | NH2 | ARG | 362 | 10.960 | 49.582 | 32.230 | 1.00 36.06 |
| ATOM | 2781 | C | ARG | 362 | 11.614 | 55.959 | 28.994 | 1.00 27.88 |
| ATOM | 2782 | O | ARG | 362 | 12.016 | 55.032 | 28.289 | 1.00 29.02 |
| ATOM | 2783 | N | ARG | 363 | 10.586 | 56.728 | 28.660 | 1.00 27.31 |
| ATOM | 2784 | CA | ARG | 363 | 9.866 | 56.564 | 27.400 | 1.00 25.77 |
| ATOM | 2785 | CB | ARG | 363 | 8.641 | 57.486 | 27.374 | 1.00 26.51 |
| ATOM | 2786 | CG | ARG | 363 | 7.530 | 57.084 | 28.318 | 1.00 26.30 |
| ATOM | 2787 | CD | ARG | 363 | 6.730 | 55.929 | 27.739 | 1.00 28.36 |
| ATOM | 2788 | NE | ARG | 363 | 6.259 | 56.216 | 26.380 | 1.00 30.91 |
| ATOM | 2789 | CZ | ARG | 363 | 6.872 | 55.826 | 25.260 | 1.00 31.55 |

*FIG. 4WW*

| ATOM | 2790 | NH1 | ARG | 363 | 7.992 | 55.112 | 25.315 | 1.00 | 33.18 |
|---|---|---|---|---|---|---|---|---|---|
| ATOM | 2791 | NH2 | ARG | 363 | 6.370 | 56.158 | 24.077 | 1.00 | 32.30 |
| ATOM | 2792 | C | ARG | 363 | 10.817 | 56.949 | 26.272 | 1.00 | 24.71 |
| ATOM | 2793 | O | ARG | 363 | 10.748 | 56.392 | 25.175 | 1.00 | 24.40 |
| ATOM | 2794 | N | ALA | 364 | 11.706 | 57.905 | 26.540 | 1.00 | 23.90 |
| ATOM | 2795 | CA | ALA | 364 | 12.653 | 58.339 | 25.507 | 1.00 | 24.48 |
| ATOM | 2796 | CB | ALA | 364 | 13.463 | 59.545 | 25.969 | 1.00 | 23.15 |
| ATOM | 2797 | C | ALA | 364 | 13.571 | 57.176 | 25.226 | 1.00 | 25.01 |
| ATOM | 2798 | O | ALA | 364 | 13.854 | 56.872 | 24.069 | 1.00 | 26.22 |
| ATOM | 2799 | N | CYS | 365 | 14.023 | 56.518 | 26.290 | 1.00 | 25.03 |
| ATOM | 2800 | CA | CYS | 365 | 14.902 | 55.370 | 26.157 | 1.00 | 24.77 |
| ATOM | 2801 | CB | CYS | 365 | 15.450 | 54.970 | 27.528 | 1.00 | 23.03 |
| ATOM | 2802 | SG | CYS | 365 | 16.728 | 56.114 | 28.173 | 1.00 | 21.60 |
| ATOM | 2803 | C | CYS | 365 | 14.140 | 54.206 | 25.514 | 1.00 | 26.44 |
| ATOM | 2804 | O | CYS | 365 | 14.661 | 53.535 | 24.617 | 1.00 | 27.49 |
| ATOM | 2805 | N | GLU | 366 | 12.906 | 53.956 | 25.944 | 1.00 | 26.87 |
| ATOM | 2806 | CA | GLU | 366 | 12.145 | 52.859 | 25.342 | 1.00 | 27.98 |
| ATOM | 2807 | CB | GLU | 366 | 10.757 | 52.743 | 25.988 | 1.00 | 28.74 |
| ATOM | 2808 | CG | GLU | 366 | 10.785 | 52.431 | 27.490 | 1.00 | 30.75 |
| ATOM | 2809 | CD | GLU | 366 | 9.427 | 51.981 | 28.041 | 1.00 | 32.09 |
| ATOM | 2810 | OE1 | GLU | 366 | 8.444 | 52.757 | 27.970 | 1.00 | 32.39 |
| ATOM | 2811 | OE2 | GLU | 366 | 9.342 | 50.841 | 28.547 | 1.00 | 33.30 |
| ATOM | 2812 | C | GLU | 366 | 12.005 | 53.056 | 23.815 | 1.00 | 28.15 |
| ATOM | 2813 | O | GLU | 366 | 12.117 | 52.104 | 23.029 | 1.00 | 27.63 |
| ATOM | 2814 | N | SER | 367 | 11.776 | 54.304 | 23.407 | 1.00 | 28.42 |
| ATOM | 2815 | CA | SER | 367 | 11.612 | 54.650 | 21.993 | 1.00 | 27.23 |
| ATOM | 2816 | CB | SER | 367 | 11.368 | 56.156 | 21.833 | 1.00 | 27.45 |
| ATOM | 2817 | OG | SER | 367 | 10.161 | 56.552 | 22.447 | 1.00 | 27.44 |
| ATOM | 2818 | C | SER | 367 | 12.824 | 54.276 | 21.165 | 1.00 | 26.52 |
| ATOM | 2819 | O | SER | 367 | 12.724 | 53.567 | 20.162 | 1.00 | 27.99 |
| ATOM | 2820 | N | VAL | 368 | 13.977 | 54.773 | 21.581 | 1.00 | 24.30 |
| ATOM | 2821 | CA | VAL | 368 | 15.194 | 54.499 | 20.849 | 1.00 | 22.45 |
| ATOM | 2822 | CB | VAL | 368 | 16.324 | 55.395 | 21.375 | 1.00 | 20.96 |
| ATOM | 2823 | CG1 | VAL | 368 | 17.623 | 55.075 | 20.682 | 1.00 | 18.44 |
| ATOM | 2824 | CG2 | VAL | 368 | 15.928 | 56.843 | 21.190 | 1.00 | 18.99 |
| ATOM | 2825 | C | VAL | 368 | 15.605 | 53.019 | 20.888 | 1.00 | 23.13 |
| ATOM | 2826 | O | VAL | 368 | 15.850 | 52.420 | 19.832 | 1.00 | 23.88 |
| ATOM | 2827 | N | SER | 369 | 15.660 | 52.405 | 22.071 | 1.00 | 22.54 |
| ATOM | 2828 | CA | SER | 369 | 16.071 | 51.003 | 22.106 | 1.00 | 21.93 |
| ATOM | 2829 | CB | SER | 369 | 16.248 | 50.476 | 23.542 | 1.00 | 23.39 |
| ATOM | 2830 | OG | SER | 369 | 15.011 | 50.251 | 24.197 | 1.00 | 25.91 |
| ATOM | 2831 | C | SER | 369 | 15.109 | 50.112 | 21.348 | 1.00 | 20.54 |
| ATOM | 2832 | O | SER | 369 | 15.526 | 49.063 | 20.850 | 1.00 | 20.31 |
| ATOM | 2833 | N | THR | 370 | 13.832 | 50.499 | 21.259 | 1.00 | 18.40 |
| ATOM | 2834 | CA | THR | 370 | 12.878 | 49.682 | 20.496 | 1.00 | 17.32 |
| ATOM | 2835 | CB | THR | 370 | 11.400 | 49.976 | 20.859 | 1.00 | 16.46 |
| ATOM | 2836 | OG1 | THR | 370 | 11.053 | 49.298 | 22.073 | 1.00 | 15.81 |
| ATOM | 2837 | CG2 | THR | 370 | 10.473 | 49.487 | 19.774 | 1.00 | 14.39 |
| ATOM | 2838 | C | THR | 370 | 13.076 | 49.936 | 19.001 | 1.00 | 17.03 |
| ATOM | 2839 | O | THR | 370 | 12.977 | 49.008 | 18.186 | 1.00 | 17.38 |
| ATOM | 2840 | N | ARG | 371 | 13.358 | 51.177 | 18.617 | 1.00 | 16.71 |
| ATOM | 2841 | CA | ARG | 371 | 13.562 | 51.423 | 17.201 | 1.00 | 16.54 |
| ATOM | 2842 | CB | ARG | 371 | 13.810 | 52.905 | 16.882 | 1.00 | 17.42 |
| ATOM | 2843 | CG | ARG | 371 | 14.013 | 53.123 | 15.374 | 1.00 | 17.76 |
| ATOM | 2844 | CD | ARG | 371 | 14.283 | 54.559 | 14.943 | 1.00 | 17.40 |
| ATOM | 2845 | NE | ARG | 371 | 15.567 | 55.076 | 15.412 | 1.00 | 18.85 |
| ATOM | 2846 | CZ | ARG | 371 | 16.159 | 56.154 | 14.896 | 1.00 | 18.99 |

*FIG. 4XX*

| ATOM | 2847 | NH1 | ARG | 371 | 15.583 | 56.810 | 13.892 | 1.00 | 17.43 |
|------|------|-----|-----|-----|--------|--------|--------|------|-------|
| ATOM | 2848 | NH2 | ARG | 371 | 17.303 | 56.605 | 15.406 | 1.00 | 19.19 |
| ATOM | 2849 | C   | ARG | 371 | 14.763 | 50.607 | 16.759 | 1.00 | 15.91 |
| ATOM | 2850 | O   | ARG | 371 | 14.689 | 49.929 | 15.748 | 1.00 | 17.14 |
| ATOM | 2851 | N   | ALA | 372 | 15.856 | 50.644 | 17.519 | 1.00 | 15.40 |
| ATOM | 2852 | CA  | ALA | 372 | 17.061 | 49.883 | 17.148 | 1.00 | 16.23 |
| ATOM | 2853 | CB  | ALA | 372 | 18.152 | 50.046 | 18.197 | 1.00 | 15.66 |
| ATOM | 2854 | C   | ALA | 372 | 16.775 | 48.407 | 16.957 | 1.00 | 16.83 |
| ATOM | 2855 | O   | ALA | 372 | 17.125 | 47.838 | 15.923 | 1.00 | 18.06 |
| ATOM | 2856 | N   | ALA | 373 | 16.149 | 47.790 | 17.955 | 1.00 | 16.86 |
| ATOM | 2857 | CA  | ALA | 373 | 15.817 | 46.367 | 17.912 | 1.00 | 17.10 |
| ATOM | 2858 | CB  | ALA | 373 | 15.027 | 45.976 | 19.156 | 1.00 | 16.66 |
| ATOM | 2859 | C   | ALA | 373 | 15.024 | 46.018 | 16.665 | 1.00 | 18.79 |
| ATOM | 2860 | O   | ALA | 373 | 15.301 | 45.004 | 16.018 | 1.00 | 20.02 |
| ATOM | 2861 | N   | HIS | 374 | 14.037 | 46.841 | 16.316 | 1.00 | 19.22 |
| ATOM | 2862 | CA  | HIS | 374 | 13.243 | 46.560 | 15.122 | 1.00 | 20.89 |
| ATOM | 2863 | CB  | HIS | 374 | 12.025 | 47.489 | 15.052 | 1.00 | 20.98 |
| ATOM | 2864 | CG  | HIS | 374 | 10.948 | 47.131 | 16.029 | 1.00 | 19.79 |
| ATOM | 2865 | CD2 | HIS | 374 | 10.813 | 46.065 | 16.855 | 1.00 | 19.53 |
| ATOM | 2866 | ND1 | HIS | 374 |  9.833 | 47.914 | 16.229 | 1.00 | 19.92 |
| ATOM | 2867 | CE1 | HIS | 374 |  9.057 | 47.347 | 17.137 | 1.00 | 18.78 |
| ATOM | 2868 | NE2 | HIS | 374 |  9.629 | 46.223 | 17.532 | 1.00 | 18.61 |
| ATOM | 2869 | C   | HIS | 374 | 14.075 | 46.696 | 13.866 | 1.00 | 21.57 |
| ATOM | 2870 | O   | HIS | 374 | 14.136 | 45.789 | 13.058 | 1.00 | 21.42 |
| ATOM | 2871 | N   | MSE | 375 | 14.722 | 47.835 | 13.698 | 1.00 | 24.00 |
| ATOM | 2872 | CA  | MSE | 375 | 15.561 | 48.027 | 12.528 | 1.00 | 26.05 |
| ATOM | 2873 | CB  | MSE | 375 | 16.390 | 49.311 | 12.666 | 1.00 | 28.31 |
| ATOM | 2874 | CG  | MSE | 375 | 15.671 | 50.558 | 12.197 | 1.00 | 31.46 |
| ATOM | 2875 | SE  | MSE | 375 | 15.246 | 50.448 | 10.400 | 1.00 | 41.26 |
| ATOM | 2876 | CE  | MSE | 375 | 16.340 | 51.745 |  9.680 | 1.00 | 36.51 |
| ATOM | 2877 | C   | MSE | 375 | 16.476 | 46.810 | 12.390 | 1.00 | 25.84 |
| ATOM | 2878 | O   | MSE | 375 | 16.501 | 46.159 | 11.351 | 1.00 | 26.84 |
| ATOM | 2879 | N   | CYS | 376 | 17.200 | 46.489 | 13.455 | 1.00 | 25.61 |
| ATOM | 2880 | CA  | CYS | 376 | 18.107 | 45.349 | 13.436 | 1.00 | 25.11 |
| ATOM | 2881 | CB  | CYS | 376 | 18.693 | 45.117 | 14.831 | 1.00 | 26.04 |
| ATOM | 2882 | SG  | CYS | 376 | 20.038 | 43.879 | 14.876 | 1.00 | 27.98 |
| ATOM | 2883 | C   | CYS | 376 | 17.445 | 44.058 | 12.931 | 1.00 | 24.01 |
| ATOM | 2884 | O   | CYS | 376 | 18.015 | 43.369 | 12.078 | 1.00 | 24.35 |
| ATOM | 2885 | N   | SER | 377 | 16.251 | 43.741 | 13.443 | 1.00 | 22.14 |
| ATOM | 2886 | CA  | SER | 377 | 15.519 | 42.531 | 13.038 | 1.00 | 20.58 |
| ATOM | 2887 | CB  | SER | 377 | 14.203 | 42.399 | 13.811 | 1.00 | 20.36 |
| ATOM | 2888 | OG  | SER | 377 | 13.233 | 43.325 | 13.338 | 1.00 | 20.95 |
| ATOM | 2889 | C   | SER | 377 | 15.210 | 42.535 | 11.542 | 1.00 | 20.00 |
| ATOM | 2890 | O   | SER | 377 | 15.154 | 41.484 | 10.900 | 1.00 | 19.23 |
| ATOM | 2891 | N   | ALA | 378 | 14.995 | 43.715 | 10.980 | 1.00 | 19.64 |
| ATOM | 2892 | CA  | ALA | 378 | 14.723 | 43.787 |  9.549 | 1.00 | 19.32 |
| ATOM | 2893 | CB  | ALA | 378 | 14.521 | 45.243 |  9.119 | 1.00 | 18.02 |
| ATOM | 2894 | C   | ALA | 378 | 15.958 | 43.186 |  8.874 | 1.00 | 19.40 |
| ATOM | 2895 | O   | ALA | 378 | 15.860 | 42.230 |  8.093 | 1.00 | 18.55 |
| ATOM | 2896 | N   | GLY | 379 | 17.123 | 43.740 |  9.222 | 1.00 | 20.18 |
| ATOM | 2897 | CA  | GLY | 379 | 18.381 | 43.271 |  8.669 | 1.00 | 20.06 |
| ATOM | 2898 | C   | GLY | 379 | 18.547 | 41.762 |  8.734 | 1.00 | 19.52 |
| ATOM | 2899 | O   | GLY | 379 | 18.754 | 41.113 |  7.704 | 1.00 | 20.07 |
| ATOM | 2900 | N   | LEU | 380 | 18.442 | 41.201 |  9.936 | 1.00 | 18.61 |
| ATOM | 2901 | CA  | LEU | 380 | 18.596 | 39.763 | 10.110 | 1.00 | 18.74 |
| ATOM | 2902 | CB  | LEU | 380 | 18.489 | 39.371 | 11.579 | 1.00 | 18.49 |
| ATOM | 2903 | CG  | LEU | 380 | 18.774 | 37.881 | 11.816 | 1.00 | 17.82 |

*FIG. 4YY*

| ATOM | 2904 | CD1 | LEU | 380 | 20.215 | 37.586 | 11.383 | 1.00 | 16.94 |
| --- | --- | --- | --- | --- | --- | --- | --- | --- | --- |
| ATOM | 2905 | CD2 | LEU | 380 | 18.557 | 37.512 | 13.285 | 1.00 | 16.34 |
| ATOM | 2906 | C | LEU | 380 | 17.580 | 38.938 | 9.341 | 1.00 | 19.56 |
| ATOM | 2907 | O | LEU | 380 | 17.895 | 37.833 | 8.892 | 1.00 | 20.67 |
| ATOM | 2908 | N | ALA | 381 | 16.354 | 39.447 | 9.211 | 1.00 | 19.83 |
| ATOM | 2909 | CA | ALA | 381 | 15.311 | 38.713 | 8.496 | 1.00 | 20.17 |
| ATOM | 2910 | CB | ALA | 381 | 13.961 | 39.327 | 8.759 | 1.00 | 19.87 |
| ATOM | 2911 | C | ALA | 381 | 15.638 | 38.746 | 7.009 | 1.00 | 21.06 |
| ATOM | 2912 | O | ALA | 381 | 15.421 | 37.773 | 6.269 | 1.00 | 21.05 |
| ATOM | 2913 | N | GLY | 382 | 16.174 | 39.874 | 6.567 | 1.00 | 21.33 |
| ATOM | 2914 | CA | GLY | 382 | 16.561 | 39.965 | 5.175 | 1.00 | 22.63 |
| ATOM | 2915 | C | GLY | 382 | 17.670 | 38.954 | 4.903 | 1.00 | 23.10 |
| ATOM | 2916 | O | GLY | 382 | 17.708 | 38.319 | 3.832 | 1.00 | 23.74 |
| ATOM | 2917 | N | VAL | 383 | 18.579 | 38.778 | 5.859 | 1.00 | 21.83 |
| ATOM | 2918 | CA | VAL | 383 | 19.642 | 37.828 | 5.615 | 1.00 | 22.47 |
| ATOM | 2919 | CB | VAL | 383 | 20.786 | 37.967 | 6.643 | 1.00 | 22.80 |
| ATOM | 2920 | CG1 | VAL | 383 | 21.737 | 36.777 | 6.525 | 1.00 | 21.04 |
| ATOM | 2921 | CG2 | VAL | 383 | 21.562 | 39.298 | 6.396 | 1.00 | 21.85 |
| ATOM | 2922 | C | VAL | 383 | 19.075 | 36.423 | 5.639 | 1.00 | 22.92 |
| ATOM | 2923 | O | VAL | 383 | 19.199 | 35.681 | 4.675 | 1.00 | 23.65 |
| ATOM | 2924 | N | ILE | 384 | 18.414 | 36.061 | 6.724 | 1.00 | 23.52 |
| ATOM | 2925 | CA | ILE | 384 | 17.853 | 34.721 | 6.835 | 1.00 | 24.64 |
| ATOM | 2926 | CB | ILE | 384 | 17.124 | 34.551 | 8.179 | 1.00 | 24.17 |
| ATOM | 2927 | CG2 | ILE | 384 | 16.533 | 33.143 | 8.283 | 1.00 | 22.50 |
| ATOM | 2928 | CG1 | ILE | 384 | 18.112 | 34.810 | 9.318 | 1.00 | 23.69 |
| ATOM | 2929 | CD1 | ILE | 384 | 17.476 | 34.861 | 10.661 | 1.00 | 24.39 |
| ATOM | 2930 | C | ILE | 384 | 16.910 | 34.324 | 5.691 | 1.00 | 26.04 |
| ATOM | 2931 | O | ILE | 384 | 17.029 | 33.233 | 5.144 | 1.00 | 26.98 |
| ATOM | 2932 | N | ASN | 385 | 15.974 | 35.182 | 5.310 | 1.00 | 26.88 |
| ATOM | 2933 | CA | ASN | 385 | 15.097 | 34.785 | 4.218 | 1.00 | 27.99 |
| ATOM | 2934 | CB | ASN | 385 | 13.984 | 35.819 | 3.998 | 1.00 | 25.92 |
| ATOM | 2935 | CG | ASN | 385 | 13.038 | 35.918 | 5.174 | 1.00 | 23.68 |
| ATOM | 2936 | OD1 | ASN | 385 | 12.721 | 34.921 | 5.820 | 1.00 | 21.60 |
| ATOM | 2937 | ND2 | ASN | 385 | 12.567 | 37.128 | 5.448 | 1.00 | 23.03 |
| ATOM | 2938 | C | ASN | 385 | 15.888 | 34.579 | 2.915 | 1.00 | 29.62 |
| ATOM | 2939 | O | ASN | 385 | 15.610 | 33.647 | 2.143 | 1.00 | 29.62 |
| ATOM | 2940 | N | ARG | 386 | 16.869 | 35.440 | 2.660 | 1.00 | 31.30 |
| ATOM | 2941 | CA | ARG | 386 | 17.660 | 35.301 | 1.442 | 1.00 | 33.07 |
| ATOM | 2942 | CB | ARG | 386 | 18.840 | 36.261 | 1.446 | 1.00 | 32.62 |
| ATOM | 2943 | CG | ARG | 386 | 19.697 | 36.147 | 0.214 | 1.00 | 33.28 |
| ATOM | 2944 | CD | ARG | 386 | 20.908 | 37.059 | 0.284 | 1.00 | 34.52 |
| ATOM | 2945 | NE | ARG | 386 | 21.923 | 36.698 | -0.704 | 1.00 | 35.29 |
| ATOM | 2946 | CZ | ARG | 386 | 21.812 | 36.910 | -2.014 | 1.00 | 36.32 |
| ATOM | 2947 | NH1 | ARG | 386 | 20.729 | 37.492 | -2.518 | 1.00 | 35.95 |
| ATOM | 2948 | NH2 | ARG | 386 | 22.782 | 36.525 | -2.832 | 1.00 | 37.07 |
| ATOM | 2949 | C | ARG | 386 | 18.178 | 33.875 | 1.362 | 1.00 | 34.69 |
| ATOM | 2950 | O | ARG | 386 | 18.077 | 33.232 | 0.320 | 1.00 | 35.70 |
| ATOM | 2951 | N | MSE | 387 | 18.710 | 33.383 | 2.480 | 1.00 | 35.94 |
| ATOM | 2952 | CA | MSE | 387 | 19.250 | 32.036 | 2.560 | 1.00 | 37.39 |
| ATOM | 2953 | CB | MSE | 387 | 19.903 | 31.828 | 3.927 | 1.00 | 39.78 |
| ATOM | 2954 | CG | MSE | 387 | 21.099 | 32.754 | 4.186 | 1.00 | 42.37 |
| ATOM | 2955 | SE | MSE | 387 | 21.873 | 32.552 | 5.859 | 1.00 | 49.18 |
| ATOM | 2956 | CE | MSE | 387 | 21.738 | 30.694 | 6.097 | 1.00 | 44.67 |
| ATOM | 2957 | C | MSE | 387 | 18.179 | 30.976 | 2.311 | 1.00 | 38.50 |
| ATOM | 2958 | O | MSE | 387 | 18.463 | 29.927 | 1.721 | 1.00 | 37.80 |
| ATOM | 2959 | N | ARG | 388 | 16.954 | 31.255 | 2.769 | 1.00 | 40.15 |
| ATOM | 2960 | CA | ARG | 388 | 15.808 | 30.352 | 2.586 | 1.00 | 41.28 |

*FIG. 4ZZ*

| | | | | | | | | |
|---|---|---|---|---|---|---|---|---|
| ATOM | 2961 | CB | ARG | 388 | 14.554 | 30.941 | 3.245 | 1.00 42.50 |
| ATOM | 2962 | CG | ARG | 388 | 13.268 | 30.115 | 3.069 | 1.00 42.73 |
| ATOM | 2963 | CD | ARG | 388 | 12.266 | 30.443 | 4.178 | 1.00 43.15 |
| ATOM | 2964 | NE | ARG | 388 | 10.965 | 29.787 | 4.012 | 1.00 44.47 |
| ATOM | 2965 | CZ | ARG | 388 | 10.049 | 30.134 | 3.104 | 1.00 44.46 |
| ATOM | 2966 | NH1 | ARG | 388 | 10.283 | 31.139 | 2.269 | 1.00 44.11 |
| ATOM | 2967 | NH2 | ARG | 388 | 8.895 | 29.478 | 3.033 | 1.00 44.15 |
| ATOM | 2968 | C | ARG | 388 | 15.579 | 30.210 | 1.094 | 1.00 41.39 |
| ATOM | 2969 | O | ARG | 388 | 15.516 | 29.104 | 0.554 | 1.00 40.76 |
| ATOM | 2970 | N | GLU | 389 | 15.460 | 31.355 | 0.439 | 1.00 41.88 |
| ATOM | 2971 | CA | GLU | 389 | 15.275 | 31.405 | -0.997 | 1.00 43.37 |
| ATOM | 2972 | CB | GLU | 389 | 15.211 | 32.867 | -1.448 | 1.00 45.21 |
| ATOM | 2973 | CG | GLU | 389 | 15.227 | 33.079 | -2.957 | 1.00 48.22 |
| ATOM | 2974 | CD | GLU | 389 | 13.894 | 32.754 | -3.632 | 1.00 50.35 |
| ATOM | 2975 | OE1 | GLU | 389 | 13.850 | 32.799 | -4.891 | 1.00 51.00 |
| ATOM | 2976 | OE2 | GLU | 389 | 12.900 | 32.464 | -2.912 | 1.00 50.86 |
| ATOM | 2977 | C | GLU | 389 | 16.476 | 30.713 | -1.635 | 1.00 43.77 |
| ATOM | 2978 | O | GLU | 389 | 16.325 | 29.726 | -2.355 | 1.00 43.53 |
| ATOM | 2979 | N | SER | 390 | 17.671 | 31.227 | -1.335 | 1.00 43.84 |
| ATOM | 2980 | CA | SER | 390 | 18.925 | 30.697 | -1.878 | 1.00 43.61 |
| ATOM | 2981 | CB | SER | 390 | 20.112 | 31.549 | -1.425 | 1.00 43.41 |
| ATOM | 2982 | OG | SER | 390 | 20.229 | 32.703 | -2.241 | 1.00 43.45 |
| ATOM | 2983 | C | SER | 390 | 19.243 | 29.234 | -1.607 | 1.00 43.62 |
| ATOM | 2984 | O | SER | 390 | 20.126 | 28.671 | -2.251 | 1.00 44.11 |
| ATOM | 2985 | N | ARG | 391 | 18.555 | 28.614 | -0.660 | 1.00 43.22 |
| ATOM | 2986 | CA | ARG | 391 | 18.815 | 27.213 | -0.396 | 1.00 43.67 |
| ATOM | 2987 | CB | ARG | 391 | 19.174 | 26.994 | 1.078 | 1.00 42.72 |
| ATOM | 2988 | CG | ARG | 391 | 20.440 | 27.699 | 1.512 | 1.00 41.51 |
| ATOM | 2989 | CD | ARG | 391 | 20.907 | 27.245 | 2.892 | 1.00 39.51 |
| ATOM | 2990 | NE | ARG | 391 | 22.183 | 27.864 | 3.231 | 1.00 37.99 |
| ATOM | 2991 | CZ | ARG | 391 | 22.940 | 27.512 | 4.266 | 1.00 37.81 |
| ATOM | 2992 | NH1 | ARG | 391 | 22.545 | 26.540 | 5.070 | 1.00 36.05 |
| ATOM | 2993 | NH2 | ARG | 391 | 24.105 | 28.121 | 4.482 | 1.00 37.12 |
| ATOM | 2994 | C | ARG | 391 | 17.578 | 26.404 | -0.756 | 1.00 44.95 |
| ATOM | 2995 | O | ARG | 391 | 17.458 | 25.241 | -0.372 | 1.00 45.05 |
| ATOM | 2996 | N | SER | 392 | 16.666 | 27.023 | -1.502 | 1.00 46.71 |
| ATOM | 2997 | CA | SER | 392 | 15.420 | 26.367 | -1.895 | 1.00 48.25 |
| ATOM | 2998 | CB | SER | 392 | 15.631 | 25.468 | -3.121 | 1.00 48.10 |
| ATOM | 2999 | OG | SER | 392 | 15.610 | 26.216 | -4.326 | 1.00 48.60 |
| ATOM | 3000 | C | SER | 392 | 14.880 | 25.536 | -0.737 | 1.00 49.61 |
| ATOM | 3001 | O | SER | 392 | 14.601 | 24.344 | -0.882 | 1.00 49.37 |
| ATOM | 3002 | N | GLU | 393 | 14.749 | 26.175 | 0.420 | 1.00 51.58 |
| ATOM | 3003 | CA | GLU | 393 | 14.237 | 25.510 | 1.617 | 1.00 53.54 |
| ATOM | 3004 | CB | GLU | 393 | 15.085 | 25.897 | 2.842 | 1.00 54.33 |
| ATOM | 3005 | CG | GLU | 393 | 16.586 | 25.655 | 2.701 | 1.00 54.92 |
| ATOM | 3006 | CD | GLU | 393 | 17.057 | 24.420 | 3.450 | 1.00 55.87 |
| ATOM | 3007 | OE1 | GLU | 393 | 16.845 | 24.347 | 4.683 | 1.00 55.29 |
| ATOM | 3008 | OE2 | GLU | 393 | 17.646 | 23.523 | 2.806 | 1.00 56.69 |
| ATOM | 3009 | C | GLU | 393 | 12.793 | 25.961 | 1.838 | 1.00 54.20 |
| ATOM | 3010 | O | GLU | 393 | 12.482 | 27.151 | 1.693 | 1.00 53.70 |
| ATOM | 3011 | N | ASP | 394 | 11.907 | 25.026 | 2.173 | 1.00 55.42 |
| ATOM | 3012 | CA | ASP | 394 | 10.519 | 25.404 | 2.419 | 1.00 56.88 |
| ATOM | 3013 | CB | ASP | 394 | 9.585 | 24.194 | 2.400 | 1.00 58.69 |
| ATOM | 3014 | CG | ASP | 394 | 8.111 | 24.602 | 2.415 | 1.00 61.23 |
| ATOM | 3015 | OD1 | ASP | 394 | 7.691 | 25.298 | 3.376 | 1.00 62.29 |
| ATOM | 3016 | OD2 | ASP | 394 | 7.374 | 24.237 | 1.466 | 1.00 62.03 |
| ATOM | 3017 | C | ASP | 394 | 10.489 | 26.041 | 3.795 | 1.00 56.57 |

*FIG. 4AAA*

| ATOM | 3018 | O | ASP | 394 | 10.023 | 27.164 | 3.959 | 1.00 | 56.22 |
|---|---|---|---|---|---|---|---|---|---|
| ATOM | 3019 | N | VAL | 395 | 10.994 | 25.298 | 4.773 | 1.00 | 56.79 |
| ATOM | 3020 | CA | VAL | 395 | 11.086 | 25.756 | 6.153 | 1.00 | 57.23 |
| ATOM | 3021 | CB | VAL | 395 | 10.166 | 24.949 | 7.093 | 1.00 | 57.72 |
| ATOM | 3022 | CG1 | VAL | 395 | 10.444 | 25.320 | 8.548 | 1.00 | 57.64 |
| ATOM | 3023 | CG2 | VAL | 395 | 8.708 | 25.221 | 6.749 | 1.00 | 58.46 |
| ATOM | 3024 | C | VAL | 395 | 12.534 | 25.538 | 6.575 | 1.00 | 57.01 |
| ATOM | 3025 | O | VAL | 395 | 12.968 | 24.407 | 6.793 | 1.00 | 56.90 |
| ATOM | 3026 | N | MSE | 396 | 13.280 | 26.626 | 6.690 | 1.00 | 56.80 |
| ATOM | 3027 | CA | MSE | 396 | 14.682 | 26.536 | 7.058 | 1.00 | 56.12 |
| ATOM | 3028 | CB | MSE | 396 | 15.463 | 27.645 | 6.375 | 1.00 | 57.66 |
| ATOM | 3029 | CG | MSE | 396 | 16.932 | 27.623 | 6.690 | 1.00 | 60.51 |
| ATOM | 3030 | SE | MSE | 396 | 17.716 | 29.077 | 6.002 | 1.00 | 65.26 |
| ATOM | 3031 | CE | MSE | 396 | 17.988 | 28.564 | 4.293 | 1.00 | 64.74 |
| ATOM | 3032 | C | MSE | 396 | 14.964 | 26.600 | 8.545 | 1.00 | 54.59 |
| ATOM | 3033 | O | MSE | 396 | 14.487 | 27.491 | 9.245 | 1.00 | 54.08 |
| ATOM | 3034 | N | ARG | 397 | 15.740 | 25.637 | 9.025 | 1.00 | 53.05 |
| ATOM | 3035 | CA | ARG | 397 | 16.134 | 25.613 | 10.426 | 1.00 | 51.13 |
| ATOM | 3036 | CB | ARG | 397 | 16.226 | 24.181 | 10.951 | 1.00 | 52.77 |
| ATOM | 3037 | CG | ARG | 397 | 14.888 | 23.520 | 11.244 | 1.00 | 55.36 |
| ATOM | 3038 | CD | ARG | 397 | 15.132 | 22.079 | 11.671 | 1.00 | 58.69 |
| ATOM | 3039 | NE | ARG | 397 | 13.985 | 21.448 | 12.326 | 1.00 | 61.28 |
| ATOM | 3040 | CZ | ARG | 397 | 14.056 | 20.294 | 12.990 | 1.00 | 62.10 |
| ATOM | 3041 | NH1 | ARG | 397 | 15.215 | 19.651 | 13.078 | 1.00 | 62.57 |
| ATOM | 3042 | NH2 | ARG | 397 | 12.978 | 19.793 | 13.583 | 1.00 | 62.49 |
| ATOM | 3043 | C | ARG | 397 | 17.509 | 26.252 | 10.397 | 1.00 | 48.33 |
| ATOM | 3044 | O | ARG | 397 | 18.273 | 26.029 | 9.466 | 1.00 | 47.77 |
| ATOM | 3045 | N | ILE | 398 | 17.825 | 27.064 | 11.395 | 1.00 | 45.82 |
| ATOM | 3046 | CA | ILE | 398 | 19.120 | 27.721 | 11.396 | 1.00 | 43.01 |
| ATOM | 3047 | CB | ILE | 398 | 19.202 | 28.791 | 10.293 | 1.00 | 43.25 |
| ATOM | 3048 | CG2 | ILE | 398 | 18.161 | 29.864 | 10.532 | 1.00 | 43.18 |
| ATOM | 3049 | CG1 | ILE | 398 | 20.594 | 29.417 | 10.279 | 1.00 | 43.75 |
| ATOM | 3050 | CD1 | ILE | 398 | 20.768 | 30.466 | 9.206 | 1.00 | 44.64 |
| ATOM | 3051 | C | ILE | 398 | 19.441 | 28.381 | 12.717 | 1.00 | 40.64 |
| ATOM | 3052 | O | ILE | 398 | 18.557 | 28.890 | 13.404 | 1.00 | 40.10 |
| ATOM | 3053 | N | THR | 399 | 20.722 | 28.360 | 13.060 | 1.00 | 37.78 |
| ATOM | 3054 | CA | THR | 399 | 21.185 | 28.954 | 14.290 | 1.00 | 35.36 |
| ATOM | 3055 | CB | THR | 399 | 22.052 | 27.988 | 15.079 | 1.00 | 35.02 |
| ATOM | 3056 | OG1 | THR | 399 | 21.280 | 26.832 | 15.425 | 1.00 | 34.92 |
| ATOM | 3057 | CG2 | THR | 399 | 22.570 | 28.666 | 16.345 | 1.00 | 34.73 |
| ATOM | 3058 | C | THR | 399 | 22.001 | 30.197 | 13.994 | 1.00 | 34.71 |
| ATOM | 3059 | O | THR | 399 | 22.736 | 30.254 | 13.005 | 1.00 | 35.10 |
| ATOM | 3060 | N | VAL | 400 | 21.858 | 31.184 | 14.871 | 1.00 | 32.96 |
| ATOM | 3061 | CA | VAL | 400 | 22.539 | 32.457 | 14.759 | 1.00 | 31.07 |
| ATOM | 3062 | CB | VAL | 400 | 21.514 | 33.593 | 14.592 | 1.00 | 31.21 |
| ATOM | 3063 | CG1 | VAL | 400 | 22.211 | 34.934 | 14.415 | 1.00 | 31.76 |
| ATOM | 3064 | CG2 | VAL | 400 | 20.628 | 33.298 | 13.405 | 1.00 | 31.47 |
| ATOM | 3065 | C | VAL | 400 | 23.336 | 32.685 | 16.039 | 1.00 | 30.19 |
| ATOM | 3066 | O | VAL | 400 | 22.779 | 32.640 | 17.144 | 1.00 | 30.96 |
| ATOM | 3067 | N | GLY | 401 | 24.641 | 32.905 | 15.888 | 1.00 | 28.35 |
| ATOM | 3068 | CA | GLY | 401 | 25.482 | 33.150 | 17.041 | 1.00 | 24.47 |
| ATOM | 3069 | C | GLY | 401 | 25.487 | 34.641 | 17.235 | 1.00 | 23.04 |
| ATOM | 3070 | O | GLY | 401 | 25.595 | 35.388 | 16.260 | 1.00 | 20.38 |
| ATOM | 3071 | N | VAL | 402 | 25.367 | 35.086 | 18.482 | 1.00 | 23.36 |
| ATOM | 3072 | CA | VAL | 402 | 25.338 | 36.514 | 18.751 | 1.00 | 23.38 |
| ATOM | 3073 | CB | VAL | 402 | 23.927 | 36.960 | 19.124 | 1.00 | 22.79 |
| ATOM | 3074 | CG1 | VAL | 402 | 23.790 | 38.458 | 18.909 | 1.00 | 22.85 |

*FIG. 4BBB*

| ATOM | 3075 | CG2 | VAL | 402 | 22.895 | 36.176 | 18.320 | 1.00 | 22.42 |
| --- | --- | --- | --- | --- | --- | --- | --- | --- | --- |
| ATOM | 3076 | C | VAL | 402 | 26.252 | 36.899 | 19.893 | 1.00 | 24.25 |
| ATOM | 3077 | O | VAL | 402 | 26.484 | 36.098 | 20.794 | 1.00 | 25.20 |
| ATOM | 3078 | N | ASP | 403 | 26.770 | 38.124 | 19.848 | 1.00 | 24.83 |
| ATOM | 3079 | CA | ASP | 403 | 27.637 | 38.649 | 20.894 | 1.00 | 27.11 |
| ATOM | 3080 | CB | ASP | 403 | 29.078 | 38.212 | 20.691 | 1.00 | 30.98 |
| ATOM | 3081 | CG | ASP | 403 | 30.003 | 38.739 | 21.787 | 1.00 | 34.48 |
| ATOM | 3082 | OD1 | ASP | 403 | 29.887 | 39.938 | 22.122 | 1.00 | 36.02 |
| ATOM | 3083 | OD2 | ASP | 403 | 30.842 | 37.960 | 22.311 | 1.00 | 36.05 |
| ATOM | 3084 | C | ASP | 403 | 27.562 | 40.154 | 20.763 | 1.00 | 27.24 |
| ATOM | 3085 | O | ASP | 403 | 27.550 | 40.667 | 19.645 | 1.00 | 29.15 |
| ATOM | 3086 | N | GLY | 404 | 27.519 | 40.863 | 21.888 | 1.00 | 26.60 |
| ATOM | 3087 | CA | GLY | 404 | 27.410 | 42.316 | 21.863 | 1.00 | 26.50 |
| ATOM | 3088 | C | GLY | 404 | 26.750 | 42.829 | 23.137 | 1.00 | 27.10 |
| ATOM | 3089 | O | GLY | 404 | 25.810 | 42.193 | 23.665 | 1.00 | 26.90 |
| ATOM | 3090 | N | SER | 405 | 27.209 | 43.972 | 23.644 | 1.00 | 26.72 |
| ATOM | 3091 | CA | SER | 405 | 26.638 | 44.496 | 24.887 | 1.00 | 27.96 |
| ATOM | 3092 | CB | SER | 405 | 27.409 | 45.722 | 25.371 | 1.00 | 28.04 |
| ATOM | 3093 | OG | SER | 405 | 27.164 | 46.828 | 24.521 | 1.00 | 30.53 |
| ATOM | 3094 | C | SER | 405 | 25.168 | 44.857 | 24.738 | 1.00 | 28.25 |
| ATOM | 3095 | O | SER | 405 | 24.341 | 44.473 | 25.573 | 1.00 | 27.96 |
| ATOM | 3096 | N | VAL | 406 | 24.844 | 45.591 | 23.675 | 1.00 | 27.79 |
| ATOM | 3097 | CA | VAL | 406 | 23.465 | 45.992 | 23.445 | 1.00 | 28.13 |
| ATOM | 3098 | CB | VAL | 406 | 23.281 | 46.667 | 22.074 | 1.00 | 28.02 |
| ATOM | 3099 | CG1 | VAL | 406 | 21.814 | 47.063 | 21.908 | 1.00 | 27.91 |
| ATOM | 3100 | CG2 | VAL | 406 | 24.197 | 47.877 | 21.940 | 1.00 | 26.07 |
| ATOM | 3101 | C | VAL | 406 | 22.535 | 44.789 | 23.488 | 1.00 | 28.35 |
| ATOM | 3102 | O | VAL | 406 | 21.484 | 44.826 | 24.120 | 1.00 | 28.48 |
| ATOM | 3103 | N | TYR | 407 | 22.934 | 43.718 | 22.811 | 1.00 | 28.72 |
| ATOM | 3104 | CA | TYR | 407 | 22.130 | 42.493 | 22.736 | 1.00 | 28.45 |
| ATOM | 3105 | CB | TYR | 407 | 22.613 | 41.643 | 21.558 | 1.00 | 26.86 |
| ATOM | 3106 | CG | TYR | 407 | 21.831 | 40.373 | 21.341 | 1.00 | 25.29 |
| ATOM | 3107 | CD1 | TYR | 407 | 20.700 | 40.358 | 20.535 | 1.00 | 25.44 |
| ATOM | 3108 | CE1 | TYR | 407 | 19.964 | 39.189 | 20.346 | 1.00 | 25.93 |
| ATOM | 3109 | CD2 | TYR | 407 | 22.213 | 39.192 | 21.955 | 1.00 | 24.93 |
| ATOM | 3110 | CE2 | TYR | 407 | 21.488 | 38.021 | 21.780 | 1.00 | 25.18 |
| ATOM | 3111 | CZ | TYR | 407 | 20.362 | 38.024 | 20.974 | 1.00 | 26.03 |
| ATOM | 3112 | OH | TYR | 407 | 19.626 | 36.868 | 20.822 | 1.00 | 25.67 |
| ATOM | 3113 | C | TYR | 407 | 22.175 | 41.651 | 24.014 | 1.00 | 28.83 |
| ATOM | 3114 | O | TYR | 407 | 21.202 | 40.988 | 24.369 | 1.00 | 28.62 |
| ATOM | 3115 | N | LYS | 408 | 23.306 | 41.674 | 24.705 | 1.00 | 29.64 |
| ATOM | 3116 | CA | LYS | 408 | 23.440 | 40.881 | 25.916 | 1.00 | 30.07 |
| ATOM | 3117 | CB | LYS | 408 | 24.904 | 40.477 | 26.118 | 1.00 | 30.08 |
| ATOM | 3118 | CG | LYS | 408 | 25.442 | 39.556 | 25.030 | 1.00 | 30.61 |
| ATOM | 3119 | CD | LYS | 408 | 26.597 | 38.698 | 25.529 | 1.00 | 30.05 |
| ATOM | 3120 | CE | LYS | 408 | 26.799 | 37.515 | 24.601 | 1.00 | 30.22 |
| ATOM | 3121 | NZ | LYS | 408 | 27.828 | 36.573 | 25.097 | 1.00 | 30.20 |
| ATOM | 3122 | C | LYS | 408 | 22.940 | 41.551 | 27.185 | 1.00 | 30.82 |
| ATOM | 3123 | O | LYS | 408 | 22.327 | 40.901 | 28.038 | 1.00 | 31.98 |
| ATOM | 3124 | N | LEU | 409 | 23.176 | 42.853 | 27.296 | 1.00 | 30.97 |
| ATOM | 3125 | CA | LEU | 409 | 22.823 | 43.598 | 28.501 | 1.00 | 31.11 |
| ATOM | 3126 | CB | LEU | 409 | 24.006 | 44.482 | 28.875 | 1.00 | 30.54 |
| ATOM | 3127 | CG | LEU | 409 | 25.305 | 43.700 | 28.962 | 1.00 | 29.31 |
| ATOM | 3128 | CD1 | LEU | 409 | 26.372 | 44.591 | 29.597 | 1.00 | 29.41 |
| ATOM | 3129 | CD2 | LEU | 409 | 25.067 | 42.423 | 29.785 | 1.00 | 28.16 |
| ATOM | 3130 | C | LEU | 409 | 21.548 | 44.441 | 28.611 | 1.00 | 31.44 |
| ATOM | 3131 | O | LEU | 409 | 20.978 | 44.542 | 29.708 | 1.00 | 31.86 |

*FIG. 4CCC*

| ATOM | 3132 | N | HIS | 410 | 21.122 | 45.077 | 27.519 | 1.00 | 31.34 |
|---|---|---|---|---|---|---|---|---|---|
| ATOM | 3133 | CA | HIS | 410 | 19.929 | 45.912 | 27.572 | 1.00 | 30.80 |
| ATOM | 3134 | CB | HIS | 410 | 19.732 | 46.635 | 26.247 | 1.00 | 30.36 |
| ATOM | 3135 | CG | HIS | 410 | 18.703 | 47.717 | 26.303 | 1.00 | 29.89 |
| ATOM | 3136 | CD2 | HIS | 410 | 18.815 | 49.060 | 26.179 | 1.00 | 29.29 |
| ATOM | 3137 | ND1 | HIS | 410 | 17.362 | 47.457 | 26.508 | 1.00 | 30.79 |
| ATOM | 3138 | CE1 | HIS | 410 | 16.691 | 48.595 | 26.505 | 1.00 | 29.88 |
| ATOM | 3139 | NE2 | HIS | 410 | 17.548 | 49.583 | 26.309 | 1.00 | 30.87 |
| ATOM | 3140 | C | HIS | 410 | 18.728 | 45.031 | 27.900 | 1.00 | 31.41 |
| ATOM | 3141 | O | HIS | 410 | 18.467 | 44.055 | 27.207 | 1.00 | 31.97 |
| ATOM | 3142 | N | PRO | 411 | 17.985 | 45.376 | 28.969 | 1.00 | 31.63 |
| ATOM | 3143 | CD | PRO | 411 | 18.173 | 46.690 | 29.610 | 1.00 | 31.32 |
| ATOM | 3144 | CA | PRO | 411 | 16.798 | 44.708 | 29.518 | 1.00 | 31.33 |
| ATOM | 3145 | CB | PRO | 411 | 16.111 | 45.815 | 30.299 | 1.00 | 31.27 |
| ATOM | 3146 | CG | PRO | 411 | 17.257 | 46.599 | 30.822 | 1.00 | 32.32 |
| ATOM | 3147 | C | PRO | 411 | 15.827 | 44.037 | 28.571 | 1.00 | 32.09 |
| ATOM | 3148 | O | PRO | 411 | 15.362 | 42.920 | 28.838 | 1.00 | 32.76 |
| ATOM | 3149 | N | SER | 412 | 15.519 | 44.684 | 27.457 | 1.00 | 31.73 |
| ATOM | 3150 | CA | SER | 412 | 14.527 | 44.094 | 26.573 | 1.00 | 31.92 |
| ATOM | 3151 | CB | SER | 412 | 13.210 | 44.834 | 26.771 | 1.00 | 32.51 |
| ATOM | 3152 | OG | SER | 412 | 13.368 | 46.200 | 26.390 | 1.00 | 33.27 |
| ATOM | 3153 | C | SER | 412 | 14.838 | 44.047 | 25.082 | 1.00 | 31.91 |
| ATOM | 3154 | O | SER | 412 | 14.039 | 43.520 | 24.304 | 1.00 | 32.59 |
| ATOM | 3155 | N | PHE | 413 | 15.974 | 44.601 | 24.679 | 1.00 | 30.72 |
| ATOM | 3156 | CA | PHE | 413 | 16.348 | 44.615 | 23.271 | 1.00 | 30.13 |
| ATOM | 3157 | CB | PHE | 413 | 17.778 | 45.105 | 23.130 | 1.00 | 28.18 |
| ATOM | 3158 | CG | PHE | 413 | 18.213 | 45.285 | 21.716 | 1.00 | 25.96 |
| ATOM | 3159 | CD1 | PHE | 413 | 18.085 | 46.522 | 21.094 | 1.00 | 25.70 |
| ATOM | 3160 | CD2 | PHE | 413 | 18.772 | 44.233 | 21.015 | 1.00 | 24.47 |
| ATOM | 3161 | CE1 | PHE | 413 | 18.517 | 46.711 | 19.787 | 1.00 | 25.13 |
| ATOM | 3162 | CE2 | PHE | 413 | 19.208 | 44.408 | 19.707 | 1.00 | 24.84 |
| ATOM | 3163 | CZ | PHE | 413 | 19.082 | 45.652 | 19.092 | 1.00 | 24.48 |
| ATOM | 3164 | C | PHE | 413 | 16.232 | 43.228 | 22.645 | 1.00 | 31.20 |
| ATOM | 3165 | O | PHE | 413 | 15.571 | 43.026 | 21.612 | 1.00 | 31.56 |
| ATOM | 3166 | N | LYS | 414 | 16.888 | 42.268 | 23.275 | 1.00 | 31.75 |
| ATOM | 3167 | CA | LYS | 414 | 16.851 | 40.906 | 22.790 | 1.00 | 32.75 |
| ATOM | 3168 | CB | LYS | 414 | 17.626 | 39.999 | 23.755 | 1.00 | 33.66 |
| ATOM | 3169 | CG | LYS | 414 | 17.570 | 38.526 | 23.429 | 1.00 | 34.45 |
| ATOM | 3170 | CD | LYS | 414 | 18.732 | 37.744 | 24.049 | 1.00 | 36.05 |
| ATOM | 3171 | CE | LYS | 414 | 18.845 | 37.909 | 25.558 | 1.00 | 35.80 |
| ATOM | 3172 | NZ | LYS | 414 | 19.972 | 38.817 | 25.920 | 1.00 | 36.66 |
| ATOM | 3173 | C | LYS | 414 | 15.412 | 40.411 | 22.600 | 1.00 | 33.19 |
| ATOM | 3174 | O | LYS | 414 | 15.054 | 39.927 | 21.518 | 1.00 | 33.30 |
| ATOM | 3175 | N | GLU | 415 | 14.577 | 40.542 | 23.627 | 1.00 | 33.81 |
| ATOM | 3176 | CA | GLU | 415 | 13.193 | 40.071 | 23.513 | 1.00 | 34.53 |
| ATOM | 3177 | CB | GLU | 415 | 12.462 | 40.251 | 24.838 | 1.00 | 37.66 |
| ATOM | 3178 | CG | GLU | 415 | 13.062 | 39.497 | 26.002 | 1.00 | 42.83 |
| ATOM | 3179 | CD | GLU | 415 | 14.376 | 40.090 | 26.520 | 1.00 | 45.68 |
| ATOM | 3180 | OE1 | GLU | 415 | 14.523 | 41.339 | 26.526 | 1.00 | 47.31 |
| ATOM | 3181 | OE2 | GLU | 415 | 15.245 | 39.293 | 26.956 | 1.00 | 47.44 |
| ATOM | 3182 | C | GLU | 415 | 12.409 | 40.776 | 22.401 | 1.00 | 33.23 |
| ATOM | 3183 | O | GLU | 415 | 11.676 | 40.137 | 21.649 | 1.00 | 33.06 |
| ATOM | 3184 | N | ARG | 416 | 12.551 | 42.092 | 22.299 | 1.00 | 31.77 |
| ATOM | 3185 | CA | ARG | 416 | 11.841 | 42.825 | 21.264 | 1.00 | 30.32 |
| ATOM | 3186 | CB | ARG | 416 | 12.066 | 44.328 | 21.427 | 1.00 | 31.27 |
| ATOM | 3187 | CG | ARG | 416 | 11.645 | 44.875 | 22.796 | 1.00 | 33.92 |
| ATOM | 3188 | CD | ARG | 416 | 11.783 | 46.393 | 22.901 | 1.00 | 35.48 |

*FIG. 4DDD*

```
ATOM   3189  NE   ARG   416      11.545  46.866  24.267  1.00 38.24
ATOM   3190  CZ   ARG   416      11.982  48.030  24.746  1.00 39.11
ATOM   3191  NH1  ARG   416      12.676  48.850  23.967  1.00 39.89
ATOM   3192  NH2  ARG   416      11.754  48.365  26.009  1.00 38.52
ATOM   3193  C    ARG   416      12.379  42.354  19.916  1.00 29.08
ATOM   3194  O    ARG   416      11.620  42.159  18.964  1.00 28.85
ATOM   3195  N    PHE   417      13.694  42.144  19.862  1.00 27.59
ATOM   3196  CA   PHE   417      14.377  41.707  18.648  1.00 25.70
ATOM   3197  CB   PHE   417      15.886  41.687  18.890  1.00 23.64
ATOM   3198  CG   PHE   417      16.687  41.310  17.680  1.00 20.59
ATOM   3199  CD1  PHE   417      16.910  42.230  16.671  1.00 18.99
ATOM   3200  CD2  PHE   417      17.183  40.018  17.540  1.00 19.41
ATOM   3201  CE1  PHE   417      17.610  41.870  15.540  1.00 19.87
ATOM   3202  CE2  PHE   417      17.884  39.641  16.413  1.00 18.04
ATOM   3203  CZ   PHE   417      18.100  40.563  15.409  1.00 20.04
ATOM   3204  C    PHE   417      13.943  40.342  18.099  1.00 25.74
ATOM   3205  O    PHE   417      13.568  40.225  16.927  1.00 25.24
ATOM   3206  N    HIS   418      14.012  39.301  18.922  1.00 26.11
ATOM   3207  CA   HIS   418      13.612  37.962  18.459  1.00 26.79
ATOM   3208  CB   HIS   418      13.638  36.973  19.615  1.00 28.01
ATOM   3209  CG   HIS   418      14.973  36.854  20.279  1.00 28.81
ATOM   3210  CD2  HIS   418      16.168  37.425  19.989  1.00 29.42
ATOM   3211  ND1  HIS   418      15.182  36.067  21.389  1.00 28.15
ATOM   3212  CE1  HIS   418      16.446  36.157  21.755  1.00 29.43
ATOM   3213  NE2  HIS   418      17.067  36.974  20.924  1.00 29.74
ATOM   3214  C    HIS   418      12.209  37.985  17.876  1.00 26.41
ATOM   3215  O    HIS   418      11.976  37.565  16.733  1.00 26.40
ATOM   3216  N    ALA   419      11.284  38.487  18.688  1.00 25.83
ATOM   3217  CA   ALA   419       9.885  38.603  18.328  1.00 25.05
ATOM   3218  CB   ALA   419       9.182  39.454  19.352  1.00 24.80
ATOM   3219  C    ALA   419       9.731  39.215  16.943  1.00 25.35
ATOM   3220  O    ALA   419       9.146  38.601  16.029  1.00 25.99
ATOM   3221  N    SER   420      10.249  40.425  16.777  1.00 25.26
ATOM   3222  CA   SER   420      10.159  41.078  15.481  1.00 25.31
ATOM   3223  CB   SER   420      10.897  42.405  15.515  1.00 23.85
ATOM   3224  OG   SER   420      10.692  43.089  14.303  1.00 23.43
ATOM   3225  C    SER   420      10.751  40.170  14.391  1.00 26.14
ATOM   3226  O    SER   420      10.145  39.976  13.331  1.00 25.95
ATOM   3227  N    VAL   421      11.926  39.602  14.670  1.00 27.34
ATOM   3228  CA   VAL   421      12.602  38.699  13.733  1.00 28.41
ATOM   3229  CB   VAL   421      13.919  38.127  14.346  1.00 27.63
ATOM   3230  CG1  VAL   421      14.479  37.020  13.475  1.00 26.36
ATOM   3231  CG2  VAL   421      14.953  39.232  14.469  1.00 28.22
ATOM   3232  C    VAL   421      11.689  37.535  13.325  1.00 29.65
ATOM   3233  O    VAL   421      11.557  37.227  12.130  1.00 28.72
ATOM   3234  N    ARG   422      11.069  36.886  14.310  1.00 30.74
ATOM   3235  CA   ARG   422      10.165  35.775  14.014  1.00 32.79
ATOM   3236  CB   ARG   422       9.419  35.328  15.265  1.00 33.29
ATOM   3237  CG   ARG   422      10.259  35.197  16.512  1.00 34.47
ATOM   3238  CD   ARG   422      11.081  33.927  16.558  1.00 34.54
ATOM   3239  NE   ARG   422      11.862  33.905  17.795  1.00 35.75
ATOM   3240  CZ   ARG   422      12.824  33.028  18.066  1.00 35.45
ATOM   3241  NH1  ARG   422      13.127  32.085  17.180  1.00 35.35
ATOM   3242  NH2  ARG   422      13.490  33.108  19.215  1.00 33.55
ATOM   3243  C    ARG   422       9.123  36.277  13.019  1.00 33.41
ATOM   3244  O    ARG   422       8.949  35.728  11.929  1.00 33.68
ATOM   3245  N    ARG   423       8.446  37.348  13.417  1.00 34.00
```

*FIG. 4EEE*

| ATOM | 3246 | CA  | ARG | 423 | 7.394  | 37.946 | 12.622 | 1.00 | 34.13 |
| ATOM | 3247 | CB  | ARG | 423 | 7.022  | 39.301 | 13.207 | 1.00 | 35.16 |
| ATOM | 3248 | CG  | ARG | 423 | 5.538  | 39.584 | 13.202 | 1.00 | 36.10 |
| ATOM | 3249 | CD  | ARG | 423 | 5.212  | 40.831 | 14.012 | 1.00 | 37.57 |
| ATOM | 3250 | NE  | ARG | 423 | 5.482  | 40.682 | 15.441 | 1.00 | 38.90 |
| ATOM | 3251 | CZ  | ARG | 423 | 6.274  | 41.503 | 16.133 | 1.00 | 40.51 |
| ATOM | 3252 | NH1 | ARG | 423 | 6.874  | 42.523 | 15.513 | 1.00 | 41.42 |
| ATOM | 3253 | NH2 | ARG | 423 | 6.461  | 41.324 | 17.440 | 1.00 | 38.76 |
| ATOM | 3254 | C   | ARG | 423 | 7.754  | 38.100 | 11.165 | 1.00 | 33.94 |
| ATOM | 3255 | O   | ARG | 423 | 6.919  | 37.849 | 10.295 | 1.00 | 35.59 |
| ATOM | 3256 | N   | LEU | 424 | 8.993  | 38.494 | 10.884 | 1.00 | 32.85 |
| ATOM | 3257 | CA  | LEU | 424 | 9.418  | 38.699 | 9.497  | 1.00 | 31.57 |
| ATOM | 3258 | CB  | LEU | 424 | 10.474 | 39.788 | 9.450  | 1.00 | 28.75 |
| ATOM | 3259 | CG  | LEU | 424 | 10.030 | 41.129 | 10.003 | 1.00 | 27.64 |
| ATOM | 3260 | CD1 | LEU | 424 | 11.220 | 42.080 | 10.066 | 1.00 | 26.47 |
| ATOM | 3261 | CD2 | LEU | 424 | 8.942  | 41.686 | 9.115  | 1.00 | 27.23 |
| ATOM | 3262 | C   | LEU | 424 | 9.950  | 37.479 | 8.747  | 1.00 | 32.00 |
| ATOM | 3263 | O   | LEU | 424 | 10.232 | 37.562 | 7.551  | 1.00 | 31.15 |
| ATOM | 3264 | N   | THR | 425 | 10.065 | 36.343 | 9.424  | 1.00 | 33.88 |
| ATOM | 3265 | CA  | THR | 425 | 10.615 | 35.153 | 8.778  | 1.00 | 35.30 |
| ATOM | 3266 | CB  | THR | 425 | 11.886 | 34.722 | 9.495  | 1.00 | 35.17 |
| ATOM | 3267 | OG1 | THR | 425 | 11.580 | 34.463 | 10.874 | 1.00 | 35.24 |
| ATOM | 3268 | CG2 | THR | 425 | 12.939 | 35.817 | 9.399  | 1.00 | 35.16 |
| ATOM | 3269 | C   | THR | 425 | 9.711  | 33.923 | 8.675  | 1.00 | 37.00 |
| ATOM | 3270 | O   | THR | 425 | 10.059 | 32.854 | 9.182  | 1.00 | 37.54 |
| ATOM | 3271 | N   | PRO | 426 | 8.562  | 34.040 | 7.982  | 1.00 | 38.04 |
| ATOM | 3272 | CD  | PRO | 426 | 8.144  | 35.123 | 7.073  | 1.00 | 38.49 |
| ATOM | 3273 | CA  | PRO | 426 | 7.663  | 32.890 | 7.856  | 1.00 | 38.85 |
| ATOM | 3274 | CB  | PRO | 426 | 6.745  | 33.295 | 6.700  | 1.00 | 38.23 |
| ATOM | 3275 | CG  | PRO | 426 | 6.699  | 34.772 | 6.802  | 1.00 | 38.07 |
| ATOM | 3276 | C   | PRO | 426 | 8.445  | 31.615 | 7.527  | 1.00 | 39.83 |
| ATOM | 3277 | O   | PRO | 426 | 9.378  | 31.641 | 6.728  | 1.00 | 40.28 |
| ATOM | 3278 | N   | SER | 427 | 8.073  | 30.510 | 8.158  | 1.00 | 40.72 |
| ATOM | 3279 | CA  | SER | 427 | 8.713  | 29.232 | 7.892  | 1.00 | 41.82 |
| ATOM | 3280 | CB  | SER | 427 | 8.358  | 28.785 | 6.474  | 1.00 | 42.86 |
| ATOM | 3281 | OG  | SER | 427 | 6.954  | 28.802 | 6.287  | 1.00 | 44.69 |
| ATOM | 3282 | C   | SER | 427 | 10.234 | 29.228 | 8.068  | 1.00 | 42.10 |
| ATOM | 3283 | O   | SER | 427 | 10.981 | 28.899 | 7.140  | 1.00 | 41.85 |
| ATOM | 3284 | N   | CYS | 428 | 10.679 | 29.586 | 9.267  | 1.00 | 42.60 |
| ATOM | 3285 | CA  | CYS | 428 | 12.096 | 29.608 | 9.601  | 1.00 | 42.43 |
| ATOM | 3286 | CB  | CYS | 428 | 12.724 | 30.960 | 9.258  | 1.00 | 42.59 |
| ATOM | 3287 | SG  | CYS | 428 | 12.860 | 31.327 | 7.492  | 1.00 | 44.02 |
| ATOM | 3288 | C   | CYS | 428 | 12.195 | 29.381 | 11.096 | 1.00 | 42.45 |
| ATOM | 3289 | O   | CYS | 428 | 11.671 | 30.169 | 11.879 | 1.00 | 43.76 |
| ATOM | 3290 | N   | GLU | 429 | 12.846 | 28.296 | 11.494 | 1.00 | 42.34 |
| ATOM | 3291 | CA  | GLU | 429 | 13.014 | 27.995 | 12.909 | 1.00 | 41.23 |
| ATOM | 3292 | CB  | GLU | 429 | 13.030 | 26.486 | 13.146 | 1.00 | 42.97 |
| ATOM | 3293 | CG  | GLU | 429 | 11.699 | 25.796 | 12.933 | 1.00 | 45.48 |
| ATOM | 3294 | CD  | GLU | 429 | 11.847 | 24.282 | 12.925 | 1.00 | 47.43 |
| ATOM | 3295 | OE1 | GLU | 429 | 12.518 | 23.756 | 13.847 | 1.00 | 48.77 |
| ATOM | 3296 | OE2 | GLU | 429 | 11.298 | 23.623 | 12.005 | 1.00 | 48.07 |
| ATOM | 3297 | C   | GLU | 429 | 14.341 | 28.587 | 13.346 | 1.00 | 39.77 |
| ATOM | 3298 | O   | GLU | 429 | 15.370 | 27.902 | 13.352 | 1.00 | 39.92 |
| ATOM | 3299 | N   | ILE | 430 | 14.315 | 29.864 | 13.708 | 1.00 | 38.09 |
| ATOM | 3300 | CA  | ILE | 430 | 15.514 | 30.560 | 14.142 | 1.00 | 36.48 |
| ATOM | 3301 | CB  | ILE | 430 | 15.341 | 32.070 | 13.998 | 1.00 | 35.17 |
| ATOM | 3302 | CG2 | ILE | 430 | 16.659 | 32.770 | 14.280 | 1.00 | 34.48 |

*FIG. 4FFF*

| | | | | | | | | |
|---|---|---|---|---|---|---|---|---|
| ATOM | 3303 | CG1 | ILE | 430 | 14.839 | 32.390 | 12.589 | 1.00 35.30 |
| ATOM | 3304 | CD1 | ILE | 430 | 14.669 | 33.866 | 12.310 | 1.00 34.88 |
| ATOM | 3305 | C | ILE | 430 | 15.872 | 30.254 | 15.591 | 1.00 37.06 |
| ATOM | 3306 | O | ILE | 430 | 15.044 | 30.399 | 16.495 | 1.00 38.13 |
| ATOM | 3307 | N | THR | 431 | 17.109 | 29.823 | 15.808 | 1.00 36.61 |
| ATOM | 3308 | CA | THR | 431 | 17.600 | 29.520 | 17.146 | 1.00 36.17 |
| ATOM | 3309 | CB | THR | 431 | 18.067 | 28.053 | 17.240 | 1.00 36.58 |
| ATOM | 3310 | OG1 | THR | 431 | 16.950 | 27.180 | 17.031 | 1.00 36.34 |
| ATOM | 3311 | CG2 | THR | 431 | 18.692 | 27.774 | 18.604 | 1.00 36.38 |
| ATOM | 3312 | C | THR | 431 | 18.796 | 30.441 | 17.396 | 1.00 36.13 |
| ATOM | 3313 | O | THR | 431 | 19.705 | 30.513 | 16.569 | 1.00 36.10 |
| ATOM | 3314 | N | PHE | 432 | 18.804 | 31.157 | 18.514 | 1.00 35.79 |
| ATOM | 3315 | CA | PHE | 432 | 19.926 | 32.054 | 18.794 | 1.00 35.93 |
| ATOM | 3316 | CB | PHE | 432 | 19.443 | 33.450 | 19.232 | 1.00 34.31 |
| ATOM | 3317 | CG | PHE | 432 | 18.643 | 34.194 | 18.188 | 1.00 32.53 |
| ATOM | 3318 | CD1 | PHE | 432 | 17.271 | 33.977 | 18.048 | 1.00 31.59 |
| ATOM | 3319 | CD2 | PHE | 432 | 19.262 | 35.124 | 17.353 | 1.00 31.00 |
| ATOM | 3320 | CE1 | PHE | 432 | 16.527 | 34.676 | 17.092 | 1.00 30.53 |
| ATOM | 3321 | CE2 | PHE | 432 | 18.525 | 35.826 | 16.395 | 1.00 30.25 |
| ATOM | 3322 | CZ | PHE | 432 | 17.154 | 35.600 | 16.266 | 1.00 30.11 |
| ATOM | 3323 | C | PHE | 432 | 20.767 | 31.483 | 19.917 | 1.00 37.08 |
| ATOM | 3324 | O | PHE | 432 | 20.248 | 30.772 | 20.779 | 1.00 38.85 |
| ATOM | 3325 | N | ILE | 433 | 22.063 | 31.774 | 19.906 | 1.00 37.32 |
| ATOM | 3326 | CA | ILE | 433 | 22.933 | 31.321 | 20.983 | 1.00 38.46 |
| ATOM | 3327 | CB | ILE | 433 | 23.526 | 29.890 | 20.722 | 1.00 39.06 |
| ATOM | 3328 | CG2 | ILE | 433 | 22.398 | 28.863 | 20.624 | 1.00 38.62 |
| ATOM | 3329 | CG1 | ILE | 433 | 24.367 | 29.861 | 19.449 | 1.00 39.03 |
| ATOM | 3330 | CD1 | ILE | 433 | 25.028 | 28.520 | 19.227 | 1.00 38.32 |
| ATOM | 3331 | C | ILE | 433 | 24.039 | 32.358 | 21.161 | 1.00 39.33 |
| ATOM | 3332 | O | ILE | 433 | 24.429 | 33.034 | 20.201 | 1.00 39.15 |
| ATOM | 3333 | N | GLU | 434 | 24.527 | 32.505 | 22.388 | 1.00 40.58 |
| ATOM | 3334 | CA | GLU | 434 | 25.559 | 33.498 | 22.669 | 1.00 42.92 |
| ATOM | 3335 | CB | GLU | 434 | 25.152 | 34.312 | 23.885 | 1.00 43.91 |
| ATOM | 3336 | CG | GLU | 434 | 23.769 | 34.883 | 23.744 | 1.00 45.53 |
| ATOM | 3337 | CD | GLU | 434 | 23.342 | 35.640 | 24.965 | 1.00 46.68 |
| ATOM | 3338 | OE1 | GLU | 434 | 23.436 | 35.072 | 26.074 | 1.00 47.18 |
| ATOM | 3339 | OE2 | GLU | 434 | 22.910 | 36.802 | 24.816 | 1.00 48.77 |
| ATOM | 3340 | C | GLU | 434 | 26.965 | 32.950 | 22.865 | 1.00 44.01 |
| ATOM | 3341 | O | GLU | 434 | 27.206 | 32.058 | 23.680 | 1.00 44.48 |
| ATOM | 3342 | N | SER | 435 | 27.901 | 33.518 | 22.119 | 1.00 45.00 |
| ATOM | 3343 | CA | SER | 435 | 29.284 | 33.075 | 22.167 | 1.00 46.11 |
| ATOM | 3344 | CB | SER | 435 | 30.077 | 33.779 | 21.057 | 1.00 46.95 |
| ATOM | 3345 | OG | SER | 435 | 29.839 | 35.186 | 21.053 | 1.00 47.94 |
| ATOM | 3346 | C | SER | 435 | 29.984 | 33.274 | 23.507 | 1.00 46.36 |
| ATOM | 3347 | O | SER | 435 | 30.043 | 34.396 | 24.022 | 1.00 46.31 |
| ATOM | 3348 | N | GLU | 436 | 30.505 | 32.180 | 24.069 | 1.00 46.22 |
| ATOM | 3349 | CA | GLU | 436 | 31.248 | 32.250 | 25.330 | 1.00 46.33 |
| ATOM | 3350 | CB | GLU | 436 | 31.322 | 30.884 | 26.020 | 1.00 47.64 |
| ATOM | 3351 | CG | GLU | 436 | 32.144 | 30.908 | 27.317 | 1.00 50.83 |
| ATOM | 3352 | CD | GLU | 436 | 32.726 | 29.541 | 27.711 | 1.00 52.03 |
| ATOM | 3353 | OE1 | GLU | 436 | 31.951 | 28.585 | 27.970 | 1.00 52.84 |
| ATOM | 3354 | OE2 | GLU | 436 | 33.972 | 29.428 | 27.765 | 1.00 52.07 |
| ATOM | 3355 | C | GLU | 436 | 32.650 | 32.671 | 24.912 | 1.00 45.58 |
| ATOM | 3356 | O | GLU | 436 | 33.446 | 31.843 | 24.463 | 1.00 45.50 |
| ATOM | 3357 | N | GLU | 437 | 32.950 | 33.956 | 25.051 | 1.00 44.67 |
| ATOM | 3358 | CA | GLU | 437 | 34.252 | 34.462 | 24.643 | 1.00 44.13 |
| ATOM | 3359 | CB | GLU | 437 | 35.328 | 34.050 | 25.652 | 1.00 43.61 |

*FIG. 4GGG*

| | | | | | | | | |
|---|---|---|---|---|---|---|---|---|
| ATOM | 3360 | CG | GLU | 437 | 36.745 | 34.334 | 25.190 | 1.00 43.39 |
| ATOM | 3361 | CD | GLU | 437 | 36.931 | 35.752 | 24.678 | 1.00 43.50 |
| ATOM | 3362 | OE1 | GLU | 437 | 36.976 | 36.680 | 25.514 | 1.00 44.49 |
| ATOM | 3363 | OE2 | GLU | 437 | 37.025 | 35.940 | 23.441 | 1.00 42.17 |
| ATOM | 3364 | C | GLU | 437 | 34.569 | 33.880 | 23.264 | 1.00 43.56 |
| ATOM | 3365 | O | GLU | 437 | 35.530 | 33.131 | 23.108 | 1.00 45.30 |
| ATOM | 3366 | N | GLY | 438 | 33.757 | 34.225 | 22.266 | 1.00 41.68 |
| ATOM | 3367 | CA | GLY | 438 | 33.958 | 33.700 | 20.926 | 1.00 39.44 |
| ATOM | 3368 | C | GLY | 438 | 34.748 | 34.538 | 19.934 | 1.00 38.11 |
| ATOM | 3369 | O | GLY | 438 | 34.932 | 34.130 | 18.791 | 1.00 37.45 |
| ATOM | 3370 | N | SER | 439 | 35.213 | 35.713 | 20.329 | 1.00 37.14 |
| ATOM | 3371 | CA | SER | 439 | 35.980 | 36.502 | 19.386 | 1.00 36.86 |
| ATOM | 3372 | CB | SER | 439 | 35.916 | 37.983 | 19.714 | 1.00 36.81 |
| ATOM | 3373 | OG | SER | 439 | 36.825 | 38.678 | 18.878 | 1.00 35.32 |
| ATOM | 3374 | C | SER | 439 | 37.420 | 36.053 | 19.444 | 1.00 36.74 |
| ATOM | 3375 | O | SER | 439 | 38.192 | 36.265 | 18.513 | 1.00 36.37 |
| ATOM | 3376 | N | GLY | 440 | 37.774 | 35.439 | 20.562 | 1.00 36.58 |
| ATOM | 3377 | CA | GLY | 440 | 39.126 | 34.957 | 20.746 | 1.00 36.42 |
| ATOM | 3378 | C | GLY | 440 | 39.207 | 33.518 | 20.302 | 1.00 36.28 |
| ATOM | 3379 | O | GLY | 440 | 40.146 | 33.140 | 19.613 | 1.00 36.20 |
| ATOM | 3380 | N | ARG | 441 | 38.224 | 32.714 | 20.699 | 1.00 36.09 |
| ATOM | 3381 | CA | ARG | 441 | 38.190 | 31.309 | 20.312 | 1.00 37.16 |
| ATOM | 3382 | CB | ARG | 441 | 37.151 | 30.562 | 21.138 | 1.00 37.34 |
| ATOM | 3383 | CG | ARG | 441 | 37.312 | 30.717 | 22.632 | 1.00 39.57 |
| ATOM | 3384 | CD | ARG | 441 | 36.334 | 29.806 | 23.375 | 1.00 42.28 |
| ATOM | 3385 | NE | ARG | 441 | 35.270 | 29.339 | 22.488 | 1.00 44.36 |
| ATOM | 3386 | CZ | ARG | 441 | 34.240 | 28.585 | 22.862 | 1.00 45.80 |
| ATOM | 3387 | NH1 | ARG | 441 | 34.103 | 28.192 | 24.127 | 1.00 45.87 |
| ATOM | 3388 | NH2 | ARG | 441 | 33.346 | 28.214 | 21.955 | 1.00 47.26 |
| ATOM | 3389 | C | ARG | 441 | 37.848 | 31.179 | 18.821 | 1.00 37.42 |
| ATOM | 3390 | O | ARG | 441 | 38.103 | 30.151 | 18.189 | 1.00 37.52 |
| ATOM | 3391 | N | GLY | 442 | 37.270 | 32.234 | 18.262 | 1.00 37.34 |
| ATOM | 3392 | CA | GLY | 442 | 36.906 | 32.204 | 16.863 | 1.00 37.39 |
| ATOM | 3393 | C | GLY | 442 | 38.165 | 32.308 | 16.048 | 1.00 37.47 |
| ATOM | 3394 | O | GLY | 442 | 38.483 | 31.410 | 15.278 | 1.00 37.51 |
| ATOM | 3395 | N | ALA | 443 | 38.887 | 33.408 | 16.241 | 1.00 38.17 |
| ATOM | 3396 | CA | ALA | 443 | 40.134 | 33.660 | 15.526 | 1.00 38.50 |
| ATOM | 3397 | CB | ALA | 443 | 40.739 | 34.999 | 15.967 | 1.00 36.50 |
| ATOM | 3398 | C | ALA | 443 | 41.127 | 32.521 | 15.759 | 1.00 39.03 |
| ATOM | 3399 | O | ALA | 443 | 42.015 | 32.297 | 14.941 | 1.00 39.36 |
| ATOM | 3400 | N | ALA | 444 | 40.977 | 31.807 | 16.875 | 1.00 39.93 |
| ATOM | 3401 | CA | ALA | 444 | 41.864 | 30.685 | 17.172 | 1.00 40.31 |
| ATOM | 3402 | CB | ALA | 444 | 41.724 | 30.242 | 18.623 | 1.00 39.25 |
| ATOM | 3403 | C | ALA | 444 | 41.427 | 29.569 | 16.246 | 1.00 40.97 |
| ATOM | 3404 | O | ALA | 444 | 42.146 | 29.210 | 15.312 | 1.00 41.31 |
| ATOM | 3405 | N | LEU | 445 | 40.233 | 29.038 | 16.501 | 1.00 41.41 |
| ATOM | 3406 | CA | LEU | 445 | 39.678 | 27.960 | 15.690 | 1.00 41.97 |
| ATOM | 3407 | CB | LEU | 445 | 38.195 | 27.776 | 16.024 | 1.00 40.09 |
| ATOM | 3408 | CG | LEU | 445 | 37.954 | 26.806 | 17.182 | 1.00 39.14 |
| ATOM | 3409 | CD1 | LEU | 445 | 36.750 | 27.233 | 17.982 | 1.00 39.27 |
| ATOM | 3410 | CD2 | LEU | 445 | 37.781 | 25.399 | 16.647 | 1.00 37.36 |
| ATOM | 3411 | C | LEU | 445 | 39.860 | 28.156 | 14.176 | 1.00 43.29 |
| ATOM | 3412 | O | LEU | 445 | 39.918 | 27.179 | 13.427 | 1.00 43.28 |
| ATOM | 3413 | N | VAL | 446 | 39.955 | 29.406 | 13.729 | 1.00 44.66 |
| ATOM | 3414 | CA | VAL | 446 | 40.136 | 29.684 | 12.307 | 1.00 46.32 |
| ATOM | 3415 | CB | VAL | 446 | 39.687 | 31.120 | 11.948 | 1.00 46.15 |
| ATOM | 3416 | CG1 | VAL | 446 | 40.356 | 31.578 | 10.653 | 1.00 46.15 |

*FIG. 4HHH*

| | | | | | | | | |
|---|---|---|---|---|---|---|---|---|
| ATOM | 3417 | CG2 | VAL | 446 | 38.164 | 31.160 | 11.793 | 1.00 45.75 |
| ATOM | 3418 | C | VAL | 446 | 41.597 | 29.503 | 11.944 | 1.00 48.03 |
| ATOM | 3419 | O | VAL | 446 | 41.929 | 29.105 | 10.825 | 1.00 48.75 |
| ATOM | 3420 | N | SER | 447 | 42.465 | 29.802 | 12.904 | 1.00 49.63 |
| ATOM | 3421 | CA | SER | 447 | 43.902 | 29.657 | 12.725 | 1.00 50.76 |
| ATOM | 3422 | CB | SER | 447 | 44.635 | 30.267 | 13.918 | 1.00 50.76 |
| ATOM | 3423 | OG | SER | 447 | 44.377 | 31.659 | 14.021 | 1.00 50.83 |
| ATOM | 3424 | C | SER | 447 | 44.259 | 28.173 | 12.612 | 1.00 52.07 |
| ATOM | 3425 | O | SER | 447 | 44.923 | 27.753 | 11.662 | 1.00 52.17 |
| ATOM | 3426 | N | ALA | 448 | 43.804 | 27.387 | 13.584 | 1.00 53.51 |
| ATOM | 3427 | CA | ALA | 448 | 44.071 | 25.953 | 13.621 | 1.00 55.46 |
| ATOM | 3428 | CB | ALA | 448 | 43.273 | 25.306 | 14.745 | 1.00 55.02 |
| ATOM | 3429 | C | ALA | 448 | 43.751 | 25.263 | 12.300 | 1.00 57.02 |
| ATOM | 3430 | O | ALA | 448 | 44.599 | 24.564 | 11.726 | 1.00 57.18 |
| ATOM | 3431 | N | VAL | 449 | 42.523 | 25.457 | 11.825 | 1.00 58.39 |
| ATOM | 3432 | CA | VAL | 449 | 42.093 | 24.841 | 10.579 | 1.00 59.69 |
| ATOM | 3433 | CB | VAL | 449 | 40.571 | 24.977 | 10.382 | 1.00 59.67 |
| ATOM | 3434 | CG1 | VAL | 449 | 40.152 | 24.262 | 9.112 | 1.00 60.28 |
| ATOM | 3435 | CG2 | VAL | 449 | 39.833 | 24.384 | 11.577 | 1.00 59.48 |
| ATOM | 3436 | C | VAL | 449 | 42.821 | 25.482 | 9.403 | 1.00 60.70 |
| ATOM | 3437 | O | VAL | 449 | 42.903 | 24.898 | 8.321 | 1.00 61.00 |
| ATOM | 3438 | N | ALA | 450 | 43.361 | 26.677 | 9.627 | 1.00 61.41 |
| ATOM | 3439 | CA | ALA | 450 | 44.093 | 27.392 | 8.591 | 1.00 62.12 |
| ATOM | 3440 | CB | ALA | 450 | 43.981 | 28.889 | 8.814 | 1.00 62.32 |
| ATOM | 3441 | C | ALA | 450 | 45.558 | 26.973 | 8.606 | 1.00 63.02 |
| ATOM | 3442 | O | ALA | 450 | 46.437 | 27.748 | 8.217 | 1.00 62.75 |
| ATOM | 3443 | N | CYS | 451 | 45.807 | 25.744 | 9.061 | 1.00 64.03 |
| ATOM | 3444 | CA | CYS | 451 | 47.160 | 25.183 | 9.148 | 1.00 65.19 |
| ATOM | 3445 | CB | CYS | 451 | 47.530 | 24.440 | 7.850 | 1.00 65.75 |
| ATOM | 3446 | SG | CYS | 451 | 46.901 | 22.720 | 7.723 | 1.00 66.86 |
| ATOM | 3447 | C | CYS | 451 | 48.239 | 26.217 | 9.474 | 1.00 65.22 |
| ATOM | 3448 | O | CYS | 451 | 47.929 | 27.230 | 10.144 | 1.00 65.18 |
| ATOM | 3449 | OXT | CYS | 451 | 49.398 | 25.979 | 9.073 | 1.00 65.50 |
| ATOM | 3450 | C1 | HEX | 1 | 31.023 | 47.521 | 12.611 | 1.00 25.83 |
| ATOM | 3451 | C2 | HEX | 1 | 32.239 | 47.182 | 11.801 | 1.00 25.25 |
| ATOM | 3452 | C3 | HEX | 1 | 32.203 | 45.697 | 11.565 | 1.00 25.11 |
| ATOM | 3453 | C4 | HEX | 1 | 32.071 | 44.939 | 12.862 | 1.00 24.99 |
| ATOM | 3454 | C5 | HEX | 1 | 31.030 | 45.591 | 13.785 | 1.00 25.34 |
| ATOM | 3455 | C6 | HEX | 1 | 30.772 | 44.921 | 15.126 | 1.00 25.58 |
| ATOM | 3456 | O1 | HEX | 1 | 30.750 | 48.942 | 12.579 | 1.00 27.04 |
| ATOM | 3457 | O2 | HEX | 1 | 32.183 | 47.912 | 10.609 | 1.00 24.71 |
| ATOM | 3458 | O3 | HEX | 1 | 33.337 | 45.251 | 10.836 | 1.00 25.99 |
| ATOM | 3459 | O4 | HEX | 1 | 31.699 | 43.621 | 12.545 | 1.00 25.85 |
| ATOM | 3460 | O5 | HEX | 1 | 31.267 | 46.968 | 13.935 | 1.00 25.37 |
| ATOM | 3461 | O6 | HEX | 1 | 31.835 | 45.222 | 16.009 | 1.00 27.23 |
| ATOM | 3462 | C1 | LIG | 1 | 30.034 | 26.620 | 8.669 | 1.00 35.87 |
| ATOM | 3463 | C2 | LIG | 1 | 29.909 | 27.259 | 10.064 | 1.00 34.82 |
| ATOM | 3464 | C3 | LIG | 1 | 31.308 | 27.852 | 10.344 | 1.00 35.54 |
| ATOM | 3465 | C4 | LIG | 1 | 32.212 | 27.447 | 9.148 | 1.00 35.52 |
| ATOM | 3466 | C5 | LIG | 1 | 31.520 | 26.207 | 8.584 | 1.00 35.20 |
| ATOM | 3467 | C6 | LIG | 1 | 33.670 | 27.245 | 9.637 | 1.00 36.33 |
| ATOM | 3468 | C7 | LIG | 1 | 34.562 | 26.321 | 8.758 | 1.00 37.11 |
| ATOM | 3469 | C8 | LIG | 1 | 35.946 | 26.832 | 8.778 | 1.00 36.91 |
| ATOM | 3470 | N9 | LIG | 1 | 36.382 | 27.317 | 7.570 | 1.00 36.92 |
| ATOM | 3471 | C10 | LIG | 1 | 37.668 | 27.907 | 7.331 | 1.00 36.42 |
| ATOM | 3472 | N11 | LIG | 1 | 38.035 | 28.336 | 6.087 | 1.00 37.39 |
| ATOM | 3473 | C12 | LIG | 1 | 39.058 | 28.930 | 6.462 | 1.00 36.99 |

*FIG. 4III*

| | | | | | | | | |
|---|---|---|---|---|---|---|---|---|
| ATOM | 3474 | C13 | LIG | 1 | 39.426 | 29.003 | 7.575 | 1.00 37.10 |
| ATOM | 3475 | S14 | LIG | 1 | 38.681 | 28.342 | 8.700 | 1.00 37.86 |
| ATOM | 3476 | O15 | LIG | 1 | 36.640 | 26.843 | 9.817 | 1.00 38.32 |
| ATOM | 3477 | C16 | LIG | 1 | 34.538 | 24.890 | 9.296 | 1.00 37.59 |
| ATOM | 3478 | C17 | LIG | 1 | 34.906 | 24.620 | 10.610 | 1.00 37.22 |
| ATOM | 3479 | C18 | LIG | 1 | 34.658 | 23.346 | 11.130 | 1.00 38.09 |
| ATOM | 3480 | N19 | LIG | 1 | 34.084 | 22.371 | 10.404 | 1.00 38.80 |
| ATOM | 3481 | C20 | LIG | 1 | 33.729 | 22.598 | 9.128 | 1.00 38.90 |
| ATOM | 3482 | C21 | LIG | 1 | 33.942 | 23.860 | 8.546 | 1.00 38.73 |
| ATOM | 3483 | K1 | K | 1 | 32.471 | 32.037 | -7.104 | 1.00 46.91 |

*FIG. 4JJJ* ured by the identification of
patients that express a mutant form of GK with increased
enzymatic activity. These patients exhibit a fasting hypoglycemia associated with an inappropriately elevated level of
plasma insulin (Glaser, B., Kesavan, P., Heyman, M. et al.,
*New England J. Med.* 338, 226–230, 1998). While mutations
of the GK gene are not found in the majority of patients with
type II diabetes, compounds that activate GK and, thereby,
increase the sensitivity of the GK sensor system will still be
CRYSTALS OF GLUCOKINASE AND METHODS OF GROWING THEM This application claims priority of Provisional application Serial No. 60/341,988, filed Dec. 19, 2001.

FIELD OF THE INVENTION

The invention relates to crystalline forms of Gluckokinase of sufficient size and quality to obtain structural data by X-ray crystallography and to methods of growing such crystals.

BACKGROUND OF THE INVENTION

Glucokinase (GK) is one of four hexokinases found in mammals [Colowick, S. P., in *The Enzymes*, Vol. 9 (P. Boyer, ed.) Academic Press, New York, N.Y., pages 1–48, 1973]. The hexokinases catalyze the first step in the metabolism of glucose, i.e., the conversion of glucose to glucose-6-phosphate. Glucokinase has a limited cellular distribution, being found principally in pancreatic β-cells and liver parenchymal cells. In addition, GK is a rate-controlling enzyme for glucose metabolism in these two cell types that are known to play critical roles in whole-body glucose homeostasis [Chipkin, S. R., Kelly, K. L., and Ruderman, N. B. in *Joslin's Diabetes* (C. R. Khan and G. C. Wier, eds.), Lea and Febiger, Philadelphia, Pa., pages 97–115, 1994]. The concentration of glucose at which GK demonstrates half-maximal activity is approximately 8 mM. The other three hexokinases are saturated with glucose at much lower concentrations (<1 mM). Therefore, the flux of glucose through the GK pathway rises as the concentration of glucose in the blood increases from fasting (5 mM) to postprandial (≈10–15 mM) levels following a carbohydrate-containing meal [Printz, R. G., Magnuson, M. A., and Granner, D. K. in *Ann. Rev. Nutrition* Vol. 13 (R. E. Olson, D. M. Bier, and D. B. McCormick, eds.), Annual Review, Inc., Palo Alto, Calif., pages 463–496, 1993]. These findings contributed over a decade ago to the hypothesis that GK functions as a glucose sensor in β-cells and hepatocytes (Meglasson, M. D. and Matschinsky, F. M. *Amer. J. Physiol.* 246, E1–E13, 1984). In recent years, studies in transgenic animals have confirmed that GK does indeed play a critical role in whole-body glucose homeostasis. Animals that do not express GK die within days of birth with severe diabetes while animals overexpressing GK have improved glucose tolerance (Grupe, A., Hultgren, B., Ryan, A. et al., *Cell* 83, 69–78, 1995; Ferrie, T., Riu, E., Bosch, F. et al., *FASEB J.*, 10, 1213–1218, 1996). An increase in glucose exposure is coupled through GK in β-cells to increased insulin secretion and in hepatocytes to increased glycogen deposition and perhaps decreased glucose production.

The finding that type II maturity-onset diabetes of the young (MODY-2) is caused by loss of function mutations in the GK gene suggests that GK also functions as a glucose sensor in humans (Liang, Y., Kesavan, P., Wang, L. et al., *Biochem. J.* 309, 167–173, 1995). Additional evidence supporting an important role for GK in the regulation of glucose metabolism in humans was provided by the identification of patients that express a mutant form of GK with increased enzymatic activity. These patients exhibit a fasting hypoglycemia associated with an inappropriately elevated level of plasma insulin (Glaser, B., Kesavan, P., Heyman, M. et al., *New England J. Med.* 338, 226–230, 1998). While mutations of the GK gene are not found in the majority of patients with type II diabetes, compounds that activate GK and, thereby, increase the sensitivity of the GK sensor system will still be useful in the treatment of the hyperglycemia characteristic of all type II diabetes. Glucokinase activators will increase the flux of glucose metabolism in β-cells and hepatocytes, which will be coupled to increased insulin secretion. Such agents would be useful for treating type II diabetes.

In an effort to elucidate the mechanisms underlying kinase activation, the crystal structure of such proteins is often sought to be determined. The crystal structures of several hexokinases have been reported. See, e.g. A. E. Aleshin, C. Zeng, G. P. Bourenkov, H. D. Bartunik, H. J. Fromm & R. B. Honzatko 'The mechanism of regulation of hexokinase: new insights from the crystal structure of recombinant human brain hexokinase complexed with glucose and glucose-6-phosphate' *Structure* 6, 39–50 (1998); W. S. Bennett, Jr. & T. A. Steitz 'Structure of a complex between yeast hexokinase A and glucose I. Structure determination and refinement at 3.5 Å resolution' *J. Mol. Biol.* 140, 183–209 (1978); and S. Ito, S. Fushinobu, I. Yoshioka, S. Koga, H. Matsuzawa & T. Wakagi 'Structural Basis for the ADP-Specificity of a Novel Glucokinase from a Hyperthermophilic Archaeon' *Structure* 9, 205–214 (2001). Despite these reports, researchers armed with the knowledge of how to obtain crystals of related hexokinases have attempted to obtain crystals of any mammalian Glucokinase without success.

SUMMARY OF THE INVENTION

Applicants have discovered protocols which allow crystallization of mammalian Glucokinase with or without a bound allosteric ligand. The crystal structure has been solved by X-ray crystallography to a resolution of 2.7 Å. See FIGS. 3 and 4. Thus the invention relates to a crystalline form of Gluckokinase and a crystalline form of a complex of Glucokinase and an allosteric ligand. The invention further relates to a method of forming crystals of Glucokinase, with or without a bound allosteric ligand.

BRIEF DESCRIPTION OF THE FIGURES

FIG. 2 shows the amino acid sequence of an expressed Glucokinase used for crystallization.

FIGS. 4A–JJJ shows the atomic structure coordinates for Glucokinase bound to 3-Cyclopentyl-2-pyridin-4-yl-N-thiazol-2-yl-propionamide.

DETAILED DESCRIPTION OF THE INVENTION

Figure 1:
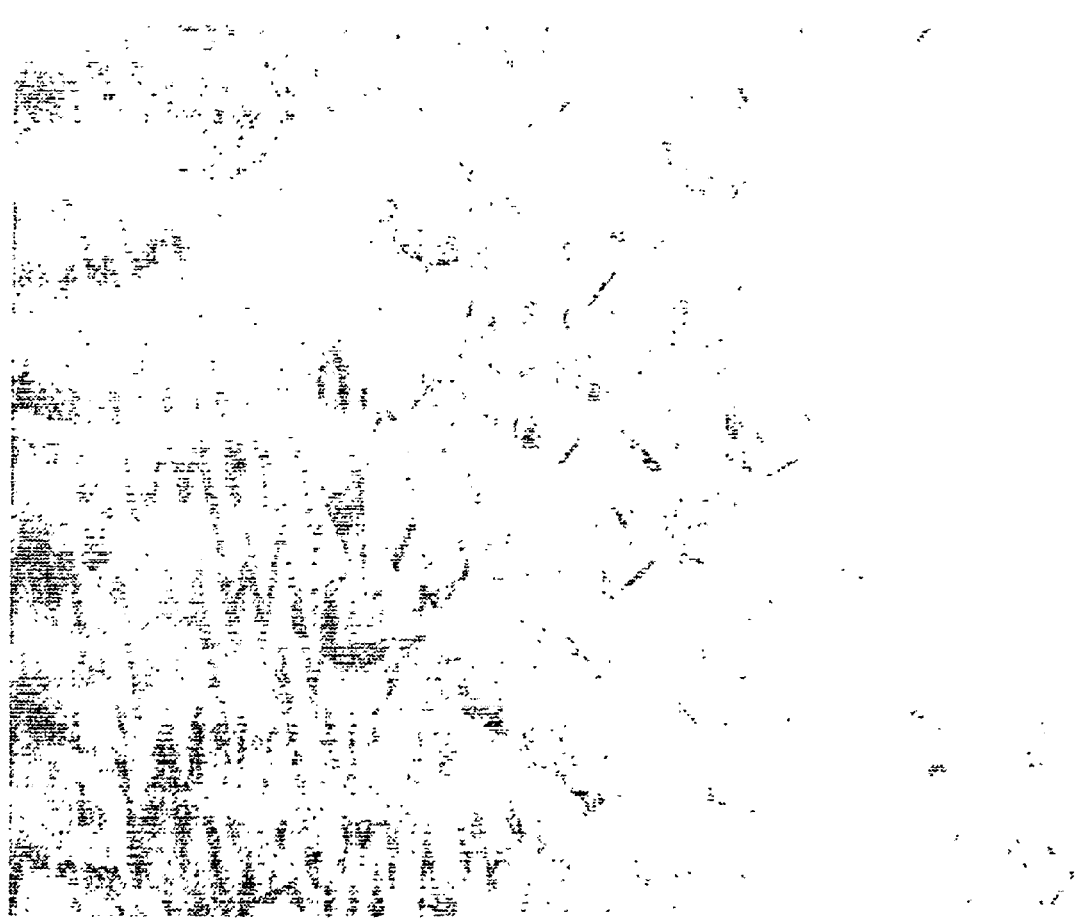
FIG. 1 shows Glucokinase co-crystals having P6(5)22 symmetry.

The present invention relates to crystalline forms of mammalian Glucokinase, with or without a ligand bound in the allosteric site, where the crystals are of sufficient quality and size to allow for the determination of the three-dimensional X-ray diffraction structure to a resolution of about 2.0 Å to about 3.5 Å. The invention also relates to methods for preparing and crystallizing the Glucokinase. The crystalline forms of Glucokinase, as well as information derived from their crystal structures can be used to analyze and modify glucokinase activity as well as to identify compounds that interact with the allosteric site.

The crystals of the invention include apo crystals and co-crystals. The apo crystals of the invention generally comprise substantially pure Glucokinase. The co-crystals generally comprise substantially pure Glucokinase with a ligand bound to the allosteric site.

It is to be understood that the crystalline Glucokinases of the invention are not limited to naturally occurring or native Glucokinases. Indeed, the crystals of the invention include mutants of the native Glucokinases. Mutants of native Glucokinases are obtained by replacing at lest one amino acid residue in a native Glucokinase domain with a different amino acid residue, or by adding or deleting amino acid residues within the native polypeptide or at the N- or C-terminus of the native polypeptide, and have substantially the same three-dimensional structure as the native Glucokinase from which the mutant is derived.

By having substantially the same three-dimensional structure is meant having a set of atomic structure coordinates from an apo- or co-crystal that have a root mean square deviation of less than or equal to about 2 Å when superimposed with the atomic structure coordinates of the native Glucokinase from which the mutant is derived when at least about 50% to about 100% of the alpha carbon atoms of the native Glucokinase are included in the superposition.

In some instances, it may be particularly advantageous or convenient to substitute, delete and/or add amino acid residues to a native Glucokinase domain in order to provide convenient cloning sites in cDNA encoding the polypeptide, to aid in purification of the polypeptide, etc. Such substitutions, deleteions and/or additions which do not substantially alter the three dimensional structure of the native Glucokinase will be apparent to those having skills in the art.

It should be noted that the mutants contemplated herein need not exhibit glucokinase activity. Indeed, amino acid substitutions, additions or deletions that interfere with the kinase activity of the glucokinase but which do not significantly alter the three-dimensional structure of the domain are specifically contemplated by the invention. Such crystalline polypeptides, or the atomic structure coordinates obtained therefrom, can be used to identify compounds that bind to the native domain. These compounds may affect the activity or the native domain.

The derivative crystals of the invention generally comprise a crystalline glucokinase polypeptide in covalent association with one or more heavy metal atoms. The polypeptide may correspond to a native or a mutated Glucokinase. Heavy metal atoms useful for providing derivative crystals include, by way of example and not limitation, gold and mercury. Alternatively, derivative crystals can be formed from proteins which have heavy atoms incorporated into one or more amino acids, such as seleno-methionine substitutions for methionine.

The co-crystals of the invention generally comprise a crystalline Glucokinase polypeptide in association with one or more compounds at an allosteric site of the polypeptide. The association may be covalent or non-covalent.

Production of Polypeptides

The native and mutated glucokinase polypeptides described herein may be isolated from natural sources or produced by methods well known to those skilled in the art of molecular biology. Expression vectors to be used may contain a native or mutated Glucokinase polypeptide coding sequence and appropriate transcriptional and/or translational control signals. These methods include in vitro recombinant DNA techniques, synthetic techniques and in vivo recombination/genetic recombination. See, for example, the techniques described in Maniatis et al., 1989, *Molecular Cloning: A Laboratory Manual*, Cold Spring Harbor Laboratory, NY; and Ausubel et al., 1989, *Current Protocols in Molecular Biology*, Greene Publishing Associates and Wiley Interscience, NY.

A variety of host-expression vector systems may be utilized to express the Glucokinase coding sequence. These include but are not limited to microorganisms such as bacteria transformed with recombinant bacteriophage DNA, plasmid DNA or cosmid DNA expression vectors containing the Glucokinase coding sequence; yeast transformed with recombinant yeast expression vectors containing the Glucokinase coding sequence; insect cell systems infected with recombinant virus expression vectors (e.g. baculovirus) containing the Glucokinase coding sequence; plant cell systems infected with recombinant virus expression vectors (e.g., cauliflower mosaic virus, CaMV; tobacco mosiac virus, TMV) or transformed with recombinant plasmid expression vectors (e.g., Ti plasmid) containing the glucokinase coding sequence; or animal cell systems. The expression elements of these systems vary in their strength and specificities. Depending on the host/vector system utilized, any of a number of suitable transcription and translation elements, including constitutive and inducible promoters such as pL of bacteriophage $\mu$, plac, ptrp, ptac (ptrp-lac hybrid promoter) and the like may be used; when cloning in insect cell systems, promoters such as the baculovirus polyhedrin promoter may be used; when cloingin in plant cell systems, promoters derived from the genome of plant cells (e.g., heat shock promoters; the promoter for the small subunit of RUBISCO; the promoter for the chlorophyll a/b binding protein) or from plant viruses (e.g., the 35 S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5 K promoter) may be used; when generating cell lines that contain multiple copies of the glucokinase coding sequence, SV40-, BPV- and EBV-based vectors may be used with an appropriate selectable marker.

Crystallization of Polypeptides and Characterization of Crystal Structure

The apo, derivative and co-crystals of the invention can be obtained by techniques well-known in the art of protein cystallography, including batch, liquid bridge, dialysis, vapor diffusion and hanging drop methods (see e.g. McPherson, 1982, *Preparation and Analysis of Protein Crystals*, John Wiley, NY; McPherson, 1990, *Eur. J. Biochem.* 189:1–23; Webber, 1991, *Adv. Protein Chem.* 41:1–36; Crystallization of Nucleic Acids and Proteins, Edited by Arnaud Ducruix and Richard Giege, Oxford University Press; Protein Crystallization Techniques, Strategies, and Tips, Edited by Terese Bergfors, International University Line, 1999). Generally, the apo- or co-crystals of the invention are grown by placing a substantially pure Glucokinase polypeptide in an aqueous buffer containing a precipitant at a concentration just below that necessary to precipitate the protein. Water is then removed from the solution by controlled evaporation to produce crystallizing conditions, which are maintained until crystal growth ceases.

In a preferred embodiment of the invention, apo or co-crystals are grown by vapor diffusion. In this method, the polypeptide/precipitant solution is allowed to equilibrate in a closed container with a larger aqueous reservoir having a precipitant concentration optimal for producing crystals. Generally, less than about 10 $\mu$L of subtantially pure polypeptide solution is mixed with an equal volume of reservoir solution, giving a precipitant concentration about half that required for crystallization. This solution is suspended as a droplet underneath a coverslip, which is sealed onto the top of a reservoir. The sealed container is allowed to stand, from one day to one year, usually for about 2–6 weeks, until crystals grow.

For crystals of the invention, it has been found that hanging drops containing about 2–5 µl of Glucokinase (9–22 mg/ml in 20 mM tris pH 7.1 measured at room temperature, 50 mM NaCl, 50 mM glucose, 10 mM DTT and optionally 0.2 mM EDTA) and an equal amount of reservoir solution (16–25% w/v polyethylene glycol with an average molecular weight from about 8000 to about 10000 Daltons, 0.1–0.2 M tris or bistris or Hepes or ammonium phosphate buffer, pH 6.9–7.5, 8–10 mM DTT, 0–30% saturated glucose) suspended over 0.5 to 1.0 mL reservoir buffer for about 3-4 weeks at 4–6° C. provided crystals suitable for high resolution X-ray structure determination. Particularly preferred conditions were: about 2–5 µl of Glucokinase (10 mg/ml in 20 mM tris pH 7.1 measured at room temperature, 50 mM NaCl, 50 mM glucose, 10 mM DTT and optionally 0.2 mM EDTA) and an equal amount of reservoir solution (22.5% w/v polyethylene glycol with an average molecular weight of about 10000 Daltons, 0.1 M tris pH 7.08, 10 mM DTT, 20% glucose) were suspended over 0.5 to 1.0 mL reservoir buffer for about 3–4 weeks at 4–6° C.

The optimum procedure for growing crystals large enough to collect data from involved first streaking 3–4 µl of protein solution on the coverslip, followed by streaking 3–4 µl of well solution across the elongated droplet of protein, forming a droplet shaped like the letter 'X'. Before discovering this crossed droplet technique, most droplets yielded showers of small crystals which were not large enough for data collection purposes. The crossed droplets allow gradients of protein and precipitating agent to form as the two solutions slowly mix, and the resulting kinetics of crystal nucleation and growth are optimal for the growth of a small number of large crystals in each crossed droplet. Simply mixing the protein and precipitant solutions together in a single round droplet often produced an overabundance of nuclei which grew to a final size too small for data collection purposes. Crystals usually appeared within 5 days of setup. The crystals grow in the form of hexagonal bipyramids, reaching dimensions of 0.2×0.2×0.4 mm typically, although larger crystals are often observed. FIG. 1 shows grown crystals.

Crystals may be frozen prior to data collection. The crystals were cryo-protected with either (a) 20–30% saturated glucose present in the crystallization setup, (b) ethanol added to 15–20%, (c) ethylene glycol added to 10–20% and PEG10,000 brought up to 25%, or (d) glycerol added to 15%. The crystals were either briefly immersed in the cryo-protectant or soaked in the cryo-protectant for periods as long as a day. Freezing was accomplished by immersing the crystal in a bath of liquid nitrogen or by placing the crystal in a stream of nitrogen gas at 100 K.

The mosaic spread of the frozen crystals could sometimes be reduced by annealing, wherein the stream of cold nitrogen gas is briefly blocked, allowing the frozen crystal to thaw momentarily before re-freezing in the nitrogen gas stream. Another technique which was sometimes helpful in data collection was to center one of the ends of the hexagonal bipyramid in the x-ray beam, rather than the mid portion of the crystal. The mosaic spread could sometimes be reduced by this technique.

Figure 3:
FIG. 3 shows a ribbon diagram of the structure of Glucokinase colored according to secondary structure. Light blue represents α-helix, dark blue represents $3_{10}$-helix, green represents β-sheet and orange is coil.

Diffraction data typically extending to 2.7 Å was collected from the frozen crystals at the synchrotron beamline X8C of the National Synchrotron Light Source in Brookhaven, N.Y. Under optimum conditions, data extending to 2.2 Å was recorded. See FIGS. 3 and 4 for solution. The space group of the crystals was determined to be P6(5)22 during the course of the solution of the crystal structure. The crystals have unit cell dimensions a=b=79.62+/−0.60 Å, c=321.73+/−3.70 Å, α=β=90°, γ=120°. The crystals are in a hexagonal system with P6(5)22 symmetry.

Of course, those having skill in the art will recognize that the above-described crystallization conditions can be varied. Such variations may be used alone or in combination, and include polypeptide solutions containing polypeptide concentrations between 1 mg/mL and 60 mg/mL, any commercially available buffer systems which can maintain pH from about 6.5 to about 7.6, Tris-HCl concentrations between 10 mM and 200 mM, dithiothreitol concentrations between 0 mM and 20 mM, substitution of dithiothreitol with beta mercapto ethanol or other art-recognized equivalents, or substitution of glucose with other sugars known to bind to Glucokinase; and reservoir solutions containing polyethylene glycol concentrations between about 10% and about 30%, polyethylene glycol average molecular weights between about 1000 and about 20,000 daltons, any commercially available buffer systems which can maintain pH from about 6.5 to about 7.6, dithiothreitol concentrations between 0 mM and 20 mM, substitution of dithiothreitol with beta mercapto ethanol or other art-recognized —SH group containing equivalents, or substitution of glucose with other sugars known to bind to Glucokinase, and temperature ranges between 4 and 20° C.

Derivative crystals of the invention can be obtained by soaking apo or co-crystals in mother liquor containing salts of heavy metal atoms, according to procedures known to those of skill in the art of X-ray crystallography.

Co-crystals of the invention can be obtained by soaking an apo crystal in mother liquor containing a ligand that binds to the allosteric site, or can be obtained by co-crystallizing the Glucokinase polypeptide in the presence of one or more ligands that bind to the allosteric site. Preferably, co-crystals are formed with a glucokinase activator disclosed in U.S. Pat. No. 6,320,050; U.S. patent application Ser. No. 09/532,506 filed Mar. 21, 2000; U.S. patent application Ser. No. 09/675,781 filed Sep. 28, 2000; U.S. patent application Ser. No. 09/727,624, filed Dec. 1, 2000; U.S. patent application Ser. No. 09/841,983, filed Apr. 25, 2001; U.S. patent application Ser. No. 09/843,466, filed Apr. 26, 2001; U.S. patent application Ser. No. 09/846,820, filed May 1, 2001; U.S. patent application Ser. No. 09/846,821, filed May 1, 2001; U.S. patent application Ser. No. 09/905,152, filed Jul. 13, 2001; U.S. patent application Ser. No. 09/924,247, filed Aug. 8, 2001; U.S. Provisional Pat. Appl. No. 60/251,637, filed Dec. 6, 2000; or U.S. Provisional Pat. Appl. No. 60/318,715, filed Sep. 13, 2001, each of which is incorporated herein by reference.

Methods for obtaining the three-dimensional structure of the crystalline glucokinases described herein, as well as the atomic structure coordinates, are well-known in the art (see, e.g., D. E. McRee, Practical Protein Crystallography, published by Academic Press, San Diego (1993), and references cited therein).

Uses of the Crystals and Atomic Structure Coordinates

The crystals of the invention, and particularly the atomic structure coordinates obtained therefrom, have a wide variety of uses. For example, the crystals and structure coordinates described herein are particularly useful for identifying compounds that activate Glucokinases as an approach towards developing new therapeutic agents.

The structure coordinates described herein can be used as phasing models in determining the crystal structures of additional native or mutated glucokinases, as well as the structures of co-crystals of such glucokinases with allosteric inhibitors or activators bound. The structure coordinates, as well as models of the three-dimensional structures obtained therefrom, can also be used to aid the elucidation of solution-based structures of native or mutated glucokinases, such as those obtained via NMR. Thus, the crystals and atomic structure coordinates of the invention provide a convenient means for elucidating the structures and functions of glucokinases.

For purposes of clarity and discussion, the crystals of the invention will be described by reference to specific Glucokinase exemplary apo crystals and co-crystals. Those skilled in the art will appreciate that the principles described herein are generally applicable to crystals of any mammalian Glucokinase, including, but not limited to the Glucokinase of FIG. 2.

Definitions

As used herein, "allosteric site" refers in general to any ligand binding site on a mammalian Glucokinase other than the active site of the enzyme.

As used herein, "apo crystal" refers to crystals of mammalian Glucokinase formed without a bound allosteric ligand.

As used herein, "allosteric ligand" refers to any molecule which specifically binds an allosteric site on a mammalian Glucokinase.

EXAMPLES

Example 1

Expression and Purification of Glucokinase
Expression of GK

Glucokinase (GK) was expressed as a glutathione S-transferase (GST) fusion protein in *Escherichia coli*. The amino-acid sequence of the fusion protein is given in FIG. 2. The expression construct is based on the pGEX-3X vector from Pharmacia, as described in Y. Liang, P. Kesavan, L. Wang, K. Niswender, Y. Tanizawa, M. A. Permutt, M. A. Magnuson, F. M. Matschinsky, *Biochem. J.* 309, 167 (1995). The construct codes for one of the two liver isozymes of human GK. The GST tag is at the N-terminus of the construct, and is separated from the coding sequence for GK by a Factor Xa cleavage site. After purification of the GST fusion protein, the GST fusion tag was removed with Factor Xa protease, which also removes five residues from the N-terminus of GK.

Purification of GK

*E. coli* cells expressing GST-GK were suspended in lysis buffer (50 mM tris, 200 mM NaCl, 5 mM EDTA, 5 mM DTT, 1% NP-40, pH 7.7) in the presence of protease inhibitors, incubated with lysozyme at 200 $\mu$/ml for 30 minutes at room temperature, and sonicated 4×30 sec. at 4° C. After centrifugation to remove insoluble material, the supernatant was loaded onto glutathione-Sepharose, washed with lysis buffer and then with lysis buffer minus NP-40. GST-GK was eluted with lysis buffer (minus NP-40) containing 50 mM D-glucose and 20 mM glutathione. The eluted protein was concentrated and dialyzed into 20 mM tris, 100 mM NaCl, 0.2 mM EDTA, 50 mM D-glucose, 1 mM DTT, pH 7.7. Factor Xa was added at a protein ratio of 1:100 GST-GK followed by the addition of CaCl$_2$ to 1 mM, and the sample was incubated at 4° C. for 48 hours. The sample was added to glutathione Sepharose and the unbound fraction collected and concentrated. The sample was then incubated with benzamidine Sepharose to remove Factor Xa, and the unbound fraction was collected and loaded on a Q Sepharose column equilibrated with 25 mM bis-tris propane, 50 mM NaCl, 5 mM DTT, 50 mM D-glucose and 5% glycerol (pH 7.0). The protein was eluted with a NaCl gradient from 50–400 mM. Fractions containing purified GK were pooled and concentrated and filtered.

Example 2

Formation of Apo Crystal

4 $\mu$l of glucokinase and 4 $\mu$l of precipitant were mixed and equilibrated against the precipitant solution at 4° C. The glucokinase solution consisted of 22 mg/ml glucokinase prepared in Example 1 in 20 mM hepes pH 7.5, 50 mM NaCl, 10 mM DTT, and 50 mM glucose. The precipitant consisted of 22.5% PEG10000, 0.1 M tris pH 7.08, 10 mM DTT, 20% glucose; the precipitant solution contained seed crystals in order to microseed the droplets. Crystals appeared in the droplets after leaving the crystallization plates at 4° C.

Example 3

Formation of Co-crystal with 3-Cyclopentyl-2-pyridin-4-yl-N-thiazol-2-yl-propionamide 3(a):

4 $\mu$l of glucokinase and 4 $\mu$l of precipitant were mixed and equilibrated against the precipitant solution at 4° C. The glucokinase solution consisted of 13 mg/ml glucokinase prepared in Example 1 in 20 mM tris pH 7.0, 50 mM NaCl, 10 mM DTT, 50 mM glucose, and the glucokinase activator 3-Cyclopentyl-2-pyridin-4-yl-N-thiazol-2-yl-propionamide at a concentration 5 times that of the protein. The precipitant consisted of 22.5% PEG10000, 0.1 M tris pH 7.08, 10 mM DTT, 20% glucose. Crystals appeared in the droplets after leaving the crystallization plates at 4° C.

3(b):

Alternatively, crystals were grown as in Example 3(a) with the following changes: instead of 4 $\mu$l glucokinase and 4 $\mu$l precipitant, 2 $\mu$l of each were used; the glucokinase solution contained 11 mg/ml glucokinase in tris buffer at pH 7.08 instead of 7.0; the glucokinase solution included 0.2 mM EDTA; in place of 22.5% PEG10000 as precipitant 18% PEG8000 was used; the precipitant solution contained seed crystals in order to microseed the droplets.

3(c):

In another alternative, crystals were grown as in Example 3(a) with the following changes: instead of 4 $\mu$l glucokinase and 4 $\mu$l precipitant, 2 $\mu$l of each were used; the glucokinase solution contained 11 mg/ml glucokinase in tris buffer at pH 7.08 instead of 7.0; the glucokinase solution included 0.2 mM EDTA; in place of 22.5% PEG10000 as precipitant 20% PEG8000 was used; the precipitant solution contained seed crystals in order to microseed the droplets.

3(d):

In yet another alternative, crystals were grown as in Example 3(a) with the following changes: instead of 4 $\mu$l glucokinase and 4 $\mu$l precipitant, 2 $\mu$l of each were used; the glucokinase solution contained 12 mg/ml glucokinase in tris buffer at pH 7.08 instead of 7.0; the glucokinase solution included 0.2 mM EDTA; in place of 22.5% PEG10000 as precipitant 16% PEG10000 was used; glucose was not present as a component of the precipitant; the precipitant solution contained seed crystals in order to microseed the droplets.

3(e):

In still another alternative, crystals were grown as in Example 3(a) with the following changes: the glucokinase solution contained 11 mg/ml glucokinase in tris buffer at pH 7.1 instead of 7.0; the glucokinase solution included 0.2 mM EDTA; in place of 22.5% PEG10000 as precipitant 25% PEG10000 was used.

3(f):

In still another alternative, crystals were grown as in Example 3(a) with the following changes: the glucokinase solution contained 11 mg/ml glucokinase in tris buffer at pH 7.1 instead of 7.0; the glucokinase solution included 0.2 mM EDTA; in place of 22.5% PEG10000 as precipitant 21.25% PEG10000 was used; in place of tris buffered at pH 7.08 in the precipitant tris buffered at pH 7.52 was used.

3(g):

In still another alternative, crystals were grown as in Example 3(a) with the following changes: the glucokinase solution contained 12 mg/ml glucokinase in tris buffer at pH 7.08 instead of 7.0; the glucokinase solution included 0.2 mM EDTA; in place of tris buffered at pH 7.08 in the precipitant, hepes buffered at pH 6.89 was used; in place of 20% glucose in the precipitant, 200 mM glucose was used.

3(h):

In still another alternative, crystals were grown as in Example 3(a) with the following changes: the glucokinase solution contained 12 mg/ml glucokinase in tris buffer at pH 7.08 instead of 7.0; the glucokinase solution included 0.2 mM EDTA; in place of 0.1 M tris buffered at pH 7.08 in the precipitant, 0.2 M ammonium phosphate buffered at pH 7.03 was used; in place of 20% glucose in the precipitant, 200 mM glucose was used.

3(i):

In still another alternative, crystals were grown as in Example 3(a) with the following changes: the glucokinase solution contained 10 mg/ml glucokinase in tris buffer at pH 7.08 instead of 7.0; the glucokinase solution included 0.2 mM EDTA; in place of 22.5% PEG10000 as precipitant, 20% PEG10000 was used; in place of tris buffered at pH 7.08 in the precipitant, tris buffered at pH 7.05 was used; in place of 10 mM DTT in the precipitant, 8 mM DTT was used; glucose was not present as a component of the precipitant.

3(j):

In still another alternative, crystals were grown as in Example 3(a) with the following changes: the glucokinase solution contained 12 mg/ml glucokinase in tris buffer at pH 7.08 instead of 7.0; the glucokinase solution included 0.2 mM EDTA; in place of 22.5% PEG10000 as precipitant, 22% PEG8000 was used; glucose was not present as a component of the precipitant; the precipitant solution contained seed crystals in order to microseed the droplets.

3(k):

In still another alternative, crystals were grown as in Example 3(a) with the following changes: the glucokinase solution contained 11 mg/ml glucokinase in tris buffer at pH 7.1 instead of 7.0; the glucokinase solution included 0.2 mM EDTA; in place of 20% glucose in the precipitant, 30% glucose was used.

Example 4

Formation of Co-crystal with N-(5-Bromo-pyridin-2-yl)-2-(3-chloro-4-methanesulfonyl-phenyl)-3-cyclopentyl-propionamide Crystals were grown as in Example 3(a) with the following changes: the glucokinase solution contained 9 mg/ml glucokinase in tris buffer at pH 7.1 instead of 7.0; the glucokinase solution included 0.2 mM EDTA; in place of the glucokinase activator of Example 3(a), the glucokinase solution contained the glucokinase activator N-(5-Bromo-pyridin-2-yl)-2-(3-chloro-4-methanesulfonyl-phenyl)-3-cyclopentyl-propionamide; in place of 20% glucose in the precipitant, 200 mM glucose was used.

Example 5

Formation of Co-crystal with 2-(3-Chloro-4-methanesulfonyl-phenyl)-3-cyclopentyl-N-(5-trifluoromethyl-pyridin-2-yl)-propionamide Crystals were grown as in Example 3(a) with the following changes: the glucokinase solution contained 10 mg/ml glucokinase in tris buffer at pH 7.1 instead of 7.0; the glucokinase solution included 0.2 mM EDTA; in place of the glucokinase activator of Example 3(a), the glucokinase solution contained the glucokinase activator 2-(3-Chloro-4-methanesulfonyl-phenyl)-3-cyclopentyl-N-(5-trifluoromethyl-pyridin-2-yl)-propionamide; in place of 22.5% PEG10000 as precipitant, 21.25% PEG1000 was used.

Example 6

Formation of Co-crystal with (2S)-2-[3-Cyclopentyl-2-(3,4-dichloro-phenyl)-propionylamino]-thiazole-4-carboxylic Acid Methyl Ester Crystals were grown as in Example 3(a) with the following changes: the glucokinase solution contained 10 mg/ml glucokinase in tris buffer at pH 7.1 instead of 7.0; the glucokinase solution included 0.2 mM EDTA; in place of the glucokinase activator of Example 3(a), the glucokinase solution contained the glucokinase activator (2S)-2-[3-Cyclopentyl-2-(3,4-dichloro-phenyl)-propionylamino]-thiazole-4-carboxylic acid methyl ester; in place of 22.5% PEG10000 as precipitant, 21.25% PEG10000 was used; in place of tris buffered at pH 7.08 in the precipitant, bistris buffered at pH 7.0 was used.

Example 7

Formation of Co-crystal with (2S)-{2-[3-Cyclopentyl-2-(3,4-dichloro-phenyl)-propionylamino]-thiazol-5-yl}-oxo-acetic Acid Ethyl Ester Crystals were grown as in Example 3(a) with the following changes: the glucokinase solution contained 10 mg/ml glucokinase in tris buffer at pH 7.1 instead of 7.0; the glucokinase solution included 0.2 mM EDTA; in place of the glucokinase activator of Example 3(a), the glucokinase solution contained the glucokinase activator (2S)-{2-[3-Cyclopentyl-2-(3,4-dichloro-phenyl)-propionylamino]-thiazol-5-yl}-oxo-acetic acid ethyl ester; in place of 22.5% PEG10000 as precipitant, 21.25% PEG10000 was used.

Example 8

Formation of Co-crystal with (2S)-{3-[3-Cyclopentyl-2-(3,4-dichloro-phenyl)-propionyl]-ureido}-acetic Acid Methyl-ester Crystals were grown as in Example 3(a) with the following changes: the glucokinase solution contained 9 mg/ml glucokinase in tris buffer at pH 7.08 instead of 7.0; the glucokinase solution included 0.2 mM EDTA; in place of the glucokinase activator of Example 3(a), the glucokinase solution contained the glucokinase activator (2S)-{3-[3-Cyclopentyl-2-(3,4-dichloro-phenyl)-propionyl]-ureido}-acetic acid methylester; in place of 20% glucose in the precipitant, 200 mM glucose was used.

Example 9

Formation of Co-crystal with (2S)-1-[3-Cyclopentyl-2-(3,4-dichloro-phenyl)-propionyl]-3-(3-hydroxy-propyl)-urea Crystals were grown as in Example 3(a) with the following changes: the glucokinase solution contained 14 mg/ml glucokinase in tris buffer at pH 7.08 instead of 7.0; the glucokinase solution included 0.2 mM EDTA; in place of the glucokinase activator of Example 3(a), the glucokinase solution contained the glucokinase activator (2S)-1-[3-Cyclopentyl-2-(3,4-dichloro-phenyl)-propionyl]-3-(3-hydroxy-propyl)-urea; in place of 20% glucose in the precipitant, 200 mM glucose was used.

Example 10

Formation of Co-crystal with (2S)-{3-[3-Cyclopentyl-2-(3,4-dichloro-phenyl)-propionyl]-ureido}-acetic Acid Ethyl Ester Crystals were grown as in Example 3(a) with the following changes: the glucokinase solution contained 14 mg/ml glucokinase in tris buffer at pH 7.08 instead of 7.0; the glucokinase solution included 0.2 mM EDTA; in place of the glucokinase activator of Example 3(a), the glucokinase solution contained the glucokinase activator (2S)-{3-[3-Cyclopentyl-2-(3,4-dichloro-phenyl)-propionyl]-ureido}-acetic acid ethyl ester; in place of tris buffered at pH 7.08 in the precipitant, tris buffered at pH 7.05 was used.

Example 11

Synthesis of 3-Cyclopentyl-2-pyridin-4-yl-N-thiazol-2-yl-propionamide

3-Cyclopentyl-2-pyridin-4-yl-N-thiazol-2-yl-propionamide can be prepared using well-known organic synthesis techniques according to the following reaction scheme:

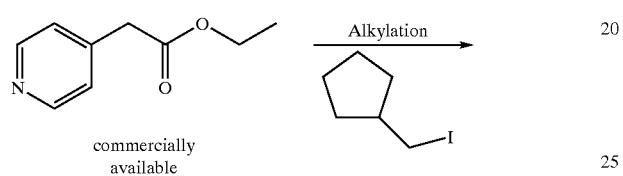

commercially available

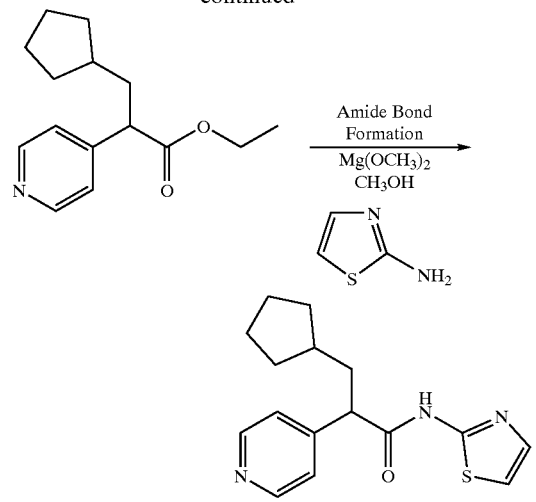

3-Cyclopentyl-2-pyridin-4-yl-N-thiazol-2-yl-propionamide is useful as an allosteric activator of Glucokinase and to assist the formation of co-crystals of Glucokinase.

We claim:
1. The compound

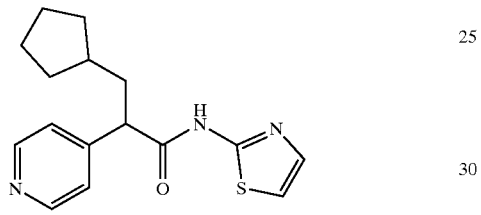

and pharmaceutically acceptable salts thereof.

* * * * *

UNITED STATES PATENT AND TRADEMARK OFFICE
CERTIFICATE OF CORRECTION

PATENT NO. : 6,911,545 B2
DATED : June 28, 2005
INVENTOR(S) : Corbett et al.

It is certified that error appears in the above-identified patent and that said Letters Patent is hereby corrected as shown below:

Title page,
Item [73], Assignee, "Hoffman-La Roche Inc., Nutley, NJ" should be -- Hoffmann-La Roche Inc., Nutley, NJ --.

Signed and Sealed this

Sixth Day of September, 2005

JON W. DUDAS
*Director of the United States Patent and Trademark Office*

SEQUENCE LISTING

<160> NUMBER OF SEQ ID NOS: 1

<210> SEQ ID NO 1
<211> LENGTH: 692
<212> TYPE: PRT
<213> ORGANISM: Escherichia coli

<400> SEQUENCE: 1

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175
```

```
Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
            195                 200                 205

Thr Phe Gly Gly Gly Asp His Pro Pro Lys Ser Asp Leu Ile Glu Gly
            210                 215                 220

Arg Gly Ile His Met Pro Arg Pro Arg Ser Gln Leu Pro Gln Pro Asn
225                 230                 235                 240

Ser Gln Val Glu Gln Ile Leu Ala Glu Phe Gln Leu Gln Glu Glu Asp
                245                 250                 255

Leu Lys Lys Val Met Arg Arg Met Gln Lys Glu Met Asp Arg Gly Leu
                260                 265                 270

Arg Leu Glu Thr His Glu Glu Ala Ser Val Lys Met Leu Pro Thr Tyr
            275                 280                 285

Val Arg Ser Thr Pro Glu Gly Ser Glu Val Gly Asp Phe Leu Ser Leu
290                 295                 300

Asp Leu Gly Gly Thr Asn Phe Arg Val Met Leu Val Lys Val Gly Glu
305                 310                 315                 320

Gly Glu Glu Gly Gln Trp Ser Val Lys Thr Lys His Gln Met Tyr Ser
                325                 330                 335

Ile Pro Glu Asp Ala Met Thr Gly Thr Ala Glu Met Leu Phe Asp Tyr
            340                 345                 350

Ile Ser Glu Cys Ile Ser Asp Phe Leu Asp Lys His Gln Met Lys His
            355                 360                 365

Lys Lys Leu Pro Leu Gly Phe Thr Phe Ser Phe Pro Val Arg His Glu
            370                 375                 380

Asp Ile Asp Lys Gly Ile Leu Leu Asn Trp Thr Lys Gly Phe Lys Ala
385                 390                 395                 400

Ser Gly Ala Glu Gly Asn Asn Val Val Gly Leu Leu Arg Asp Ala Ile
                405                 410                 415

Lys Arg Arg Gly Asp Phe Glu Met Asp Val Val Ala Met Val Asn Asp
                420                 425                 430

Thr Val Ala Thr Met Ile Ser Cys Tyr Tyr Glu Asp His Gln Cys Glu
            435                 440                 445

Val Gly Met Ile Val Gly Thr Gly Cys Asn Ala Cys Tyr Met Glu Glu
            450                 455                 460

Met Gln Asn Val Glu Leu Val Glu Gly Asp Glu Gly Arg Met Cys Val
465                 470                 475                 480

Asn Thr Glu Trp Gly Ala Phe Gly Asp Ser Gly Glu Leu Asp Glu Phe
                485                 490                 495

Leu Leu Glu Tyr Asp Arg Leu Val Asp Glu Ser Ser Ala Asn Pro Gly
            500                 505                 510

Gln Gln Leu Tyr Glu Lys Leu Ile Gly Gly Lys Tyr Met Gly Glu Leu
            515                 520                 525

Val Arg Leu Val Leu Leu Arg Leu Val Asp Glu Asn Leu Leu Phe His
            530                 535                 540

Gly Glu Ala Ser Glu Gln Leu Arg Thr Arg Gly Ala Phe Glu Thr Arg
545                 550                 555                 560

Phe Val Ser Gln Val Glu Ser Asp Thr Gly Asp Arg Lys Gln Ile Tyr
                565                 570                 575

Asn Ile Leu Ser Thr Leu Gly Leu Arg Pro Ser Thr Thr Asp Cys Asp
            580                 585                 590

Ile Val Arg Arg Ala Cys Glu Ser Val Ser Thr Arg Ala Ala His Met
```

-continued

```
            595                 600                 605
Cys Ser Ala Gly Leu Ala Gly Val Ile Asn Arg Met Arg Glu Ser Arg
    610                 615                 620

Ser Glu Asp Val Met Arg Ile Thr Val Gly Val Asp Gly Ser Val Tyr
625                 630                 635                 640

Lys Leu His Pro Ser Phe Lys Glu Arg Phe His Ala Ser Val Arg Arg
                645                 650                 655

Leu Thr Pro Ser Cys Glu Ile Thr Phe Ile Glu Ser Glu Glu Gly Ser
                660                 665                 670

Gly Arg Gly Ala Ala Leu Val Ser Ala Val Ala Cys Lys Lys Ala Cys
            675                 680                 685

Met Leu Gly Gln
    690
```